(12) United States Patent
Chen et al.

(10) Patent No.: US 11,999,976 B2
(45) Date of Patent: Jun. 4, 2024

(54) ENGINEERED KETOREDUCTASE POLYPEPTIDES AND USES THEREOF

(71) Applicant: Enzymaster (Ningbo) Bio-Engineering Co., Ltd, Ningbo (CN)

(72) Inventors: Haibin Chen, Ningbo (CN); Chuanyang Shang, Ningbo (CN); Baoqin Cai, Ningbo (CN); Marco Bocola, Ningbo (CN); Shumin Shi, Ningbo (CN); Ruimei Hong, Ningbo (CN); Lei Sun, Ningbo (CN); Yong Koy Bong, Ningbo (CN)

(73) Assignee: Enzymaster (Ningbo) Bio-Engineering Co., Ltd, Ningbo (CN)

( * ) Notice: Subject to any disclaimer, the term of this patent is extended or adjusted under 35 U.S.C. 154(b) by 0 days.

(21) Appl. No.: 17/290,916

(22) PCT Filed: Dec. 11, 2019

(86) PCT No.: PCT/CN2019/124709
§ 371 (c)(1),
(2) Date: May 3, 2021

(87) PCT Pub. No.: WO2020/119740
PCT Pub. Date: Jun. 18, 2020

(65) Prior Publication Data
US 2021/0371829 A1 Dec. 2, 2021

(30) Foreign Application Priority Data
Dec. 15, 2018 (CN) .......................... 201811537509.4

(51) Int. Cl.
| | | |
|---|---|---|
| *C12N 9/04* | (2006.01) | |
| *C12N 11/02* | (2006.01) | |
| *C12P 7/22* | (2006.01) | |
| *C12P 7/62* | (2022.01) | |
| *C12P 41/00* | (2006.01) | |

(52) U.S. Cl.
CPC ............ *C12N 9/0006* (2013.01); *C12N 11/02* (2013.01); *C12P 7/22* (2013.01); *C12P 7/62* (2013.01); *C12P 41/002* (2013.01); *C12Y 101/01184* (2013.01)

(58) Field of Classification Search
CPC ...... C12N 9/0006; C12N 11/02; C12N 11/00; C12P 7/22; C12P 7/62; C12P 41/002; C12P 7/18; C12P 41/001; C12Y 101/01184; Y02P 20/582
See application file for complete search history.

(56) References Cited

FOREIGN PATENT DOCUMENTS

| CN | 105062985 A | 11/2015 |
|---|---|---|
| CN | 106047828 A | 10/2016 |
| CN | 107254454 A | 10/2017 |

OTHER PUBLICATIONS

GenBank accession No. WP_089998481, Jul. 29, 2017.*
Gkorezis et al., GenBank accession No. APU96915 Jan. 17, 2017.*
Zhao, Feng-Jiao et al., "Single Mutations of Ketoreductase ChKRED20 Enhance the Bioreductive Production of (1S)-2-chloro-1-(3, 4 difluorophenyl) ethanol", *Appl. Microbiol. Biotechnol.*, vol. 101 (Nov. 11, 2009).

* cited by examiner

*Primary Examiner* — Delia M Ramirez
(74) *Attorney, Agent, or Firm* — Smith Patent, LLC; Chalin A. Smith

(57) ABSTRACT

Provided are amino acid sequences of ketoreductase polypeptides that are useful for asymmetrically synthesizing chiral alcohol compounds, its preparation process as well as reaction process under industrial-relevant conditions. Also provided are polynucleotide sequences encoding engineered ketoreductase polypeptides, engineered host cells capable of expressing engineered ketoreductase polypeptides, and methods of producing chiral alcohol compounds using engineered ketoreductase polypeptides. Compared to other enzymes, the engineered ketoreductase polypeptides provided by the invention have better catalytic activity and thermal stability, allowing purification of the enzyme solution by heat treatment, which is advantageous for the production of enzymes and the industrial application of enzymatic reactions. The use of the engineered polypeptides of the present invention greatly simplifies the production process of chiral alcohol compounds, reduces the cost of production and the impact on the environment, and has good industrial application prospects.

19 Claims, 2 Drawing Sheets
Specification includes a Sequence Listing.

ENGINEERED KETOREDUCTASE POLYPEPTIDES AND USES THEREOF

PRIORITY

This application corresponds to the U.S. National phase of International Application No. PCT/CN2019/124709, filed Dec. 11, 2019, which, in turn, claims priority to Chinese Patent Application No. 201811537509.4 filed Dec. 15, 2018, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Apr. 8, 2021, is named LNK_229US_SEQ_LIST.txt and is 559,072 bytes in size.

TECHNICAL FIELD OF THE PRESENT INVENTION

The present invention relates to the field of biotechnology, in particular to engineered ketoreductase polypeptides and their applications.

BACKGROUND OF THE PRESENT INVENTION

Chiral alcohols are widely used compounds. Many natural or biologically active compounds contain a chiral alcohol structure. In industrial production, chemical and enzymatic methods are the main methods for the preparation of chiral alcohols. In the enzymatic catalysis method, a carbonyl compound is usually used as a substrate, and the carbonyl substrate is asymmetrically reduced by a keto reductase (KRED) or an alcohol dehydrogenase (ADH) to obtain a chiral alcohol. The enzymatic method is favored in the industry for its high selectivity, high conversion, mild reaction conditions, low cost and low pollution. In terms of reaction mechanism, the ketoreductase or alcohol dehydrogenase catalyzes the reduction of a carbonyl (or keto) compound to an alcohol compound by the reducing power H$^-$ provided by the cofactor NADH or NADPH, and the cofactor NADH or NADPH is converted into NAD+ or NADP+ respectively. While this process is being carried out, NAD+ or NADP+ can also be converted back to NADH or NADPH by another enzymatic reaction, that regenerates NADH or NADPH. There are usually three ways to convert NAD+ or NADP+ to NADH or NADPH, respectively. The first is to add an alcohol compound in the reaction of FIG. 1, in the process of converting this alcohol compound (such as isopropanol) into a carbonyl compound (such as acetone) by the same ketoreductase or alcohol dehydrogenase, NAD+ or NADP+ is reduced to NADH or NADPH respectively. The second is to add glucose dehydrogenase and glucose in the reaction of FIG. 1, in the process of glucose dehydrogenase catalyzing the conversion of glucose to gluconic acid, NAD+ or NADP+ is converted to NADH or NADPH respectively. The third is to add formate dehydrogenase and formic acid in the reaction of FIG. 1, in the process of formate dehydrogenase catalyzing the conversion of formic acid to carbon dioxide, NAD+ or NADP+ is converted to NADH or NADPH, respectively.

(R)-(−)-1,3-butanediol is a relatively expensive chiral alcohol compound whose synthesis is difficult. Currently, the highly-pure (R)-(−)-1,3-butanediol required in the domestic market is dependent on imports. The current industrial production of (R)-(−)-1,3-butanediol is mainly based on chemical methods, represented by the method of Japan Daicel Chemical Co., Ltd. This process starts with hydrogenation of 3-hydroxybutyraldehyde by Raney Ni catalyst to obtain racemic 1,3-butanediol, which is then subjected to resolution to obtain (R)-(−)-1,3-butanediol and (S)-(−)-1,3-butanediol, respectively. This method involves cumbersome resolution and recrystallization steps, which generate large amount of waste water and solid waste, resulting in high cost and heavy pollution, and the theoretical yield of (R)-(−)-1,3-butanediol in this method is up to 50%. For the enzymatic method, the asymmetric conversion of 4-hydroxy-2-butanone to (R)-(−)-1,3-butanediol could reach the highest theoretical yield of 100% through suitable ketoreductase. However, the ketoreductase or alcohol dehydrogenase reported so far exhibits low activity or insufficient stability when applied to the asymmetric reduction of 4-hydroxy-2-butanone to prepare (R)-(−)-1,3-butanediol, which makes them not applicable to industrial production.

SUMMARY OF THE PRESENT INVENTION

The invention provides engineered ketoreductase polypeptides with high stereoselectivity, high catalytic activity and good stability, which can be used for preparing chiral alcohol compounds, in particular (R)-(−)-1,3-butanediol. The present invention also provides gene sequences of engineered polypeptides, recombinant expression vectors containing the genes, engineered strains and efficient methods for the production thereof, as well as reaction processes for the synthesis of chiral alcohol compounds using engineered ketoreductase polypeptides.

The inventors have experimentally verified that a wild type ketoreductase ChKRED20, derived from *Chryseobacterium* sp. CA49 (Journal of Molecular Catalysis B: Enzymatic, 102 (2014) 1-8 was reported in the literature), is active on 4-hydroxy-2-butanone. In the presence of the cofactor NADH, ChKRED20 can asymmetrically reduce 4-hydroxy-2-butanone to (R)-(−)-1,3-butanediol. The amino acid sequence of ChKRED20 is shown given as SEQ ID NO: 2. However, the activity and stability of ChKRED20 do not meet the requirements of the manufacture process in industrial production, and its performance needs to be improved (Applied Microbiology and Biotechnology, 100 (2016) 3567-3575). In industrial production, the manufacture of enzymes is generally accomplished by liquid fermentation of microorganisms. In the fermentation process, in addition to producing the target enzyme, the host microorganisms simultaneously produce a large amount of non-target proteins (i.e., contaminating proteins). It is often desirable to remove contaminating proteins by heat treatment as a means of purification for the target enzyme. Heat treatment is a very simple, effective and economical method for purifying the enzyme solution, and contaminating proteins will be inactivated, precipitated and removed from the enzyme solution through heat treatment. Using the enzyme solution purified by the heat treatment method in the catalytic reaction not only avoids the undesired influence of the contaminating proteins on the reaction process, but also the separation and purification process of the product obtained after the catalytic reaction will be greatly simplified due to dramatical reduction of the total protein loading in the reaction. If *Escherichia coli* is used as a host microorganism to produce target enzyme, it has been verified by the inventors that the contaminating proteins can be precipitated very efficiently by heating the enzyme solution at 85° C. under industrial production conditions. However, the premise of heat treatment of the enzyme solution at 85° C. is that the target enzyme has very good thermal stability. The better the thermal stability of the target enzyme is, the more target enzyme will survive the heat treatment at 85° C. In order to obtain a ketone reductase with good thermal stability and high activity for industrial synthesis of chiral alcohol compounds, the present invention used the reaction of asymmetric reduction of 4-hydroxy-2-butanone to (R)-(−)-1,3-butanediol as a reference, and employed enzyme directed evolution technology to engineer ChKRED20. The present invention developed a series of engineered ketoreductase polypeptides with high stability, high activity, high stereoselectivity which are suitable for a wider spectrum of substrates. For an introduction to directed evolution techniques, see "Directed Evolution: Bringing New Chemistry to Life" Frances H. Arnold, Angewandte Chemie, Nov. 28, 2017. Frances H. Arnold received 2018 Nobel Prize in Chemistry due to her pioneering contribution to enzyme directed evolution technology.

Compared to the wild-type ketoreductase as of SEQ ID NO: 2, the engineered ketoreductase polypeptides provided by present invention has better activity and/or stability, and is capable of asymmetrically synthesizing chiral alcohols with extremely high stereoselectivity. Especially, the engineered ketoreductase polypeptides provided by present invention can convert 4-hydroxy-2-butanone to (R)-(−)-1,3-butanediol more efficiently, while simultaneously converting isopropanol to acetone in order to achieve the regeneration of NADH (FIG. 2). These engineered ketoreductase polypeptides can comprise an amino acid sequence that differs from the sequence of SEQ ID NO: 2 in one or more residue positions selected from: X10, X16, X18, X20, X22, X30, X35, X38, X39, X42, X46, X52, X53, X54, X60, X64, X65, X73, X78, X80, X86, X93, X94, X97, X104, X114, X125, X126, X134, X140, X141, X142, X150, X152, X153, X164, X169, X173, X184, X185, X187, X190, X201, X204, X206, X211, X216, X218, X224, X228, X235, X239, X244. In some embodiments, the engineered ketoreductase polypeptides comprise an amino acid sequence comprising at least one of the following features (these features are substitutions of amino acid residues to the reference sequence of SEQ ID NO: 2): L10V, S16R, S16K, S16N, I18V, L20Q, V22S, G30A, V35A, I38C, I38W, I38V, I38R, N39S, H42P, H42K, H42R, H42T, H42S, A46V, A46T, A52S, A52H, A52G, Q53T, G54N, V60S, V60M, T64I, S65A, S65T, L73M, V78R, I80N, I80K, I86V, I93V, G94R, G94L, G94V, G94Q, G94K, G94A, Q97K, Q97R, G104K, G104R, G104P, G104T, G104H, I114V, I114S, Y125F, E126S, E126T, E126A, E126V, G134K, G134H, G134T, G134R, N140V, M141I, M141N, M141T, A142S, A150Y, A150R, A150K, A150O, A150N, L152Y, S153R, S153N, S153M, S153L, S153Q, V164I, V164L, N169H, E173D, V184T, G185C, G185A, A187G, E190D, M201A, M201E, A204D, A204N, I206A, M211S, M211N, K216R, E218S, V224S, V224T, S228A, M235V, M235I, Y239A, Y239S, Y239D, Y239T, Y239P, G244A, G244T, G244P; Or, in addition to the abovementioned differences, engineered ketoreductase polypeptides comprise insertions or deletions of 1, 2, 3, 4, 5, 6, 7, 8, 9, 10, 11, 12, 13, 14, 15, 16, 18, 20, 21, 22, 23, 24, 25 or more amino acid residues.

More specifically, in some embodiments, the engineered ketoreductase polypeptides which were improved over SEQ ID NO: 2 comprise a sequence corresponding to SEQ ID No: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332.

In some embodiments, the engineered ketoreductase polypeptides comprise an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99% or more identical to the reference sequence of SEQ ID Nos: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332.

The identity between two amino acid sequences or two nucleotide sequences can be obtained by commonly used algorithms in the art and can be calculated according to default parameters by using NCBI Blastp and Blastn software, or by using the Clustal W algorithm (Nucleic Acid Research, 22 (22): 4673-4680, 1994). For example, using the Clustal W algorithm, the amino acid sequence identity of SEQ ID NO: 2 to SEQ ID NO: 330 is 95.6%.

In another aspect, this invention provides polynucleotide sequences encoding engineered ketoreductase polypeptides. In some embodiments, a polynucleotide can be part of an expression vector having one or more control sequences for the expression of an engineered ketoreductase polypeptide. In some embodiments, polynucleotides can comprise sequences corresponding to SEQ ID No: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331.

As known to people skilled in the art, due to the degeneracy of the nucleotide codons, the polynucleotide sequences encoding amino acid sequences SEQ ID No: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332 are not limited to SEQ ID No: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331. The polynucleotide sequences of the engineered ketoreductase polypeptides of the present invention may also be any other polynucleotide sequences encoding amino acid sequences SEQ ID No: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332.

In another aspect, this disclosure provides polynucleotides comprising sequences encoding engineered ketoreductase polypeptides, expression vectors and host cells capable of expressing engineered ketoreductase polypeptides. In some embodiments, the host cell can be bacterial host cell, such as E. coli. The host cell can be used to express and isolate the engineered ketoreductase described herein, or alternatively be directly used in the reaction for conversion of substrates to products.

In some embodiments, the engineered ketoreductase polypeptides in the form of whole cell, crude extract, isolated enzyme, or purified enzyme can be used alone or in an immobilized form, such as immobilization on a resin.

The present disclosure also provides the process of converting a carbonyl substrate of formula (II) to a chiral alcohol compound of formula (I) using the engineered ketoreductase polypeptides disclosed herein:

$$\underset{R^2}{\overset{OH}{\underset{*}{\bigwedge}}}R^1 \quad (I)$$

$$\underset{R^2}{\overset{O}{\bigwedge}}R^1 \quad (II)$$

where the alcohol products of formula (I) has the indicated stereochemical configuration shown at the chiral center marked with an *;

the alcohol products of formula (I) are in enantiomeric excess over the other isomer, wherein $R^1$ is optionally substituted or unsubstituted aryl or heteroaryl, or optionally substituted or unsubstituted $C_1$-$C_8$ hydrocarbyl, or may also be a cycloalkyl or a heterocyclic group;

$R^2$ is optionally substituted or unsubstituted $C_1$-$C_6$ hydrocarbyl, halogen (such as —F, —Cl, —Br, and —I), alkenyl, alkynyl, aryl, heteroaryl, —NO$_2$, —NO, —SO$_2$R' or —SOR', —SR', —NR'R', —OR', —CO$_2$R$^1$ or —COR', —C(O)NR', —SO$_2$NH$_2$ or —SONH$_2$, —CN, CF$_3$; wherein each R' is independently selected from —H or ($C_1$-$C_4$) hydrocarbyl, halogen, ($C_1$-$C_8$) hydrocarbyl, ($C_2$-$C_{12}$) alkenyl, ($C_2$-$C_{12}$) alkynyl, cycloalkyl, aryl or heterocyclic;

the process comprising that, under suitable reaction conditions of converting the carbonyl substrate to an alcohol product, the carbonyl substrate of structural formula (II) was contacted with ketoreductase polypeptides, wherein the ketoreductase polypeptides are engineered ketoreductase polypeptides as described herein. In some embodiments, the engineered ketoreductase polypeptides have at least 80%, 81%, 82%, 83%, 84%, 85%, 86%, 87%, 88%, 89%, 90%, 91%, 92%, 93%, 94%, 95%, 96%, 97%, 98%, 99% or more of sequence identity to a reference sequence that is an even sequence identifier of SEQ ID NO: 2-332 and are capable of converting carbonyl substrate of structural formula (II) to alcohol product of structural formula (I) with better performance (including higher activity, tolerance to higher temperatures, tolerance to higher organic solvent concentrations) compared to SEQ ID NO:2.

In some embodiments, the alcohol products of formula (I) are present in an enantiomeric excess of at least 90%, 91%, 92%, 93%, 94%, 95%, 96%, 97%, 98% or 99% or greater.

In some embodiments of this process, the alcohol product of formula (I) is:

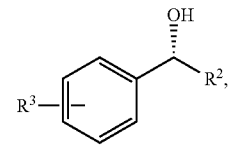

wherein $R^3$ is an optionally substituted or non-substituted $C_1$-$C_4$ hydrocarbyl, —H, halogen (such as —F, —Cl, —Br and —I), aryl, heteroaryl, —NO$_2$, —NO, —SO$_2$R' or —SOR', —SR', —NRR', —OR', —CO$_2$R' or —COR', —C(O)NR', —SO$_2$NH$_2$ or —SONH$_2$, —CN, —CF$_3$, wherein each R' is independently selected from —H, ($C_1$-$C_4$) hydrocarbyl, cycloalkyl, aryl or heterocyclic;

$R^2$ is as defined above, and the carbonyl substrate of formula (II) is:

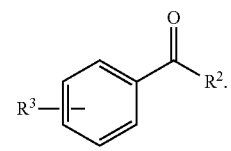

In some embodiments, $R^3$ is in the para position of the phenyl ring. In some embodiments, $R^3$ is in the meta position of the phenyl ring. In some embodiments, $R^3$ is ortho to the phenyl ring. In some embodiments, $R^3$ is both para and meta to the phenyl ring. In some embodiments, $R^3$ is both para and ortho to the phenyl ring. In some embodiments, $R^3$ is both meta and ortho to the phenyl ring.

In some embodiments of the process, the alcohol product of formula (I) is:

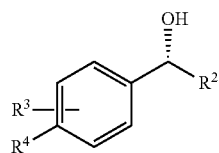

wherein $R^4$ is defined the same as $R^3$ above, $R^3$ and $R^2$ are as defined above, and the carbonyl substrate of structural formula (II) is:

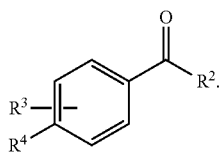

In some embodiments, $R^3$ is in the meta position of the phenyl ring. In some embodiments, $R^3$ is ortho to the phenyl ring.

In some embodiments, the engineered ketoreductase polypeptides can be used in the production process of enantiomeric excess of the compound of formula A2, (R)-(−)-1,3-butanediol:

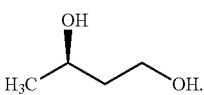

In these embodiments, the production process comprises that, under suitable reaction conditions for converting compound of formula A1 to compound of formula A2, in the presence of a cofactor, the compound of formula A1, 4-hydroxy-2-butanone

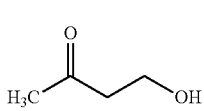

was contacted with the engineered ketoreductase polypeptides disclosed herein.

In some embodiments of the above processes, the compound of formula (I) or the compound of formula A2 is present in an enantiomeric excess of at least 90%, 91%, 92%, 93%, 94%, 95%, 96%, 97%, 98%, or 99% or more.

Specific embodiments of engineered ketoreductase polypeptides for use in these processes are further provided in the detailed description. An engineered ketoreductase polypeptide that can be used in the above process can comprise one or more sequences selected from the amino acid sequences corresponding to SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322.

Any of the processes for the preparation of a compound of formula (I) or a compound of formula A2 using an engineered polypeptide as disclosed herein can be performed under a range of suitable reaction conditions, which include, but are not limited to, pH, temperature, buffer, solvent system, substrate loading, polypeptide loading, cofactor loading, recycling process of cofactor, pressure and reaction time range. For example, in some embodiments, preparing a compound of formula (I) or a compound of formula A2 may be performed, wherein suitable reaction conditions include: (a) about 1 g/L to 500 g/L of the substrate of compound (II) or A1; (b) about 0.1 g/L to 50 g/L of engineered polypeptide; (c) about 5 g/L to 500 g/L of isopropanol; (d) 0.01 g/L to 1.0 g/L of cofactor; (e) 0% (v/v) to about 99% (v/v) of an organic solvent, including but not limited to 4-hydroxy-2-butanone, Isopropanol, dimethyl sulfoxide (DMSO), dimethylformamide (DMF), methyl tert-butyl ether (MTBE), isopropyl acetate, methanol, ethanol or propanol; (f) a pH of about 4.0 to about 11.0; and (g) a temperature of about 10° C. to 60° C.

DETAILED DESCRIPTION OF THE PRESENT INVENTION

1 Definitions

Figure 1:
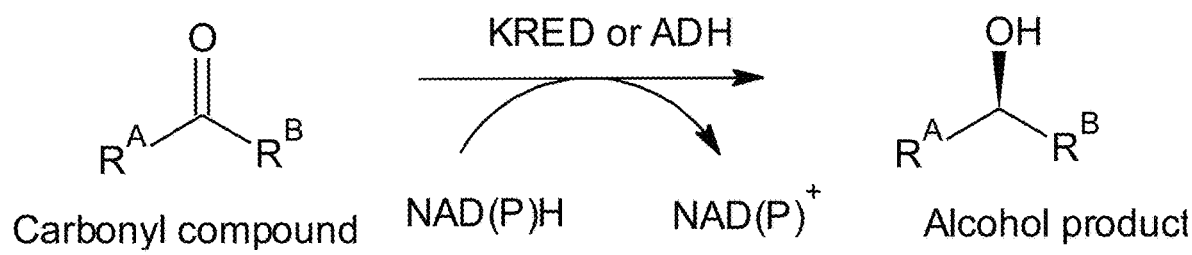
FIG. 1 depicts the reduction of carbonyl compounds to chiral alcohols catalyzed by ketoreductase.
Figure 2:
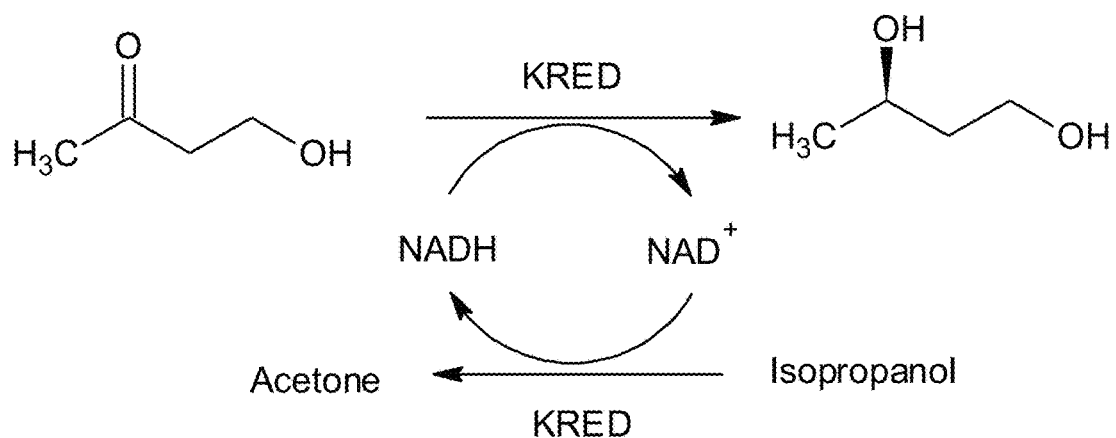
FIG. 2 depicts the conversion of 4-hydroxy-2-butanone to (R)-(−)-1,3-butanediol catalyzed by ketoreductase, with simultaneous conversion of isopropanol to acetone catalyzed by the same ketoreductase to achieve regeneration of NADH.

Unless explicitly defined otherwise, technical and scientific terms used in this disclosure have the meanings that are commonly understood by people skilled in the art.

"Protein", "polypeptide" and "peptide" are used interchangeably herein to denote a polymer of at least two amino acids covalently linked by an amide bond, regardless of length or post-translational modification (e.g., glycosylation, phosphorylation, lipidation, myristoylation, ubiquitination, etc.). This definition includes D-amino acids and L-amino acids, as well as mixtures of D-amino acids and L-amino acids.

"Engineered ketoreductase", "engineered ketoreductase polypeptide", "improved ketoreductase polypeptide" and "engineered polypeptide" are used interchangeably herein.

Ketoreductase or alcohol dehydrogenase can be used interchangeably herein.

"Polynucleotide" and "nucleic acid" are used interchangeably herein.

"Cofactor" as used herein refers to a non-protein compound that operates in conjunction with an enzyme in a catalytic reaction. As used herein, "cofactor" includes NADH (nicotinamide adenine dinucleotide) or NADPH (nicotinamide adenine dinucleotide phosphate) and its oxidized form NAD+ or NADP+, which are sometimes also referred to as coenzymes.

"Coding sequence" refers to that portion of a nucleic acid (e.g., a gene) that encodes an amino acid sequence of a protein.

"Naturally occurring" or "wild-type" refers to the form found in nature. For example, a naturally occurring or wild-type polypeptide or polynucleotide sequence is a sequence that is present in an organism that can be isolated from sources in nature and which has not been intentionally modified by manual procedures.

"Recombinant" or "engineered" or "non-naturally occurring" when used with reference to, for example, a cell, nucleic acid or polypeptide, refers to a material or material corresponding to the native or native form of the material, that has been modified in a manner that would not otherwise exist in nature, or is identical thereto but produced or derived from synthetic material and/or by manipulation using recombinant techniques.

"Sequence identity" and "homology" are used interchangeably herein to refer to comparisons between polynucleotide sequences or polypeptide sequences ("sequence identity" is generally expressed as a percentage), and are determined by comparing two optimally aligned sequences over a comparison window, where the portion of the polynucleotide or polypeptide sequence in the comparison window may comprise additions or deletions (i.e., gaps) as compared to the reference sequence for optimal alignment of the two sequences. The percentage can be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those skilled in the art will appreciate that there are many established algorithms available to align two sequences. The optimal alignment of sequences for comparison can be conducted, for example, by the local homology algorithm of Smith and Waterman, 1981, Adv. Appl. Math. 2: 482, by the Homology alignment algorithm of Needleman and Wunsch, 1970, J. Mol. Biol. 48: 443, by the search for similarity method of Pearson and Lipman, 1988, Proc. Natl. Acad. Sci. USA 85: 2444, by computerized implementations of these algorithms (GAP, BESTFIT, FASTA, and TFASTA in the GCG Wisconsin Package) or by visual inspection (see generally, Current Protocols in Molecular Biology, FM Ausubel et al. eds., Current Protocols, a Joint Venture between Greene Publishing Associates, Inc. and John Wiley & Sons, Inc., (1995 Supplement) (Ausubel)). Examples of algorithms that are suitable for determining the percent sequence identity and percent sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analysis is publicly available through the National Center for Biotechnology Information website. The algorithm involves first identifying high scoring sequence pairs (HSPs) by identifying short words of length W in the query sequence, which either match or satisfy some positive-valued threshold scores T when aligned with a word of the same length in the database sequence. T is referred to as, the neighborhood word score threshold (Altschul et al., Supra). These initial neighborhood word hits serve as seeds for initiating searches to find longer HSPs that contain them. The word hits are then extended in both directions along each sequence for as far as the cumulative alignment score can be increased. For nucleotide sequences, the cumulative scores are calculated using the parameters M (reward score for matched pair of residues; always >0) and N (penalty score for mismatched residues; always <0). For amino acid sequences, a scoring matrix is used to calculate the cumulative score. The extension of the word hits in each direction are halted when: the cumulative alignment score falls off by the quality X from its maximum achieved value; the cumulative score goes 0 or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, the expected value (E) of 10, M=5, N=−4, and a comparison of both strands as a default value. For amino acid sequences, the BLASTP program uses as defaults the wordlength (W) of 3, the expected value (E) of 10 and the BLOSUM62 scoring matrix (see Henikoff and Henikoff, 1989, Proc Natl Acad Sci USA 89: 10915). Exemplary determination of sequence alignments and % sequence identity can employ the BESTFIT or GAP programs in the GCG Wisconsin Software package (Accelrys, Madison Wis.), using the default parameters provided.

"Reference sequence" refers to a defined sequence that is used as a basis for sequence comparison. The reference sequence may be a subset of a larger sequence, for example, a full-length gene or a fragment of a polypeptide sequence. In general, a reference sequence is at least 20 nucleotides or amino acid residues in length, at least 25 residues long, at least 50 residues in length, or the full length of the nucleic acid or polypeptide. Because two polynucleotides or polypeptides may each (1) comprise a sequence (i.e., a portion of the complete sequence) that is similar between two sequences, and (2) may further comprise sequences that is divergent between the two sequences, sequence comparisons between two (or more) polynucleotides or polypeptides are typically performed by comparing the sequences of the two polynucleotides or polypeptides over a "comparison window" to identify and compare local regions of sequence similarity. In some embodiments, a "reference sequence" is not intended to be limited to a wild-type sequence, and may comprise engineered or altered sequences. For example, "a reference sequence with lysine at the residue corresponding to X94 based on SEQ ID NO: 2" refers to a reference sequence wherein the corresponding residue at position X94 in SEQ ID NO: 2 which is a glycine, has been altered to lysine.

A "comparison window" refers to a conceptual segment of at least about 20 contiguous nucleotide positions or amino acid residues, wherein the sequence may be compared to a reference sequence of at least 20 contiguous nucleotides or amino acids and wherein the portions of the sequence in the comparison window may comprise additions or deletions (i.e., gaps) of 20% or less as compared to a reference sequence (which does not comprise additions or deletions) for optimal alignment of the two sequences. The comparison window can be longer than 20 contiguous residues, and optionally include 30, 40, 50, 100 or more residues.

In the context of the numbering for a given amino acid or polynucleotide sequence, "corresponding to," "reference to" or "relative to" refers to the numbering of the residues of a specified reference when the given amino acid or polynucleotide sequence is compared to the reference sequence. In other words, the residue number or residue position of a given sequence is designated with respect to the reference sequence, rather than by the actual numerical position of the residue within the given amino acid or polynucleotide sequence. For example, a given amino acid sequence such as an engineered ketoreductase can be aligned to a reference sequence by introducing gaps to optimize residue matches between the two sequences. In these cases, although there are gaps, the numbering of the residue in a given amino acid or polynucleotide sequence is made with respect to the reference sequence to which they have been aligned.

"Amino acid difference" or "residue difference" refers to the difference in amino acid residues at a position of a polypeptide sequence relative to the amino acid residue at a corresponding position in the reference sequence. The positions of amino acid differences are generally referred to herein as "Xn", where n refers to the corresponding position in the reference sequence on which the residue differences are based. For example, "a residue difference at position X94 as compared to SEQ ID NO: 2" refers to the difference in amino acid residues at the polypeptide position corresponding to position 94 of SEQ ID NO: 2. Thus, if the reference polypeptide of SEQ ID NO: 2 has a glycine at position 94, then "a residue difference at position X94 as compared to SEQ ID NO: 2" refers to an amino acid substitution of any residue other than glycine at the position of the polypeptide corresponding to position 94 of SEQ ID NO: 2. In most of the examples herein, the specific amino acid residue difference at the position is indicated as "XnY", wherein "Xn" specified to the corresponding position as described above, and "Y" is the single letter identifier of the amino acid found in the engineered polypeptide (i.e., a different residue than in the reference polypeptide). In some examples (e.g., in Table 1), the present disclosure also provides specific amino acid differences denoted by the conventional notation "AnB", where A is a single letter identifier of a residue in the reference sequence, "n" is the number of residue position in the reference sequence, and B is the single letter identifier for the residue substitution in the sequence of the engineered polypeptide. In some examples, an engineered polypeptide of this disclosure may comprise one or more amino acid residue differences relative to a reference sequence, which is indicated by a list of specific positions at which residue differences are present relative to a reference sequence.

"Deletion" refers to the modification of a polypeptide by removing one or more amino acids from a reference polypeptide. Deletions can include the removal of one or more amino acids, two or more amino acids, five or more amino acids, ten or more amino acids, fifteen or more amino acids, or twenty or more amino acids, up to 10% of the total number of amino acids of the enzyme, or up to 20% of the total number of amino acids making up the reference enzyme while retaining the enzymatic activity of the engineered ketoreductase and/or retaining the improved properties of the engineered ketoreductase. Deletion may involve the internal portion and/or the terminal portion of the polypeptide. In various embodiments, deletions may include a contiguous segment or may be discontinuous.

"Insertion" refers to the modification of a polypeptide by adding one or more amino acids from a reference polypeptide. In some embodiments, the improved engineered ketoreductase comprises insertions of one or more amino acids to a naturally occurring ketoreductase polypeptide as well as insertions of one or more amino acids to other engineered ketoreductase polypeptides. It can be inserted in the internal portions of the polypeptide or inserted to the carboxyl or amino terminus. As used herein, insertions include fusion proteins known in the art. The insertion can be a contiguous segment of amino acids or separated by one or more amino acids in naturally occurring or engineered polypeptides.

"Fragment" as used herein refers to a polypeptide having an amino terminal and/or carboxyl terminal deletion, but where the remaining amino acid sequence is identical to the corresponding position in the sequence. Fragments may be at least 10 amino acids long, at least 20 amino acids long, at least 50 amino acids long or longer, and up to 70%, 80%, 90%, 95%, 98% and 99% of the full-length ketoreductase polypeptide.

An "isolated polypeptide" refers to a polypeptide that is substantially separated from other substances with which it is naturally associated, such as proteins, lipids, and polynucleotides. The term comprises polypeptides that have been removed or purified from their naturally occurring environment or expression system (e.g., in host cells or in vitro synthesis). Engineered ketoreductase polypeptides may be present in the cell, in the cell culture medium, or prepared in various forms, such as lysates or isolated preparations. As such, in some embodiments, the engineered ketoreductase polypeptide may be an isolated polypeptide.

"Chiral center" refers to a carbon atom connecting four different groups.

"Stereoselectivity" refers to the preferential formation of one stereoisomer over the other in a chemical or enzymatic reaction. Stereoselectivity can be partial, with the formation of one stereoisomer is favored over the other; or it may be complete where only one stereoisomer is formed. When the stereoisomers are enantiomers, the stereoselectivity is referred to as enantioselectivity. The excess fraction of one enantiomer in a mixture of two enantiomers is usually optionally reported as "enantiomeric excess" (ee for short). The fraction, typically a percentage, is generally reported in the art as the enantiomeric excess (i.e., ee) derived therefrom according to the following formula: [major enantiomer−minor enantiomer]/[major enantiomer+minor enantiomer].

"Stereoisomers," "stereoisomeric forms," and similar expressions are used interchangeably herein to refer to all isomers resulting from a difference in orientation of atoms in their space only. It includes enantiomers and compounds that have more than one chiral center and are not mirror images of one another (i.e., diastereomers).

"Improved enzyme properties" refers to an enzyme property that is better or more desirable for a specific purpose as compared to a reference ketoreductase such as a wild-type ketoreductase or another improved engineered ketoreductase. Improved enzyme properties are exhibited by engineered ketoreductase polypeptides in this disclosure. Enzyme properties that are expected to be improved include, but are not limited to, enzyme activity (which can be expressed as a percentage of substrate conversion), thermal stability, solvent stability, pH activity characteristics, cofactor requirements, tolerance to inhibitors (e.g., substrate or product inhibition), stereospecificity and stereoselectivity.

"Conversion" refers to the enzymatic transformation of a substrate to the corresponding product. "Percent conversion" or "conversion" refers to the percentage of substrate that is converted to product within a period of time under the specified conditions. Thus, "enzymatic activity" or "activity" of a ketoreductase polypeptide can be expressed as the "percent conversion" of the substrate to the product. The conversion is generally calculated by sampling to determine the product concentration and substrate concentration in the reaction system: {product molar concentration}/{substrate molar concentration+product molar concentration}.

"Thermostable" means that a ketoreductase polypeptide that retains similar activity after being exposed to an elevated temperature (e.g., 72° C. or higher) for a period of time (e.g., 2.5 hours or longer) compared to a wild-type enzyme.

"Solvent-stable" or "solvent-tolerant" refers to, compared to a wild-type enzyme, a ketoreductase polypeptide that maintains similar activity after exposure to different concentrations (e.g., 5-99%) of varying solvent (methanol, ethanol, isopropanol, dimethylsulfoxide (DMSO), tetrahydrofuran, 2-methyltetrahydrofuran, acetone, toluene, butyl acetate, methyl tert-butyl ether, etc.) for a period of time (e.g., 0.5-24 hours).

"Suitable reaction conditions" refer to those conditions (e.g., enzyme loading, substrate loading, cofactor loading, temperature, pH, buffer, co-solvent, etc.) in the biocatalytic reaction system, under which the ketoreductase polypeptide of the present disclosure can convert a substrate to a desired product compound. Exemplary "suitable reaction conditions" are provided in the present disclosure and illustrated by examples.

"Hydrocarbyl" refers to a straight or branched aliphatic hydrocarbon chain. The number of subscripts following the symbol "C" specifies the number of carbon atoms that a particular chain may contain. For example, "$C_1$-$C_8$" refers to a straight or branched chain hydrocarbyl group having 1 to 8 carbon atoms. Hydrocarbyl groups may optionally be substituted with one or more substituent groups. "Aryl" means a monovalent aromatic hydrocarbon group of 6 to about 20 carbon atoms. "Heteroaryl" and "heteroaromatic" refer to an aryl group in which one or more of the carbon atoms of the parent aromatic ring system is/are replaced by a heteroatom (O, N, or S). "Substituted", when used to modify a specified group, means that one or more hydrogen atoms of the specified group are replaced, each independently of one another, by identical or different substituents. "Substituted hydrocarbyl, aryl, or heteroaryl" refers to a hydrocarbyl, aryl, or heteroaryl group in which one or more hydrogen atoms are replaced by other substituents. "Optional" or "optionally" means that the described event or circumstance may or may not occur; for example, "optionally substituted aryl" refers to an aryl group that may or may not be substituted. This description includes both substituted aryl groups and unsubstituted aryl groups.

As used herein, "compound" refers to any compound encompassed by the structural formulas and/or chemical names indicated with the compounds disclosed herein. Compounds may be identified by their chemical structure and/or chemical name. When the chemical structure and chemical name conflict, the chemical structure determines the identity of the compound. Unless specifically stated or indicated otherwise, the chemical structures described herein encompass all possible isomeric forms of the described compounds.

2 Engineered Ketoreductase

Table 1 below illustrates the engineered ketoreductase polypeptides developed by the present invention. Each row gives the polynucleotide sequence number and amino acid sequence number of a particular engineered ketoreductase polypeptide, as well as the residue difference compared to SEQ ID No: 2. The level of catalytic performance of each exemplified engineered ketoreductase polypeptide (the overall performance in the reaction, including but not limited to activity, thermal stability, stability in the reaction system, stereoselectivity to the product, etc.) is indicated as "+", with the specific meanings given in Table 2 or Table 3.

TABLE 1

| Polynucleotide SEQ ID No | Amino acid SEQ ID No | Residue difference relative to SEQ ID No: 2 | Catalytic performance of the enzyme |
|---|---|---|---|
| 1 | 2 | — | # |
| 3 | 4 | S153R; | + |
| 5 | 6 | Q97K; | + |
| 7 | 8 | S153N; | + |
| 9 | 10 | A150Y; | + |
| 11 | 12 | A150R; | + |
| 13 | 14 | Q97R; | + |
| 15 | 16 | G94R; | + |
| 17 | 18 | G94L; | + |
| 19 | 20 | G94V; | + |
| 21 | 22 | G94Q; | + |
| 23 | 24 | G94K; | + |
| 25 | 26 | A150K; | + |
| 27 | 28 | S153M; | + |
| 29 | 30 | S153L; | + |
| 31 | 32 | S153Q; | + |
| 33 | 34 | L152Y; | + |
| 35 | 36 | A46V; I86V; G185C; A187G; | + |
| 37 | 38 | A46V; I86V; G185C; A187G; S228A; Y239A; | + |
| 39 | 40 | A46T; | + |
| 41 | 42 | A46T; G185C; A187G; M235V; | + |
| 43 | 44 | G185C; A187G; S228A; | + |
| 45 | 46 | A46T; G185C; A187G; | + |
| 47 | 48 | A187G; S228A; M235I; Y239A; | + |
| 49 | 50 | A46T; G185C; A187G; S228A; | + |
| 51 | 52 | G185C; A187G; Y239A; | + |
| 53 | 54 | I86V; G185C; A187G; S228A; | + |
| 55 | 56 | A46V; G185C; A187G; Y239A; | + |
| 57 | 58 | A46V; I86V; G185C; | + |

TABLE 1-continued

| Polynucleotide SEQ ID No | Amino acid SEQ ID No | Residue difference relative to SEQ ID No: 2 | Catalytic performance of the enzyme |
|---|---|---|---|
| 59 | 60 | A46T; I86V; G185C; A187G; S228A; | + |
| 61 | 62 | A46V; G185C; | + |
| 63 | 64 | A46V; I86V; Y239A; | + |
| 65 | 66 | A46T; G185C; | + |
| 67 | 68 | A46T; A187G; | + |
| 69 | 70 | A46V; G185C; A187G; S228A; | + |
| 71 | 72 | I86V; S228A; Y239A; | + |
| 73 | 74 | I86V; G185C; A187G; Y239A; | + |
| 75 | 76 | A46V; | + |
| 77 | 78 | A46V; G185C; S228A; M235I; Y239A; | + |
| 79 | 80 | I86V; G185C; A187G; | + |
| 81 | 82 | A46T; I86V; G185C; S228A; | + |
| 83 | 84 | A46V; G185C; A187G; | + |
| 85 | 86 | A46V; S228A; M235I; | + |
| 87 | 88 | A46T; I86V; G185C; S228A; Y239A; | + |
| 89 | 90 | G185C; A187G; | + |
| 91 | 92 | S228A; M235I; | + |
| 93 | 94 | A46V; G185C; Y239A; | + |
| 95 | 96 | A46V; G185C; A187G; S228A; Y239A; | + |
| 97 | 98 | A187G; S228A; M235I; | + |
| 99 | 100 | A46T; G185C; S228A; | + |
| 101 | 102 | A46T; I86V; G185C; A187G; | + |
| 103 | 104 | A46V; G185C; A187G; S228A; M235V; | + |
| 105 | 106 | A46V; I86V; G185C; A187G; M235V; | + |
| 107 | 108 | A46V; I86V; G185C; A187G; S228A; | + |
| 109 | 110 | S16R; | + |
| 111 | 112 | S65A; | + |
| 113 | 114 | I114V; | + |
| 115 | 116 | M141I; | + |
| 117 | 118 | S16K; | + |
| 119 | 120 | I38C; | + |
| 121 | 122 | I38W; | + |
| 123 | 124 | S16N; | + |
| 125 | 126 | A46T; I86V; Q97K; A150K; G185C; A187G; | ++ |
| 127 | 128 | A46T; I86V; Q97K; S153R; G185C; A187G; | ++ |
| 129 | 130 | A46T; I86V; A150Q; S153N; G185C; A187G; | ++ |
| 131 | 132 | A46T; I86V; Q97K; A150R; G185C; A187G; | ++ |
| 133 | 134 | A46T; I86V; A150K; G185C; A187G; | ++ |
| 135 | 136 | A46T; I86V; Q97R; A150N; S153Q; G185C; A187G; | ++ |
| 137 | 138 | A46T; I86V; Q97R; S153Q; G185C; A187G; | ++ |
| 139 | 140 | A46T; I86V; Q97K; S153Q; G185C; A187G; | ++ |
| 141 | 142 | A46T; I86V; Q97K; A150Q; S153N; G185C; A187G; | ++ |
| 143 | 144 | A46T; I86V; S153Q; G185C; A187G; | ++ |
| 145 | 146 | A46T; I86V; A150K; S153N; G185C; A187G; | ++ |
| 147 | 148 | A46T; I86V; G185A; A187G; Y239S; | ++ |
| 149 | 150 | A46T; I86V; G185A; A187G; Y239D; | ++ |
| 151 | 152 | A46T; I86V; G185A; A187G; Y239T; | ++ |
| 153 | 154 | A46T; I86V; G185A; A187G; Y239P; | ++ |
| 155 | 156 | H42P; A46T; I86V; G185C; A187G; | ++ |
| 157 | 158 | I38V; H42K; A46T; I86V; G185C; A187G; | ++ |
| 159 | 160 | H42R; A46T; I86V; G185C; A187G; | ++ |
| 161 | 162 | H42T; A46T; I86V; G185C; A187G; | ++ |
| 163 | 164 | N39S; H42K; A46T; I86V; G185C; A187G; | ++ |
| 165 | 166 | I38R; A46T; I86V; G185C; A187G; | ++ |
| 167 | 168 | H42K; A46T; I86V; G185C; A187G; | ++ |
| 169 | 170 | I38R; H42T; A46T; I86V; G185C; A187G; | ++ |
| 171 | 172 | I38R; H42S; A46T; I86V; G185C; A187G; | ++ |
| 173 | 174 | N39S; A46T; I86V; G185C; A187G; | ++ |
| 175 | 176 | A46T; I86V; M141N; G185C; A187G; | ++ |
| 177 | 178 | I18V; A46T; I86V; G185C; A187G; | ++ |
| 179 | 180 | A46T; I86V; M141I; G185C; A187G; | ++ |
| 181 | 182 | A46T; I86V; M141T; G185C; A187G; | ++ |
| 183 | 184 | H42K; A46T; S65A; I86V; G94L; Q97K; I114V; A150Q; S153N; G185A; A187G; | +++ |
| 185 | 186 | A46T; S65A; I86V; Q97K; A150Q; S153N; G185C; A187G; | +++ |
| 187 | 188 | H42R; A46T; I86V; Q97K; I114V; A150Q; S153N; G185C; A187G; | +++ |
| 189 | 190 | H42K; A46T; S65A; I86V; G94L; Q97K; M141N; A150Q; S153N; G185C; A187G; | +++ |
| 191 | 192 | H42R; A46T; S65A; I86V; Q97K; I114V; A150Q; S153N; G185C; A187G; Y239P; | +++ |
| 193 | 194 | H42K; A46T; I86V; Q97K; I114V; A150Q; S153N; G185C; A187G; | +++ |
| 195 | 196 | H42K; A46T; S65A; I86V; Q97K; A150Q; S153N; G185C; A187G; | +++ |
| 197 | 198 | H42R; A46T; S65A; I86V; G94L; Q97K; I114V; A150Q; S153N; G185C; A187G; Y239P; | +++ |

TABLE 1-continued

| Polynucleotide SEQ ID No | Amino acid SEQ ID No | Residue difference relative to SEQ ID No: 2 | Catalytic performance of the enzyme |
|---|---|---|---|
| 199 | 200 | H42R; A46T; S65A; I86V; G94L; Q97K; I114V; M141N; A150Q; S153N; G185C; A187G; | +++ |
| 201 | 202 | H42R; A46T; T64I; I86V; G94L; Q97K; I114V; A150Q; S153N; G185C; A187G; Y239P; | +++ |
| 203 | 204 | H42R; A46T; I86V; Q97K; I114V; A150Q; S153N; G185C; A187G; Y239P; | +++ |
| 205 | 206 | H42K; A46T; I86V; G94L; Q97K; I114V; A150Q; S153N; G185C; A187G; | +++ |
| 207 | 208 | H42R; A46T; I86V; G94L; Q97K; I114V; A150Q; S153N; G185C; A187G; | +++ |
| 209 | 210 | H42K; A46T; S65A; I86V; G94L; Q97K; I114V; A150Q; S153N; G185C; A187G; | +++ |
| 211 | 212 | H42R; A46T; S65A; I86V; Q97K; I114V; A150Q; S153N; G185C; A187G; | +++ |
| 213 | 214 | H42R; A46T; I86V; G94L; Q97K; I114V; A150Q; S153N; G185C; A187G; Y239P; | +++ |
| 215 | 216 | A46T; I86V; Q97K; I114V; A150Q; S153N; G185C; A187G; | +++ |
| 217 | 218 | A46T; S65A; I86V; Q97K; I114V; A150Q; S153N; G185C; A187G; | +++ |
| 219 | 220 | A46T; I86V; Q97K; I114S; A150Q; S153N; G185C; A187G; | +++ |
| 221 | 222 | A46T; S65T; I86V; Q97K; A150Q; S153N; G185C; A187G; | +++ |
| 223 | 224 | A46T; I86V; G94A; Q97K; A150Q; S153N; G185C; A187G; | +++ |
| 225 | 226 | A46T; I86V; Q97K; A150Q; S153N; E173D; G185C; A187G; | +++ |
| 227 | 228 | A46T; I86V; Q97K; A150Q; S153N; E173D; G185C; A187G; G244A; | +++ |
| 229 | 230 | A46T; I86V; Q97K; A150Q; S153N; N169H; G185C; A187G; M211S; G244T; | +++ |
| 231 | 232 | A46T; I86V; I93V; Q97K; A150Q; S153N; G185C; A187G; | +++ |
| 233 | 234 | A46T; I86V; Q97K; A150Q; S153N; G185C; A187G; G244P; | +++ |
| 235 | 236 | A46T; I86V; Q97K; A150Q; S153N; E173D; G185C; A187G; M211N; | +++ |
| 237 | 238 | L20Q; H42K; A46T; I86V; Q97K; I114V; A150Q; S153N; G185C; A187G; | ++++ |
| 239 | 240 | G30A; H42K; A46T; I86V; Q97K; I114V; A150Q; S153N; G185C; A187G; | ++++ |
| 241 | 242 | H42K; A46T; A52S; I86V; Q97K; I114V; A150Q; S153N; G185C; A187G; | ++++ |
| 243 | 244 | H42K; A46T; V78R; I86V; Q97K; I114V; A150Q; S153N; G185C; A187G; | ++++ |
| 245 | 246 | H42K; A46T; G54N; I86V; Q97K; I114V; A150Q; S153N; G185C; A187G; | ++++ |
| 247 | 248 | H42K; A46T; A52H; I86V; Q97K; I114V; A150Q; S153N; G185C; A187G; | ++++ |
| 249 | 250 | H42K; A46T; A52G; I86V; Q97K; I114V; A150Q; S153N; G185C; A187G; | ++++ |
| 251 | 252 | H42K; A46T; I80N; I86V; Q97K; I114V; A150Q; S153N; G185C; A187G; | ++++ |
| 253 | 254 | H42K; A46T; I80K; I86V; Q97K; I114V; A150Q; S153N; G185C; A187G; | ++++ |
| 255 | 256 | H42K; A46T; I86V; Q97K; G104K; I114V; A150Q; S153N; G185C; A187G; | ++++ |
| 257 | 258 | H42K; A46T; I86V; Q97K; G104R; I114V; A150Q; S153N; G185C; A187G; | ++++ |
| 259 | 260 | H42K; A46T; I86V; Q97K; G104P; I114V; A150Q; S153N; G185C; A187G; | ++++ |
| 261 | 262 | H42K; A46T; I86V; Q97K; G104T; I114V; A150Q; S153N; G185C; A187G; | ++++ |
| 263 | 264 | H42K; A46T; I86V; Q97K; G104H; I114V; A150Q; S153N; G185C; A187G; | ++++ |
| 265 | 266 | H42K; A46T; I86V; Q97K; I114V; G134K; A150Q; S153N; G185C; A187G; | ++++ |
| 267 | 268 | H42K; A46T; I86V; Q97K; I114V; G134H; A150Q; S153N; G185C; A187G; | ++++ |
| 269 | 270 | H42K; A46T; I86V; Q97K; I114V; G134T; A150Q; S153N; G185C; A187G; | ++++ |
| 271 | 272 | H42K; A46T; I86V; Q97K; I114V; G134R; A150Q; S153N; G185C; A187G; | ++++ |
| 273 | 274 | H42K; A46T; I86V; Q97K; I114V; A150Q; S153N; G185C; A187G; M201A; | ++++ |
| 275 | 276 | H42K; A46T; I86V; Q97K; I114V; A150Q; S153N; G185C; A187G; M201E; | ++++ |
| 277 | 278 | H42K; A46T; I86V; Q97K; I114V; A150Q; S153N; G185C; A187G; A204D; | ++++ |
| 279 | 280 | H42K; A46T; I86V; Q97K; I114V; A150Q; S153N; G185C; A187G; A204N; | ++++ |
| 281 | 282 | H42K; A46T; I86V; Q97K; I114V; A150Q; S153N; G185C; A187G; I206A; | ++++ |
| 283 | 284 | L10V; H42K; A46T; I86V; Q97K; I114V; A150Q; S153N; G185C; A187G; | ++++ |
| 285 | 286 | V22S; H42K; A46T; I86V; Q97K; I114V; A150Q; S153N; G185C; A187G; | ++++ |
| 287 | 288 | V35A; H42K; A46T; I86V; Q97K; I114V; A150Q; S153N; G185C; A187G; | ++++ |
| 289 | 290 | H42K; A46T; V60S; I86V; Q97K; I114V; A150Q; S153N; G185C; A187G; | ++++ |
| 291 | 292 | H42K; A46T; V60M; I86V; Q97K; I114V; A150Q; S153N; G185C; A187G; | ++++ |
| 293 | 294 | H42K; A46T; L73M; I86V; Q97K; I114V; A150Q; S153N; G185C; A187G; | ++++ |
| 295 | 296 | H42K; A46T; I86V; Q97K; I114V; A142S; A150Q; S153N; G185C; A187G; | ++++ |
| 297 | 298 | H42K; A46T; Q53T; I86V; Q97K; I114V; A150Q; S153N; G185C; A187G; | ++++ |
| 299 | 300 | H42K; A46T; I86V; Q97K; I114V; A150Q; S153N; G185C; A187G; K216R; | ++++ |
| 301 | 302 | H42K; A46T; I86V; Q97K; I114V; A150Q; S153N; G185C; A187G; E218S; | ++++ |
| 303 | 304 | H42K; A46T; I86V; Q97K; I114V; A150Q; S153N; G185C; A187G; E190D; | ++++ |
| 305 | 306 | H42K; A46T; I86V; Q97K; I114V; A150Q; S153N; V164I; G185C; A187G; | ++++ |
| 307 | 308 | H42K; A46T; I86V; Q97K; I114V; A150Q; S153N; V164L; G185C; A187G; | ++++ |
| 309 | 310 | H42K; A46T; I86V; Q97K; I114V; A150Q; S153N; V184T; G185C; A187G; | ++++ |
| 311 | 312 | H42K; A46T; I86V; Q97K; I114V; A150Q; S153N; G185C; A187G; V224S; | ++++ |
| 313 | 314 | H42K; A46T; I86V; Q97K; I114V; A150Q; S153N; G185C; A187G; V224T; | ++++ |
| 315 | 316 | H42K; A46T; I86V; Q97K; I114V; Y125F; E126S; A150Q; S153N; G185C; A187G; | ++++ |
| 317 | 318 | H42K; A46T; I86V; Q97K; I114V; Y125F; A150Q; S153N; G185C; A187G; | ++++ |
| 319 | 320 | H42K; A46T; I86V; Q97K; I114V; E126T; A150Q; S153N; G185C; A187G; | ++++ |
| 321 | 322 | H42K; A46T; I86V; Q97K; I114V; N140V; A150Q; S153N; G185C; A187G; | ++++ |
| 323 | 324 | H42K; A46T; I86V; Q97K; I114V; E126A; A150Q; S153N; G185C; A187G; | ++++ |
| 325 | 326 | H42K; A46T; I86V; Q97K; I114V; E126S; A150Q; S153N; G185C; A187G; | ++++ |
| 327 | 328 | H42K; A46T; I86V; Q97K; I114V; Y125F; E126V; A150Q; S153N; G185C; A187G; | ++++ |
| 329 | 330 | H42K; A46T; I86V; G94A; Q97K; I114V; A150Q; S153N; E173D; G185C; A187G; | ++++ |
| 331 | 332 | H42K; A46T; I86V; Q97K; I114V; A150Q; S153N; E173D; G185C; A187G; | ++++ |

TABLE 2

| Catalytic performance of the enzyme | Description | Reaction conditions (loading of each substance in the reaction system) |
|---|---|---|
| # | Conversion ≤50%, Reaction time ≤24 h, ee >99% | Enzyme solution 30% (v/v), 4-hydroxy-2-butanone 200 g/L, Isopropanol 50% (v/v), NAD+ 0.2 g/L |
| + | Conversion ≤75%, Reaction time ≤24 h, ee >99% | Enzyme solution 30% (v/v), 4-hydroxy-2-butanone 200 g/L, Isopropanol 50% (v/v), NAD+ 0.2 g/L |
| ++ | Conversion ≥90%, Reaction time ≤24 h, ee >99% | Enzyme solution 20% (v/v), 4-hydroxy-2-butanone 200 g/L, Isopropanol 50% (v/v), NAD+ 0.2 g/L |
| +++ | Conversion ≥95%, Reaction time ≤24 h, ee >99% | Enzyme solution 10% (v/v), 4-hydroxy-2-butanone 200 g/L, Isopropanol 50% (v/v), NAD+ 0.1 g/L |
| ++++ | Conversion ≥95%, Reaction time ≤24 h, ee >99% | Enzyme solution 8% (v/v), 4-hydroxy-2-butanone 200 g/L, Isopropanol 50% (v/v), NAD+ 0.05 g/L |

The enzyme solution in the reaction conditions described in Table 2 was prepared according to Example 2. The enzyme solution is not subjected to any heat treatment, and the protein concentration in the enzyme solution is about 10 g/L (the protein concentration was determined by well-known Bradford method) which contains an equivalent amount of ketoreductase polypeptide corresponding to the amino acid sequence in Table 1. The reactions in Table 2 were carried out at 40° C., neutral pH, and the operation of the reaction can be referred to Example 10.

TABLE 3

| Catalytic performance of the enzyme | Description | Reaction conditions (loading of each substance in the reaction system) |
|---|---|---|
| # | Conversion ≤25%, Reaction time ≤24 h, ee >99% | [72° C., 2.5 h] Heat-treated enzyme solution 30% (v/v), 4-hydroxy-2-butanone 200 g/L, Isopropanol 50% (v/v), NAD+ 0.2 g/L |
| + | Conversion ≥50%, Reaction time ≤24 h, ee >99% | [72° C., 2.5 h] Heat-treated enzyme solution 30% (v/v), 4-hydroxy-2-butanone 200 g/L, Isopropanol 50% (v/v), NAD+ 0.2 g/L |
| ++ | Conversion ≥75%, Reaction time ≤24 h, ee >99% | [75° C., 2 h] Heat-treated enzyme solution 20% (v/v), 4-hydroxy-2-butanone 200 g/L, Isopropanol 50% (v/v), NAD+ 0.2 g/L |
| +++ | Conversion ≥85%, Reaction time ≤24 h, ee >99% | [80° C., 2 h] Heat-treated enzyme solution 10% (v/v), 4-hydroxy-2-butanone 200 g/L, Isopropanol 50% (v/v), NAD+ 0.1 g/L |
| ++++ | Conversion ≥95%, Reaction time ≤24 h, ee >99% | [85° C., 2 h] Heat-treated enzyme solution 8% (v/v), 4-hydroxy-2-butanone 200 g/L, Isopropanol 50% (v/v), NAD+ 0.05 g/L |

The heat-treated enzyme solution described in the reaction conditions in Table 3 is obtained by heat treatment of the enzyme solution as described in Table 2. The operation of the heat treatment can be referred to Example 3. The reactions in Table 3 were carried out at 40° C., neutral pH, and the operation of the reaction can be referred to Example 10.

Since the thermal stability of the ketoreductase polypeptides corresponding to the amino acid sequences in Table 1 are different, after the heat treatment, different ketoreductase polypeptides will exhibit different degrees of inactivation and lead to changes in catalytic performance. Such changes are reflected in conversion as shown in Table 2 and in Table 3.

3 Polynucleotides, Control Sequences, Expression Vectors and Host Cells that can be Used to Produce Engineered Ketoreductase Polypeptides In another aspect, this disclosure provides polynucleotides encoding engineered polypeptides having ketoreductase activity described herein. The polynucleotides can be linked to one or more heterologous regulatory sequences that control gene expression to produce recombinant polynucleotides that are capable of expressing the engineered polypeptides. Expression constructs comprising a heterologous polynucleotide encoding an engineered ketoreductase may be introduced into a suitable host cell to express the corresponding engineered ketoreductase polypeptide.

As apparent to one skilled in the art, the availability of protein sequences and knowledge of codons corresponding to a variety of amino acids provide an illustration of all possible polynucleotides that encode the protein sequence of interest. The degeneracy of the genetic code, in which the same amino acid is encoded by selectable or synonymous codons, allows for the production of an extremely large number of polynucleotides, all of which encode the engineered ketoreductase polypeptides disclosed herein. Thus, upon determination of a particular amino acid sequence, one skilled in the art can generate any number of different polynucleotides by merely modifying one or more codons in a manner that does not alter the amino acid sequence of the protein. In this regard, this disclosure specifically contemplates each and every possible alteration of a polynucleotide that can be made by selecting a combination based on possible codon selections, for any of the polypeptides disclosed herein, comprising those amino acid sequences of exemplary engineered polypeptides listed in Table 1, and any of the polypeptides disclosed as even sequence identifiers of SEQ ID NO: 4 to 332 in the Sequence Listing incorporated by reference, all of which are believed to be particularly disclosed or public.

In various embodiments, the codons are preferably selected to accommodate the host cell in which the recombinant protein is produced. For example, codons preferred for bacteria are used to express genes in bacteria; codons preferred for yeast are used to express genes in yeast; and codons preferred for mammals are used for gene expression in mammalian cells.

In some embodiments, the polynucleotides encode polypeptides comprising amino acid sequences that are at least about 80%, 81%, 82%, 83%, 84%, 85%, 86%, 87%, 88%, 89%, 90%, 91%, 92%, 93%, 94%, 95%, 96%, 97%, 98%, 99% or more identical to a reference sequence that is an even sequence identifier of SEQ ID NO: 4-332, wherein the polypeptides have ketoreductase activity and one or more of the improved properties described herein, for example, the ability of converting compound A1 to compound A2 with increased activity and/or stability compared to the polypeptide of SEQ ID NO: 2.

In some embodiments, the polynucleotides encode engineered ketoreductase polypeptides comprising amino acid sequences having a percentage of identity described above and having one or more amino acid residue differences as compared to SEQ ID NO: 2. In some embodiments, the present disclosure provides engineered polypeptides having ketoreductase activity, wherein the engineered polypeptides comprise a combination that has at least 80% sequence identity to the reference sequence of SEQ ID NO: 2 with residue differences that is selected from the following positions: X10, X16, X18, X20, X22, X30, X35, X38, X39, X42, X46, X52, X53, X54, X60, X64, X65, X73, X78, X80, X86, X93, X94, X97, X104, X114, X125, X126, X134, X140, X141, X142, X150, X152, X153, X164, X169, X173, X184, X185, X187, X190, X201, X204, X206, X211, X216, X218, X224, X228, X235, X239, X244.

In some embodiments, the polynucleotides encoding the engineered ketoreductase polypeptides comprise sequences having odd sequence identifiers of SEQ ID NO: 3-331.

In some embodiments, the polynucleotides encode polypeptides as described herein, but at the nucleotide level, the polynucleotides have about 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity to reference polynucleotides encoding engineered ketoreductase polypeptides as described herein. In some embodiments, the reference polynucleotides are selected from the sequences having the odd sequence identifiers of SEQ ID NO: 3-331.

The isolated polynucleotides encoding engineered ketoreductase polypeptides can be manipulated to enable the expression of the engineered polypeptides in a variety of ways, which comprises further modification of the sequences by codon optimization to improve expression, insertion into suitable expression elements with or without additional control sequences, and transformation into a host cell suitable for expression and production of the engineered polypeptides.

Depending on the expression vector, manipulation of the isolated polynucleotide prior to insertion of the isolated polynucleotide into the vector may be desirable or necessary. Techniques for modifying polynucleotides and nucleic acid sequences using recombinant DNA methods are well known in the art. Guidance is provided below: Sambrook et al., 2001, Molecular Cloning: A Laboratory Manual, Third Edition, Cold Spring Harbor Laboratory Press; and Current Protocols in Molecular Biology, Edited by Ausubel. F. et al., GreenePub. Associates, 1998, 2010.

In another aspect, this disclosure also relates to recombinant expression vectors, depending on the type of host they are to be introduced into, including a polynucleotide encoding an engineered ketoreductase polypeptide or variant thereof, and one or more expression regulatory regions, such as promoters and terminators, origin of replication and the like. Alternatively, the nucleic acid sequence of the present disclosure can be expressed by inserting the nucleic acid sequence or the nucleic acid construct comprising the sequence into an appropriate expression vector. In generating the expression vector, the coding sequence is located in the vector such that the coding sequence is linked to a suitable control sequence for expression.

The recombinant expression vector can be any vector (e.g., a plasmid or virus) that can be conveniently used in recombinant DNA procedures and can result in the expression of a polynucleotide sequence. The choice of vector will generally depend on the compatibility of the vector with the host cell to be introduced into. The vector can be linear or closed circular plasmid. The expression vector may be an autonomously replicating vector, i.e., a vector that exists as an extrachromosomal entity whose replication is independent of chromosomal replication such as plasmids, extrachromosomal elements, mini-chromosomes, or artificial chromosomes. The vector may contain any tools for ensuring self-copying. Alternatively, the vector may be a vector that, when introduced into a host cell, integrates into the genome and replicates with the chromosome into which it is integrated. Moreover, a single vector or plasmid or two or more vectors or plasmids that together comprise the total DNA to be introduced into the genome of the host cell may be used.

Many expression vectors useful to the embodiments of the present disclosure are commercially available. An exemplary expression vector can be prepared by inserting a polynucleotide encoding an engineered ketoreductase polypeptide to plasmid pACYC-Duet-1 (Novagen).

In another aspect, this disclosure provides host cells comprising polynucleotides encoding engineered ketoreductase polypeptides of the present disclosure. The polynucleotide is linked to one or more control sequences for expression of ketoreductase polypeptides in a host cell. Host cells for expression of polypeptides encoded by the expression vectors of the present disclosure are well known in the art, including, but not limited to, bacterial cells such as *E. coli, Arthrobacter* KNK168, *Streptomyces*, and *Salmonella typhimurium* cells; fungal cells such as yeast cells (e.g., *Saccharomyces cerevisiae* or *Pichia pastoris*); insect cells such as *Drosophila* S2 and *Spodoptera* Sf9 cells; animal cells such as CHO, COS, BHK, 293 and Bowes melanoma cells; and plant cells. An exemplary host cell is *E. coli* BL21 (DE3). The above host cells may be wild-type or may be engineered cells through genomic edition, such as knockout of the wild-type ketoreductase gene carried in the host cell's genome. Suitable media and growth conditions for the above host cells are well known in the art.

Polynucleotides used to express engineered ketoreductases can be introduced into cells by a variety of methods known in the art. Techniques comprise, among others, electroporation, bio-particle bombardment, liposome-mediated transfection, calcium chloride transfection, and protoplast fusion. Different methods of introducing polynucleotides into cells are obvious to those skilled in the art.

4 Process of Producing an Engineered Ketoreductase Polypeptide

Engineered ketoreductase can be developed by subjecting a polynucleotide encoding a ketoreductase to mutagenesis and/or directed evolution. An illustration of direction evolution technique can be found in "Biocatalysis for the Pharmaceutical Industry: Discovery, Development, and Manufacturing" (2009 John Wiley & Sons Asia (Pte) Ltd. ISBN: 978-0-470-82314-9).

When the sequence of an engineered polypeptide is known, the encoding polynucleotide may be prepared by standard solid-phase methods according to known synthetic methods. In some embodiments, fragments of up to about 100 bases can be synthesized separately and then ligated (e.g., by enzymatic or chemical ligation methods or polymerase-mediated methods) to form any desired contiguous sequence. For example, the polynucleotides and oligonucleotides of the present disclosure can be prepared by chemical synthesis using, for example, the classic phosphoramidite methods described by Beaucage et al., 1981, Tet Lett 22: 1859-69, or Matthes et al. People, 1984, EMBO J. 3: 801-05, as typically practiced in automated synthesis methods. According to the phosphoramidite method, oligonucleotides are synthesized, purified, annealed, ligated, and cloned into a suitable vector, for example, in an automated DNA synthesizer. In addition, essentially any nucleic acid is available from any of a variety of commercial sources.

In some embodiments, the present disclosure also provides a process for preparing or producing an engineered ketoreductase polypeptide, wherein the process comprises culturing a host cell capable of expressing a polynucleotide encoding an engineered polypeptide under culture conditions suitable for the expression of the polypeptide. In some embodiments, the process of preparing a polypeptide further comprises isolating the polypeptide. Engineered polypeptides may be expressed in suitable cells and isolated (or recovered) from the host cell and/or culture medium using any one or more of the well-known techniques for protein purification, the techniques for protein purification include, among others, lysozyme treatment, sonication, filtration, salting out, ultracentrifugation and chromatography. Engineered polypeptides may also be expressed via in vitro transcription & translation (ivTT) systems.

5 Methods of Using an Engineered Ketoreductase and Compounds Prepared Therewith In another aspect, the engineered ketoreductase polypeptides described herein can convert a carbonyl compound to a chiral alcohol compound in the presence of a cofactor NADH or NADPH. The present disclosure also provides process of preparing a wide range of compounds (I) or structural analogs thereof using an engineered ketoreductase polypeptide disclosed herein. In some embodiments, engineered ketoreductase polypeptides can be used in a process of preparing a compound of formula (I):

The alcohol of formula (I) has the indicated stereochemical configuration at the chiral center marked with an *; the alcohol of formula (I) is in enantiomer excess over the other isomer, wherein $R^1$ is optionally substituted or unsubstituted aryl or heteroaryl, or optionally substituted or unsubstituted $C_1$-$C_8$ hydrocarbyl; or it may be cycloalkyl or heterocyclic;

$R^2$ is optionally substituted or unsubstituted $C_1$-$C_6$ hydrocarbyl, halogen (such as —F, —Cl, —Br, and —I), alkenyl, alkynyl, aryl, heteroaryl, —$NO_2$, —NO, —$SO_2R'$ or —SOR', —SR', —NR'R', —OR', —$CO_2R^1$ or —COR', —C(O)NR', —$SO_2NH_2$ or —$SONH_2$, —CN, $CF_3$; wherein each R' is independently selected from —H or ($C_1$-$C_4$) hydrocarbyl, halogen, $C_1$-$C_8$ hydrocarbyl, $C_2$-$C_{12}$ alkenyl, $C_2$-$C_{12}$ alkynyl, cycloalkyl, aryl or heterocyclic.

The process herein comprises that, under reaction conditions suitable for converting the carbonyl substrate to an alcohol product, the carbonyl substrate of formula (II)

is contacted with a ketoreductase polypeptide, wherein the ketoreductase polypeptide is an engineered ketoreductase polypeptide as described herein.

In some embodiments, the engineered ketoreductase polypeptides have at least 80%, 81%, 82%, 83%, 84%, 85%, 86%, 87%, 88%, 89%, 90%, 91%, 92%, 93%, 94%, 95%, 96%, 97%, 98%, 99% or more of sequence identity to even sequence identifiers of SEQ ID NO: 2-332, and are capable of converting carbonyl substrate of formula (II) to alcohol product of formula (I) with better performance (including higher activity, tolerance to higher temperatures, tolerance to higher organic solvent concentrations) compared to SEQ ID NO:2.

In some embodiments, the chiral alcohol products of formula (I) are present in an enantiomeric excess of at least 90%, 91%, 92%, 93%, 94%, 95%, 96%, 97%, 98% or 99% or greater.

As noted above, engineered ketoreductase polypeptides useful in the process of the present disclosure may be characterized according to the ability of converting 4-hydroxy-2-butanone to (R)-(-)-1,3-butanediol. Thus, in any of the embodiments of the process disclosed herein, the process may be carried out, wherein the ketoreductase polypeptides are capable of converting 4-hydroxy-2-butanone to (R)-(-)-1,3-butanediol with better catalytic performance than SEQ ID NO: 2 and have at least 80%, 81%, 82%, 83%, 84%, 85%, 86%, 87%, 88%, 89%, 90%, 91%, 92%, 93%, 94%, 95%, 96%, 97%, 98%, 99% or more of sequence identity to even sequence identifiers of SEQ ID NO: 2-332.

In some embodiments of the process, the alcohol product of formula (I) is:

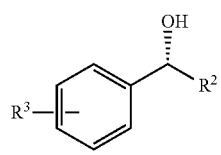

wherein $R^3$ is an optionally substituted or non-substituted $C_1$-$C_4$ hydrocarbyl, —H, halogen (such as —F, —Cl, —Br, and —I), aryl, heteroaryl, —$NO_2$, —NO, —$SO_2R'$ or —SOR', —SR', —NR'R', —OR', —$CO_2R'$ or —COR', —C(O)NR', —$SO_2NH_2$ or —$SONH_2$, —CN, $CF_3$, wherein each R' is independently selected from —H or ($C_1$-$C_4$) hydrocarbyl, cycloalkyl, aryl or heterocyclic;
$R^2$ is as defined above, and the carbonyl substrate of formula (II) is:

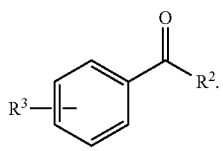

In some embodiments, $R^3$ is in the para position of the phenyl ring. In some embodiments, $R^3$ is in the meta position of the phenyl ring. In some embodiments, $R^3$ is ortho to the phenyl ring. In some embodiments, $R^3$ is both para and meta to the phenyl ring. In some embodiments, $R^3$ is both para and ortho to the phenyl ring. In some embodiments, $R^3$ is both meta and ortho to the phenyl ring.

In some embodiments of this process, the alcohol product of formula (I) is:

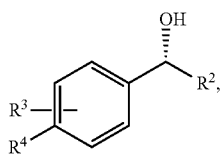

wherein $R^4$ is $R^3$ as defined above, $R^3$ and $R^2$ are as defined above, and the carbonyl substrate of formula (II) is:

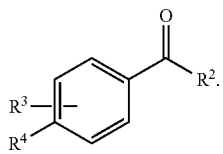

In some embodiments, $R^3$ is in the meta position of the phenyl ring. In some embodiments, $R^3$ is ortho to the phenyl ring.

In some embodiments of this process, the chiral alcohol product of formula (I) is methyl (R)-(−)-3-hydroxybutyrate:

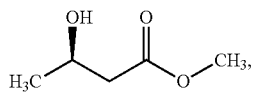

and the carbonyl substrate of formula (II) is methyl acetoacetate:

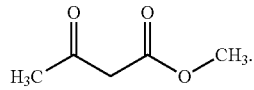

In some embodiments of this process, the chiral alcohol product of formula (I) is ethyl (R)-(−)-3-hydroxybutyrate:

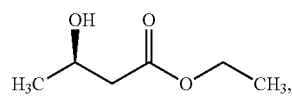

and the carbonyl substrate of formula (II) is ethyl acetoacetate:

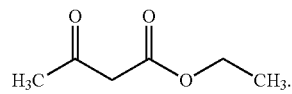

In some embodiments of this process, the chiral alcohol product of formula (I) is ethyl (S)-(−)-4-chloro-3-hydroxybutyrate:

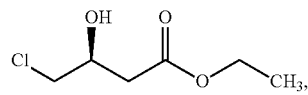

and the carbonyl substrate of formula (II) is ethyl 4-chloroacetoacetate:

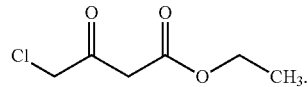

In some embodiments of this process, the chiral alcohol product of formula (I) is (R)-1-[3,5-bis(trifluoromethyl)phenyl]ethanol:

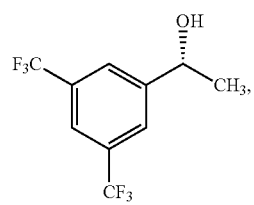

and the carbonyl substrate of formula (II) is 3,5-bistrifluoromethylacetophenone:

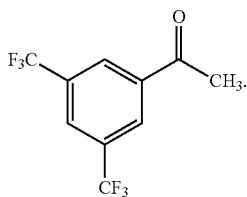

In some embodiments of the process, the chiral alcohol product of formula (I) is:

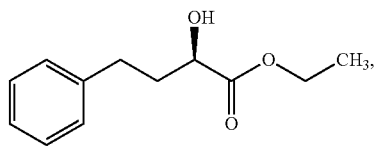 [SMILES: CCOC(=O)[C@H](O)CCc1ccccc1]

and the carbonyl substrate of formula (II) is:

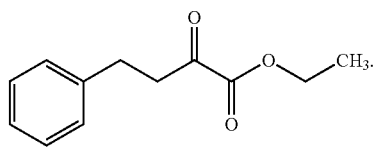 [SMILES: CCOC(=O)C(=O)CCc1ccccc1]

In some embodiments, the alcohol product of formula (I) produced in the above processes is present in an enantiomeric excess of at least 90%, 91%, 92%, 93%, 94%, 95%, 96%, 97%, 98%, 99% or more.

Specific embodiments of engineered ketoreductase polypeptides for use in the above processes are further provided in the detailed description. Engineered ketoreductase polypeptides that can be used in the above processes comprise amino acid sequences selected from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332.

In some embodiments, an engineered ketoreductase polypeptide can be used in a process of preparing an enantiomeric excess of the compound of formula A2 (R)-(−)-1,3-butanediol:

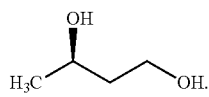

In these embodiments, the process comprises that, under reaction conditions suitable for converting a compound of formula A1 to a compound of formula A2, in the presence of a cofactor NADH, the compound of formula A1, 4-hydroxy-2-butanone:

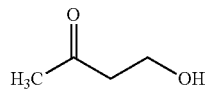

was contacted with the engineered ketoreductase polypeptide disclosed herein.

In some embodiments of the above process, the compound of Formula A2 is produced in an enantiomeric excess of at least 90%, 91%, 92%, 93%, 94%, 95%, 96%, 97%, 98%, 99% or more.

Specific embodiments of engineered ketoreductase polypeptides for use in the above process are further provided in the detailed description.

Engineered ketoreductase polypeptides that can be used in the above process comprise amino acid sequences selected from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332.

In the process described herein, the engineered ketoreductase polypeptide catalyzes the conversion of a carbonyl substrate to a chiral alcohol product in the presence of the cofactor NADH. In some embodiments, the regeneration of the cofactor NADH during the reaction is accomplished by converting another alcohol compound (such as isopropanol) to a carbonyl compound (such as acetone) under the action of the same engineered ketoreductase polypeptide. In the process, NAD+ is converted to NADH. In some embodiments, regeneration of the cofactor NADH during the reaction is accomplished through catalyzing the conversion of glucose to gluconic acid by glucose dehydrogenase. In the process, NAD+ is converted to NADH; a specific example of this method is described in Example 9. In some embodiments, the regeneration of the cofactor NADH during the reaction is accomplished through catalyzing the conversion of formic acid to carbon dioxide by formate dehydrogenase. In the process, NAD+ is converted to NADH.

As is known to those skilled in the art, ketoreductase catalyzed reactions are reversible. In some embodiments, in the presence of the cofactor NAD+, the engineered ketoreductase polypeptides disclosed herein can also convert a chiral alcohol compound of Formula (I) or Formula A2 to Compound (II) or A1, respectively:

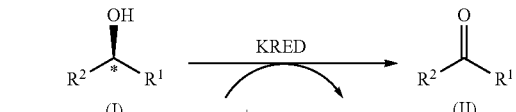

or

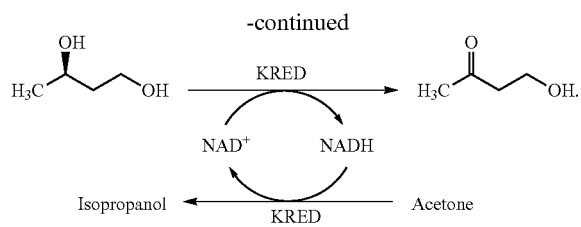

In some embodiments of the process, the substrate is a racemic alcohol compound, and the engineered ketoreductase polypeptide disclosed herein selectively converts one of the enantiomers to a carbonyl compound while retaining the other enantiomer, thus achieving chiral resolution of the racemic alcohol compound. In the process of converting an alcohol compound into a carbonyl compound by a ketoreductase, regeneration of NAD+ can be simultaneously achieved, for example, by converting acetone to isopropanol by the same ketoreductase. A specific example of this method is referred to Example 15.

As described herein and exemplified in the examples, the present disclosure contemplates a range of suitable reaction conditions that may be used in the process herein, including but not limited to, co-factor regeneration process, temperature, solvent system, substrate loading, polypeptide loading, buffer, pH, and reaction time. Additional suitable reaction conditions for performing a method of biocatalytically converting substrate compounds to product compounds using engineered ketoreductase polypeptides described herein can be readily optimized by routine experimentation, which includes but is not limited to, the engineered ketoreductase polypeptide is contacted with the substrate compound under experimental reaction conditions of varying the loading of individual reaction components, pH, temperature, solvent conditions, and co-factor regeneration process, and the product compound is detected, for example, using the methods described in the Examples provided herein.

As described above, engineered polypeptides having ketoreductase activity for use in the process of the present disclosure generally comprise amino acid sequences that have at least 80%, 81%, 82%, 83%, 84%, 85%, 86%, 87%, 88%, 89%, 90%, 91%, 92%, 93%, 94%, 95%, 96%, 97%, 98%, 99% or more sequence identity to the reference amino acid sequence selected from any one of the even numbered sequences of SEQ ID NOs: 2-332.

The loading of substrate compounds in the reaction mixture can be varied, taking into consideration of, for example, the amount of the desired product compound, the effect of the substrate concentration on the enzyme activity, the stability of the enzyme under the reaction conditions, and the conversion of substrate to product. In some embodiments of the process, the suitable reaction conditions include at least 0.5 g/L, at least about 1 g/L, at least about 5 g/L, at least about 10 g/L, at least about 15 g/L, at least about 20 g/L, at least about 30 g/L, at least about 50 g/L, at least about 75 g/L, at least about 100 g/L, at least about 150 g/L, at least about 200 g/L, at least about 250 g/L, at least about 300 g/L, at least about 350 g/L, at least about 400 g/L or even more of loading of substrate (II) or substrate A1. The values for the substrate loading provided herein are based on the molecular weight of compound (II) or A1, however it is also contemplated that the equivalent molar amounts of various hydrates and salts of compound (II) or A1 may also be used in the process.

In some embodiments of the reaction, the reaction conditions may include a suitable pH. The desired pH or desired pH range can be maintained by using an acid or base, a suitable buffer, or a combination of buffer and added acid or base. The pH of the reaction mixture can be controlled before and/or during the reaction. In some embodiments, suitable reaction conditions include a solution pH of about 4 to about 11. In some embodiments, the reaction conditions include a solution pH of about 4.0, 4.5, 5.0, 5.5, 6.0, 6.5, 7, 7.5, 8, 8.5, 9, 9.5, 10, 10.5, 11.0.

In embodiments of the processes herein, suitable temperatures can be used for the reaction conditions, taking into consideration of, for example, the increase in reaction rate at higher temperatures, and the activity of the enzyme for sufficient duration of reaction. Accordingly, in some embodiments, suitable reaction conditions include a temperature of about 10° C. to about 60° C., about 25° C. to about 50° C., about 25° C. to about 40° C., or about 25° C. to about 30° C. In some embodiments, suitable reaction temperatures include temperature of about 10° C., 15° C., 20° C., 25° C., 30° C., 35° C., 40° C., 45° C., 50° C., 55° C., or 60° C. In some embodiments, the temperature during the enzymatic reaction can be maintained at a certain temperature throughout the reaction. In some embodiments, the temperature during the enzymatic reaction may be adjusted over a temperature profile during the course of the reaction.

The processes of using the engineered ketoreductase are generally carried out in a solvent. Suitable solvents include water, aqueous buffer solutions, organic solvents, and/or co-solvent systems, which generally include aqueous solvents and organic solvents. The aqueous solutions (water or aqueous co-solvent systems) can be pH-buffered or unbuffered. In some embodiments, the processes of using an engineered ketoreductase polypeptide are generally carried out in an aqueous co-solvent system comprising an organic solvent (e.g., methanol, ethanol, propanol, isopropanol, dimethyl sulfoxide (DMSO), dimethylformamide (DMF), isopropyl acetate, ethyl acetate, butyl acetate, 1-octanol, heptane, octane, methyl tert-butyl ether (MTBE), Toluene, etc.), ionic liquids (for example, 1-ethyl 4-methylimidazolium tetrafluoroborate, 1-butyl-3-methylimidazolium tetrafluoroborate, 1-butyl-3-methylimidazolium hexafluorophosphate, and the like). The organic solvent component of the aqueous co-solvent system may be miscible with the aqueous component, providing a single liquid phase, or may be partially miscible or immiscible with the aqueous component, providing two liquid phases. Exemplary aqueous co-solvent system comprises water and one or more organic solvents. In general, the organic solvent component of the aqueous co-solvent system is selected such that it does not completely inactivate the ketoreductase. Suitable co-solvent system can be readily identified by measuring the enzymatic activity of a particular engineered ketoreductase with a defined substrate of interest in the candidate solvent system, utilizing enzymatic activity assays, such as those described herein. In some embodiments of the process, suitable reaction conditions include an aqueous co-solvent comprising an organic solvent having a concentration of about 1% to about 95% (v/v), about 1% to about 60% (v/v), about 2% to about 60% (v/v), about 5% to about 60% (v/v), about 10% to about 60% (v/v), about 10% to about 50% (v/v) or about 10% to about 40% (v/v). In some embodiments of the process, suitable reaction conditions comprise a organic solvent having a concentration of at least about 1%, 5%, 10%, 15%, 20%, 25%, 30%, 35%, 40%, 45%, 50%, 55%, 60%, 65%, 70%, 75%, 80%, 85%, 90% or 95% (v/v).

Suitable reaction conditions can include a combination of reaction parameters that allows the biocatalytic conversion of the substrate compound to its corresponding product compound. Accordingly, in some embodiments of the process, the combination of reaction parameters comprises: (a) substrate A1 loading of about 10 g/L to about 600 g/L; (b) engineered polypeptide concentration of about 1 g/L to about 50 g/L; (c) pH of about 4.0 to 11.0; and (d) temperature of about 10 to 60° C.

In some embodiments, the ketoreductase polypeptides capable of performing the above reactions comprise the amino acid sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332.

Exemplary reaction conditions include the conditions provided in Table 2, Table 3, and Examples 8-14.

In carrying out the reactions described herein, the engineered ketoreductase polypeptide may be added to the reaction mixture in the partially purified or purified forms, a heat-treated enzyme solution, whole cells transformed with the gene encoding the engineered ketoreductase polypeptide, and/or as cell extracts and/or lysates of such cells. Whole cells transformed with the gene encoding the engineered ketoreductase or cell extracts, lysates thereof, and isolated enzymes can be used in a wide variety of different forms, including solids (e.g., lyophilized, spray dried, or the like) or semisolid (e.g., a crude paste of wet cells). The cell extract or cell lysate may be partially purified by precipitation (e.g., ammonium sulfate, polyethyleneimine, heat treatment or the like), followed by desalting procedures (e.g., ultrafiltration, dialysis, and the like) prior to lyophilization. Any of the enzyme preparations can be stabilized by cross-linking using known crosslinking agents, such as glutaraldehyde, or immobilization to a solid phase material (such as a resin).

In some embodiments of the reactions described herein, the reaction is performed under suitable reaction conditions described herein, wherein the engineered ketoreductase polypeptide is immobilized on a solid support. Solid supports useful for immobilizing the engineered ketoreductase enzyme for carrying out the reaction including but not limited to beads or resins such as polymethacrylates with epoxy functional groups, polymethacrylates with amino epoxy functional groups, polymethacrylates, styrene/DVB copolymer or polymethacrylates with octadecyl functional groups. Exemplary solid supports include, but are not limited to, chitosan beads, Eupergit C, and SEPABEAD5 (Mitsubishi), including the following different types of SEPA-BEAD: EC-EP, EC-HFA/S, EXA252, EXE119 and EXE120.

In some embodiments, wherein the engineered polypeptide is expressed in the form of a secreted polypeptide, a culture medium containing the secreted polypeptide can be used in the process herein.

In some embodiments, the solid reactants (e.g., enzymes, salts, etc.) can be provided to the reaction in a variety of different forms, including powders (e.g., lyophilized, spray dried, etc.), solutions, emulsions, suspensions and the like. The reactants can be readily lyophilized or spray-dried using methods and instrumentation known to one skilled in the art. For example, the protein solution can be frozen at −80° C. in small aliquots, and then added to the pre-chilled lyophilization chamber, followed by the application of a vacuum.

In some embodiments, the order of addition of reactants is not critical. The reactants may be added together to the solvent at the same time (e.g., monophasic solvent, a biphasic aqueous co-solvent system, etc.), or alternatively, some reactants may be added separately, and some may be added at different time points. For example, ketoreductase and substrate may be added first to the solvent, and the organic solvent can then be added and mixed. Alternatively, the substrates can be premixed in the organic solvent prior to addition to the aqueous phase.

Different features and embodiments of the present disclosure are exemplified in the following representative examples, which are intended to be illustrative and not restrictive.

EXAMPLES

The following examples further illustrate the present invention, but the present invention is not limited thereto. In the following examples, experimental methods with conditions not specified, were conducted at the commonly used conditions or according to the suppliers' suggestion.

Example 1: Gene Cloning and Construction of Expression Vectors

The amino acid sequence of the wild-type ChKRED20 ketoreductase from *Chryseobacterium* sp. CA49 can be retrieved from NCBI, and the corresponding nucleic acids were then synthesized by a vendor using conventional techniques in the art and cloned into the expression vector pACYC-Duet-1. The recombinant expression plasmid was transformed into *E. coli* BL21 (DE3) competent cells under the conditions of 42° C. and thermal shock for 90 seconds. The transformation was plated on LB agar plates containing chloramphenicol which was then incubated overnight at 37° C. Recombinant transformants were obtained.

Example 2: Expression of Ketoreductase Polypeptides, and Preparation of an Enzyme Solution Containing Ketoreductase Polypeptides The preparation procedure of enzyme solution in the present invention is as follows: the recombinant transformant obtained in Example 1 was inoculated into 50 mL LB medium containing chloramphenicol (peptone 10 g/L, yeast extract powder 5 g/L, sodium chloride 10 g/L, pH 7.0±0.2, 25° C.) in a 250 mL Erlenmeyer flask, which was then cultured in a shaking incubator at 30° C., 250 rpm overnight. When the $OD_{600}$ of this overnight culture reached 2, it was subcultured at the inoculum of 5% (v/v) into a 1.0 L flask containing 250 mL of TB medium (tryptone 12 g/L, yeast extract 24 g/L, disodium hydrogen phosphate 9.4 g/L, dipotassium hydrogen phosphate 2.2 g/L, lactose 6 g/L, pH 7.2±0.2, 30° C.), and this expression culture was placed in a shaking incubator at 30° C., 250 rpm, during which lactose induced the expression of ketoreductase polypeptide. After about 20 h, the expression culture was harvested and centrifuged (8000 rpm, 10 minutes); the supernatant was discarded and wet cells were collected. The obtained wet cells were suspended with 30 mL of phosphate buffer (PBS, pH 7.0) and sonicated in an ice bath, and then the supernatant was collected by centrifugation (4000 rpm, 15 min) to obtain an enzyme solution containing ketoreductase polypeptides.

According to the recombinant expression process using shaking flasks as mentioned above, a miniaturized expression process in 96-well plate was performed by proportionally reducing the scale and the culture broth was centrifuged to obtain wet cells. The wet cells can be lysed by a chemical, mechanical or enzymatic method commonly known in this field, and enzyme solution can be obtained as clear supernatant after centrifuging the cell lysate.

Figure 3:
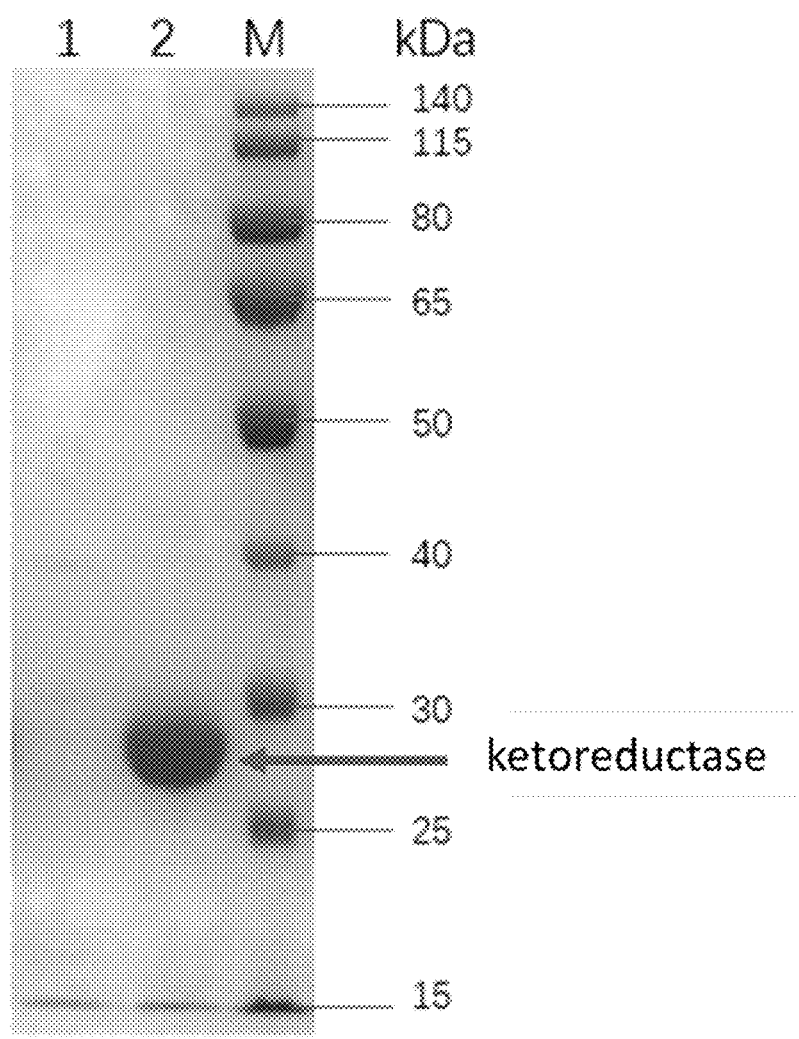
FIG. 3 depicts an SDA-PAGE image of the enzyme solution after heat treatment.

Example 3: Heat Treatment of Enzyme Solution 25 mL of each of the enzyme solutions of the ketoreductase polypeptides of SEQ ID No: 2 and SEQ ID No: 330 were prepared by the preparation method described in Example 2. The enzyme solution was separately put into a 50 mL centrifuge tube and placed in a water bath at 85° C., and the enzyme solution was heated uniformly by stirring. After 2 hours, the enzyme solution was centrifuged (4000 rpm, 30 min), and the supernatant was collected to obtain a heat-treated enzyme solution. The heat-treated enzyme solution sample was subjected to SDS-PAGE electrophoresis analysis, and the electrophoresis result was shown in FIG. 3: sample 1 is the heat-treated enzyme solution corresponding to SEQ ID No: 2, and sample 2 is the heat-treated enzyme solution corresponding to SEQ ID No: 330. The result in FIG. 3 showed that after heat treatment at [85° C., 2 h], the contaminating proteins in the enzyme solution have been completely removed, and the ketoreductase corresponding to SEQ ID No: 2 was also removed, but the ketoreductase corresponding to SEQ ID No: 330 remained in the enzyme solution.

Example 4: Construction of a Ketoreductase Mutant Library

Quikchange kit (supplier: Agilent) was used here. The sequence design of the mutagenesis primers was performed according to the instructions of the kit. The construction of a site-saturation mutagenesis library is as following. The PCR reaction consisted of 10 μl of 5× Buffer, 1 μl of 10 mM dNTP, 1 μl of plasmid DNA template (50 ng/μl), 0.75 μl (10 uM) each of the upstream and downstream primers, 0.5 μl of high fidelity enzyme and 36 μl of ddH2O, The PCR primer has a NNK codon at the mutation position.

PCR amplification steps: (1) 98° C. pre-denaturation 3 min; (2) 98° C. denaturation 10s; (3) annealing and extension 3 min at 72° C.; steps of (2)~(3) repeated 25 times; (5) extension 10 min at 72° C.; (6) cooling to 4° C., 2 μl of DpnI was added to the PCR product and the plasmid template was eliminated by overnight digestion at 37° C. The digested PCR product was transformed into *E. coli* BL21 (DE3) competent cells and plated on LB agar plates containing chloramphenicol to obtain a site-saturation mutagenesis library.

Example 5: High-Throughput Screening of Ketoreductase Mutant Libraries

The expression of ketoreductase mutant library was done in 96-well plates. The operation procedure was as follows: mutant colonies (as described in Example 4) were picked from the agar plates, inoculated into LB medium containing chloramphenicol in a 96-well shallow plate (1500 LB medium per well), and cultured overnight (18 to 20 hours) at 180 rpm, 80% humidity, 30° C.

When $OD_{600}$ of shallow plate culture reached 2.0, 20 μl of this culture were used to inoculate a TB medium (containing 400 μL of TB medium and 6 g/L of lactose per well) in a 96-well deep-well plate as expression culture, and it was shaken overnight for 18 to 20 hours at 250 rpm in a shaking incubator under 30° C. and humidity of 80%. Once the overnight expression was done, the expression culture was centrifuged at 4000 rpm for 10 min to collect cell pellets (i.e. wet cells).

Next, 200 μL/well of cell lysis buffer (100 mM phosphate buffer, pH 7.5, containing 1 mg/mL lysozyme) was added to the deep well plate, and the plate was sealed, placed on a plate shaker at 700 rpm for 1 h to break the cells. Then, the cell lysate was centrifuged (4000 rpm, 10 min), and 160 μL/well of supernatant enzyme solution was collected into a new plate which subsequently sealed and subjected to heat treatment by shaking in a water bath shaker at 72° C. for 2.5 h (for high-throughput screening of the ketoreductase polypeptides corresponding to "+" in Table 2 or Table 3).

After the heat treatment, the enzyme solution was centrifuged at 4000 rpm for 15 minutes, and 30 μL of supernatant was transferred to a 96-well plate pre-loaded with reaction stock solution (170 μL/well). The reaction plate was then heat-sealed with an aluminum film and placed in a shaker at 45° C., 200 rpm to start the reaction. After 15 h of reaction, 50 μL of the reaction solution was transferred into a new 96-deep well plate, and the reaction was quenched by adding 1 mL of ethyl acetate. The reaction was shaken on a plate shaker for 30 min (800 rpm), then centrifuged (4000 rpm, 30 min) and the supernatant was subject to GC analysis to determine the conversion.

For the reaction conditions of the high-throughput screening of the ketoreductase polypeptide corresponding to "+" in Table 2 or Table 3, the reaction stock solution is prepared as follows: a) dissolving 4-hydroxy-2-butanone in isopropanol, b) dissolving NAD+ in PBS buffer, mix a) and b) with water to give a final concentration of reaction stock solution [4-hydroxy-2-butanone 118 g/L, isopropanol 59% (v/v), NAD+0.24 g/L, PBS 0.01 M, pH 7.0].

Example 6: Analytical Method of (R)-(−)-1,3-Butanediol

GC analysis method: the column is DB-WAX 15 m*0.25 mm*0.25 μm, the carrier gas is $N_2$, the detector is FID, the inlet temperature is 250° C., the split ratio is 28:1, and the detector temperature is 300° C. The injection volume is 1 μL, the column temperature is 130° C., the temperature is raised to 150° C. at 10° C./min and then raised to 160° C. at 20° C./min, wherein the retention time of 4-hydroxy-2-butanone is 1.5 min, and the retention time of (R)-(−)-1,3-butanediol is 2.3 min.

GC chiral analysis method. Before injection, sample was prepared as following: 50 μL of MSTFA and 30 μL of anhydrous pyridine were added to 200 μL of sample and well mixed in a 1.5 mL centrifuge tube, and the reaction was shaken for 30 min. The column is CP-Chirasil Dex CB (CP7502) 25 m*0.25 mm*0.25 μm, the carrier gas is $N_2$, the detector is FID, the inlet temperature is 250° C., the split ratio is 28:1, and the detector temperature is 300° C. The injection volume is 1 μL, the column temperature was 105° C., and the stop time is 9 min, wherein the retention time of (R)-(−)-1,3-butanediol is 6.5 min, and the retention time of (S)-(−)-1,3-butanediol is 5.82 min.

Example 7: Fermentation Process and Downstream Processing

A single colony of *E. coli* BL21 (DE3) containing a plasmid bearing the gene of target engineered ketoreductase polypeptide was inoculated into 50 mL of LB medium (5.0 g/L Yeast Extract, 10 g/L Tryptone, 10 g/L sodium chloride) containing 30 μg/mL chloramphenicol. It was shaken at 250 rpm in a 30° C. shaker for at least 16 hours. When the $OD_{600}$ of the culture reached 3.5 to 5.0, the culture was used to inoculate a fermentor.

A 1.0 L fermentor containing 0.6 L of fermentation base medium was sterilized in an autoclave at 121° C. for 30 min. The fermentor was inoculated with the abovementioned culture. Temperature of fermentor was maintained at 37° C., the stirring paddle speed was in the range of 200-1000 rpm, and air was supplied to the fermentation vessel at 0.4-0.8 L/min to maintain the dissolved oxygen level at 35% saturation or greater. The pH of culture medium was maintained at pH7.0 by addition of 25-28% v/v ammonium hydroxide. Cell growth was maintained by feeding a feed solution containing 500 g/L of dextrose glucose monohydrate, 12 g/L of ammonium chloride, and 5 g/L of magnesium sulfate heptahydrate. In about 8 h from the start, the $OD_{600}$ of culture would reach 35±5, the temperature of the fermentor was decreased and maintained at 30° C., and the expression of ketoreductase was induced by the addition of monohydrate-α-lactose, added to a final concentration of 15 g/L. Fermentation process then continued for additional 16 hours and fermentation broth was collected. Cells were harvested using a Thermo Multifuge X3R centrifuge at 8000 rpm for 10 min at 4° C. Harvested cells were used directly in the following downstream process or stored frozen at −20° C.

To wash the wet cell, the wet cells were resuspended in 10 mM potassium phosphate buffer pH 7.0 at 4° C., centrifuged at 8000 rpm for 10 min at 4° C. using a Thermo Multifuge X3R centrifuge, and the wet cells were again collected. 10 g of the wet cells after the above washing were resuspended in 50 mL of 10 mM pH 7.0 potassium phosphate buffer, disrupted twice by a pressure homogenizer to release the ketoreductase from the cells. The cell lysate was heat-treated at 85° C. for 2 h (for the ketoreductase polypeptide corresponding to "++++" in Table 2 or Table 3). The heat-treated cell lysate was centrifuged at 4000 rpm for 30 min, and the supernatant was collected to obtain the heat-treated enzyme solution.

Example 8: Reaction Process for Producing (R)-(−)-1,3-Butanediol Catalyzed by Engineering Ketoreductase The following is a representative reaction process and workup process at 200 mL reaction volume. In a 500 mL reaction flask, 80 g of substrate 4-hydroxy-2-butanone and 80 mL of isopropanol were added, and stirring was started. Then, 16 mL of the heat-treated enzyme solution corresponding to SEQ ID No: 330 and 4 mg of cofactor NAD+ were charged. The final reaction volume in the reaction flask was made up to 200 mL with pure water. The temperature of reaction was maintained at 40° C. 1.0 with a water bath, the stirring speed was 200 rpm. From the 12th hour of the reaction, a vacuum of 0.09~0.1 Mpa was applied intermittently to remove the acetone produced in the reaction, and the fraction was collected. In-between the vacuum, isopropyl alcohol was supplemented into the reaction flask for 5 times, and the amount of each supplementation was 40 mL. After 24 hours of reaction, the vacuum was stopped and the reaction was completed. By analyzing the reaction sample, the conversion was 99%, and ee 99.5%.

The reaction was subject to distillation under reduced pressure, and isopropyl alcohol and water were firstly collected; then the product (R)-(−)-1,3-butanediol was collected by heating under reduced pressure. Finally, about 64 g of pure (R)-(−)-1,3-butanediol was obtained, and ee 99.5%.

Example 9: Reaction Process for Recycling NADH by Using Glucose Dehydrogenase

The following is a representative reaction and workup process at 200 mL reaction volume. In a 500 mL reaction flask, 20 g of substrate 4-hydroxy-2-butanone, 40 mL of pure water, 20 mL of the heat-treated enzyme solution corresponding to SEQ ID No: 102, and 20 mL of an enzyme solution containing glucose dehydrogenase (GDH), 82 g of glucose, 4 mg of cofactor NAD+ were added, and the final reaction volume in the reaction flask was made up to 200 mL with pure water. The temperature of reaction was maintained at 40° C. with a water bath, the stirring speed was 200 rpm, and the pH of the system was maintained at about 7.0 with a 1 M NaOH solution during the reaction. After 24 hours of reaction, the conversion was 68%, and ee≥99.5%.

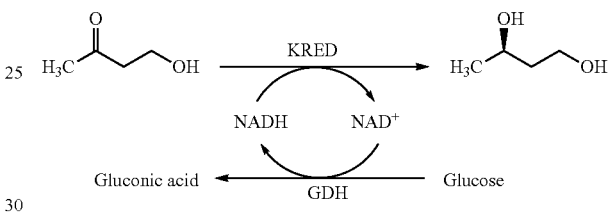

Example 10: Comparison of Catalytic Performance of Engineered Ketoreductase SEQ ID No: 330 with Wild-Type Ketoreductase SEQ ID No: 2 in the Context of Producing (R)-(−)-1,3-Butanediol According to the method described in Example 2, the following enzyme solutions were prepared: a) the enzyme solution of SEQ ID No: 2 and c) the enzyme solution of SEQ ID No: 330; a portion of a) or c) was heat treated at [85° C., 2 h] to produce b) or d), respectively.

Four reaction flasks with a volume of 250 mL were used. To each reaction flask, 10.0 g of 4-hydroxy-2-butanone and 25 mL of isopropanol were added, and then four different enzyme solutions (as shown in Table 4) were added to the four reaction flasks, each flask containing a different enzyme: a) 15 mL, b) 15 mL, c) 4 mL, d) 4 mL. Then 0.2 mL of NAD+ cofactor stock solution (12.5 g/L) was added to each reaction flask. Each reaction flask was filled up to a final reaction volume of 50 mL with pure water, so that the final concentration of the substrate is 200 g/L, the final concentration of isopropanol is 50% v/v, and the final concentration of NAD+ is 0.05 g/L in each reaction flask. The temperature of reaction was maintained at 40° C. with a water bath, the stirring speed was 200 rpm. From the 12th hour of the reaction, a vacuum of 0.09~0.1 Mpa was applied intermittently to remove the acetone produced in the reaction, and isopropanol was supplemented to maintain the concentration of isopropanol in the reaction system at 50% v/v. After 24 hours of the reaction, the reaction was stopped. A sample of 50 μL of the reaction mixture was taken from each reaction flask, and the sample was quenched by mixing with 1 mL of ethyl acetate. The conversion and ee values were measured and calculated according to the analysis method of Example 6, the results obtained are shown in Table 4.

TABLE 4

| Enzyme solution | Enzyme solution loading | Conversions | ee |
|---|---|---|---|
| a) SEQ. ID No: 2 enzyme solution without heat treatment | 30% v/v | 44.9% | >99% |
| b) [85° C., 2 h] heat-treatment enzyme solution of SEQ. ID No: 2 | 30% v/v | 0 | — |
| c) SEQ. ID No: 330 enzyme solution without heat treatment | 8% v/v | 99.1% | >99% |
| d) [85° C., 2 h] heat-treatment enzyme solution of SEQ. ID No: 330 | 8% v/v | 96.8% | >99% |

Example 11: Ketoreductase-Catalyzed Reaction to Prepare Methyl (R)-(−)-3-Hydroxybutyrate Four reaction flasks with a volume of 30 mL were used. To each reaction flask, 1.0 g of methyl acetoacetate and 2.0 mL of isopropanol were added, and then four different enzyme solutions (as shown in Table 5) were added to the four reaction flasks, each flask containing one of the enzymes: e) 0.25 mL, f) 0.25 mL, g) 0.1 mL, h) 0.1 mL. Then 0.04 mL of NAD+ cofactor stock solution (12.5 g/L) was added to each reaction flask. Each reaction flask was filled up to a final reaction volume of 5.0 mL with pure water, so that the final concentration of the substrate (methyl acetoacetate) was 200 g/L, the final concentration of isopropanol was 40% v/v, the final concentration of NAD+ was 0.1 g/L in each reaction flask. The reaction flask was placed on an IKA magnetic stirrer at 40° C., and the stirring speed was set to 400 rpm to start the reaction. After the reaction was carried out for 24 hours, the reaction was sampled and measured for conversion and ee. The results are shown in Table 5.

TABLE 5

| Enzyme solution | Enzyme solution loading | Conversions | ee |
|---|---|---|---|
| e) SEQ. ID No: 2 enzyme solution without heat treatment | 5% v/v | 84.7% | >99% |
| f) [72° C., 2.5 h] heat-treatment enzyme solution of SEQ. ID No: 2 | 5% v/v | 40.5% | >99% |
| g) SEQ. ID No: 188 enzyme solution without heat treatment | 2% v/v | 98.8% | >99% |
| h) [80° C., 2 h] heat-treatment enzyme solution of SEQ. ID No: 188 | 2% v/v | 97.0% | >99% |

Analytical Method:
GC analysis method: the column was CP-ChiraSil-DEX CB 25 m*0.25 mm*0.25 μm, the carrier gas was N$_2$, the detector was FID, the inlet temperature was 250° C., the split ratio was 100:1, the detector temperature was 250° C., the injection volume was 1 μL, the column temperature was 120° C. and maintained for 5 min. The retention time of methyl acetoacetate was 2.7 min. The retention time of methyl (R)-(−)-3-hydroxybutyrate was 3.1 min.

GC chiral analysis method. Before injection, sample was prepared as following: 50 μL of MSTFA and 30 μL of anhydrous pyridine were added with 200 μL of the diluted sample in a 1.5 mL centrifuge tube, and the mixture was well mixed and shaken for 30 minutes. The column was CP-Chirasil Dex CB (CP7502) 25 m*0.25 mm*0.25 μm, the carrier gas was N$_2$, the detector was FID, the inlet temperature was 250° C., the split ratio was 50:1, and the detector temperature was 250° C. The injection volume was 1 μL, the column temperature was 110° C., the stop time was 8 min, and the retention time of methyl (R)-(−)-3-hydroxybutyrate was 3.7 min, the retention time of methyl (S)-(−)-3-hydroxybutyrate was 3.9 min.

Example 12: Ketoreductase-Catalyzed Reaction to Prepare Ethyl (R)-(−)-3-Hydroxybutyrate Four reaction flasks with a volume of 30 mL were used. To each reaction flask, 1.0 g of ethyl acetoacetate and 2.0 mL of isopropanol were added, and then four different enzyme solutions (as shown in Table 6) were added to the four reaction flasks, each flask containing one of the enzymes: i) 0.25 mL, j) 0.25 mL, k) 0.1 mL, l) 0.1 mL. Then, 0.04 mL of NAD+ cofactor stock solution (12.5 g/L) was added to each reaction flask. Each reaction flask was filled up to a final reaction volume of 5.0 mL with pure water, so that the final concentration of the substrate (ethyl acetoacetate) was 200 g/L, the final concentration of isopropanol was 40% v/v, the final concentration of NAD+ was 0.1 g/L in each reaction flask. The reaction flask was placed on an IKA magnetic stirrer at 40° C., and the stirring speed was set to 400 rpm to start the reaction. After the reaction was carried out for 24 hours, the reaction was sampled and measured for conversion and ee. The results are shown in Table 6.

TABLE 6

| Enzyme solution | Enzyme solution loading | Conversions | ee |
|---|---|---|---|
| i) SEQ. ID No: 2 enzyme solution without heat treatment | 5% v/v | 81.4% | >99% |
| j) [72° C., 2.5 h] heat-treatment enzyme solution of SEQ. ID No: 2 | 5% v/v | 41.5% | >99% |
| k) SEQ. ID No: 240 enzyme solution without heat treatment | 2% v/v | 99.0% | >99% |
| l) [85° C., 2 h] heat-treatment enzyme solution of SEQ. ID No: 240 | 2% v/v | 98.3% | >99% |

Analytical Method:
GC analysis method: the column was CP-ChiraSil-DEX CB 25 m*0.25 mm*0.25 μm, the carrier gas was N$_2$, the detector is FID, the inlet temperature was 250° C., the split ratio was 50:1, the detector temperature was 250° C., the injection volume was 1 μL, the column temperature was 120° C. and maintained for 4 min. The retention time of ethyl acetoacetate was 3.2 min. The retention time of ethyl (R)-(−)-3-hydroxybutyrate was 3.7 min.

GC chiral analysis method: the column is CP-Chirasil Dex CB (CP7502) 25 m*0.25 mm*0.25 μm, the carrier gas is N$_2$, the detector is FID, the inlet temperature is 250° C., and the split ratio is 100:1. The detector temperature was 250° C., the injection volume was 1 μL, the column temperature was 100° C., the stop time was 15 min, and the retention time of ethyl (R)-(−)-3-hydroxybutyrate was 10.3 min, the retention time of ethyl (S)-(−)-3-hydroxybutanoate was 10.8 min.

Example 13: Ketoreductase-Catalyzed Reaction to Prepare Ethyl (S)-(−)-4-Chloro-3-Hydroxybutyrate Four reaction flasks with a volume of 30 mL were used. To each reaction flask, 0.3 g of ethyl 4-chloroacetoacetate, 2.0 mL of isopropanol and 2.6 mL of triethanolamine buffer (0.1 M pH=8.5) were added, and then four different enzyme solutions (as shown in Table 7) were added to the four reaction flasks, each flask containing one of the enzymes: m)

0.25 mL, n) 0.25 mL, o) 0.05 mL, p) 0.05 mL. Then, 0.04 mL of NAD+ cofactor stock solution (12.5 g/L) was added to each reaction flask. Each reaction flask was filled up to a final reaction volume of 5.0 mL with pure water, so that the final concentration of the substrate (ethyl 4-chloroacetoacetate) was 60 g/L, the final concentration of isopropanol was 40% v/v, the final concentration of NAD+ was 0.1 g/L in each reaction flask. The reaction flask was placed on an IKA magnetic stirrer at 40° C., and the stirring speed was set to 400 rpm to start the reaction. After the reaction was carried out for 24 hours, the reaction was sampled and measured for conversion and ee. The results are shown in Table 7.

TABLE 7

| Enzyme solution | Enzyme solution loading | Conversions | ee |
|---|---|---|---|
| m) SEQ. ID No: 2 enzyme solution without heat treatment | 5% v/v | 74.8% | >99% |
| n) [72° C., 2.5 h] heat-treated enzyme solution of SEQ. ID No: 2 | 5% v/v | 35.6% | >99% |
| o) SEQ. ID No: 332 enzyme solution without heat treatment | 1% v/v | 99.5% | >99% |
| p) [85° C., 2 h] heat-treated enzyme solution of SEQ. ID No: 332 | 1% v/v | 99.2% | >99% |

Analytical Method:

GC analysis method: the column was CP-ChiraSil-DEX CB 25 m*0.25 mm*0.25 μm, the carrier gas was $N_2$, the detector was FID, the inlet temperature was 250° C., the split ratio was 98:1, the detector temperature was 250° C., the injection volume was 1 μL, the column temperature was 50° C., and the temperature was raised to 180° C. at 30° C./min, wherein the retention time of ethyl 4-chloroacetoacetate was 10.4 min, the retention time of ethyl (S)-(−)-4-chloro-3-hydroxybutyrate was 9.9 min.

GC chiral analysis method: the column was CP-Chirasil Dex CB (CP7502) 25 m*0.25 mm*0.25 μm, the carrier gas was $N_2$, the detector was FID, the inlet temperature was 250° C., and the split ratio was 100:1. The detector temperature was 250° C., the injection volume was 1 μL, the column temperature was 105° C., the stop time was 15 min, and the retention time of ethyl (S)-(−)-4-chloro-3-hydroxybutyrate was 11.5 min. The retention time of ethyl (R)-(−)-4-chloro-3-hydroxybutyrate was 11.9 min.

Example 14: Ketoreductase-Catalyzed Reaction to Prepare (R)-1-[3,5-Bis(Trifluoromethyl)Phenyl]Ethanol A reaction flask of 30 mL was used. To this reaction flask, 1.0 g of 3,5-bis-trifluoromethylacetophenone, 1.0 mL of isopropanol and 0.08 mL of NAD+ cofactor stock solution (12.5 g/L) were added, then 0.5 mL of [75° C., 2 h] heat-treated enzyme solution of SEQ ID No: 142 was added. The reaction flask was filled up to a final reaction volume of 5.0 mL with pure water, so that the final concentration of substrate(3,5-bistrifluoromethylacetophenone) in the reaction flask was 200 g/L, the final concentration of isopropanol was 20% v/v, and the final concentration of NAD+ was 0.2 g/L. The reaction flask was placed on an IKA magnetic stirrer at 40° C., and the stirring speed was set to 400 rpm to start the reaction. After 24 h of reaction, the conversion was >95%, and the product (R)-1-[3,5-bis(trifluoromethyl)phenyl]ethanol had an ee≥99.9%.

Analytical Method:

HPLC analysis method: column: ZORBAX SB-C18, mobile phase: 60% acetonitrile+40% water, column temperature: 30° C., injection volume: 10 μL, flow rate: 1 ml/min, wavelength: 218 nm, The retention time of (R)-1-[3,5-bis(trifluoromethyl)phenyl]ethanol was 4.9 min, and the retention time of 3,5-bistrifluoromethylacetophenone was 6.7 min.

GC chiral analysis method: column: Beta DEX™ 225 (30 m*0.25 mm*0.25 μm), column temperature: 110° C. constant temperature for 20 min, column flow rate: 1.0 ml/min, gasification chamber: 250° C., detector: FID 330° C., split ratio: 1:30, injection amount: 1.0 μl. Wherein the retention time of (S)-1-[3,5-bis(trifluoromethyl)phenyl]ethanol was 15.77 min, the retention time of (R)-1-[3,5-bis(trifluoromethyl)phenyl ethanol was 16.33 min.

Example 15: Reaction Process for Resolution of Racemic 1,3-Butanediol by Ketoreductase The following is a representative reaction and workup process at 200 mL volume. Racemic 1,3-butanediol was used as a substrate (containing an equivalent amount of (R)-(−)-1,3-butanediol and (S)-(−)-1,3-butanediol). To a 500 mL reaction flask, 10 g of racemic 1,3-butanediol, 20 g of acetone, 20 mL of [85° C., 2 h] heat-treated enzyme solution of SEQ ID No: 330, and 4 mg of cofactor NAD+ were added. The reaction flask was filled up to a final reaction volume of 200 mL with pure water. The temperature of the reaction was at 40° C. controlled by a water bath and the stirring speed was 200 rpm. The reaction was completed after 24 hours and was sampled for analysis. ≥99.5% of (R)-(−)-1,3-butanediol in the substrate was converted into 4-hydroxy-2-butanone, and the ee value of (S)-(−)-1,3-butanediol in the reaction is ≥99%.

It should be understood that after reading the above contents of the present invention, those skilled in the art may make various modifications or changes to the present invention. And these equivalent forms also fall within the scope of the appended claims of the present invention.

The invention claimed is:

1. An engineered ketoreductase polypeptide which is, under suitable reaction conditions, capable of catalyzing the conversion of 4-hydroxy-2-butanone to (R)-(-)-1,3-butanediol, wherein the amino acid sequence of said polypeptide comprises one or more of substitutions selected from the group consisting of substitutions corresponding to substitutions X46T, X185C, and X228A in the polypeptide of SEQ ID NO 2, wherein the numbering refers to SEQ ID NO:2, wherein said amino acid sequence is selected from the group consisting of SEQ ID NO: 36, 38, 40, 42, 44, 46, 48, 50, 52, 54, 56, 58, 60, 62, 66, 68, 70, 72, 74, 78, 80, 82, 84, 86, 88, 90, 92, 94, 96, 98, 100, 102, 104, 106, 108, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, and 332.

2. The engineered ketoreductase polypeptide of claim 1, wherein said suitable reaction conditions include the provision of about 5 g/L to 400 g/L of 4-hydroxy-2-butanone, about 0.01 g/L to 0.2 g/L of NADH, and about 10%-50% (v/v) of isopropanol, at a temperature of about 10-60° C.

3. An engineered polypeptide, wherein said polypeptide is:
(a) a polypeptide comprising an amino acid sequence selected from the group consisting of SEQ ID NO: 36, 38, 40, 42, 44, 46, 48, 50, 52, 54, 56, 58, 60, 62, 66, 68, 70, 72, 74, 78, 80, 82, 84, 86, 88, 90, 92, 94, 96, 98, 100, 102, 104, 106, 108, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, and 332; or
(b) a polypeptide having ketoreductase activity, which comprises an amino acid sequence having (i) at least 95% sequence identity to one of the amino acid sequences recited in (a), and (ii) one or more substitutions selected from the group consisting of substitutions corresponding to substitutions X46T, X185C and X228A in the polypeptide of SEQ ID NO: 2.

4. The engineered ketoreductase polypeptide of claim 3, wherein said polypeptide is capable of catalyzing the conversion of 4-hydroxy-2-butanone to (R)-(-)-1,3-butanediol under suitable reaction conditions with greater catalytic activity and/or stability than the polypeptide of SEQ ID NO: 2, and producing (R)-(-)-1,3-butanediol in an enantiomeric excess of at least 90%.

5. A polypeptide immobilized on a solid material by a chemical bond or a physical adsorption method, wherein the polypeptide is the engineered ketoreductase polypeptide according to claim 1.

6. A ketoreductase catalyst obtained by culturing a host cell comprising an expression vector comprising a polynucleotide encoding the engineered ketoreductase polypeptide of claim 1, wherein said ketoreductase catalyst comprises (a) cells or culture fluid obtained from said host cell culture and that contain said engineered ketoreductase polypeptide, (b) an extract that contains said engineered ketoreductase polypeptide and is obtained from said host cell culture, (c) an isolated product that contains said engineered ketoreductase polypeptide and is obtained by isolating or purifying said engineered ketoreductase from said extract, or (d) an immobilization product that contains said engineered ketoreductase polypeptide and is obtained by immobilizing said host cell, an extract of said host cell, or isolated product of the host cell extract.

7. A process for converting a carbonyl substrate of formula (II)

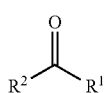

to a chiral alcohol compound of formula (I)

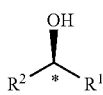

using the engineered ketoreductase polypeptide of claim 1, wherein said chiral alcohol compound of formula (I) has the indicated stereochemical configuration shown at the chiral center marked with an * and is in an enantiomeric excess over its other isomer, further wherein:

$R^1$ is an optionally substituted or unsubstituted aryl or heteroaryl, an optionally substituted or unsubstituted $C_1$-$C_8$ hydrocarbyl, a cycloalkyl or a heterocyclic group; and $R_2$ is (a) an optionally substituted or unsubstituted $C_1$-$C_6$ hydrocarbyl, (b) a halogen selected from —F, —Cl, —Br, and —I, (c) an alkenyl, an alkynyl, an aryl, or a heteroaryl, or (d) —$NO_2$, —NO, —$SO_2R'$, —SOR', —SR', —NR'R', —OR', —$CO_2R'$, —COR', —C(O)NR', —$SO_2NH_2$, —$SONH_2$, —CN, or —$CF_3$, wherein each R' is independently selected from hydrogen, a $C_1$-$C_4$ hydrocarbyl, a halogen, a $C_1$-$C_8$ hydrocarbyl, a $C_2$-$C_{12}$ alkenyl, a $C_2$-$C_{12}$ alkynyl, a cycloalkyl, an aryl, and a heterocyclic substituent;

further wherein the process comprises the step of contacting under suitable reaction conditions said carbonyl substrate of formula (II) with the engineered ketoreductase polypeptide of claim 1.

8. The process of claim 7, wherein the chiral alcohol compound of formula (I) is

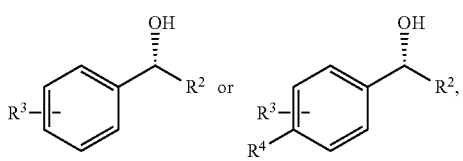

further wherein, (i) $R^2$ is as defined in claim 7; and (ii) $R^3$ and $R^4$ are each (a) hydrogen, (b) an optionally substituted or non-substituted $C_1$-$C_4$ hydrocarbyl, (c) a halogen selected from —F, —Cl, —Br, and —I, (d) an aryl or a heteroaryl, or (e) —$NO_2$, —NO, —$SO_2R'$, —SOR', —SR', —NR'R', —OR', —$CO_2R'$, —COR', —C(O)NR', —$SO_2NH_2$, —$SONH_2$, —CN, or —$CF_3$, wherein each R' is independently selected from hydrogen, a $C_1$-$C_4$ hydrocarbyl, a cycloalkyl, an aryl, and a heterocyclic substituent; and (iii) the carbonyl substrate of formula (II) is:

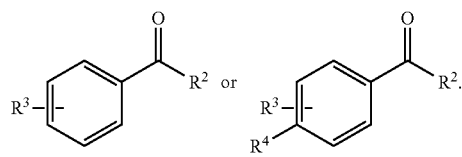

9. The process of claim 8, wherein $R^3$ is (a) in the para position of the phenyl ring, (b) in the meta position of the phenyl ring, or (c) in the ortho position of the phenyl ring.

10. The process of claim 7, wherein the compound of formula (I) is:

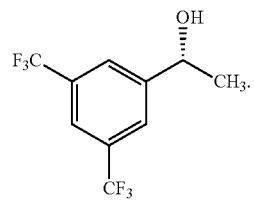

11. A process of preparing an (R)-(-)-1,3-butanediol of formula A2:

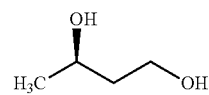

wherein the process comprises the step of converting, under suitable reaction conditions, a 4-hydroxy-2-butanone compound of formula A1 to (R)-(-)-1,3-butanediol,

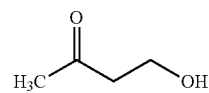

by reacting said 4-hydroxy-2-butanone compound of formula A1 with the engineered ketoreductase polypeptide of claim 1.

12. The process of claim 7, wherein the chiral alcohol compound is present in an enantiomeric excess of at least 90%.

13. The process of claim 7, wherein said engineered ketoreductase polypeptide converts said carbonyl substrate to said chiral alcohol in the presence of a co-factor NADH is regenerated during the conversion by (a) a process of converting isopropanol to acetone by a ketoreductase; (b) a process of converting glucose to gluconic acid by glucose dehydrogenase; or (c) by converting formic acid to carbon dioxide by formate dehydrogenase.

14. The process of claim 7, wherein the process requires a reaction solvent selected from water, methanol, ethanol, propanol, isopropanol, isopropyl acetate, dimethyl sulfoxide (DMSO) and dimethylformamide (DMF).

15. The process of claim 7, wherein the reaction conditions include a temperature of 10° C. to 60° C.

16. The process of claim 7, wherein the reaction conditions include a pH 4.0 to pH 11.0.

17. The process of claim 7, wherein the carbonyl substrate is present at a loading of 5 g/L to 400 g/L.

18. A process for the resolution of racemic 1,3-butanediol, said process comprising the step of contacting under suitable reaction conditions a racemic 1,3-butanediol with an the engineered polypeptide of claim 1.

19. The process of claim 18, wherein the reaction conditions include a loading of about 5 g/L to 400 g/L of racemic 1,3-butanediol, about 0.01 g/L to 0.2 g/L of NAD+, and about 10%-50% v/v of acetone, at a temperature of about 10-60° C.

* * * * *

SEQUENCE LISTING

<160> NUMBER OF SEQ ID NOS: 332

<210> SEQ ID NO 1
<211> LENGTH: 747
<212> TYPE: DNA
<213> ORGANISM: Artificial sequence
<220> FEATURE:
<223> OTHER INFORMATION: Engineered sequence

<400> SEQUENCE: 1

-continued

| | |
|---|---|
| atgggtatcc tggacaacaa agtcgcactg gttacgggcg ctggttcggg catcggtctg | 60 |
| gcggtggcac actcctacgc taaagaaggc gctaaagtca ttgtgtcaga tatcaacgaa | 120 |
| gaccatggta ataaagcggt tgaagatatt aaagcacagg gcggtgaagc tagttttgtg | 180 |
| aaagcggaca ccagcaaccc ggaagaagtg gaagccctgg ttaaacgtac ggtcgaaatt | 240 |
| tatggtcgcc tggatatcgc atgcaacaat gctggcattg gcggtgaaca ggcactggct | 300 |
| ggtgattacg gcctggacag ctggcgtaaa gttctgtcta tcaatctgga cggtgtcttc | 360 |
| tatggctgta atacgaact ggaacaaatg gagaaaacg gcggtggcgt tatcgtcaat | 420 |
| atggccagca ttcatggtat cgttgcggcc ccgctgagct ctgcatatac ctctgcgaaa | 480 |
| cacgccgtgg ttggcctgac gaaaaacatt ggtgctgaat atggccagaa aaacatccgt | 540 |
| tgcaatgcgg tgggcccggc ctacattgaa accccgctgc tggaatcact gacgaaagaa | 600 |
| atgaaagaag ccctgatctc gaaacacccg atgggtcgcc tgggcaaacc ggaagaagtg | 660 |
| gcagaactgg ttctgtttct gagttccgaa aaatcatcgt tcatgaccgg tggctattac | 720 |
| ctggtcgatg gtggctacac ggcagtg | 747 |

<210> SEQ ID NO 2
<211> LENGTH: 249
<212> TYPE: PRT
<213> ORGANISM: Chryseobacterium sp.CA49

<400> SEQUENCE: 2

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245

<210> SEQ ID NO 3
<211> LENGTH: 747
<212> TYPE: DNA
<213> ORGANISM: Artificial sequence
<220> FEATURE:
<223> OTHER INFORMATION: Engineered sequence

<400> SEQUENCE: 3

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaagcggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact  ggaacaaatg gagaaaacg  gcggtggcgt tatcgtcaat     420
atggccagca ttcatggtat cgttgcggcc ccgctgcgct ctgcatatac ctctgcgaaa     480
cacgccgtgg ttggcctgac gaaaaacatt ggtgctgaat atggccagaa aacatccgt      540
tgcaatgcgg tgggcccggc ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747
```

<210> SEQ ID NO 4
<211> LENGTH: 249
<212> TYPE: PRT
<213> ORGANISM: Artificial sequence
<220> FEATURE:
<223> OTHER INFORMATION: Engineered sequence

<400> SEQUENCE: 4

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Arg Ser Ala Tyr Thr Ser Ala Lys
145                 150                 155                 160

His Ala Val Val Gly Leu Thr Lys Asn Ile Gly Ala Glu Tyr Gly Gln
            165                 170                 175

Lys Asn Ile Arg Cys Asn Ala Val Gly Pro Ala Tyr Ile Glu Thr Pro
        180                 185                 190

Leu Leu Glu Ser Leu Thr Lys Glu Met Lys Glu Ala Leu Ile Ser Lys
            195                 200                 205

His Pro Met Gly Arg Leu Gly Lys Pro Glu Glu Val Ala Glu Leu Val
        210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245

<210> SEQ ID NO 5
<211> LENGTH: 747
<212> TYPE: DNA
<213> ORGANISM: Artificial sequence
<220> FEATURE:
<223> OTHER INFORMATION: Engineered sequence

<400> SEQUENCE: 5

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagcggt tgaagatatt aaagcacagg gtggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg cggtgaaaaa ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgggcccggc ctacattgaa accccgctgc tggaatcact gacgaaagaa     600
atgaaagaag ccctgatctc gaaacacccg atgggtcgcc tgggcaaacc ggaagaagtg     660
gcagaactgg ttctgttct gagttccgaa aaatcatcgt tcatgaccgg tggctattac     720
ctggtcgatg gtggctacac ggcagtg                                          747
```

<210> SEQ ID NO 6
<211> LENGTH: 249
<212> TYPE: PRT
<213> ORGANISM: Artificial sequence
<220> FEATURE:
<223> OTHER INFORMATION: Engineered sequence

<400> SEQUENCE: 6

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

```
Tyr Gly Arg Leu Asp Ile Ala Cys Asn Asn Ala Gly Ile Gly Gly Glu
                85                  90                  95
Lys Ala Leu Ala Gly Asp Tyr Gly Leu Asp Ser Trp Arg Lys Val Leu
            100                 105                 110
Ser Ile Asn Leu Asp Gly Val Phe Tyr Gly Cys Lys Tyr Glu Leu Glu
        115                 120                 125
Gln Met Glu Lys Asn Gly Gly Val Ile Val Asn Met Ala Ser Ile
    130                 135                 140
His Gly Ile Val Ala Ala Pro Leu Ser Ser Ala Tyr Thr Ser Ala Lys
145                 150                 155                 160
His Ala Val Val Gly Leu Thr Lys Asn Ile Gly Ala Glu Tyr Gly Gln
                165                 170                 175
Lys Asn Ile Arg Cys Asn Ala Val Gly Pro Ala Tyr Ile Glu Thr Pro
            180                 185                 190
Leu Leu Glu Ser Leu Thr Lys Glu Met Lys Glu Ala Leu Ile Ser Lys
        195                 200                 205
His Pro Met Gly Arg Leu Gly Lys Pro Glu Glu Val Ala Glu Leu Val
    210                 215                 220
Leu Phe Leu Ser Ser Glu Lys Ser Ser Phe Met Thr Gly Gly Tyr Tyr
225                 230                 235                 240
Leu Val Asp Gly Gly Tyr Thr Ala Val
                245
```

<210> SEQ ID NO 7
<211> LENGTH: 747
<212> TYPE: DNA
<213> ORGANISM: Artificial sequence
<220> FEATURE:
<223> OTHER INFORMATION: Engineered sequence

<400> SEQUENCE: 7

```
atgggtatcc tggacaacaa agtcgcactg gttacgggcg ctggttcggg catcggtctg    60
gcggtggcac actcctacgc taaagaaggc gctaaagtca ttgtgtcaga tatcaacgaa   120
gaccatggta taaagcggt tgaagatatt aaagcacagg gcggtgaagc tagttttgtg   180
aaagcggaca ccagcaaccc ggaagaagtg aaagccctgg ttaaacgtac ggtcgaaatt   240
tatggtcgcc tggatatcgc atgcaacaat gctggcattg gcggtgaaca ggcactggct   300
ggtgattacg gcctggacag ctggcgtaaa gttctgtcta tcaatctgga cggtgtcttc   360
tatggctgta atacgaact ggaacaaatg gagaaaacg gcggtggcgt tatcgtcaat   420
atggccagca ttcatggtat cgttgcggcc ccgctgaact ctgcatatac ctctgcgaaa   480
cacgccgtgg ttggcctgac gaaaaacatt ggtgctgaat atggccagaa aaacatccgt   540
tgcaatgcgg tgggcccggc ctacattgaa accccgctgc tggaatcact gacgaaagaa   600
atgaaagaag ccctgatctc gaaacacccg atgggtcgcc tgggcaaacc ggaagaagtg   660
gcagaactgg ttctgtttct gagttccgaa aaatcatcgt tcatgaccgg tggctattac   720
ctggtcgatg gtggctacac ggcagtg                                      747
```

<210> SEQ ID NO 8
<211> LENGTH: 249
<212> TYPE: PRT
<213> ORGANISM: Artificial sequence
<220> FEATURE:
<223> OTHER INFORMATION: Engineered sequence

<400> SEQUENCE: 8

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
            35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
            115                 120                 125

Gln Met Glu Lys Asn Gly Gly Val Ile Val Asn Met Ala Ser Ile
            130                 135                 140

His Gly Ile Val Ala Ala Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
            195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 9
<211> LENGTH: 747
<212> TYPE: DNA
<213> ORGANISM: Artificial sequence
<220> FEATURE:
<223> OTHER INFORMATION: Engineered sequence

<400> SEQUENCE: 9

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagcggt tgaagatatt aaagcacagg gcggtgaagc tagttttgtg     180
aaagcggaca ccagcaaccc ggaagaagtg aagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta aatacgaact ggaacaaatg gagaaaaacg gcggtggcgt atcgtcaat     420
atggccagca ttcatggtat cgttgcgtac ccgctgagct ctgcatatac ctctgcgaaa     480
cacgccgtgg ttggcctgac gaaaaacatt ggtgctgaat atggccagaa aaacatccgt     540
tgcaatgcgg tgggcccggc ctacattgaa acccgctgc tggaatcact gacgaaagaa     600
atgaaagaag ccctgatctc gaaacacccg atgggtcgcc tgggcaaacc ggaagaagtg     660
```

```
gcagaactgg ttctgtttct gagttccgaa aaatcatcgt tcatgaccgg tggctattac    720
ctggtcgatg gtggctacac ggcagtg                                        747
```

<210> SEQ ID NO 10
<211> LENGTH: 249
<212> TYPE: PRT
<213> ORGANISM: Artificial sequence
<220> FEATURE:
<223> OTHER INFORMATION: Engineered sequence

<400> SEQUENCE: 10

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Tyr Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 11
<211> LENGTH: 747
<212> TYPE: DNA
<213> ORGANISM: Artificial sequence
<220> FEATURE:
<223> OTHER INFORMATION: Engineered sequence

<400> SEQUENCE: 11

```
atgggtatcc tggacaacaa agtcgcactg gttacgggcg ctggttcggg catcggtctg    60
gcggtggcac actcctacgc taaagaaggc gctaaagtca ttgtgtcaga tatcaacgaa   120
gaccatggta taaagcggt tgaagatatt aaagcacagg gcggtgaagc tagttttgtg   180
```

```
aaagcggaca ccagcaaccc ggaagaagtg gaagccctgg ttaaacgtac ggtcgaaatt    240
tatggtcgcc tggatatcgc atgcaacaat gctggcattg gcggtgaaca ggcactggct    300
ggtgattacg gcctggacag ctggcgtaaa gttctgtcta tcaatctgga cggtgtcttc    360
tatggctgta atacgaact ggaacaaatg gagaaaaacg gcggtggcgt tatcgtcaat    420
atggccagca ttcatggtat cgttgcgcgc ccgctgagct ctgcatatac ctctgcgaaa    480
cacgccgtgg ttggcctgac gaaaaacatt ggtgctgaat atggccagaa aaacatccgt    540
tgcaatgcgg tgggcccggc ctacattgaa accccgctgc tggaatcact gacgaaagaa    600
atgaaagaag ccctgatctc gaaacacccg atgggtcgcc tgggcaaacc ggaagaagtg    660
gcagaactgg ttctgttct gagttccgaa aaatcatcgt tcatgaccgg tggctattac    720
ctggtcgatg gtggctacac ggcagtg                                        747
```

<210> SEQ ID NO 12
<211> LENGTH: 249
<212> TYPE: PRT
<213> ORGANISM: Artificial sequence
<220> FEATURE:
<223> OTHER INFORMATION: Engineered sequence

<400> SEQUENCE: 12

```
Met Gly Ile Leu Asp Asn Lys Val Ala Leu Val Thr Gly Ala Gly Ser
1               5                  10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Arg Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 13
<211> LENGTH: 747
<212> TYPE: DNA
<213> ORGANISM: Artificial sequence
<220> FEATURE:
<223> OTHER INFORMATION: Engineered sequence

<400> SEQUENCE: 13

```
atgggtatcc tggacaacaa agtcgcactg gttacgggcg ctggttcggg catcggtctg    60
gcggtggcac actcctacgc taaagaaggc gctaaagtca ttgtgtcaga tatcaacgaa   120
gaccatggta ataaagcggt tgaagatatt aaagcacagg gcggtgaagc tagttttgtg   180
aaagcggaca ccagcaaccc ggaagaagtg gaagccctgg ttaaacgtac ggtcgaaatt   240
tatggtcgcc tggatatcgc atgcaacaat gctggcattg gcggtgaacg cgcactggct   300
ggtgattacg gcctggacag ctggcgtaaa gttctgtcta tcaatctgga cggtgtcttc   360
tatggctgta atacgaact ggaacaaatg gagaaaaacg gcggtggcgt tatcgtcaat   420
atggccagca ttcatggtat cgttgcggcc ccgctgagct ctgcatatac ctctgcgaaa   480
cacgccgtgg ttggcctgac gaaaaacatt ggtgctgaat atggccagaa aacatccgt   540
tgcaatgcgg tgggccccggc ctacattgaa accccgctgc tggaatcact gacgaaagaa   600
atgaaagaag ccctgatctc gaaacacccg atgggtcgcc tgggcaaacc ggaagaagtg   660
gcagaactgg ttctgtttct gagttccgaa aaatcatcgt tcatgaccgg tggctattac   720
ctggtcgatg gtggctacac ggcagtg                                        747
```

<210> SEQ ID NO 14
<211> LENGTH: 249
<212> TYPE: PRT
<213> ORGANISM: Artificial sequence
<220> FEATURE:
<223> OTHER INFORMATION: Engineered sequence

<400> SEQUENCE: 14

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Arg Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro

```
                180              185              190
Leu Leu Glu Ser Leu Thr Lys Glu Met Lys Glu Ala Leu Ile Ser Lys
                    195              200              205
His Pro Met Gly Arg Leu Gly Lys Pro Glu Glu Val Ala Glu Leu Val
        210              215              220
Leu Phe Leu Ser Ser Glu Lys Ser Ser Phe Met Thr Gly Gly Tyr Tyr
225             230              235              240
Leu Val Asp Gly Gly Tyr Thr Ala Val
                245
```

<210> SEQ ID NO 15
<211> LENGTH: 747
<212> TYPE: DNA
<213> ORGANISM: Artificial sequence
<220> FEATURE:
<223> OTHER INFORMATION: Engineered sequence

<400> SEQUENCE: 15

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagcggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcatta ggggtgaaca ggcactggct     300
ggtgattacg gcctggacag ctggcgtaaa gttctgtcta tcaatctgga cggtgtcttc     360
tatggctgta aatacgaact ggaacaaatg gagaaaaacg gcggtggcgt atcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aacatccgt     540
tgcaatgcgg tgggcccggc ctacattgaa accccgctgc tggaatcact gacgaaagaa     600
atgaaagaag ccctgatctc gaaacacccg atgggtcgcc tggcaaaacc ggaagaagtg     660
gcagaactgg ttctgtttct gagttccgaa aaatcatcgt tcatgaccgg tggctattac     720
ctggtcgatg gtggctacac ggcagtg                                        747
```

<210> SEQ ID NO 16
<211> LENGTH: 249
<212> TYPE: PRT
<213> ORGANISM: Artificial sequence
<220> FEATURE:
<223> OTHER INFORMATION: Engineered sequence

<400> SEQUENCE: 16

```
Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
                    20                  25                  30
Val Ile Val Ser Asp Ile Asn Glu Asp His Gly Asn Lys Ala Val Glu
                35                  40                  45
Asp Ile Lys Ala Gln Gly Gly Glu Ala Ser Phe Val Lys Ala Asp Thr
            50                  55                  60
Ser Asn Pro Glu Glu Val Glu Ala Leu Val Lys Arg Thr Val Glu Ile
65                  70                  75                  80
Tyr Gly Arg Leu Asp Ile Ala Cys Asn Asn Ala Gly Ile Arg Gly Glu
                85                  90                  95
Gln Ala Leu Ala Gly Asp Tyr Gly Leu Asp Ser Trp Arg Lys Val Leu
```

```
              100                 105                 110
Ser Ile Asn Leu Asp Gly Val Phe Tyr Gly Cys Lys Tyr Glu Leu Glu
            115                 120                 125

Gln Met Glu Lys Asn Gly Gly Val Ile Val Asn Met Ala Ser Ile
        130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 17
<211> LENGTH: 747
<212> TYPE: DNA
<213> ORGANISM: Artificial sequence
<220> FEATURE:
<223> OTHER INFORMATION: Engineered sequence

<400> SEQUENCE: 17

```
atgggtatcc tggacaacaa agtcgcactg gttacgggcg ctggttcggg catcggtctg    60
gcggtggcac actcctacgc taaagaaggc gctaaagtca ttgtgtcaga tatcaacgaa   120
gaccatggta ataaagcggt tgaagatatt aaagcacagg gcggtgaagc tagttttgtg   180
aaagcggaca ccagcaaccc ggaagaagtg aaagccctgg ttaaacgtac ggtcgaaatt   240
tatggtcgcc tggatatcgc atgcaacaat gctggcattc tgggtgaaca ggcactggct   300
ggtgattacg gcctggacag ctggcgtaaa gttctgtcta tcaatctgga cggtgtcttc   360
tatggctgta atacgaact ggaacaaatg gagaaaaacg gcggtggcgt atcgtcaat   420
atggccagca ttcatggtat cgttgcggcc ccgctgagct ctgcatatac ctctgcgaaa   480
cacgccgtgg ttggcctgac gaaaaacatt ggtgctgaat atggccagaa aacatccgt   540
tgcaatgcgg tgggcccggc ctacattgaa accccgctgc tggaatcact gacgaaagaa   600
atgaaagaag ccctgatctc gaaacacccg atgggtcgcc tgggcaaacc ggaagaagtg   660
gcagaactgg ttctgtttct gagttccgaa aaatcatcgt tcatgaccgg tggctattac   720
ctggtcgatg gtggctacac ggcagtg                                       747
```

<210> SEQ ID NO 18
<211> LENGTH: 249
<212> TYPE: PRT
<213> ORGANISM: Artificial sequence
<220> FEATURE:
<223> OTHER INFORMATION: Engineered sequence

<400> SEQUENCE: 18

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
```

```
                20                  25                  30
        Val Ile Val Ser Asp Ile Asn Glu Asp His Gly Asn Lys Ala Val Glu
                         35                  40                  45

Asp Ile Lys Ala Gln Gly Gly Glu Ala Ser Phe Val Lys Ala Asp Thr
                 50                  55                  60

Ser Asn Pro Glu Glu Val Glu Ala Leu Val Lys Arg Thr Val Glu Ile
        65                  70                  75                  80

Tyr Gly Arg Leu Asp Ile Ala Cys Asn Asn Ala Gly Ile Leu Gly Glu
                         85                  90                  95

Gln Ala Leu Ala Gly Asp Tyr Gly Leu Asp Ser Trp Arg Lys Val Leu
                    100                 105                 110

Ser Ile Asn Leu Asp Gly Val Phe Tyr Gly Cys Lys Tyr Glu Leu Glu
                    115                 120                 125

Gln Met Glu Lys Asn Gly Gly Val Ile Val Asn Met Ala Ser Ile
                    130                 135                 140

His Gly Ile Val Ala Ala Pro Leu Ser Ser Ala Tyr Thr Ser Ala Lys
        145                 150                 155                 160

His Ala Val Val Gly Leu Thr Lys Asn Ile Gly Ala Glu Tyr Gly Gln
                        165                 170                 175

Lys Asn Ile Arg Cys Asn Ala Val Gly Pro Ala Tyr Ile Glu Thr Pro
                        180                 185                 190

Leu Leu Glu Ser Leu Thr Lys Glu Met Lys Ala Leu Ile Ser Lys
                    195                 200                 205

His Pro Met Gly Arg Leu Gly Lys Pro Glu Glu Val Ala Glu Leu Val
                    210                 215                 220

Leu Phe Leu Ser Ser Glu Lys Ser Ser Phe Met Thr Gly Tyr Tyr
        225                 230                 235                 240

Leu Val Asp Gly Gly Tyr Thr Ala Val
                         245
```

<210> SEQ ID NO 19
<211> LENGTH: 747
<212> TYPE: DNA
<213> ORGANISM: Artificial sequence
<220> FEATURE:
<223> OTHER INFORMATION: Engineered sequence

<400> SEQUENCE: 19

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaagcggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg ttggtgaaca ggcactggct     300
ggtgattacg gcctggacag ctggcgtaaa gttctgtcta tcaatctgga cggtgtcttc     360 tatgctgta  aatacgaact ggaacaaatg gagaaaaacg gcggtggcgt tatcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgggcccggc ctacattgaa accccgctgc tggaatcact gacgaaagaa     600
atgaaagaag ccctgatctc gaaacacccg atgggtcgcc tggcaaaacc ggaagaagtg     660
gcagaactgg ttctgtttct gagttccgaa aaatcatcgt tcatgaccgg tggctattac     720
ctggtcgatg gtggctacac ggcagtg                                          747
```

<210> SEQ ID NO 20
<211> LENGTH: 249
<212> TYPE: PRT
<213> ORGANISM: Artificial sequence
<220> FEATURE:
<223> OTHER INFORMATION: Engineered sequence

<400> SEQUENCE: 20

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Val Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 21
<211> LENGTH: 747
<212> TYPE: DNA
<213> ORGANISM: Artificial sequence
<220> FEATURE:
<223> OTHER INFORMATION: Engineered sequence

<400> SEQUENCE: 21

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaagcggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg agggtgaaca ggcactggct     300
```

| | |
|---|---|
| ggtgattacg gcctggacag ctggcgtaaa gttctgtcta tcaatctgga cggtgtcttc | 360 |
| tatggctgta aatacgaact ggaacaaatg gagaaaaacg gcggtggcgt tatcgtcaat | 420 |
| atggccagca ttcatggtat cgttgcggcc ccgctgagct ctgcatatac ctctgcgaaa | 480 |
| cacgccgtgg ttggcctgac gaaaaacatt ggtgctgaat atggccagaa aaacatccgt | 540 |
| tgcaatgcgg tgggcccggc ctacattgaa accccgctgc tggaatcact gacgaaagaa | 600 |
| atgaaagaag ccctgatctc gaaacacccg atgggtcgcc tgggcaaacc ggaagaagtg | 660 |
| gcagaactgg ttctgtttct gagttccgaa aaatcatcgt tcatgaccgg tggctattac | 720 |
| ctggtcgatg gtggctacac ggcagtg | 747 |

<210> SEQ ID NO 22
<211> LENGTH: 249
<212> TYPE: PRT
<213> ORGANISM: Artificial sequence
<220> FEATURE:
<223> OTHER INFORMATION: Engineered sequence

<400> SEQUENCE: 22

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gln Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 23
<211> LENGTH: 747
<212> TYPE: DNA
<213> ORGANISM: Artificial sequence
<220> FEATURE:
<223> OTHER INFORMATION: Engineered sequence

<400> SEQUENCE: 23

| | | |
|---|---|---|
| atgggtatcc tggacaacaa agtcgcactg gttacgggcg ctggttcggg catcggtctg | 60 |
| gcggtggcac actcctacgc taaagaaggc gctaaagtca ttgtgtcaga tatcaacgaa | 120 |
| gaccatggta ataaagcggt tgaagatatt aaagcacagg gcggtgaagc tagttttgtg | 180 |
| aaagcggaca ccagcaaccc ggaagaagtg gaagccctgg ttaaacgtac ggtcgaaatt | 240 |
| tatggtcgcc tggatatcgc atgcaacaat gctggcatta agggtgaaca ggcactggct | 300 |
| ggtgattacg gcctggacag ctggcgtaaa gttctgtcta tcaatctgga cggtgtcttc | 360 |
| tatggctgta atacgaact ggaacaaatg gagaaaaacg gcggtggcgt tatcgtcaat | 420 |
| atggccagca ttcatggtat cgttgcggcc ccgctgagct ctgcatatac ctctgcgaaa | 480 |
| cacgccgtgg ttggcctgac gaaaaacatt ggtgctgaat atggccagaa aaacatccgt | 540 |
| tgcaatgcgg tgggcccggc ctacattgaa accccgctgc tggaatcact gacgaaagaa | 600 |
| atgaaagaag ccctgatctc gaaacaccecg atgggtcgcc tgggcaaacc ggaagaagtg | 660 |
| gcagaactgg ttctgtttct gagttccgaa aaatcatcgt tcatgaccgg tggctattac | 720 |
| ctggtcgatg gtggctacac ggcagtg | 747 |

<210> SEQ ID NO 24
<211> LENGTH: 249
<212> TYPE: PRT
<213> ORGANISM: Artificial sequence
<220> FEATURE:
<223> OTHER INFORMATION: Engineered sequence

<400> SEQUENCE: 24

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Lys Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245

<210> SEQ ID NO 25
<211> LENGTH: 747
<212> TYPE: DNA
<213> ORGANISM: Artificial sequence
<220> FEATURE:
<223> OTHER INFORMATION: Engineered sequence

<400> SEQUENCE: 25

| atgggtatcc tggacaacaa agtcgcactg gttacgggcg ctggttcggg catcggtctg | 60 |
| gcggtggcac actcctacgc taaagaaggc gctaaagtca ttgtgtcaga tatcaacgaa | 120 |
| gaccatggta taaagcggt tgaagatatt aaagcacagg gcggtgaagc tagttttgtg | 180 |
| aaagcggaca ccagcaaccc ggaagaagtg gaagccctgg ttaaacgtac ggtcgaaatt | 240 |
| tatggtcgcc tggatatcgc atgcaacaat gctggcattg gcggtgaaca ggcactggct | 300 |
| ggtgattacg gcctggacag ctggcgtaaa gttctgtcta tcaatctgga cggtgtcttc | 360 |
| tatggctgta atacgaact ggaacaaatg gagaaaaacg gcggtggcgt tatcgtcaat | 420 |
| atggccagca ttcatggtat cgttgcgaag ccgctgagct ctgcatatac ctctgcgaaa | 480 |
| cacgccgtgg ttggcctgac gaaaaacatt ggtgctgaat atggccagaa aaacatccgt | 540 |
| tgcaatgcgg tgggcccggc ctacattgaa accccgctgc tggaatcact gacgaaagaa | 600 |
| atgaaagaag ccctgatctc gaaacacccg atgggtcgcc tgggcaaacc ggaagaagtg | 660 |
| gcagaactgg ttctgtttct gagttccgaa aaatcatcgt tcatgaccgg tggctattac | 720 |
| ctggtcgatg gtggctacac ggcagtg | 747 |

<210> SEQ ID NO 26
<211> LENGTH: 249
<212> TYPE: PRT
<213> ORGANISM: Artificial sequence
<220> FEATURE:
<223> OTHER INFORMATION: Engineered sequence

<400> SEQUENCE: 26

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

```
Gln Met Glu Lys Asn Gly Gly Val Ile Val Asn Met Ala Ser Ile
    130                 135                 140

His Gly Ile Val Ala Lys Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 27
<211> LENGTH: 747
<212> TYPE: DNA
<213> ORGANISM: Artificial sequence
<220> FEATURE:
<223> OTHER INFORMATION: Engineered sequence

<400> SEQUENCE: 27

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagcggt tgaagatatt aaagcacagg gcggtgaagc tagttttgtg      180
aaagcggaca ccagcaaccc ggaagaagtg aagccctgg ttaaacgtac ggtcgaaatt      240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat      420
atggccagca ttcatggtat cgttgcggcc ccgctgatgt ctgcatatac ctctgcgaaa     480
cacgccgtgg ttggcctgac gaaaaacatt ggtgctgaat atggccagaa aaacatccgt     540
tgcaatgcgg tgggcccggc ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747
```

<210> SEQ ID NO 28
<211> LENGTH: 249
<212> TYPE: PRT
<213> ORGANISM: Artificial sequence
<220> FEATURE:
<223> OTHER INFORMATION: Engineered sequence

<400> SEQUENCE: 28

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45
```

Asp Ile Lys Ala Gln Gly Gly Glu Ala Ser Phe Val Lys Ala Asp Thr
 50                  55                  60

Ser Asn Pro Glu Glu Val Glu Ala Leu Val Lys Arg Thr Val Glu Ile
 65                  70                  75                  80

Tyr Gly Arg Leu Asp Ile Ala Cys Asn Asn Ala Gly Ile Gly Gly Glu
                 85                  90                  95

Gln Ala Leu Ala Gly Asp Tyr Gly Leu Asp Ser Trp Arg Lys Val Leu
                100                 105                 110

Ser Ile Asn Leu Asp Gly Val Phe Tyr Gly Cys Lys Tyr Glu Leu Glu
            115                 120                 125

Gln Met Glu Lys Asn Gly Gly Val Ile Val Asn Met Ala Ser Ile
        130                 135                 140

His Gly Ile Val Ala Ala Pro Leu Met Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
                180                 185                 190

Leu Leu Glu Ser Leu Thr Lys Glu Met Lys Ala Leu Ile Ser Lys
            195                 200                 205

His Pro Met Gly Arg Leu Gly Lys Pro Glu Glu Val Ala Glu Leu Val
210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 29
<211> LENGTH: 747
<212> TYPE: DNA
<213> ORGANISM: Artificial sequence
<220> FEATURE:
<223> OTHER INFORMATION: Engineered sequence

<400> SEQUENCE: 29
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaagcggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta aatacgaact ggaacaaatg gagaaaaacg gcggtggcgt tatcgtcaat     420
atggccagca ttcatggtat cgttgcggcc ccgctgttgt ctgcatatac ctctgcgaaa     480
cacgccgtgg ttggcctgac gaaaaacatt ggtgctgaat atggccagaa aaacatccgt     540
tgcaatgcgg tgggcccggc ctacattgaa acccgctgc tggaatcact gacgaaagaa     600
atgaaagaag ccctgatctc gaaacaccg atgggtcgcc tgggcaaacc ggaagaagtg     660
gcagaactgg ttctgttttct gagttccgaa aaatcatcgt tcatgaccgg tggctattac     720
ctggtcgatg gtggctacac ggcagtg                                          747

<210> SEQ ID NO 30
<211> LENGTH: 249

```
<212> TYPE: PRT
<213> ORGANISM: Artificial sequence
<220> FEATURE:
<223> OTHER INFORMATION: Engineered sequence

<400> SEQUENCE: 30

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Leu Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 31
<211> LENGTH: 747
<212> TYPE: DNA
<213> ORGANISM: Artificial sequence
<220> FEATURE:
<223> OTHER INFORMATION: Engineered sequence

<400> SEQUENCE: 31
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagcggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta aatacgaact ggaacaaatg gagaaaaacg gcggtggcgt tatcgtcaat     420
```

```
atggccagca ttcatggtat cgttgcggcc ccgctgcagt ctgcatatac ctctgcgaaa    480
cacgccgtgg ttggcctgac gaaaaacatt ggtgctgaat atggccagaa aaacatccgt    540
tgcaatgcgg tgggcccggc ctacattgaa acccgctgct ggaatcact  gacgaaagaa    600 atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747
```

<210> SEQ ID NO 32
<211> LENGTH: 249
<212> TYPE: PRT
<213> ORGANISM: Artificial sequence
<220> FEATURE:
<223> OTHER INFORMATION: Engineered sequence

<400> SEQUENCE: 32

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Gln Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 33
<211> LENGTH: 747
<212> TYPE: DNA
<213> ORGANISM: Artificial sequence
<220> FEATURE:
<223> OTHER INFORMATION: Engineered sequence

<400> SEQUENCE: 33

```
atgggtatcc tggacaacaa agtcgcactg gttacgggcg ctggttcggg catcggtctg    60
gcggtggcac actcctacgc taaagaaggc gctaaagtca ttgtgtcaga tatcaacgaa   120
gaccatggta ataaagcggt tgaagatatt aaagcacagg gcggtgaagc tagttttgtg   180
aaagcggaca ccagcaaccc ggaagaagtg gaagccctgg ttaaacgtac ggtcgaaatt   240
tatggtcgcc tggatatcgc atgcaacaat gctggcattg gcggtgaaca ggcactggct   300
ggtgattacg gcctggacag ctggcgtaaa gttctgtcta tcaatctgga cggtgtcttc   360
tatggctgta atacgaact  ggaacaaatg gagaaaaacg gcggtggcgt tatcgtcaat   420
atggccagca ttcatggtat cgttgcggcc ccgtatagct ctgcatatac ctctgcgaaa   480
cacgccgtgg ttggcctgac gaaaaacatt ggtgctgaat atggccagaa aacatccgt   540 tgcaatgcgg tgggcccggc ctacattgaa accccgctgc tggaatcact gacgaaagaa   600
atgaaagaag ccctgatctc gaaacacccg atgggtcgcc tgggcaaacc ggaagaagtg   660
gcagaactgg ttctgtttct gagttccgaa aaatcatcgt tcatgaccgg tggctattac   720
ctggtcgatg gtggctacac ggcagtg                                       747
```

<210> SEQ ID NO 34
<211> LENGTH: 249
<212> TYPE: PRT
<213> ORGANISM: Artificial sequence
<220> FEATURE:
<223> OTHER INFORMATION: Engineered sequence

<400> SEQUENCE: 34

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Tyr Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220
```

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245

<210> SEQ ID NO 35
<211> LENGTH: 747
<212> TYPE: DNA
<213> ORGANISM: Artificial sequence
<220> FEATURE:
<223> OTHER INFORMATION: Engineered sequence

<400> SEQUENCE: 35
atgggtatcc tggacaacaa agtcgcactg gttacgggcg ctggttcggg catcggtctg     60
gcggtggcac actcctacgc taaagaaggc gctaaagtca ttgtgtcaga tatcaacgaa    120
gaccatggta taaagtggt tgaagatatt aaagcacagg gcggtgaagc tagttttgtg    180
aaagcggaca ccagcaaccc ggaagaagtg aagccctgg ttaaacgtac ggtcgaaatt    240
tatggtcgcc tggatgtggc atgcaacaat gctggcattg gcggtgaaca ggcactggct    300
ggtgattacg gcctggacag ctggcgtaaa gttctgtcta tcaatctgga cggtgtcttc    360
tatggctgta atacgaact ggaacaaatg gagaaaaacg gcggtggcgt tatcgtcaat    420
atggccagca ttcatggtat cgttgcggcc ccgctgagct ctgcatatac ctctgcgaaa    480
cacgccgtgg ttggcctgac gaaaaacatt ggtgctgaat atggccagaa aacatccgt    540 tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747

<210> SEQ ID NO 36
<211> LENGTH: 249
<212> TYPE: PRT
<213> ORGANISM: Artificial sequence
<220> FEATURE:
<223> OTHER INFORMATION: Engineered sequence

<400> SEQUENCE: 36

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Val Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
            165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245

<210> SEQ ID NO 37
<211> LENGTH: 747
<212> TYPE: DNA
<213> ORGANISM: Artificial sequence
<220> FEATURE:
<223> OTHER INFORMATION: Engineered sequence

<400> SEQUENCE: 37

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagtggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg cggtgaaaca ggcactggct     300
ggtgattacg gcctggacag ctggcgtaaa gttctgtcta tcaatctgga cggtgtcttc     360
tatggctgta aatacgaact ggaacaaatg gagaaaaacg gcggtggcgt atcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgttct ggcgtccgaa aaatcatcgt tcatgaccgg tggcgcgtac     720
ctggtcgatg gtggctacac ggcagtg                                         747
```

<210> SEQ ID NO 38
<211> LENGTH: 249
<212> TYPE: PRT
<213> ORGANISM: Artificial sequence
<220> FEATURE:
<223> OTHER INFORMATION: Engineered sequence

<400> SEQUENCE: 38

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Val Val Glu
        35                  40                  45

Asp Ile Lys Ala Gln Gly Gly Glu Ala Ser Phe Val Lys Ala Asp Thr
    50                  55                  60

```
Ser Asn Pro Glu Glu Val Glu Ala Leu Val Lys Arg Thr Val Glu Ile
 65                  70                  75                  80

Tyr Gly Arg Leu Asp Val Ala Cys Asn Asn Ala Gly Ile Gly Gly Glu
                 85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
            115                 120                 125

Gln Met Glu Lys Asn Gly Gly Val Ile Val Asn Met Ala Ser Ile
            130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
            195                 200                 205

His Pro Met Gly Arg Leu Gly Lys Pro Glu Glu Val Ala Glu Leu Val
210                 215                 220

Leu Phe Leu Ala Ser Glu Lys Ser Ser Phe Met Thr Gly Gly Ala Tyr
225                 230                 235                 240

Leu Val Asp Gly Gly Tyr Thr Ala Val
                245
```

<210> SEQ ID NO 39
<211> LENGTH: 747
<212> TYPE: DNA
<213> ORGANISM: Artificial sequence
<220> FEATURE:
<223> OTHER INFORMATION: Engineered sequence

<400> SEQUENCE: 39

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat      420
atggccagca ttcatggtat cgttgcggcc ccgctgagct ctgcatatac ctctgcgaaa     480
cacgccgtgg ttggcctgac gaaaaacatt ggtgctgaat atggccagaa aacatccgt     540 tgcaatgcgg tgggcccggc ctacattgaa accccgctgc tggaatcact gacgaaagaa     600
atgaaagaag ccctgatctc gaaacacccg atgggtcgcc tggcaaaacc ggaagaagtg     660
gcagaactgg ttctgtttct gagttccgaa aaatcatcgt tcatgaccgg tggctattac     720
ctggtcgatg gtggctacac ggcagtg                                         747
```

<210> SEQ ID NO 40
<211> LENGTH: 249
<212> TYPE: PRT
<213> ORGANISM: Artificial sequence
<220> FEATURE:
<223> OTHER INFORMATION: Engineered sequence

<400> SEQUENCE: 40

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 41
<211> LENGTH: 747
<212> TYPE: DNA
<213> ORGANISM: Artificial sequence
<220> FEATURE:
<223> OTHER INFORMATION: Engineered sequence

<400> SEQUENCE: 41

```
atgggtatcc tggacaacaa agtcgcactg gttacgggcg ctggttcggg catcggtctg     60
gcggtggcac actcctacgc taaagaaggc gctaaagtca ttgtgtcaga tatcaacgaa    120
gaccatggta ataaaaccgt tgaagatatt aaagcacagg gcggtgaagc tagttttgtg    180
aaagcggaca ccagcaaccc ggaagaagtg aagccctgg ttaaacgtac ggtcgaaatt     240
tatggtcgcc tggatatcgc atgcaacaat gctggcattg gcggtgaaca ggcactggct    300
ggtgattacg gcctggacag ctggcgtaaa gttctgtcta tcaatctgga cggtgtcttc    360
tatggctgta atacgaact  ggaacaaatg agaaaaacg  gcggtggcgt tatcgtcaat    420
atggccagca ttcatggtat cgttgcggcc ccgctgagct ctgcatatac ctctgcgaaa    480
cacgccgtgg ttggcctgac gaaaaacatt ggtgctgaat atggccagaa aaacatccgt    540
```

```
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcgtgaccgg tggctattac    720
ctggtcgatg gtggctacac ggcagtg                                        747
```

<210> SEQ ID NO 42
<211> LENGTH: 249
<212> TYPE: PRT
<213> ORGANISM: Artificial sequence
<220> FEATURE:
<223> OTHER INFORMATION: Engineered sequence

<400> SEQUENCE: 42

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Val Ala Glu Leu Val
    210                 215                 220

Leu Phe Leu Ser Ser Glu Lys Ser Ser Phe Val Thr Gly Gly Tyr Tyr
225                 230                 235                 240

Leu Val Asp Gly Gly Tyr Thr Ala Val
                245
```

<210> SEQ ID NO 43
<211> LENGTH: 747
<212> TYPE: DNA
<213> ORGANISM: Artificial sequence
<220> FEATURE:
<223> OTHER INFORMATION: Engineered sequence

<400> SEQUENCE: 43

```
atgggtatcc tggacaacaa agtcgcactg gttacgggcg ctggttcggg catcggtctg    60
gcggtggcac actcctacgc taaagaaggc gctaaagtca ttgtgtcaga tatcaacgaa    120
```

```
gaccatggta ataaagcggt tgaagatatt aaagcacagg gcggtgaagc tagttttgtg    180
aaagcggaca ccagcaaccc ggaagaagtg gaagccctgg ttaaacgtac ggtcgaaatt    240
tatggtcgcc tggatatcgc atgcaacaat gctggcattg gcggtgaaca ggcactggct    300
ggtgattacg gcctggacag ctggcgtaaa gttctgtcta tcaatctgga cggtgtcttc    360
tatggctgta atacgaact ggaacaaatg gagaaaaacg gcggtggcgt atcgtcaat     420 atggccagca ttcatggtat cgttgcggcc ccgctgagct ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgttct ggcgtccgaa aaatcatcgt tcatgaccgg tggctattac    720
ctggtcgatg gtggctacac ggcagtg                                        747

<210> SEQ ID NO 44
<211> LENGTH: 249
<212> TYPE: PRT
<213> ORGANISM: Artificial sequence
<220> FEATURE:
<223> OTHER INFORMATION: Engineered sequence

<400> SEQUENCE: 44

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ala Ser Glu Lys Ser Ser Phe Met Thr Gly Gly Tyr Tyr
225                 230                 235                 240

Leu Val Asp Gly Gly Tyr Thr Ala Val
```

<210> SEQ ID NO 45
<211> LENGTH: 747
<212> TYPE: DNA
<213> ORGANISM: Artificial sequence
<220> FEATURE:
<223> OTHER INFORMATION: Engineered sequence

<400> SEQUENCE: 45

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat      420
atggccagca ttcatggtat cgttgcggcc ccgctgagct ctgcatatac ctctgcgaaa     480
cacgccgtgt ttggcctgac gaaaaacatt ggtgctgaat atggccagaa aacatccgt      540
tgcaatgcgg tgtgcccggg ctacattgaa accccgctgc tggaatcact gacgaaagaa     600
atgaaagaag ccctgatctc gaaacacccg atgggtcgcc tggcaaaccc ggaagaagtg     660
gcagaactgg ttctgttct gagttccgaa aaatcatcgt tcatgaccgg tggctattac      720
ctggtcgatg gtggctacac ggcagtg                                         747
```

<210> SEQ ID NO 46
<211> LENGTH: 249
<212> TYPE: PRT
<213> ORGANISM: Artificial sequence
<220> FEATURE:
<223> OTHER INFORMATION: Engineered sequence

<400> SEQUENCE: 46

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
```

```
                165                 170                 175
Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 47
<211> LENGTH: 747
<212> TYPE: DNA
<213> ORGANISM: Artificial sequence
<220> FEATURE:
<223> OTHER INFORMATION: Engineered sequence

<400> SEQUENCE: 47
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaagcggt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat      420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgggcccggg ctacattgaa accccgctgc tggaatcact gacgaaagaa     600
atgaaagaag ccctgatctc gaaacacccg atgggtcgcc tggcaaaacc ggaagaagtg     660
gcagaactgg ttctgttctt ggcgtccgaa aaatcatcgt tcatcaccgg tggcgcgtac     720
ctggtcgatg gtggctacac ggcagtg                                        747

<210> SEQ ID NO 48
<211> LENGTH: 249
<212> TYPE: PRT
<213> ORGANISM: Artificial sequence
<220> FEATURE:
<223> OTHER INFORMATION: Engineered sequence

<400> SEQUENCE: 48

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
```

```
            85                  90                  95
Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
            115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Gly Tyr Ile Glu Thr Pro
            180                 185                 190

Leu Leu Glu Ser Leu Thr Lys Glu Met Lys Glu Ala Leu Ile Ser Lys
            195                 200                 205

His Pro Met Gly Arg Leu Gly Lys Pro Glu Glu Val Ala Glu Leu Val
    210                 215                 220

Leu Phe Leu Ala Ser Glu Lys Ser Ser Phe Ile Thr Gly Gly Ala Tyr
225                 230                 235                 240

Leu Val Asp Gly Gly Tyr Thr Ala Val
                245

<210> SEQ ID NO 49
<211> LENGTH: 747
<212> TYPE: DNA
<213> ORGANISM: Artificial sequence
<220> FEATURE:
<223> OTHER INFORMATION: Engineered sequence

<400> SEQUENCE: 49
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaacg gcggtggcgt tatcgtcaat       420
atggccagca ttcatggtat cgttgcggcc ccgctgagct ctgcatatac ctctgcgaaa     480
cacgccgtgg ttggcctgac gaaaaacatt ggtgctgaat atggccagaa aacatccgt      540 tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct ggcgtccgaa aaatcatcgt tcatgaccgg tggctattac     720
ctggtcgatg gtggctacac ggcagtg                                         747

<210> SEQ ID NO 50
<211> LENGTH: 249
<212> TYPE: PRT
<213> ORGANISM: Artificial sequence
<220> FEATURE:
<223> OTHER INFORMATION: Engineered sequence

<400> SEQUENCE: 50

Met Gly Ile Leu Asp Asn Lys Val Ala Leu Val Thr Gly Ala Gly Ser
```

```
              1               5                  10                 15
            Gly Ile Gly Leu Ala Val Ala His Ser Tyr Ala Lys Glu Gly Ala Lys
                           20                  25                  30

Val Ile Val Ser Asp Ile Asn Glu Asp His Gly Asn Lys Thr Val Glu
                           35                  40                  45

Asp Ile Lys Ala Gln Gly Gly Glu Ala Ser Phe Val Lys Ala Asp Thr
                 50                  55                  60

Ser Asn Pro Glu Glu Val Glu Ala Leu Val Lys Arg Thr Val Glu Ile
             65                  70                  75                  80

Tyr Gly Arg Leu Asp Ile Ala Cys Asn Asn Ala Gly Ile Gly Gly Glu
                               85                  90                  95

Gln Ala Leu Ala Gly Asp Tyr Gly Leu Asp Ser Trp Arg Lys Val Leu
                           100                 105                 110

Ser Ile Asn Leu Asp Gly Val Phe Tyr Gly Cys Lys Tyr Glu Leu Glu
                           115                 120                 125

Gln Met Glu Lys Asn Gly Gly Val Ile Val Asn Met Ala Ser Ile
                130                 135                 140

His Gly Ile Val Ala Ala Pro Leu Ser Ser Ala Tyr Thr Ser Ala Lys
            145                 150                 155                 160

His Ala Val Val Gly Leu Thr Lys Asn Ile Gly Ala Glu Tyr Gly Gln
                               165                 170                 175

Lys Asn Ile Arg Cys Asn Ala Val Cys Pro Gly Tyr Ile Glu Thr Pro
                           180                 185                 190

Leu Leu Glu Ser Leu Thr Lys Glu Met Lys Glu Ala Leu Ile Ser Lys
                           195                 200                 205

His Pro Met Gly Arg Leu Gly Lys Pro Glu Glu Val Ala Glu Leu Val
                210                 215                 220

Leu Phe Leu Ala Ser Glu Lys Ser Ser Phe Met Thr Gly Gly Tyr Tyr
            225                 230                 235                 240

Leu Val Asp Gly Gly Tyr Thr Ala Val
                           245
```

<210> SEQ ID NO 51
<211> LENGTH: 747
<212> TYPE: DNA
<213> ORGANISM: Artificial sequence
<220> FEATURE:
<223> OTHER INFORMATION: Engineered sequence

<400> SEQUENCE: 51

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagcggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa ccccgctgc tggaatcact gacgaaagaa     600
atgaaagaag ccctgatctc gaaacacccg atgggtcgcc tgggcaaacc ggaagaagtg     660
```

-continued

```
gcagaactgg ttctgtttct gagttccgaa aaatcatcgt tcatgaccgg tggcgcgtac    720
ctggtcgatg gtggctacac ggcagtg                                        747
```

<210> SEQ ID NO 52
<211> LENGTH: 249
<212> TYPE: PRT
<213> ORGANISM: Artificial sequence
<220> FEATURE:
<223> OTHER INFORMATION: Engineered sequence

<400> SEQUENCE: 52

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
                20                  25                  30

Val Ile Val Ser Asp Ile Asn Glu Asp His Gly Asn Lys Ala Val Glu
            35                  40                  45

Asp Ile Lys Ala Gln Gly Gly Glu Ala Ser Phe Val Lys Ala Asp Thr
        50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Ala Tyr
225                 230                 235                 240

Leu Val Asp Gly Gly Tyr Thr Ala Val
                245
```

<210> SEQ ID NO 53
<211> LENGTH: 747
<212> TYPE: DNA
<213> ORGANISM: Artificial sequence
<220> FEATURE:
<223> OTHER INFORMATION: Engineered sequence

<400> SEQUENCE: 53

```
atgggtatcc tggacaacaa agtcgcactg gttacgggcg ctggttcggg catcggtctg    60
gcggtggcac actcctacgc taaagaaggc gctaaagtca ttgtgtcaga tatcaacgaa   120
gaccatggta taaagcggt tgaagatatt aagcacagg gcggtgaagc tagttttgtg    180
aaagcggaca ccagcaaccc ggaagaagtg gaagccctgg ttaaacgtac ggtcgaaatt   240
```

```
tatggtcgcc tggatgtggc atgcaacaat gctggcattg gcggtgaaca ggcactggct    300
ggtgattacg gcctggacag ctggcgtaaa gttctgtcta tcaatctgga cggtgtcttc    360
tatggctgta atacgaact ggaacaaatg gagaaaaacg gcggtggcgt tatcgtcaat    420
atggccagca ttcatggtat cgttgcggcc ccgctgagct ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct ggcgtccgaa aaatcatcgt tcatgaccgg tggctattac    720
ctggtcgatg gtggctacac ggcagtg                                        747
```

<210> SEQ ID NO 54
<211> LENGTH: 249
<212> TYPE: PRT
<213> ORGANISM: Artificial sequence
<220> FEATURE:
<223> OTHER INFORMATION: Engineered sequence

<400> SEQUENCE: 54

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ala Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 55

<211> LENGTH: 747
<212> TYPE: DNA
<213> ORGANISM: Artificial sequence
<220> FEATURE:
<223> OTHER INFORMATION: Engineered sequence

<400> SEQUENCE: 55

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaagtggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat      420
atggccagca ttcatggtat cgttgcggcc ccgctgagct ctgcatatac ctctgcgaaa     480
cacgccgtgg ttggcctgac gaaaaacatt ggtgctgaat atggcagaa aaacatccgt      540
tgcaatgcgg tgtgcccggg ctacattgaa ccccgctgc tggaatcact gacgaaagaa      600
atgaaagaag ccctgatctc gaaacacccg atgggtcgcc tggcaaaacc ggaagaagtg     660
gcagaactgg ttctgtttct gagttccgaa aaatcatcgt tcatgaccgg tggcgcgtac     720
ctggtcgatg gtggctacac ggcagtg                                         747
```

<210> SEQ ID NO 56
<211> LENGTH: 249
<212> TYPE: PRT
<213> ORGANISM: Artificial sequence
<220> FEATURE:
<223> OTHER INFORMATION: Engineered sequence

<400> SEQUENCE: 56

```
Met Gly Ile Leu Asp Asn Lys Val Ala Leu Val Thr Gly Ala Gly Ser
1               5                  10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Val Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190
```

```
Leu Leu Glu Ser Leu Thr Lys Glu Met Lys Glu Ala Leu Ile Ser Lys
        195                 200                 205
His Pro Met Gly Arg Leu Gly Lys Pro Glu Glu Val Ala Glu Leu Val
    210                 215                 220
Leu Phe Leu Ser Ser Glu Lys Ser Ser Phe Met Thr Gly Gly Ala Tyr
225                 230                 235                 240
Leu Val Asp Gly Gly Tyr Thr Ala Val
                245
```

<210> SEQ ID NO 57
<211> LENGTH: 747
<212> TYPE: DNA
<213> ORGANISM: Artificial sequence
<220> FEATURE:
<223> OTHER INFORMATION: Engineered sequence

<400> SEQUENCE: 57

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaagtggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggc ctacattgaa accccgctgc tggaatcact gacgaaagaa     600
atgaaagaag ccctgatctc gaaacacccg atgggtcgcc tgggcaaacc ggaagaagtg     660
gcagaactgg ttctgttttct gagttccgaa aaatcatcgt tcatgaccgg tggctattac     720
ctggtcgatg gtggctacac ggcagtg                                          747
```

<210> SEQ ID NO 58
<211> LENGTH: 249
<212> TYPE: PRT
<213> ORGANISM: Artificial sequence
<220> FEATURE:
<223> OTHER INFORMATION: Engineered sequence

<400> SEQUENCE: 58

```
Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
                20                  25                  30
Val Ile Val Ser Asp Ile Asn Glu Asp His Gly Asn Lys Val Val Glu
            35                  40                  45
Asp Ile Lys Ala Gln Gly Gly Glu Ala Ser Phe Val Lys Ala Asp Thr
        50                  55                  60
Ser Asn Pro Glu Glu Val Glu Ala Leu Val Lys Arg Thr Val Glu Ile
65                  70                  75                  80
Tyr Gly Arg Leu Asp Val Ala Cys Asn Asn Ala Gly Ile Gly Gly Glu
                85                  90                  95
Gln Ala Leu Ala Gly Asp Tyr Gly Leu Asp Ser Trp Arg Lys Val Leu
                100                 105                 110
```

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 59
<211> LENGTH: 747
<212> TYPE: DNA
<213> ORGANISM: Artificial sequence
<220> FEATURE:
<223> OTHER INFORMATION: Engineered sequence

<400> SEQUENCE: 59

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat      420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacaccca atgggtcgcc tgggcaaacc ggaagaagtg     660
gcagaactgg ttctgtttct ggcgtccgaa aaatcatcgt tcatgaccgg tggctattac     720
ctggtcgatg gtggctacac ggcagtg                                          747
```

<210> SEQ ID NO 60
<211> LENGTH: 249
<212> TYPE: PRT
<213> ORGANISM: Artificial sequence
<220> FEATURE:
<223> OTHER INFORMATION: Engineered sequence

<400> SEQUENCE: 60

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
          35                  40                  45

Asp Ile Lys Ala Gln Gly Gly Glu Ala Ser Phe Val Lys Ala Asp Thr
 50                  55                  60

Ser Asn Pro Glu Glu Val Glu Ala Leu Val Lys Arg Thr Val Glu Ile
 65                  70                  75                  80

Tyr Gly Arg Leu Asp Val Ala Cys Asn Asn Ala Gly Ile Gly Gly Glu
                 85                  90                  95

Gln Ala Leu Ala Gly Asp Tyr Gly Leu Asp Ser Trp Arg Lys Val Leu
                100                 105                 110

Ser Ile Asn Leu Asp Gly Val Phe Tyr Gly Cys Lys Tyr Glu Leu Glu
                115                 120                 125

Gln Met Glu Lys Asn Gly Gly Val Ile Val Asn Met Ala Ser Ile
        130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
                180                 185                 190

Leu Leu Glu Ser Leu Thr Lys Glu Met Lys Glu Ala Leu Ile Ser Lys
                195                 200                 205

His Pro Met Gly Arg Leu Gly Lys Pro Glu Glu Val Ala Glu Leu Val
210                 215                 220

Leu Phe Leu Ala Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 61
<211> LENGTH: 747
<212> TYPE: DNA
<213> ORGANISM: Artificial sequence
<220> FEATURE:
<223> OTHER INFORMATION: Engineered sequence

<400> SEQUENCE: 61

| | |
|---|---|
| atgggtatcc tggacaacaa agtcgcactg gttacgggcg ctggttcggg catcggtctg | 60 |
| gcggtggcac actcctacgc taaagaaggc gctaaagtca ttgtgtcaga tatcaacgaa | 120 |
| gaccatggta taaagtggt tgaagatatt aaagcacagg gcggtgaagc tagttttgtg | 180 |
| aaagcggaca ccagcaaccc ggaagaagtg gaagccctgg ttaaacgtac ggtcgaaatt | 240 |
| tatggtcgcc tggatatcgc atgcaacaat gctggcattg gcggtgaaca ggcactggct | 300 |
| ggtgattacg gcctggacag ctggcgtaaa gttctgtcta tcaatctgga cggtgtcttc | 360 |
| tatgctgta aatacgaact ggaacaaatg gagaaaaacg gcggtggcgt atcgtcaat | 420 |
| atggccagca ttcatggtat cgttgcggcc ccgctgagct ctgcatatac ctctgcgaaa | 480 |
| cacgccgtgg ttggcctgac gaaaaacatt ggtgctgaat atggccagaa aaacatccgt | 540 |
| tgcaatgcgg tgtgcccggc ctacattgaa accccgctgc tggaatcact gacgaaagaa | 600 |
| atgaaagaag ccctgatctc gaaacaccccg atgggtcgcc tgggcaaacc ggaagaagtg | 660 |
| gcagaactgg ttctgtttct gagttccgaa aaatcatcgt tcatgaccgg tggctattac | 720 |
| ctggtcgatg gtggctacac ggcagtg | 747 |

<210> SEQ ID NO 62
<211> LENGTH: 249
<212> TYPE: PRT
<213> ORGANISM: Artificial sequence
<220> FEATURE:
<223> OTHER INFORMATION: Engineered sequence

<400> SEQUENCE: 62

```
Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
                20                  25                  30
Val Ile Val Ser Asp Ile Asn Glu Asp His Gly Asn Lys Val Val Glu
            35                  40                  45
Asp Ile Lys Ala Gln Gly Gly Glu Ala Ser Phe Val Lys Ala Asp Thr
        50                  55                  60
Ser Asn Pro Glu Glu Val Glu Ala Leu Val Lys Arg Thr Val Glu Ile
65                  70                  75                  80
Tyr Gly Arg Leu Asp Ile Ala Cys Asn Asn Ala Gly Ile Gly Gly Glu
                85                  90                  95
Gln Ala Leu Ala Gly Asp Tyr Gly Leu Asp Ser Trp Arg Lys Val Leu
            100                 105                 110
Ser Ile Asn Leu Asp Gly Val Phe Tyr Gly Cys Lys Tyr Glu Leu Glu
        115                 120                 125
Gln Met Glu Lys Asn Gly Gly Val Ile Val Asn Met Ala Ser Ile
    130                 135                 140
His Gly Ile Val Ala Ala Pro Leu Ser Ser Ala Tyr Thr Ser Ala Lys
145                 150                 155                 160
His Ala Val Val Gly Leu Thr Lys Asn Ile Gly Ala Glu Tyr Gly Gln
                165                 170                 175
Lys Asn Ile Arg Cys Asn Ala Val Cys Pro Ala Tyr Ile Glu Thr Pro
            180                 185                 190
Leu Leu Glu Ser Leu Thr Lys Glu Met Lys Glu Ala Leu Ile Ser Lys
        195                 200                 205
His Pro Met Gly Arg Leu Gly Lys Pro Glu Glu Val Ala Glu Leu Val
    210                 215                 220
Leu Phe Leu Ser Ser Glu Lys Ser Ser Phe Met Thr Gly Gly Tyr Tyr
225                 230                 235                 240
Leu Val Asp Gly Gly Tyr Thr Ala Val
                245
```

<210> SEQ ID NO 63
<211> LENGTH: 747
<212> TYPE: DNA
<213> ORGANISM: Artificial sequence
<220> FEATURE:
<223> OTHER INFORMATION: Engineered sequence

<400> SEQUENCE: 63

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaagtggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
```

```
tatggctgta aatacgaact ggaacaaatg agagaaaaacg gcggtggcgt tatcgtcaat    420
atggccagca ttcatggtat cgttgcggcc ccgctgagct ctgcatatac ctctgcgaaa    480
cacgccgtgg ttggcctgac gaaaaacatt ggtgctgaat atggccagaa aaacatccgt    540
tgcaatgcgg tgggcccggc ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggcgcgtac    720
ctggtcgatg gtggctacac ggcagtg                                         747
```

<210> SEQ ID NO 64
<211> LENGTH: 249
<212> TYPE: PRT
<213> ORGANISM: Artificial sequence
<220> FEATURE:
<223> OTHER INFORMATION: Engineered sequence

<400> SEQUENCE: 64

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Val Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Ala Tyr
225                 230                 235                 240

Leu Val Asp Gly Gly Tyr Thr Ala Val
                245
```

<210> SEQ ID NO 65
<211> LENGTH: 747
<212> TYPE: DNA
<213> ORGANISM: Artificial sequence
<220> FEATURE:

<223> OTHER INFORMATION: Engineered sequence

<400> SEQUENCE: 65

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaacg gcggtggcgt tatcgtcaat       420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggc ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg tgggctacac ggcagtg                                         747
```

<210> SEQ ID NO 66
<211> LENGTH: 249
<212> TYPE: PRT
<213> ORGANISM: Artificial sequence
<220> FEATURE:
<223> OTHER INFORMATION: Engineered sequence

<400> SEQUENCE: 66

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Ala Tyr Ile Glu Thr Pro
            180                 185                 190

Leu Leu Glu Ser Leu Thr Lys Glu Met Lys Glu Ala Leu Ile Ser Lys
        195                 200                 205
```

```
His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 67
<211> LENGTH: 747
<212> TYPE: DNA
<213> ORGANISM: Artificial sequence
<220> FEATURE:
<223> OTHER INFORMATION: Engineered sequence

<400> SEQUENCE: 67
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat      420 atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgggcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgttcct gagttccgaa aaatcatcgt tcatgaccgg tggctattac     720
ctggtcgatg gtggctacac ggcagtg                                        747

<210> SEQ ID NO 68
<211> LENGTH: 249
<212> TYPE: PRT
<213> ORGANISM: Artificial sequence
<220> FEATURE:
<223> OTHER INFORMATION: Engineered sequence

<400> SEQUENCE: 68

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125
```

```
Gln Met Glu Lys Asn Gly Gly Gly Val Ile Val Asn Met Ala Ser Ile
    130                 135                 140
His Gly Ile Val Ala Ala Pro Leu Ser Ser Ala Tyr Thr Ser Ala Lys
145                 150                 155                 160
His Ala Val Val Gly Leu Thr Lys Asn Ile Gly Ala Glu Tyr Gly Gln
                165                 170                 175
Lys Asn Ile Arg Cys Asn Ala Val Gly Pro Gly Tyr Ile Glu Thr Pro
            180                 185                 190
Leu Leu Glu Ser Leu Thr Lys Glu Met Lys Glu Ala Leu Ile Ser Lys
        195                 200                 205
His Pro Met Gly Arg Leu Gly Lys Pro Glu Val Ala Glu Leu Val
    210                 215                 220
Leu Phe Leu Ser Ser Glu Lys Ser Ser Phe Met Thr Gly Gly Tyr Tyr
225                 230                 235                 240
Leu Val Asp Gly Gly Tyr Thr Ala Val
                245
```

<210> SEQ ID NO 69
<211> LENGTH: 747
<212> TYPE: DNA
<213> ORGANISM: Artificial sequence
<220> FEATURE:
<223> OTHER INFORMATION: Engineered sequence

<400> SEQUENCE: 69

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagtggt tgaagatatt aaagcacagg gcggtgaagc agttttgtg      180
aaagcggaca ccagcaaccc ggaagaagtg aagccctgg ttaaacgtac ggtcgaaatt      240
tatggtcgcc tggatatcgc atgcaacaat gctggcattg cggtgaaca ggcactggct      300
ggtgattacg gcctggacag ctggcgtaaa gttctgtcta tcaatctgga cggtgtcttc     360
tatggctgta atacgaact ggaacaaatg gagaaaacg gcggtggcgt tatcgtcaat       420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgttct ggcgtccgaa aaatcatcgt tcatgaccgg tggctattac      720
ctggtcgatg gtggctacac ggcagtg                                         747
```

<210> SEQ ID NO 70
<211> LENGTH: 249
<212> TYPE: PRT
<213> ORGANISM: Artificial sequence
<220> FEATURE:
<223> OTHER INFORMATION: Engineered sequence

<400> SEQUENCE: 70

```
Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
                20                  25                  30
Val Ile Val Ser Asp Ile Asn Glu Asp His Gly Asn Lys Val Val Glu
            35                  40                  45
```

```
Asp Ile Lys Ala Gln Gly Gly Glu Ala Ser Phe Val Lys Ala Asp Thr
     50                  55                  60

Ser Asn Pro Glu Glu Val Glu Ala Leu Val Lys Arg Thr Val Glu Ile
 65                  70                  75                  80

Tyr Gly Arg Leu Asp Ile Ala Cys Asn Asn Ala Gly Ile Gly Gly Glu
                 85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ala Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 71
<211> LENGTH: 747
<212> TYPE: DNA
<213> ORGANISM: Artificial sequence
<220> FEATURE:
<223> OTHER INFORMATION: Engineered sequence

<400> SEQUENCE: 71

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagcggt tgaagatatt aaagcacagg gcggtgaagc tagttttgtg     180
aaagcggaca ccagcaaccc ggaagaagtg aagccctgg ttaaacgtac ggtcgaaatt     240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatgctgta aatacgaact ggaacaaatg gagaaaaacg gcggtggcgt tatcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgggcccggc ctacattgaa acccgctgc tggaatcact gacgaaagaa     600
atgaaagaag ccctgatctc gaaacacccg atgggtcgcc tgggcaaacc ggaagaagtg     660
gcagaactgg ttctgtttct ggcgtccgaa aaatcatcgt tcatgaccgg tggcgcgtac     720
ctggtcgatg gtggctacac ggcagtg                                         747
```

<210> SEQ ID NO 72
<211> LENGTH: 249
<212> TYPE: PRT

<213> ORGANISM: Artificial sequence
<220> FEATURE:
<223> OTHER INFORMATION: Engineered sequence

<400> SEQUENCE: 72

Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
            20                  25                  30
Val Ile Val Ser Asp Ile Asn Glu Asp His Gly Asn Lys Ala Val Glu
        35                  40                  45
Asp Ile Lys Ala Gln Gly Gly Glu Ala Ser Phe Val Lys Ala Asp Thr
50                  55                  60
Ser Asn Pro Glu Glu Val Glu Ala Leu Val Lys Arg Thr Val Glu Ile
65                  70                  75                  80
Tyr Gly Arg Leu Asp Val Ala Cys Asn Asn Ala Gly Ile Gly Gly Glu
                85                  90                  95
Gln Ala Leu Ala Gly Asp Tyr Gly Leu Asp Ser Trp Arg Lys Val Leu
            100                 105                 110
Ser Ile Asn Leu Asp Gly Val Phe Tyr Gly Cys Lys Tyr Glu Leu Glu
        115                 120                 125
Gln Met Glu Lys Asn Gly Gly Val Ile Val Asn Met Ala Ser Ile
130                 135                 140
His Gly Ile Val Ala Ala Pro Leu Ser Ser Ala Tyr Thr Ser Ala Lys
145                 150                 155                 160
His Ala Val Val Gly Leu Thr Lys Asn Ile Gly Ala Glu Tyr Gly Gln
                165                 170                 175
Lys Asn Ile Arg Cys Asn Ala Val Gly Pro Ala Tyr Ile Glu Thr Pro
            180                 185                 190
Leu Leu Glu Ser Leu Thr Lys Glu Met Lys Glu Ala Leu Ile Ser Lys
        195                 200                 205
His Pro Met Gly Arg Leu Gly Lys Pro Glu Glu Val Ala Glu Leu Val
    210                 215                 220
Leu Phe Leu Ala Ser Glu Lys Ser Ser Phe Met Thr Gly Gly Ala Tyr
225                 230                 235                 240
Leu Val Asp Gly Gly Tyr Thr Ala Val
                245

<210> SEQ ID NO 73
<211> LENGTH: 747
<212> TYPE: DNA
<213> ORGANISM: Artificial sequence
<220> FEATURE:
<223> OTHER INFORMATION: Engineered sequence

<400> SEQUENCE: 73
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagcggt tgaagatatt aaagcacagg gcggtgaagc tagttttgtg      180
aaagcggaca ccagcaaccc ggaagaagtg gaagccctgg ttaaacgtac ggtcgaaatt     240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat     420
atggccagca ttcatggtat cgttgcggcc ccgctgagct ctgcatatac ctctgcgaaa     480

| | | | |
|---|---|---|---|
| cacgccgtgg ttggcctgac gaaaaacatt ggtgctgaat atggccagaa aaacatccgt | | | 540 |
| tgcaatgcgg tgtgcccggg ctacattgaa acccgctgc tggaatcact gacgaaagaa | | | 600 |
| atgaaagaag ccctgatctc gaaacacccg atgggtcgcc tgggcaaacc ggaagaagtg | | | 660 |
| gcagaactgg ttctgtttct gagttccgaa aaatcatcgt tcatgaccgg tggcgcgtac | | | 720 |
| ctggtcgatg gtggctacac ggcagtg | | | 747 |

<210> SEQ ID NO 74
<211> LENGTH: 249
<212> TYPE: PRT
<213> ORGANISM: Artificial sequence
<220> FEATURE:
<223> OTHER INFORMATION: Engineered sequence

<400> SEQUENCE: 74

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Ala Tyr
225                 230                 235                 240

Leu Val Asp Gly Gly Tyr Thr Ala Val
                245

<210> SEQ ID NO 75
<211> LENGTH: 747
<212> TYPE: DNA
<213> ORGANISM: Artificial sequence
<220> FEATURE:
<223> OTHER INFORMATION: Engineered sequence

<400> SEQUENCE: 75

```
atgggtatcc tggacaacaa agtcgcactg gttacgggcg ctggttcggg catcggtctg    60
gcggtggcac actcctacgc taaagaaggc gctaaagtca ttgtgtcaga tatcaacgaa   120
gaccatggta ataaagtggt tgaagatatt aaagcacagg gcggtgaagc tagttttgtg   180
aaagcggaca ccagcaaccc ggaagaagtg gaagccctgg ttaaacgtac ggtcgaaatt   240
tatggtcgcc tggatatcgc atgcaacaat gctggcattg gcggtgaaca ggcactggct   300
ggtgattacg gcctggacag ctggcgtaaa gttctgtcta tcaatctgga cggtgtcttc   360
tatggctgta atacgaact ggaacaaatg gagaaaacg gcggtggcgt tatcgtcaat    420
atggccagca ttcatggtat cgttgcggcc ccgctgagct ctgcatatac ctctgcgaaa   480
cacgccgtgg ttggcctgac gaaaaacatt ggtgctgaat atggccagaa aacatccgt    540 tgcaatgcgg tgggcccggc ctacattgaa accccgctgc tggaatcact gacgaaagaa   600
atgaaagaag ccctgatctc gaaacacccg atgggtcgcc tgggcaaacc ggaagaagtg   660
gcagaactgg ttctgtttct gagttccgaa aaatcatcgt tcatgaccgg tggctattac   720
ctggtcgatg tggctacac ggcagtg                                        747
```

<210> SEQ ID NO 76
<211> LENGTH: 249
<212> TYPE: PRT
<213> ORGANISM: Artificial sequence
<220> FEATURE:
<223> OTHER INFORMATION: Engineered sequence

<400> SEQUENCE: 76

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Val Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
```

```
                225                 230                 235                 240

Leu Val Asp Gly Gly Tyr Thr Ala Val
                245

<210> SEQ ID NO 77
<211> LENGTH: 747
<212> TYPE: DNA
<213> ORGANISM: Artificial sequence
<220> FEATURE:
<223> OTHER INFORMATION: Engineered sequence

<400> SEQUENCE: 77
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaagtggt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat      420 atggccagca ttcatggtat cgttgcggcc ccgctgagct ctgcatatac ctctgcgaaa     480
cacgccgtgg ttggcctgac gaaaaacatt ggtgctgaat atggccagaa aacatccgt      540 tgcaatgcgg tgtgcccggc ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct ggcgtccgaa aaatcatcgt tcatcaccgg tggcgcgtac     720
ctggtcgatg gtggctacac ggcagtg                                         747

<210> SEQ ID NO 78
<211> LENGTH: 249
<212> TYPE: PRT
<213> ORGANISM: Artificial sequence
<220> FEATURE:
<223> OTHER INFORMATION: Engineered sequence

<400> SEQUENCE: 78

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Val Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
```

```
                145                 150                 155                 160
His Ala Val Val Gly Leu Thr Lys Asn Ile Gly Ala Glu Tyr Gly Gln
                    165                 170                 175

Lys Asn Ile Arg Cys Asn Ala Val Cys Pro Ala Tyr Ile Glu Thr Pro
                    180                 185                 190

Leu Leu Glu Ser Leu Thr Lys Glu Met Lys Glu Ala Leu Ile Ser Lys
                    195                 200                 205

His Pro Met Gly Arg Leu Gly Lys Pro Glu Val Ala Glu Leu Val
                    210                 215                 220

Leu Phe Leu Ala Ser Glu Lys Ser Ser Phe Ile Thr Gly Gly Ala Tyr
225                 230                 235                 240

Leu Val Asp Gly Gly Tyr Thr Ala Val
                    245

<210> SEQ ID NO 79
<211> LENGTH: 747
<212> TYPE: DNA
<213> ORGANISM: Artificial sequence
<220> FEATURE:
<223> OTHER INFORMATION: Engineered sequence

<400> SEQUENCE: 79
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaagcggt tgaagatatt aaagcacagg gcggtgaagc tagttttgtg     180
aaaagcggaca ccagcaaccc ggaagaagtg gaagccctgg ttaaacgtac ggtcgaaatt     240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                        747

<210> SEQ ID NO 80
<211> LENGTH: 249
<212> TYPE: PRT
<213> ORGANISM: Artificial sequence
<220> FEATURE:
<223> OTHER INFORMATION: Engineered sequence

<400> SEQUENCE: 80

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
                    20                  25                  30

Val Ile Val Ser Asp Ile Asn Glu Asp His Gly Asn Lys Ala Val Glu
                    35                  40                  45

Asp Ile Lys Ala Gln Gly Gly Glu Ala Ser Phe Val Lys Ala Asp Thr
                    50                  55                  60

Ser Asn Pro Glu Glu Val Glu Ala Leu Val Lys Arg Thr Val Glu Ile
```

```
                65                  70                  75                  80

Tyr Gly Arg Leu Asp Val Ala Cys Asn Asn Ala Gly Ile Gly Gly Glu
                    85                  90                  95

Gln Ala Leu Ala Gly Asp Tyr Gly Leu Asp Ser Trp Arg Lys Val Leu
                100                 105                 110

Ser Ile Asn Leu Asp Gly Val Phe Tyr Gly Cys Lys Tyr Glu Leu Glu
                115                 120                 125

Gln Met Glu Lys Asn Gly Gly Val Ile Val Asn Met Ala Ser Ile
        130                 135                 140

His Gly Ile Val Ala Ala Pro Leu Ser Ser Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
                180                 185                 190

Leu Leu Glu Ser Leu Thr Lys Glu Met Lys Glu Ala Leu Ile Ser Lys
                195                 200                 205

His Pro Met Gly Arg Leu Gly Lys Pro Glu Glu Val Ala Glu Leu Val
        210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 81
<211> LENGTH: 747
<212> TYPE: DNA
<213> ORGANISM: Artificial sequence
<220> FEATURE:
<223> OTHER INFORMATION: Engineered sequence

<400> SEQUENCE: 81
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatggctgta aatacgaact ggaacaaatg gagaaaaacg gcggtggcgt atcgtcaat     420 atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggc ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct ggcgtccgaa aaatcatcgt tcatgaccgg tggctattac     720
ctggtcgatg gtggctacac ggcagtg                                         747

<210> SEQ ID NO 82
<211> LENGTH: 249
<212> TYPE: PRT
<213> ORGANISM: Artificial sequence
<220> FEATURE:
<223> OTHER INFORMATION: Engineered sequence
```

<400> SEQUENCE: 82

```
Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
            20                  25                  30
Val Ile Val Ser Asp Ile Asn Glu Asp His Gly Asn Lys Thr Val Glu
        35                  40                  45
Asp Ile Lys Ala Gln Gly Gly Glu Ala Ser Phe Val Lys Ala Asp Thr
    50                  55                  60
Ser Asn Pro Glu Glu Val Glu Ala Leu Val Lys Arg Thr Val Glu Ile
65                  70                  75                  80
Tyr Gly Arg Leu Asp Val Ala Cys Asn Asn Ala Gly Ile Gly Gly Glu
                85                  90                  95
Gln Ala Leu Ala Gly Asp Tyr Gly Leu Asp Ser Trp Arg Lys Val Leu
            100                 105                 110
Ser Ile Asn Leu Asp Gly Val Phe Tyr Gly Cys Lys Tyr Glu Leu Glu
        115                 120                 125
Gln Met Glu Lys Asn Gly Gly Val Ile Val Asn Met Ala Ser Ile
    130                 135                 140
His Gly Ile Val Ala Ala Pro Leu Ser Ser Ala Tyr Thr Ser Ala Lys
145                 150                 155                 160
His Ala Val Val Gly Leu Thr Lys Asn Ile Gly Ala Glu Tyr Gly Gln
                165                 170                 175
Lys Asn Ile Arg Cys Asn Ala Val Cys Pro Ala Tyr Ile Glu Thr Pro
            180                 185                 190
Leu Leu Glu Ser Leu Thr Lys Glu Met Lys Glu Ala Leu Ile Ser Lys
        195                 200                 205
His Pro Met Gly Arg Leu Gly Lys Pro Glu Glu Val Ala Glu Leu Val
    210                 215                 220
Leu Phe Leu Ala Ser Glu Lys Ser Ser Phe Met Thr Gly Gly Tyr Tyr
225                 230                 235                 240
Leu Val Asp Gly Gly Tyr Thr Ala Val
                245
```

<210> SEQ ID NO 83
<211> LENGTH: 747
<212> TYPE: DNA
<213> ORGANISM: Artificial sequence
<220> FEATURE:
<223> OTHER INFORMATION: Engineered sequence

<400> SEQUENCE: 83

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagtggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
```

```
atgaaagaag ccctgatctc gaaacacccg atgggtcgcc tggcaaaacc ggaagaagtg    660
gcagaactgg ttctgtttct gagttccgaa aaatcatcgt tcatgaccgg tggctattac    720
ctggtcgatg gtggctacac ggcagtg                                        747
```

<210> SEQ ID NO 84
<211> LENGTH: 249
<212> TYPE: PRT
<213> ORGANISM: Artificial sequence
<220> FEATURE:
<223> OTHER INFORMATION: Engineered sequence

<400> SEQUENCE: 84

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Val Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 85
<211> LENGTH: 747
<212> TYPE: DNA
<213> ORGANISM: Artificial sequence
<220> FEATURE:
<223> OTHER INFORMATION: Engineered sequence

<400> SEQUENCE: 85

```
atgggtatcc tggacaacaa agtcgcactg gttacgggcg ctggttcggg catcggtctg     60
gcggtggcac actcctacgc taaagaaggc gctaaagtca ttgtgtcaga tatcaacgaa    120
```

```
gaccatggta ataaagtggt tgaagatatt aaagcacagg gcggtgaagc tagttttgtg      180
aaagcggaca ccagcaaccc ggaagaagtg gaagccctgg ttaaacgtac ggtcgaaatt      240
tatggtcgcc tggatatcgc atgcaacaat gctggcattg gcggtgaaca ggcactggct      300
ggtgattacg gcctggacag ctggcgtaaa gttctgtcta tcaatctgga cggtgtcttc      360
tatggctgta atacgaact ggaacaaatg gagaaaaacg gcggtggcgt tatcgtcaat      420
atggccagca ttcatggtat cgttgcggcc ccgctgagct ctgcatatac ctctgcgaaa      480
cacgccgtgg ttggcctgac gaaaaacatt ggtgctgaat atggccagaa aacatccgt      540
tgcaatgcgg tgggcccggc ctacattgaa accccgctgc tggaatcact gacgaaagaa      600
atgaaagaag ccctgatctc gaaacaccccg atgggtcgcc tgggcaaacc ggaagaagtg      660
gcagaactgg ttctgtttct ggcgtccgaa aaatcatcgt tcatcaccgg tggctattac      720
ctggtcgatg gtggctacac ggcagtg                                           747
```

<210> SEQ ID NO 86
<211> LENGTH: 249
<212> TYPE: PRT
<213> ORGANISM: Artificial sequence
<220> FEATURE:
<223> OTHER INFORMATION: Engineered sequence

<400> SEQUENCE: 86

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Val Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ala Ser Glu Lys Ser Ser Phe Ile Thr Gly Gly Tyr Tyr
225                 230                 235                 240

Leu Val Asp Gly Gly Tyr Thr Ala Val
                245
```

<210> SEQ ID NO 87
<211> LENGTH: 747
<212> TYPE: DNA
<213> ORGANISM: Artificial sequence
<220> FEATURE:
<223> OTHER INFORMATION: Engineered sequence

<400> SEQUENCE: 87

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaaaccgt tgaagatatt aaagcacagg gcggtgaagc tagttttgtg      180
aaagcggaca ccagcaaccc ggaagaagtg gaagccctgg ttaaacgtac ggtcgaaatt     240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat      420
atggccagca ttcatggtat cgttgcggcc ccgctgagct ctgcatatac ctctgcgaaa    480
cacgccgtgg ttggcctgac gaaaaacatt ggtgctgaat atggccagaa aacatccgt     540
tgcaatgcgg tgtgcccggc ctacattgaa accccgctgc tggaatcact gacgaaagaa    600
atgaaagaag ccctgatctc gaaacacccg atgggtcgcc tggcaaaacc ggaagaagtg    660
gcagaactgg ttctgtttct ggcgtccgaa aaatcatcgt tcatgaccgg tggcgcgtac    720
ctggtcgatg gtggctacac ggcagtg                                         747
```

<210> SEQ ID NO 88
<211> LENGTH: 249
<212> TYPE: PRT
<213> ORGANISM: Artificial sequence
<220> FEATURE:
<223> OTHER INFORMATION: Engineered sequence

<400> SEQUENCE: 88

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175
```

```
Lys Asn Ile Arg Cys Asn Ala Val Cys Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Val Ala Glu Leu Val
    210                 215                 220

Leu Phe Leu Ala Ser Glu Lys Ser Ser Phe Met Thr Gly Gly Ala Tyr
225                 230                 235                 240

Leu Val Asp Gly Gly Tyr Thr Ala Val
                245

<210> SEQ ID NO 89
<211> LENGTH: 747
<212> TYPE: DNA
<213> ORGANISM: Artificial sequence
<220> FEATURE:
<223> OTHER INFORMATION: Engineered sequence

<400> SEQUENCE: 89
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaagcggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat      420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                        747

<210> SEQ ID NO 90
<211> LENGTH: 249
<212> TYPE: PRT
<213> ORGANISM: Artificial sequence
<220> FEATURE:
<223> OTHER INFORMATION: Engineered sequence

<400> SEQUENCE: 90

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95
```

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
            115                 120                 125

Gln Met Glu Lys Asn Gly Gly Val Ile Val Asn Met Ala Ser Ile
130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
            165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
            195                 200                 205

His Pro Met Gly Arg Leu Gly Lys Pro Glu Glu Val Ala Glu Leu Val
210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245

<210> SEQ ID NO 91
<211> LENGTH: 747
<212> TYPE: DNA
<213> ORGANISM: Artificial sequence
<220> FEATURE:
<223> OTHER INFORMATION: Engineered sequence

<400> SEQUENCE: 91
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagcggt tgaagatatt aaagcacagg gcggtgaagc tagttttgtg      180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat      420 atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgggcccggc ctacattgaa accccgctgc tggaatcact gacgaaagaa     600
atgaaagaag ccctgatctc gaaacacccg atgggtcgcc tgggcaaacc ggaagaagtg     660
gcagaactgg ttctgttttct ggcgtccgaa aaatcatcgt tcatcaccgg tggctattac     720
ctggtcgatg gtggctacac ggcagtg                                         747

<210> SEQ ID NO 92
<211> LENGTH: 249
<212> TYPE: PRT
<213> ORGANISM: Artificial sequence
<220> FEATURE:
<223> OTHER INFORMATION: Engineered sequence

<400> SEQUENCE: 92

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Glu
                85                  90                  95

Gln Ala Leu Ala Gly Asp Tyr Gly Leu Asp Ser Trp Arg Lys Val Leu
                100                 105                 110

Ser Ile Asn Leu Asp Gly Val Phe Tyr Gly Cys Lys Tyr Glu Leu Glu
            115                 120                 125

Gln Met Glu Lys Asn Gly Gly Val Ile Val Asn Met Ala Ser Ile
130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ala Ser Glu Lys Ser Ser Phe Ile Thr Gly Gly Tyr Tyr
225                 230                 235                 240

Leu Val Asp Gly Gly Tyr Thr Ala Val
                245

<210> SEQ ID NO 93
<211> LENGTH: 747
<212> TYPE: DNA
<213> ORGANISM: Artificial sequence
<220> FEATURE:
<223> OTHER INFORMATION: Engineered sequence

<400> SEQUENCE: 93
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagtggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat     420 atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggc ctacattgaa acccgctgc tggaatcact gacgaaagaa     600
atgaaagaag ccctgatctc gaaacacccg atgggtcgcc tggcaaaacc ggaagaagtg     660
gcagaactgg ttctgtttct gagttccgaa aaatcatcgt tcatgaccgg tggcgcgtac     720
ctggtcgatg gtggctacac ggcagtg                                         747

<210> SEQ ID NO 94
<211> LENGTH: 249
<212> TYPE: PRT
<213> ORGANISM: Artificial sequence
<220> FEATURE:
<223> OTHER INFORMATION: Engineered sequence

<400> SEQUENCE: 94

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Val Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Ala Tyr
225                 230                 235                 240

Leu Val Asp Gly Gly Tyr Thr Ala Val
                245

<210> SEQ ID NO 95
<211> LENGTH: 747
<212> TYPE: DNA
<213> ORGANISM: Artificial sequence
<220> FEATURE:
<223> OTHER INFORMATION: Engineered sequence

<400> SEQUENCE: 95
atgggtatcc tggacaacaa agtcgcactg gttacgggcg ctggttcggg catcggtctg     60
gcggtggcac actcctacgc taaagaaggc gctaaagtca ttgtgtcaga tatcaacgaa    120
gaccatggta taaagtggt tgaagatatt aaagcacagg gcgttgaagc tagttttgtg    180
aaagcggaca ccagcaaccc ggaagaagtg gaagccctgg ttaaacgtac ggtcgaaatt    240

```
tatggtcgcc tggatatcgc atgcaacaat gctggcattg gcggtgaaca ggcactggct    300
ggtgattacg gcctggacag ctggcgtaaa gttctgtcta tcaatctgga cggtgtcttc    360
tatggctgta aatacgaact ggaacaaatg gagaaaaacg gcggtggcgt tatcgtcaat    420
atggccagca ttcatggtat cgttgcggcc ccgctgagct ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct ggcgtccgaa aaatcatcgt tcatgaccgg tggcgcgtac    720
ctggtcgatg gtggctacac ggcagtg                                        747
```

<210> SEQ ID NO 96
<211> LENGTH: 249
<212> TYPE: PRT
<213> ORGANISM: Artificial sequence
<220> FEATURE:
<223> OTHER INFORMATION: Engineered sequence

<400> SEQUENCE: 96

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Val Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ala Ser Glu Lys Ser Ser Phe Met Thr Gly Gly Ala Tyr
225                 230                 235                 240

Leu Val Asp Gly Gly Tyr Thr Ala Val
                245
```

<210> SEQ ID NO 97
<211> LENGTH: 747

```
<212> TYPE: DNA
<213> ORGANISM: Artificial sequence
<220> FEATURE:
<223> OTHER INFORMATION: Engineered sequence

<400> SEQUENCE: 97
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaagcggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat      420 atggccagca ttcatggtat cgttgcggcc ccgctgagct ctgcatatac ctctgcgaaa     480
cacgccgtgg ttggcctgac gaaaaacatt ggtgctgaat atggccagaa aacatccgt      540 tgcaatgcgg tgggcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct ggcgtccgaa aaatcatcgt tcatcaccgg tggctattac     720
ctggtcgatg gtggctacac ggcagtg                                         747

<210> SEQ ID NO 98
<211> LENGTH: 249
<212> TYPE: PRT
<213> ORGANISM: Artificial sequence
<220> FEATURE:
<223> OTHER INFORMATION: Engineered sequence

<400> SEQUENCE: 98

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Gly Tyr Ile Glu Thr Pro
            180                 185                 190
```

```
Leu Leu Glu Ser Leu Thr Lys Glu Met Lys Glu Ala Leu Ile Ser Lys
            195                 200                 205

His Pro Met Gly Arg Leu Gly Lys Pro Glu Val Ala Glu Leu Val
        210                 215                 220

Leu Phe Leu Ala Ser Glu Lys Ser Ser Phe Ile Thr Gly Gly Tyr Tyr
225                 230                 235                 240

Leu Val Asp Gly Gly Tyr Thr Ala Val
                245

<210> SEQ ID NO 99
<211> LENGTH: 747
<212> TYPE: DNA
<213> ORGANISM: Artificial sequence
<220> FEATURE:
<223> OTHER INFORMATION: Engineered sequence

<400> SEQUENCE: 99
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggc ctacattgaa accccgctgc tggaatcact gacgaaagaa     600
atgaaagaag ccctgatctc gaaacaccg atgggtcgcc tgggcaaacc ggaagaagtg     660
gcagaactgg ttctgttct ggcgtccgaa aaatcatcgt tcatgaccgg tggctattac      720
ctggtcgatg gtggctacac ggcagtg                                         747

<210> SEQ ID NO 100
<211> LENGTH: 249
<212> TYPE: PRT
<213> ORGANISM: Artificial sequence
<220> FEATURE:
<223> OTHER INFORMATION: Engineered sequence

<400> SEQUENCE: 100

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110
```

Ser Ile Asn Leu Asp Gly Val Phe Tyr Gly Cys Lys Tyr Glu Leu Glu
         115                 120                 125

Gln Met Glu Lys Asn Gly Gly Val Ile Val Asn Met Ala Ser Ile
     130                 135                 140

His Gly Ile Val Ala Ala Pro Leu Ser Ser Tyr Thr Ser Ala Lys
145                 150                 155                 160

His Ala Val Val Gly Leu Thr Lys Asn Ile Gly Ala Glu Tyr Gly Gln
                 165                 170                 175

Lys Asn Ile Arg Cys Asn Ala Val Cys Pro Ala Tyr Ile Glu Thr Pro
             180                 185                 190

Leu Leu Glu Ser Leu Thr Lys Glu Met Lys Glu Ala Leu Ile Ser Lys
         195                 200                 205

His Pro Met Gly Arg Leu Gly Lys Pro Glu Glu Val Ala Glu Leu Val
     210                 215                 220

Leu Phe Leu Ala Ser Glu Lys Ser Ser Phe Met Thr Gly Gly Tyr Tyr
225                 230                 235                 240

Leu Val Asp Gly Gly Tyr Thr Ala Val
                 245

<210> SEQ ID NO 101
<211> LENGTH: 747
<212> TYPE: DNA
<213> ORGANISM: Artificial sequence
<220> FEATURE:
<223> OTHER INFORMATION: Engineered sequence

<400> SEQUENCE: 101

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747
```

<210> SEQ ID NO 102
<211> LENGTH: 249
<212> TYPE: PRT
<213> ORGANISM: Artificial sequence
<220> FEATURE:
<223> OTHER INFORMATION: Engineered sequence

<400> SEQUENCE: 102

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
             20                  25                  30

Val Ile Val Ser Asp Ile Asn Glu Asp His Gly Asn Lys Thr Val Glu
            35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 103
<211> LENGTH: 747
<212> TYPE: DNA
<213> ORGANISM: Artificial sequence
<220> FEATURE:
<223> OTHER INFORMATION: Engineered sequence

<400> SEQUENCE: 103
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagtggt tgaagatatt aaagcacagg gcggtgaagc tagttttgtg     180
aaagcggaca ccagcaaccc ggaagaagtg aagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta aatacgaact ggaacaaatg gagaaaaacg gcggtggcgt tatcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct ggcgtccgaa aaatcatcgt tcgtgaccgg tggctattac     720
ctggtcgatg gtggctacac ggcagtg                                          747

<210> SEQ ID NO 104
<211> LENGTH: 249
<212> TYPE: PRT
<213> ORGANISM: Artificial sequence
<220> FEATURE:
<223> OTHER INFORMATION: Engineered sequence

<400> SEQUENCE: 104

```
Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
            20                  25                  30
Val Ile Val Ser Asp Ile Asn Glu Asp His Gly Asn Lys Val Val Glu
        35                  40                  45
Asp Ile Lys Ala Gln Gly Gly Glu Ala Ser Phe Val Lys Ala Asp Thr
    50                  55                  60
Ser Asn Pro Glu Glu Val Glu Ala Leu Val Lys Arg Thr Val Glu Ile
65                  70                  75                  80
Tyr Gly Arg Leu Asp Ile Ala Cys Asn Asn Ala Gly Ile Gly Gly Glu
                85                  90                  95
Gln Ala Leu Ala Gly Asp Tyr Gly Leu Asp Ser Trp Arg Lys Val Leu
            100                 105                 110
Ser Ile Asn Leu Asp Gly Val Phe Tyr Gly Cys Lys Tyr Glu Leu Glu
        115                 120                 125
Gln Met Glu Lys Asn Gly Gly Val Ile Val Asn Met Ala Ser Ile
    130                 135                 140
His Gly Ile Val Ala Ala Pro Leu Ser Ser Ala Tyr Thr Ser Ala Lys
145                 150                 155                 160
His Ala Val Val Gly Leu Thr Lys Asn Ile Gly Ala Glu Tyr Gly Gln
                165                 170                 175
Lys Asn Ile Arg Cys Asn Ala Val Cys Pro Gly Tyr Ile Glu Thr Pro
            180                 185                 190
Leu Leu Glu Ser Leu Thr Lys Glu Met Lys Glu Ala Leu Ile Ser Lys
        195                 200                 205
His Pro Met Gly Arg Leu Gly Lys Pro Glu Glu Val Ala Glu Leu Val
    210                 215                 220
Leu Phe Leu Ala Ser Glu Lys Ser Ser Phe Val Thr Gly Gly Tyr Tyr
225                 230                 235                 240
Leu Val Asp Gly Gly Tyr Thr Ala Val
                245
```

<210> SEQ ID NO 105
<211> LENGTH: 747
<212> TYPE: DNA
<213> ORGANISM: Artificial sequence
<220> FEATURE:
<223> OTHER INFORMATION: Engineered sequence

<400> SEQUENCE: 105

```
atgggtatcc tggacaacaa agtcgcactg gttacgggcg ctggttcggg catcggtctg     60
gcggtggcac actcctacgc taaagaaggc gctaaagtca ttgtgtcaga tatcaacgaa    120
gaccatggta taaagtggt tgaagatatt aagcacagg gcggtgaagc tagttttgtg    180
aaagcggaca ccagcaaccc ggaagaagtg gaagccctgg ttaaacgtac ggtcgaaatt    240
tatggtcgcc tggatgtggc atgcaacaat gctggcattg gcggtgaaca ggcactggct    300
ggtgattacg gcctggacag ctggcgtaaa gttctgtcta tcaatctgga cggtgtcttc    360
```

```
tatggctgta aatacgaact ggaacaaatg agaaaaacg gcggtggcgt tatcgtcaat      420
atggccagca ttcatggtat cgttgcggcc ccgctgagct ctgcatatac ctctgcgaaa      480
cacgccgtgg ttggcctgac gaaaaacatt ggtgctgaat atggccagaa aaacatccgt      540
tgcaatgcgg tgtgcccggg ctacattgaa accccgctgc tggaatcact gacgaaagaa      600
atgaaagaag ccctgatctc gaaacacccg atgggtcgcc tgggcaaacc ggaagaagtg      660
gcagaactgg ttctgtttct gagttccgaa aaatcatcgt tcgtgaccgg tggctattac      720
ctggtcgatg gtggctacac ggcagtg                                          747
```

<210> SEQ ID NO 106
<211> LENGTH: 249
<212> TYPE: PRT
<213> ORGANISM: Artificial sequence
<220> FEATURE:
<223> OTHER INFORMATION: Engineered sequence

<400> SEQUENCE: 106

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Val Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Phe Val Thr Gly Gly Tyr Tyr
225                 230                 235                 240

Leu Val Asp Gly Gly Tyr Thr Ala Val
                245
```

<210> SEQ ID NO 107
<211> LENGTH: 747
<212> TYPE: DNA
<213> ORGANISM: Artificial sequence
<220> FEATURE:
<223> OTHER INFORMATION: Engineered sequence -continued

```
<400> SEQUENCE: 107
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagtggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aacatccgt      540 tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgttct ggcgtccgaa aaatcatcgt tcatgaccgg tggctattac     720
ctggtcgatg gtggctacac ggcagtg                                          747

<210> SEQ ID NO 108
<211> LENGTH: 249
<212> TYPE: PRT
<213> ORGANISM: Artificial sequence
<220> FEATURE:
<223> OTHER INFORMATION: Engineered sequence

<400> SEQUENCE: 108

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
                20                  25                  30

Val Ile Val Ser Asp Ile Asn Glu Asp His Gly Asn Lys Val Val Glu
            35                  40                  45

Asp Ile Lys Ala Gln Gly Gly Glu Ala Ser Phe Val Lys Ala Asp Thr
        50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
```

```
Leu Phe Leu Ala Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 109
<211> LENGTH: 747
<212> TYPE: DNA
<213> ORGANISM: Artificial sequence
<220> FEATURE:
<223> OTHER INFORMATION: Engineered sequence

<400> SEQUENCE: 109

```
atgggtatcc tggacaacaa agtcgcactg gttacgggcg ctggtagggg catcggtctg      60
gcggtggcac actcctacgc taaagaaggc gctaaagtca ttgtgtcaga tatcaacgaa     120
gaccatggta taaagcggt tgaagatatt aaagcacagg gcggtgaagc tagttttgtg      180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat      420
atggccagca ttcatggtat cgttgcggcc ccgctgagct ctgcatatac ctctgcgaaa    480
cacgccgtgg ttggcctgac gaaaaacatt ggtgctgaat atggccagaa aacatccgt     540
tgcaatgcgg tgggcccggc ctacattgaa accccgctgc tggaatcact gacgaaagaa    600
atgaaagaag ccctgatctc gaaacaccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                         747
```

<210> SEQ ID NO 110
<211> LENGTH: 249
<212> TYPE: PRT
<213> ORGANISM: Artificial sequence
<220> FEATURE:
<223> OTHER INFORMATION: Engineered sequence

<400> SEQUENCE: 110

```
Met Gly Ile Leu Asp Asn Lys Val Ala Leu Val Thr Gly Ala Gly Arg
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
```

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 111
<211> LENGTH: 747
<212> TYPE: DNA
<213> ORGANISM: Artificial sequence
<220> FEATURE:
<223> OTHER INFORMATION: Engineered sequence

<400> SEQUENCE: 111

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaagcggt tgaagatatt aaagcacagg gcggtgaagc tagttttgtg     180
aaagcggaca ccgctaaccc ggaagaagtg aagccctgg ttaaacgtac ggtcgaaatt      240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat      420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgggcccggc ctacattgaa accccgctgc tggaatcact gacgaaagaa     600
atgaaagaag ccctgatctc gaaacacccg atgggtcgcc tggcaaaacc ggaagaagtg     660
gcagaactgg ttctgtttct gagttccgaa aaatcatcgt tcatgaccgg tggctattac     720
ctggtcgatg gtggctacac ggcagtg                                        747
```

<210> SEQ ID NO 112
<211> LENGTH: 249
<212> TYPE: PRT
<213> ORGANISM: Artificial sequence
<220> FEATURE:
<223> OTHER INFORMATION: Engineered sequence

<400> SEQUENCE: 112

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
                20                  25                  30

Val Ile Val Ser Asp Ile Asn Glu Asp His Gly Asn Lys Ala Val Glu
            35                  40                  45

Asp Ile Lys Ala Gln Gly Gly Glu Ala Ser Phe Val Lys Ala Asp Thr

```
                50                  55                  60
Ala Asn Pro Glu Glu Val Glu Ala Leu Val Lys Arg Thr Val Glu Ile
 65                  70                  75                  80

Tyr Gly Arg Leu Asp Ile Ala Cys Asn Asn Ala Gly Ile Gly Gly Glu
                 85                  90                  95

Gln Ala Leu Ala Gly Asp Tyr Gly Leu Asp Ser Trp Arg Lys Val Leu
                100                 105                 110

Ser Ile Asn Leu Asp Gly Val Phe Tyr Gly Cys Lys Tyr Glu Leu Glu
                115                 120                 125

Gln Met Glu Lys Asn Gly Gly Gly Val Ile Val Asn Met Ala Ser Ile
                130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
                180                 185                 190

Leu Leu Glu Ser Leu Thr Lys Glu Met Lys Glu Ala Leu Ile Ser Lys
                195                 200                 205

His Pro Met Gly Arg Leu Gly Lys Pro Glu Glu Val Ala Glu Leu Val
210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 113
<211> LENGTH: 747
<212> TYPE: DNA
<213> ORGANISM: Artificial sequence
<220> FEATURE:
<223> OTHER INFORMATION: Engineered sequence

<400> SEQUENCE: 113

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagcggt tgaagatatt aaagcacagg gcggtgaagc tagttttgtg      180
aaagcggaca ccagcaaccc ggaagaagtg aagccctgg ttaaacgtac ggtcgaaatt      240
tatggtcgcc tggatatcgc atgcaacaat gctggcattg gcggtgaaca ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt tatcgtcaat      420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgggcccggc ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747
```

<210> SEQ ID NO 114
<211> LENGTH: 249
<212> TYPE: PRT
<213> ORGANISM: Artificial sequence
<220> FEATURE:
<223> OTHER INFORMATION: Engineered sequence

<400> SEQUENCE: 114

| Met | Gly | Ile | Leu | Asp | Asn | Lys | Val | Ala | Leu | Val | Thr | Gly | Ala | Gly | Ser |
|---|---|---|---|---|---|---|---|---|---|---|---|---|---|---|---|
| 1 | | | | 5 | | | | | 10 | | | | | 15 | |

| Gly | Ile | Gly | Leu | Ala | Val | Ala | His | Ser | Tyr | Ala | Lys | Glu | Gly | Ala | Lys |
|---|---|---|---|---|---|---|---|---|---|---|---|---|---|---|---|
| | | | 20 | | | | | 25 | | | | | 30 | | |

| Val | Ile | Val | Ser | Asp | Ile | Asn | Glu | Asp | His | Gly | Asn | Lys | Ala | Val | Glu |
|---|---|---|---|---|---|---|---|---|---|---|---|---|---|---|---|
| | | | 35 | | | | | 40 | | | | | 45 | | |

| Asp | Ile | Lys | Ala | Gln | Gly | Gly | Glu | Ala | Ser | Phe | Val | Lys | Ala | Asp | Thr |
|---|---|---|---|---|---|---|---|---|---|---|---|---|---|---|---|
| | 50 | | | | | 55 | | | | | 60 | | | | |

| Ser | Asn | Pro | Glu | Glu | Val | Glu | Ala | Leu | Val | Lys | Arg | Thr | Val | Glu | Ile |
|---|---|---|---|---|---|---|---|---|---|---|---|---|---|---|---|
| 65 | | | | | 70 | | | | | 75 | | | | | 80 |

| Tyr | Gly | Arg | Leu | Asp | Ile | Ala | Cys | Asn | Asn | Ala | Gly | Ile | Gly | Gly | Glu |
|---|---|---|---|---|---|---|---|---|---|---|---|---|---|---|---|
| | | | | 85 | | | | | 90 | | | | | 95 | |

| Gln | Ala | Leu | Ala | Gly | Asp | Tyr | Gly | Leu | Asp | Ser | Trp | Arg | Lys | Val | Leu |
|---|---|---|---|---|---|---|---|---|---|---|---|---|---|---|---|
| | | | 100 | | | | | 105 | | | | | 110 | | |

| Ser | Val | Asn | Leu | Asp | Gly | Val | Phe | Tyr | Gly | Cys | Lys | Tyr | Glu | Leu | Glu |
|---|---|---|---|---|---|---|---|---|---|---|---|---|---|---|---|
| | | | 115 | | | | | 120 | | | | | 125 | | |

| Gln | Met | Glu | Lys | Asn | Gly | Gly | Gly | Val | Ile | Val | Asn | Met | Ala | Ser | Ile |
|---|---|---|---|---|---|---|---|---|---|---|---|---|---|---|---|
| | 130 | | | | | 135 | | | | | 140 | | | | |

| His | Gly | Ile | Val | Ala | Ala | Pro | Leu | Ser | Ser | Ala | Tyr | Thr | Ser | Ala | Lys |
|---|---|---|---|---|---|---|---|---|---|---|---|---|---|---|---|
| 145 | | | | | 150 | | | | | 155 | | | | | 160 |

| His | Ala | Val | Val | Gly | Leu | Thr | Lys | Asn | Ile | Gly | Ala | Glu | Tyr | Gly | Gln |
|---|---|---|---|---|---|---|---|---|---|---|---|---|---|---|---|
| | | | | 165 | | | | | 170 | | | | | 175 | |

| Lys | Asn | Ile | Arg | Cys | Asn | Ala | Val | Gly | Pro | Ala | Tyr | Ile | Glu | Thr | Pro |
|---|---|---|---|---|---|---|---|---|---|---|---|---|---|---|---|
| | | | 180 | | | | | 185 | | | | | 190 | | |

| Leu | Leu | Glu | Ser | Leu | Thr | Lys | Glu | Met | Lys | Glu | Ala | Leu | Ile | Ser | Lys |
|---|---|---|---|---|---|---|---|---|---|---|---|---|---|---|---|
| | | | 195 | | | | | 200 | | | | | 205 | | |

| His | Pro | Met | Gly | Arg | Leu | Gly | Lys | Pro | Glu | Glu | Val | Ala | Glu | Leu | Val |
|---|---|---|---|---|---|---|---|---|---|---|---|---|---|---|---|
| | 210 | | | | | 215 | | | | | 220 | | | | |

| Leu | Phe | Leu | Ser | Ser | Glu | Lys | Ser | Ser | Phe | Met | Thr | Gly | Gly | Tyr | Tyr |
|---|---|---|---|---|---|---|---|---|---|---|---|---|---|---|---|
| 225 | | | | | 230 | | | | | 235 | | | | | 240 |

| Leu | Val | Asp | Gly | Gly | Tyr | Thr | Ala | Val |
|---|---|---|---|---|---|---|---|---|
| | | | | 245 | | | | |

<210> SEQ ID NO 115
<211> LENGTH: 747
<212> TYPE: DNA
<213> ORGANISM: Artificial sequence
<220> FEATURE:
<223> OTHER INFORMATION: Engineered sequence

<400> SEQUENCE: 115

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaagcggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat     420
atcgccagca ttcatggtat cgttgcggcc ccgctgagct ctgcatatac ctctgcgaaa     480
```

```
cacgccgtgg ttggcctgac gaaaaacatt ggtgctgaat atggccagaa aaacatccgt      540
tgcaatgcgg tgggcccggc ctacattgaa accccgctgc tggaatcact gacgaaagaa      600
atgaaagaag ccctgatctc gaaacacccg atgggtcgcc tgggcaaacc ggaagaagtg      660
gcagaactgg ttctgtttct gagttccgaa aaatcatcgt tcatgaccgg tggctattac      720
ctggtcgatg gtggctacac ggcagtg                                           747
```

```
<210> SEQ ID NO 116
<211> LENGTH: 249
<212> TYPE: PRT
<213> ORGANISM: Artificial sequence
<220> FEATURE:
<223> OTHER INFORMATION: Engineered sequence

<400> SEQUENCE: 116
```

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Ile Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

```
<210> SEQ ID NO 117
<211> LENGTH: 747
<212> TYPE: DNA
<213> ORGANISM: Artificial sequence
<220> FEATURE:
<223> OTHER INFORMATION: Engineered sequence

<400> SEQUENCE: 117
atgggtatcc tggacaacaa agtcgcactg gttacgggcg ctggtaaggg catcggtctg      60
```

```
gcggtggcac actcctacgc taaagaaggc gctaaagtca ttgtgtcaga tatcaacgaa    120
gaccatggta ataaagcggt tgaagatatt aaagcacagg gcggtgaagc tagttttgtg    180
aaagcggaca ccagcaaccc ggaagaagtg aagccctgg ttaaacgtac ggtcgaaatt    240
tatggtcgcc tggatatcgc atgcaacaat gctggcattg gcggtgaaca ggcactggct    300
ggtgattacg gcctggacag ctggcgtaaa gttctgtcta tcaatctgga cggtgtcttc    360
tatggctgta aatacgaact ggaacaaatg gagaaaaacg gcggtggcgt tatcgtcaat    420
atggccagca ttcatggtat cgttgcggcc ccgctgagct ctgcatatac ctctgcgaaa    480
cacgccgtgg ttggcctgac gaaaaacatt ggtgctgaat atggccagaa aaacatccgt    540
tgcaatgcgg tgggcccggc ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                         747
```

<210> SEQ ID NO 118
<211> LENGTH: 249
<212> TYPE: PRT
<213> ORGANISM: Artificial sequence
<220> FEATURE:
<223> OTHER INFORMATION: Engineered sequence

<400> SEQUENCE: 118

```
Met Gly Ile Leu Asp Asn Lys Val Ala Leu Val Thr Gly Ala Gly Lys
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Phe Met Thr Gly Gly Tyr Tyr
225                 230                 235                 240
```

<210> SEQ ID NO 119
<211> LENGTH: 747
<212> TYPE: DNA
<213> ORGANISM: Artificial sequence
<220> FEATURE:
<223> OTHER INFORMATION: Engineered sequence

<400> SEQUENCE: 119

```
atgggtatcc tggacaacaa agtcgcactg gttacgggcg ctggttcggg catcggtctg      60
gcggtggcac actcctacgc taaagaaggc gctaaagtca ttgtgtcaga ttgcaacgaa     120
gaccatggta ataaagcggt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact  ggaacaaatg gagaaaaacg gcggtggcgt tatcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aacatccgt     540
tgcaatgcgg tgggcccggc ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747
```

<210> SEQ ID NO 120
<211> LENGTH: 249
<212> TYPE: PRT
<213> ORGANISM: Artificial sequence
<220> FEATURE:
<223> OTHER INFORMATION: Engineered sequence

<400> SEQUENCE: 120

```
Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
            20                  25                  30
Val Ile Val Ser Asp Cys Asn Glu Asp His Gly Asn Lys Ala Val Glu
        35                  40                  45
Asp Ile Lys Ala Gln Gly Gly Glu Ala Ser Phe Val Lys Ala Asp Thr
    50                  55                  60
Ser Asn Pro Glu Glu Val Glu Ala Leu Val Lys Arg Thr Val Glu Ile
65                  70                  75                  80
Tyr Gly Arg Leu Asp Ile Ala Cys Asn Asn Ala Gly Ile Gly Gly Glu
                85                  90                  95
Gln Ala Leu Ala Gly Asp Tyr Gly Leu Asp Ser Trp Arg Lys Val Leu
            100                 105                 110
Ser Ile Asn Leu Asp Gly Val Phe Tyr Gly Cys Lys Tyr Glu Leu Glu
        115                 120                 125
Gln Met Glu Lys Asn Gly Gly Gly Val Ile Val Asn Met Ala Ser Ile
    130                 135                 140
His Gly Ile Val Ala Ala Pro Leu Ser Ser Ala Tyr Thr Ser Ala Lys
145                 150                 155                 160
```

```
His Ala Val Val Gly Leu Thr Lys Asn Ile Gly Ala Glu Tyr Gly Gln
            165                 170                 175

Lys Asn Ile Arg Cys Asn Ala Val Gly Pro Ala Tyr Ile Glu Thr Pro
        180                 185                 190

Leu Leu Glu Ser Leu Thr Lys Glu Met Lys Glu Ala Leu Ile Ser Lys
    195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Tyr Tyr
225                 230                 235                 240

Leu Val Asp Gly Gly Tyr Thr Ala Val
                245

<210> SEQ ID NO 121
<211> LENGTH: 747
<212> TYPE: DNA
<213> ORGANISM: Artificial sequence
<220> FEATURE:
<223> OTHER INFORMATION: Engineered sequence

<400> SEQUENCE: 121
atgggtatcc tggacaacaa agtcgcactg gttacgggcg ctggttcggg catcggtctg      60
gcggtggcac actcctacgc taaagaaggc gctaaagtca ttgtgtcaga ttggaacgaa     120
gaccatggta ataaagcggt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta aatacgaact ggaacaaatg gagaaaaacg gcggtggcgt tatcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgggcccggc ctacattgaa accccgctgc tggaatcact gacgaaagaa     600
atgaaagaag ccctgatctc gaaacacccg atgggtcgcc tggcaaaacc ggaagaagtg     660
gcagaactgg ttctgtttct gagttccgaa aaatcatcgt tcatgaccgg tggctattac     720
ctggtcgatg gtggctacac ggcagtg                                        747

<210> SEQ ID NO 122
<211> LENGTH: 249
<212> TYPE: PRT
<213> ORGANISM: Artificial sequence
<220> FEATURE:
<223> OTHER INFORMATION: Engineered sequence

<400> SEQUENCE: 122

Met Gly Ile Leu Asp Asn Lys Val Ala Leu Val Thr Gly Ala Gly Ser
1               5                  10                  15

Gly Ile Gly Leu Ala Val Ala His Ser Tyr Ala Lys Glu Gly Ala Lys
            20                  25                  30

Val Ile Val Ser Asp Trp Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80
```

Tyr Gly Arg Leu Asp Ile Ala Cys Asn Asn Ala Gly Ile Gly Gly Glu
            85                  90                  95

Gln Ala Leu Ala Gly Asp Tyr Gly Leu Asp Ser Trp Arg Lys Val Leu
        100                 105                 110

Ser Ile Asn Leu Asp Gly Val Phe Tyr Gly Cys Lys Tyr Glu Leu Glu
    115                 120                 125

Gln Met Glu Lys Asn Gly Gly Val Ile Val Asn Met Ala Ser Ile
130                 135                 140

His Gly Ile Val Ala Ala Pro Leu Ser Ser Tyr Thr Ser Ala Lys
145                 150                 155                 160

His Ala Val Val Gly Leu Thr Lys Asn Ile Gly Ala Glu Tyr Gly Gln
            165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
            195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 123
<211> LENGTH: 747
<212> TYPE: DNA
<213> ORGANISM: Artificial sequence
<220> FEATURE:
<223> OTHER INFORMATION: Engineered sequence

<400> SEQUENCE: 123
atgggtatcc tggacaacaa agtcgcactg gttacgggcg ctggtaacgg catcggtctg      60
gcggtggcac actcctacgc taaagaaggc gctaaagtca ttgtgtcaga tatcaacgaa     120
gaccatggta ataaagcggt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatatcgc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat       420 atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgggcccggc ctacattgaa accccgctgc tggaatcact gacgaaagaa     600
atgaaagaag ccctgatctc gaaacacccg atgggtcgcc tggcaaaccc ggaagaagtg     660
gcagaactgg ttctgtttct gagttccgaa aaatcatcgt tcatgaccgg tggctattac     720
ctggtcgatg gtggctacac ggcagtg                                         747

<210> SEQ ID NO 124
<211> LENGTH: 249
<212> TYPE: PRT
<213> ORGANISM: Artificial sequence
<220> FEATURE:
<223> OTHER INFORMATION: Engineered sequence

<400> SEQUENCE: 124

```
Met Gly Ile Leu Asp Asn Lys Val Ala Leu Val Thr Gly Ala Gly Asn
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Ala Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Ile Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Gly Pro Ala Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 125
<211> LENGTH: 747
<212> TYPE: DNA
<213> ORGANISM: Artificial sequence
<220> FEATURE:
<223> OTHER INFORMATION: Engineered sequence

<400> SEQUENCE: 125
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat     420
atggccagca ttcatggtat cgttgcgaag ccgctgagct ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
```

```
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747
```

<210> SEQ ID NO 126
<211> LENGTH: 249
<212> TYPE: PRT
<213> ORGANISM: Artificial sequence
<220> FEATURE:
<223> OTHER INFORMATION: Engineered sequence

<400> SEQUENCE: 126

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Lys Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 127
<211> LENGTH: 747
<212> TYPE: DNA
<213> ORGANISM: Artificial sequence
<220> FEATURE:
<223> OTHER INFORMATION: Engineered sequence

<400> SEQUENCE: 127

```
atgggtatcc tggacaacaa agtcgcactg gttacgggcg ctggttcggg catcggtctg     60
gcggtggcac actcctacgc taagaaaggc gctaaagtca ttgtgtcaga tatcaacgaa    120
gaccatggta ataaaaccgt tgaagatatt aaagcacagg gcggtgaagc tagttttgtg    180
```

```
aaagcggaca ccagcaaccc ggaagaagtg gaagccctgg ttaaacgtac ggtcgaaatt    240
tatggtcgcc tggatgtggc atgcaacaat gctggcattg gcggtgaaaa ggcactggct    300
ggtgattacg gcctggacag ctggcgtaaa gttctgtcta tcaatctgga cggtgtcttc    360
tatggctgta aatacgaact ggaacaaatg gagaaaaacg gcggtggcgt tatcgtcaat    420
atggccagca ttcatggtat cgttgcggcc ccgctgcgct ctgcatatac ctctgcgaaa    480
cacgccgtgg ttggcctgac gaaaaacatt ggtgctgaat atggccagaa aacatccgt    540 tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                       747
```

<210> SEQ ID NO 128
<211> LENGTH: 249
<212> TYPE: PRT
<213> ORGANISM: Artificial sequence
<220> FEATURE:
<223> OTHER INFORMATION: Engineered sequence

<400> SEQUENCE: 128

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Arg Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 129
<211> LENGTH: 747
<212> TYPE: DNA
<213> ORGANISM: Artificial sequence
<220> FEATURE:
<223> OTHER INFORMATION: Engineered sequence

<400> SEQUENCE: 129

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat      420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747
```

<210> SEQ ID NO 130
<211> LENGTH: 249
<212> TYPE: PRT
<213> ORGANISM: Artificial sequence
<220> FEATURE:
<223> OTHER INFORMATION: Engineered sequence

<400> SEQUENCE: 130

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175
```

```
Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Phe Met Thr Gly Tyr Tyr
225                 230                 235                 240

Leu Val Asp Gly Gly Tyr Thr Ala Val
            245
```

<210> SEQ ID NO 131
<211> LENGTH: 747
<212> TYPE: DNA
<213> ORGANISM: Artificial sequence
<220> FEATURE:
<223> OTHER INFORMATION: Engineered sequence

<400> SEQUENCE: 131

| | |
|---|---:|
| atgggtatcc tggacaacaa agtcgcactg gttacgggcg ctggttcggg catcggtctg | 60 |
| gcggtggcac actcctacgc taaagaaggc gctaaagtca ttgtgtcaga tatcaacgaa | 120 |
| gaccatggta ataaaaccgt tgaagatatt aaagcacagg gcggtgaagc tagttttgtg | 180 |
| aaagcggaca ccagcaaccc ggaagaagtg gaagccctgg ttaaacgtac ggtcgaaatt | 240 |
| tatggtcgcc tggatgtggc atgcaacaat gctggcattg gcggtgaaaa ggcactggct | 300 |
| ggtgattacg gcctggacag ctggcgtaaa gttctgtcta tcaatctgga cggtgtcttc | 360 |
| tatggctgta aatacgaact ggaacaaatg gagaaaacg gcggtggcgt tatcgtcaat | 420 |
| atggccagca ttcatggtat cgttgcgcgc ccgctgagct ctgcatatac ctctgcgaaa | 480 |
| cacgccgtgg ttggcctgac gaaaaacatt ggtgctgaat atggccagaa aaacatccgt | 540 |
| tgcaatgcgg tgtgcccggg ctacattgaa accccgctgc tggaatcact gacgaaagaa | 600 |
| atgaaagaag ccctgatctc gaaacacccg atgggtcgcc tgggcaaacc ggaagaagtg | 660 |
| gcagaactgg ttctgtttct gagttccgaa aaatcatcgt tcatgaccgg tggctattac | 720 |
| ctggtcgatg gtggctacac ggcagtg | 747 |

<210> SEQ ID NO 132
<211> LENGTH: 249
<212> TYPE: PRT
<213> ORGANISM: Artificial sequence
<220> FEATURE:
<223> OTHER INFORMATION: Engineered sequence

<400> SEQUENCE: 132

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95
```

```
Lys Ala Leu Ala Gly Asp Tyr Gly Leu Asp Ser Trp Arg Lys Val Leu
                100                 105                 110

Ser Ile Asn Leu Asp Gly Val Phe Tyr Gly Cys Lys Tyr Glu Leu Glu
            115                 120                 125

Gln Met Glu Lys Asn Gly Gly Gly Val Ile Val Asn Met Ala Ser Ile
        130                 135                 140

His Gly Ile Val Ala Arg Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
210                 215                 220

Leu Phe Leu Ser Ser Glu Lys Ser Phe Met Thr Gly Gly Tyr Tyr
225                 230                 235                 240

Leu Val Asp Gly Gly Tyr Thr Ala Val
                245
```

<210> SEQ ID NO 133
<211> LENGTH: 747
<212> TYPE: DNA
<213> ORGANISM: Artificial sequence
<220> FEATURE:
<223> OTHER INFORMATION: Engineered sequence

<400> SEQUENCE: 133

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaaaccgt tgaagatatt aaagcacagg gcggtgaagc tagttttgtg     180
aaagcggaca ccagcaaccc ggaagaagtg aagccctgg ttaaacgtac ggtcgaaatt     240
tatggtcgcc tggatgtggc atgcaacaat gctggcattg cggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat     420
atggccagca ttcatggtat cgttgcgaag ccgctgagct ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                          747
```

<210> SEQ ID NO 134
<211> LENGTH: 249
<212> TYPE: PRT
<213> ORGANISM: Artificial sequence
<220> FEATURE:
<223> OTHER INFORMATION: Engineered sequence

<400> SEQUENCE: 134

```
Met Gly Ile Leu Asp Asn Lys Val Ala Leu Val Thr Gly Ala Gly Ser
1               5                   10                  15
```

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Lys Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

```
<210> SEQ ID NO 135
<211> LENGTH: 747
<212> TYPE: DNA
<213> ORGANISM: Artificial sequence
<220> FEATURE:
<223> OTHER INFORMATION: Engineered sequence

<400> SEQUENCE: 135
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaacg cgcactggct     300
ggtgattacg gcctggacag ctggcgtaaa gttctgtcta tcaatctgga cggtgtcttc     360 tatgctgta  aatacgaact ggaacaaatg gagaaaaacg gcggtggcgt tatcgtcaat     420
atggccagca ttcatggtat cgttgcgaac ccgctgcagt ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tggcaaaacc ggaagaagtg     660
gcagaactgg ttctgtttct gagttccgaa aaatcatcgt tcatgaccgg tggctattac     720
```
ctggtcgatg gtggctacac ggcagtg                                        747

<210> SEQ ID NO 136
<211> LENGTH: 249
<212> TYPE: PRT
<213> ORGANISM: Artificial sequence
<220> FEATURE:
<223> OTHER INFORMATION: Engineered sequence

<400> SEQUENCE: 136

Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
            20                  25                  30
Val Ile Val Ser Asp Ile Asn Glu Asp His Gly Asn Lys Thr Val Glu
        35                  40                  45
Asp Ile Lys Ala Gln Gly Gly Glu Ala Ser Phe Val Lys Ala Asp Thr
    50                  55                  60
Ser Asn Pro Glu Glu Val Glu Ala Leu Val Lys Arg Thr Val Glu Ile
65                  70                  75                  80
Tyr Gly Arg Leu Asp Val Ala Cys Asn Asn Ala Gly Ile Gly Gly Glu
                85                  90                  95
Arg Ala Leu Ala Gly Asp Tyr Gly Leu Asp Ser Trp Arg Lys Val Leu
            100                 105                 110
Ser Ile Asn Leu Asp Gly Val Phe Tyr Gly Cys Lys Tyr Glu Leu Glu
        115                 120                 125
Gln Met Glu Lys Asn Gly Gly Val Ile Val Asn Met Ala Ser Ile
    130                 135                 140
His Gly Ile Val Ala Asn Pro Leu Gln Ser Ala Tyr Thr Ser Ala Lys
145                 150                 155                 160
His Ala Val Val Gly Leu Thr Lys Asn Ile Gly Ala Glu Tyr Gly Gln
                165                 170                 175
Lys Asn Ile Arg Cys Asn Ala Val Cys Pro Gly Tyr Ile Glu Thr Pro
            180                 185                 190
Leu Leu Glu Ser Leu Thr Lys Glu Met Lys Glu Ala Leu Ile Ser Lys
        195                 200                 205
His Pro Met Gly Arg Leu Gly Lys Pro Glu Glu Val Ala Glu Leu Val
    210                 215                 220
Leu Phe Leu Ser Ser Glu Lys Ser Ser Phe Met Thr Gly Gly Tyr Tyr
225                 230                 235                 240
Leu Val Asp Gly Gly Tyr Thr Ala Val
                245

<210> SEQ ID NO 137
<211> LENGTH: 747
<212> TYPE: DNA
<213> ORGANISM: Artificial sequence
<220> FEATURE:
<223> OTHER INFORMATION: Engineered sequence

<400> SEQUENCE: 137
atgggtatcc tggacaacaa agtcgcactg gttacgggcg ctggttcggg catcggtctg    60
gcggtggcac actcctacgc taagaaggc gctaaagtca ttgtgtcaga tatcaacgaa   120
gaccatggta ataaaaccgt tgaagatatt aaagcacagg gcggtgaagc tagttttgtg   180
aaagcggaca ccagcaaccc ggaagaagtg gaagccctgg ttaaacgtac ggtcgaaatt   240
tatggtcgcc tggatgtggc atgcaacaat gctggcattg gcggtgaacg cgcactggct   300

```
ggtgattacg gcctggacag ctggcgtaaa gttctgtcta tcaatctgga cggtgtcttc    360
tatggctgta aatacgaact ggaacaaatg gagaaaaacg gcggtggcgt tatcgtcaat    420
atggccagca ttcatggtat cgttgcggcc ccgctgcagt ctgcatatac ctctgcgaaa    480
cacgccgtgg ttggcctgac gaaaaacatt ggtgctgaat atggccagaa aacatccgt    540 tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747
```

<210> SEQ ID NO 138
<211> LENGTH: 249
<212> TYPE: PRT
<213> ORGANISM: Artificial sequence
<220> FEATURE:
<223> OTHER INFORMATION: Engineered sequence

<400> SEQUENCE: 138

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Arg Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Gln Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 139
<211> LENGTH: 747
<212> TYPE: DNA

<213> ORGANISM: Artificial sequence
<220> FEATURE:
<223> OTHER INFORMATION: Engineered sequence

<400> SEQUENCE: 139

| | | | | | |
|---|---|---|---|---|---|
| atgggtatcc | tggacaacaa | agtcgcactg | gttacgggcg | ctggttcggg | catcggtctg | 60 |
| gcggtggcac | actcctacgc | taaagaaggc | gctaaagtca | ttgtgtcaga | tatcaacgaa | 120 |
| gaccatggta | taaaaaccgt | tgaagatatt | aaagcacagg | gcggtgaagc | tagttttgtg | 180 |
| aaagcggaca | ccagcaaccc | ggaagaagtg | gaagccctgg | ttaaacgtac | ggtcgaaatt | 240 |
| tatggtcgcc | tggatgtggc | atgcaacaat | gctggcattg | gcggtgaaaa | ggcactggct | 300 |
| ggtgattacg | gcctggacag | ctggcgtaaa | gttctgtcta | tcaatctgga | cggtgtcttc | 360 |
| tatggctgta | atacgaact | ggaacaaatg | gagaaaaacg | gcggtggcgt | tatcgtcaat | 420 |
| atggccagca | ttcatggtat | cgttgcggcc | ccgctgcagt | ctgcatatac | ctctgcgaaa | 480 |
| cacgccgtgg | ttggcctgac | gaaaaacatt | ggtgctgaat | atggccagaa | aaacatccgt | 540 |
| tgcaatgcgg | tgtgcccggg | ctacattgaa | acccgctgc | tggaatcact | gacgaaagaa | 600 |
| atgaaagaag | ccctgatctc | gaaacacccg | atgggtcgcc | tgggcaaacc | ggaagaagtg | 660 |
| gcagaactgg | ttctgtttct | gagttccgaa | aaatcatcgt | tcatgaccgg | tggctattac | 720 |
| ctggtcgatg | gtggctacac | ggcagtg | | | | 747 |

<210> SEQ ID NO 140
<211> LENGTH: 249
<212> TYPE: PRT
<213> ORGANISM: Artificial sequence
<220> FEATURE:
<223> OTHER INFORMATION: Engineered sequence

<400> SEQUENCE: 140

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Gln Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys

```
                195                 200                 205
His Pro Met Gly Arg Leu Gly Lys Pro Glu Glu Val Ala Glu Leu Val
    210                 215                 220

Leu Phe Leu Ser Ser Glu Lys Ser Phe Met Thr Gly Gly Tyr Tyr
225                 230                 235                 240

Leu Val Asp Gly Gly Tyr Thr Ala Val
                245
```

<210> SEQ ID NO 141
<211> LENGTH: 747
<212> TYPE: DNA
<213> ORGANISM: Artificial sequence
<220> FEATURE:
<223> OTHER INFORMATION: Engineered sequence

<400> SEQUENCE: 141

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatgtggc atgcaacaat gctggcattg gcggtgaaaa ggcactggct     300
ggtgattacg gcctggacag ctggcgtaaa gttctgtcta tcaatctgga cggtgtcttc     360
tatggctgta atacgaact ggaacaaatg gagaaaacg gcggtggcgt tatcgtcaat       420
atggccagca ttcatggtat cgttgcgcag ccgctgaact ctgcatatac ctctgcgaaa     480
cacgccgtgg ttggcctgac gaaaaacatt ggtgctgaat atggccagaa aacatccgt      540
tgcaatgcgg tgtgcccggg ctacattgaa accccgctgc tggaatcact gacgaaagaa     600
atgaaagaag ccctgatctc gaaacaccg atgggtcgcc tgggcaaacc ggaagaagtg      660
gcagaactgg ttctgtttct gagttccgaa aaatcatcgt tcatgaccgg tggctattac     720
ctggtcgatg gtggctacac ggcagtg                                        747
```

<210> SEQ ID NO 142
<211> LENGTH: 249
<212> TYPE: PRT
<213> ORGANISM: Artificial sequence
<220> FEATURE:
<223> OTHER INFORMATION: Engineered sequence

<400> SEQUENCE: 142

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
            85                  90                  95

Lys Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
```

```
                115                 120                 125
Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245
```

<210> SEQ ID NO 143
<211> LENGTH: 747
<212> TYPE: DNA
<213> ORGANISM: Artificial sequence
<220> FEATURE:
<223> OTHER INFORMATION: Engineered sequence

<400> SEQUENCE: 143

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaaaccgt tgaagatatt aaagcacagg gcggtgaagc tagttttgtg     180
aaagcggaca ccagcaaccc ggaagaagtg aagccctgg ttaaacgtac ggtcgaaatt     240
tatggtcgcc tggatgtggc atgcaacaat gctggcattg cggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat     420
atggccagca ttcatggtat cgttgcggcc ccgctgcagt ctgcatatac ctctgcgaaa     480
cacgccgtgg ttggcctgac gaaaaacatt ggtgctgaat atggccagaa aacatccgt     540
tgcaatgcgg tgtgcccggg ctacattgaa accccgctgc tggaatcact gacgaaagaa     600
atgaaagaag ccctgatctc gaaacaccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747
```

<210> SEQ ID NO 144
<211> LENGTH: 249
<212> TYPE: PRT
<213> ORGANISM: Artificial sequence
<220> FEATURE:
<223> OTHER INFORMATION: Engineered sequence

<400> SEQUENCE: 144

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
```

```
                35                  40                  45
Asp Ile Lys Ala Gln Gly Gly Glu Ala Ser Phe Val Lys Ala Asp Thr
 50                  55                  60
Ser Asn Pro Glu Glu Val Glu Ala Leu Val Lys Arg Thr Val Glu Ile
 65                  70                  75                  80
Tyr Gly Arg Leu Asp Val Ala Cys Asn Asn Ala Gly Ile Gly Gly Glu
                 85                  90                  95
Gln Ala Leu Ala Gly Asp Tyr Gly Leu Asp Ser Trp Arg Lys Val Leu
            100                 105                 110
Ser Ile Asn Leu Asp Gly Val Phe Tyr Gly Cys Lys Tyr Glu Leu Glu
            115                 120                 125
Gln Met Glu Lys Asn Gly Gly Val Ile Val Asn Met Ala Ser Ile
        130                 135                 140
His Gly Ile Val Ala Ala Pro Leu Gln Ser Ala Tyr Thr Ser Ala Lys
145                 150                 155                 160
His Ala Val Val Gly Leu Thr Lys Asn Ile Gly Ala Glu Tyr Gly Gln
                165                 170                 175
Lys Asn Ile Arg Cys Asn Ala Val Cys Pro Gly Tyr Ile Glu Thr Pro
            180                 185                 190
Leu Leu Glu Ser Leu Thr Lys Glu Met Lys Glu Ala Leu Ile Ser Lys
            195                 200                 205
His Pro Met Gly Arg Leu Gly Lys Pro Glu Val Ala Glu Leu Val
210                 215                 220
Leu Phe Leu Ser Ser Glu Lys Ser Ser Phe Met Thr Gly Gly Tyr Tyr
225                 230                 235                 240
Leu Val Asp Gly Gly Tyr Thr Ala Val
            245

<210> SEQ ID NO 145
<211> LENGTH: 747
<212> TYPE: DNA
<213> ORGANISM: Artificial sequence
<220> FEATURE:
<223> OTHER INFORMATION: Engineered sequence

<400> SEQUENCE: 145
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaaaccgt tgaagatatt aaagcacagg cggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat     420
atggccagca ttcatggtat cgttgcgaag ccgctgaact ctgcatatac ctctgcgaaa     480
cacgccgtgg ttggcctgac gaaaaacatt ggtgctgaat atggccagaa aacatccgt     540
tgcaatgcgg tgtgcccggg ctacattgaa ccccgctgc tggaatcact gacgaaagaa     600
atgaaagaag ccctgatctc gaaacacccg atgggtcgcc tggcaaaacc ggaagaagtg     660
gcagaactgg ttctgtttct gagttccgaa aaatcatcgt tcatgaccgg tggctattac     720
ctggtcgatg gtggctacac ggcagtg                                         747

<210> SEQ ID NO 146
```

<211> LENGTH: 249
<212> TYPE: PRT
<213> ORGANISM: Artificial sequence
<220> FEATURE:
<223> OTHER INFORMATION: Engineered sequence

<400> SEQUENCE: 146

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Lys Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 147
<211> LENGTH: 747
<212> TYPE: DNA
<213> ORGANISM: Artificial sequence
<220> FEATURE:
<223> OTHER INFORMATION: Engineered sequence

<400> SEQUENCE: 147

```
atgggtatcc tggacaacaa agtcgcactg gttacgggcg ctggttcggg catcggtctg    60
gcggtggcac actcctacgc taaagaaggc gctaaagtca ttgtgtcaga tatcaacgaa   120
gaccatggta taaaaccgt tgaagatatt aaagcacagg gcggtgaagc tagttttgtg   180
aaagcggaca ccagcaaccc ggaagaagtg gaagccctgg ttaaacgtac ggtcgaaatt   240
tatggtcgcc tggatgtggc atgcaacaat gctggcattg gcggtgaaca ggcactggct   300
ggtgattacg gcctgacag ctggcgtaaa gttctgtcta tcaatctgga cggtgtcttc   360
tatggctgta aatacgaact ggaacaaatg gagaaaaacg gcggtggcgt tatcgtcaat   420
```

```
atggccagca ttcatggtat cgttgcggcc ccgctgagct ctgcatatac ctctgcgaaa      480
cacgccgtgg ttggcctgac gaaaaacatt ggtgctgaat atggccagaa aaacatccgt      540
tgcaatgcgg tggcgccggg ctacattgaa accccgctgc tggaatcact gacgaaagaa      600
atgaaagaag ccctgatctc gaaacacccg atgggtcgcc tgggcaaacc ggaagaagtg      660
gcagaactgg ttctgttcct gagttccgaa aaatcatcgt tcatgaccgg tggctcttac      720
ctggtcgatg gtggctacac ggcagtg                                          747
```

<210> SEQ ID NO 148
<211> LENGTH: 249
<212> TYPE: PRT
<213> ORGANISM: Artificial sequence
<220> FEATURE:
<223> OTHER INFORMATION: Engineered sequence

<400> SEQUENCE: 148

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Ala Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Ser Tyr
225                 230                 235                 240

Leu Val Asp Gly Gly Tyr Thr Ala Val
                245
```

<210> SEQ ID NO 149
<211> LENGTH: 747
<212> TYPE: DNA
<213> ORGANISM: Artificial sequence
<220> FEATURE:
<223> OTHER INFORMATION: Engineered sequence

<400> SEQUENCE: 149

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa    120
gaccatggta ataaaaccgt tgaagatatt aaagcacagg gcggtgaagc tagttttgtg    180
aaagcggaca ccagcaaccc ggaagaagtg aaagccctgg ttaaacgtac ggtcgaaatt    240
tatggtcgcc tggatgtggc atgcaacaat gctggcattg gcggtgaaca ggcactggct    300
ggtgattacg gcctggacag ctggcgtaaa gttctgtcta tcaatctgga cggtgtcttc    360
tatggctgta atacgaact ggaacaaatg gagaaaaacg gcggtggcgt tatcgtcaat    420
atggccagca ttcatggtat cgttgcggcc ccgctgagct ctgcatatac ctctgcgaaa    480
cacgccgtgg ttggcctgac gaaaaacatt ggtgctgaat atggccagaa aaacatccgt    540
tgcaatgcgg tggcgccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggcgattac    720
ctggtcgatg gtggctacac ggcagtg                                       747
```

<210> SEQ ID NO 150
<211> LENGTH: 249
<212> TYPE: PRT
<213> ORGANISM: Artificial sequence
<220> FEATURE:
<223> OTHER INFORMATION: Engineered sequence

<400> SEQUENCE: 150

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Ala Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220
```

Leu Phe Leu Ser Ser Glu Lys Ser Ser Phe Met Thr Gly Gly Asp Tyr
225                 230                 235                 240

Leu Val Asp Gly Gly Tyr Thr Ala Val
            245

<210> SEQ ID NO 151
<211> LENGTH: 747
<212> TYPE: DNA
<213> ORGANISM: Artificial sequence
<220> FEATURE:
<223> OTHER INFORMATION: Engineered sequence

<400> SEQUENCE: 151

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatggctgta atacgaact  ggaacaaatg gagaaaaacg gcggtggcgt tatcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aacatccgt      540
tgcaatgcgg tggcgccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggcacttac     720
ctggtcgatg gtggctacac ggcagtg                                         747
```

<210> SEQ ID NO 152
<211> LENGTH: 249
<212> TYPE: PRT
<213> ORGANISM: Artificial sequence
<220> FEATURE:
<223> OTHER INFORMATION: Engineered sequence

<400> SEQUENCE: 152

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Tyr Thr Ser Ala Lys
145                 150                 155                 160

His Ala Val Val Gly Leu Thr Lys Asn Ile Gly Ala Glu Tyr Gly Gln
            165                 170                 175

Lys Asn Ile Arg Cys Asn Ala Val Ala Pro Gly Tyr Ile Glu Thr Pro
        180                 185                 190

Leu Leu Glu Ser Leu Thr Lys Glu Met Lys Glu Ala Leu Ile Ser Lys
    195                 200                 205

His Pro Met Gly Arg Leu Gly Lys Pro Glu Glu Val Ala Glu Leu Val
210                 215                 220

Leu Phe Leu Ser Ser Glu Lys Ser Ser Phe Met Thr Gly Gly Thr Tyr
225                 230                 235                 240

Leu Val Asp Gly Gly Tyr Thr Ala Val
            245

<210> SEQ ID NO 153
<211> LENGTH: 747
<212> TYPE: DNA
<213> ORGANISM: Artificial sequence
<220> FEATURE:
<223> OTHER INFORMATION: Engineered sequence

<400> SEQUENCE: 153
atgggtatcc tggacaacaa agtcgcactg gttacgggcg ctggttcggg catcggtctg     60
gcggtggcac actcctacgc taaagaaggc gctaaagtca ttgtgtcaga tatcaacgaa    120
gaccatggta taaaaccgt tgaagatatt aaagcacagg gcggtgaagc tagttttgtg    180
aaagcggaca ccagcaaccc ggaagaagtg aagccctgg ttaaacgtac ggtcgaaatt    240
tatggtcgcc tggatgtggc atgcaacaat gctggcattg cggtgaaca ggcactggct    300 ggtgattacg gcctggacag ctggcgtaaa gttctgtcta tcaatctgga cggtgtcttc    360
tatggctgta atacgaact ggaacaaatg gagaaaaacg gcggtggcgt atcgtcaat    420 atggccagca ttcatggtat cgttgcggcc ccgctgagct ctgcatatac ctctgcgaaa    480
cacgccgtgg ttggcctgac gaaaaacatt ggtgctgaat atggccagaa aaacatccgt    540
tgcaatgcgg tggcgccggg ctacattgaa accccgctgc tggaatcact gacgaaagaa    600
atgaaagaag ccctgatctc gaaacaccg atgggtcgcc tgggcaaacc ggaagaagtg    660
gcagaactgg ttctgttttct gagttccgaa aaatcatcgt tcatgaccgg tggcccgtac    720
ctggtcgatg gtggctacac ggcagtg                                        747

<210> SEQ ID NO 154
<211> LENGTH: 249
<212> TYPE: PRT
<213> ORGANISM: Artificial sequence
<220> FEATURE:
<223> OTHER INFORMATION: Engineered sequence

<400> SEQUENCE: 154

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Ala Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Pro Tyr
225                 230                 235                 240

Leu Val Asp Gly Gly Tyr Thr Ala Val
                245

<210> SEQ ID NO 155
<211> LENGTH: 747
<212> TYPE: DNA
<213> ORGANISM: Artificial sequence
<220> FEATURE:
<223> OTHER INFORMATION: Engineered sequence

<400> SEQUENCE: 155
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacccgggta ataaaaccgt tgaagatatt aaagcacagg cggtgaagc tagttttgtg     180 aaagcggaca ccagcaaccc ggaagaagtg gaagccctgg ttaaacgtac ggtcgaaatt     240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat     420 atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa acccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                          747

<210> SEQ ID NO 156
<211> LENGTH: 249
<212> TYPE: PRT
<213> ORGANISM: Artificial sequence
<220> FEATURE:

<223> OTHER INFORMATION: Engineered sequence

<400> SEQUENCE: 156

| | | | | | | | | | | | | | | | |
|---|---|---|---|---|---|---|---|---|---|---|---|---|---|---|---|
| Met | Gly | Ile | Leu | Asp | Asn | Lys | Val | Ala | Leu | Val | Thr | Gly | Ala | Gly | Ser |
| 1 | | | | 5 | | | | | 10 | | | | | 15 | |
| Gly | Ile | Gly | Leu | Ala | Val | Ala | His | Ser | Tyr | Ala | Lys | Glu | Gly | Ala | Lys |
| | | | 20 | | | | | 25 | | | | | 30 | | |
| Val | Ile | Val | Ser | Asp | Ile | Asn | Glu | Asp | Pro | Gly | Asn | Lys | Thr | Val | Glu |
| | | | 35 | | | | | 40 | | | | | 45 | | |
| Asp | Ile | Lys | Ala | Gln | Gly | Gly | Glu | Ala | Ser | Phe | Val | Lys | Ala | Asp | Thr |
| | 50 | | | | | 55 | | | | | 60 | | | | |
| Ser | Asn | Pro | Glu | Glu | Val | Glu | Ala | Leu | Val | Lys | Arg | Thr | Val | Glu | Ile |
| 65 | | | | | 70 | | | | | 75 | | | | | 80 |
| Tyr | Gly | Arg | Leu | Asp | Val | Ala | Cys | Asn | Asn | Ala | Gly | Ile | Gly | Gly | Glu |
| | | | | 85 | | | | | 90 | | | | | 95 | |
| Gln | Ala | Leu | Ala | Gly | Asp | Tyr | Gly | Leu | Asp | Ser | Trp | Arg | Lys | Val | Leu |
| | | | 100 | | | | | 105 | | | | | 110 | | |
| Ser | Ile | Asn | Leu | Asp | Gly | Val | Phe | Tyr | Gly | Cys | Lys | Tyr | Glu | Leu | Glu |
| | | | 115 | | | | | 120 | | | | | 125 | | |
| Gln | Met | Glu | Lys | Asn | Gly | Gly | Val | Ile | Val | Asn | Met | Ala | Ser | Ile |
| | 130 | | | | | 135 | | | | | 140 | | | |
| His | Gly | Ile | Val | Ala | Ala | Pro | Leu | Ser | Ser | Ala | Tyr | Thr | Ser | Ala | Lys |
| 145 | | | | | 150 | | | | | 155 | | | | | 160 |
| His | Ala | Val | Val | Gly | Leu | Thr | Lys | Asn | Ile | Gly | Ala | Glu | Tyr | Gly | Gln |
| | | | | 165 | | | | | 170 | | | | | 175 | |
| Lys | Asn | Ile | Arg | Cys | Asn | Ala | Val | Cys | Pro | Gly | Tyr | Ile | Glu | Thr | Pro |
| | | | 180 | | | | | 185 | | | | | 190 | | |
| Leu | Leu | Glu | Ser | Leu | Thr | Lys | Glu | Met | Lys | Glu | Ala | Leu | Ile | Ser | Lys |
| | | | 195 | | | | | 200 | | | | | 205 | | |
| His | Pro | Met | Gly | Arg | Leu | Gly | Lys | Pro | Glu | Glu | Val | Ala | Glu | Leu | Val |
| | 210 | | | | | 215 | | | | | 220 | | | | |
| Leu | Phe | Leu | Ser | Ser | Glu | Lys | Ser | Ser | Phe | Met | Thr | Gly | Gly | Tyr | Tyr |
| 225 | | | | | 230 | | | | | 235 | | | | | 240 |
| Leu | Val | Asp | Gly | Gly | Tyr | Thr | Ala | Val |
| | | | | 245 | | | | |

<210> SEQ ID NO 157
<211> LENGTH: 747
<212> TYPE: DNA
<213> ORGANISM: Artificial sequence
<220> FEATURE:
<223> OTHER INFORMATION: Engineered sequence

<400> SEQUENCE: 157

| | | |
|---|---|---|
| atgggtatcc tggacaacaa agtcgcactg gttacgggcg ctggttcggg catcggtctg | 60 |
| gcggtggcac actcctacgc taaagaaggc gctaaagtca ttgtgtcaga tgtgaacgaa | 120 |
| gacaagggta ataaaaccgt tgaagatatt aaagcacagg gcggtgaagc tagttttgtg | 180 |
| aaagcggaca ccagcaaccc ggaagaagtg gaagccctgg ttaaacgtac ggtcgaaatt | 240 |
| tatggtcgcc tggatgtggc atgcaacaat gctggcattg gcggtgaaca ggcactggct | 300 |
| ggtgattacg gcctggacag ctggcgtaaa gttctgtcta tcaatctgga cggtgtcttc | 360 |
| tatggctgta aatacgaact ggaacaaatg gagaaaaacg gcggtggcgt tatcgtcaat | 420 |
| atggccagca ttcatggtat cgttgcggcc ccgctgagct ctgcatatac ctctgcgaaa | 480 |
| cacgccgtgg ttggcctgac gaaaaacatt ggtgctgaat atggccagaa aaacatccgt | 540 |

```
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747
```

```
<210> SEQ ID NO 158
<211> LENGTH: 249
<212> TYPE: PRT
<213> ORGANISM: Artificial sequence
<220> FEATURE:
<223> OTHER INFORMATION: Engineered sequence

<400> SEQUENCE: 158
```

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
                20                  25                  30

Val Ile Val Ser Asp Val Asn Glu Asp Lys Gly Asn Lys Thr Val Glu
            35                  40                  45

Asp Ile Lys Ala Gln Gly Gly Glu Ala Ser Phe Val Lys Ala Asp Thr
        50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

```
<210> SEQ ID NO 159
<211> LENGTH: 747
<212> TYPE: DNA
<213> ORGANISM: Artificial sequence
<220> FEATURE:
<223> OTHER INFORMATION: Engineered sequence

<400> SEQUENCE: 159
atgggtatcc tggacaacaa agtcgcactg gttacgggcg ctggttcggg catcggtctg    60
```

```
gcggtggcac actcctacgc taaagaaggc gctaaagtca ttgtgtcaga tatcaacgaa    120
gaccgcggta ataaaaccgt tgaagatatt aaagcacagg gcggtgaagc tagttttgtg    180
aaagcggaca ccagcaaccc ggaagaagtg aagccctgg ttaaacgtac ggtcgaaatt     240
tatggtcgcc tggatgtggc atgcaacaat gctggcattg gcggtgaaca ggcactggct    300
ggtgattacg gcctggacag ctggcgtaaa gttctgtcta tcaatctgga cggtgtcttc    360
tatggctgta atacgaact ggaacaaatg gagaaaaacg gcggtggcgt tatcgtcaat     420
atggccagca ttcatggtat cgttgcggcc ccgctgagct ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgttttct gagttccgaa aaatcatcgt tcatgaccgg tggctattac   720
ctggtcgatg gtggctacac ggcagtg                                        747
```

<210> SEQ ID NO 160
<211> LENGTH: 249
<212> TYPE: PRT
<213> ORGANISM: Artificial sequence
<220> FEATURE:
<223> OTHER INFORMATION: Engineered sequence

<400> SEQUENCE: 160

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Arg Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Phe Met Thr Gly Gly Tyr Tyr
225                 230                 235                 240
```

Leu Val Asp Gly Gly Tyr Thr Ala Val
              245

<210> SEQ ID NO 161
<211> LENGTH: 747
<212> TYPE: DNA
<213> ORGANISM: Artificial sequence
<220> FEATURE:
<223> OTHER INFORMATION: Engineered sequence

<400> SEQUENCE: 161

| | | | | | |
|---|---|---|---|---|---|
| atgggtatcc | tggacaacaa | agtcgcactg | gttacgggcg | ctggttcggg | catcggtctg | 60 |
| gcggtggcac | actcctacgc | taaagaaggc | gctaaagtca | ttgtgtcaga | tatcaacgaa | 120 |
| gacaccggta | ataaaaccgt | tgaagatatt | aaagcacagg | gcggtgaagc | tagttttgtg | 180 |
| aaagcggaca | ccagcaaccc | ggaagaagtg | gaagccctgg | ttaaacgtac | ggtcgaaatt | 240 |
| tatggtcgcc | tggatgtggc | atgcaacaat | gctggcattg | gcggtgaaca | ggcactggct | 300 |
| ggtgattacg | gcctggacag | ctggcgtaaa | gttctgtcta | tcaatctgga | cggtgtcttc | 360 |
| tatggctgta | aatacgaact | ggaacaaatg | gagaaaaacg | gcggtggcgt | tatcgtcaat | 420 |
| atggccagca | ttcatggtat | cgttgcggcc | ccgctgagct | ctgcatatac | ctctgcgaaa | 480 |
| cacgccgtgg | ttggcctgac | gaaaaacatt | ggtgctgaat | atggccagaa | aaacatccgt | 540 |
| tgcaatgcgg | tgtgcccggg | ctacattgaa | accccgctgc | tggaatcact | gacgaaagaa | 600 |
| atgaaagaag | ccctgatctc | gaaacacccg | atgggtcgcc | tgggcaaacc | ggaagaagtg | 660 |
| gcagaactgg | ttctgtttct | gagttccgaa | aaatcatcgt | tcatgaccgg | tggctattac | 720 |
| ctggtcgatg | gtggctacac | ggcagtg | | | | 747 |

<210> SEQ ID NO 162
<211> LENGTH: 249
<212> TYPE: PRT
<213> ORGANISM: Artificial sequence
<220> FEATURE:
<223> OTHER INFORMATION: Engineered sequence

<400> SEQUENCE: 162

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Thr Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

```
His Ala Val Val Gly Leu Thr Lys Asn Ile Gly Ala Glu Tyr Gly Gln
            165                 170                 175

Lys Asn Ile Arg Cys Asn Ala Val Cys Pro Gly Tyr Ile Glu Thr Pro
        180                 185                 190

Leu Leu Glu Ser Leu Thr Lys Glu Met Lys Glu Ala Leu Ile Ser Lys
            195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245
```

<210> SEQ ID NO 163
<211> LENGTH: 747
<212> TYPE: DNA
<213> ORGANISM: Artificial sequence
<220> FEATURE:
<223> OTHER INFORMATION: Engineered sequence

<400> SEQUENCE: 163

```
atgggtatcc tggacaacaa agtcgcactg gttacgggcg ctggttcggg catcggtctg    60
gcggtggcac actcctacgc taaagaaggc gctaaagtca ttgtgtcaga tatcagcgaa   120
gacaagggta taaaaccgt tgaagatatt aaagcacagg gcggtgaagc tagttttgtg   180
aaagcggaca ccagcaaccc ggaagaagtg gaagccctgg ttaaacgtac ggtcgaaatt   240
tatggtcgcc tggatgtggc atgcaacaat gctggcattg cggtgaaca ggcactggct   300
ggtgattacg gcctggacag ctggcgtaaa gttctgtcta tcaatctgga cggtgtcttc   360
tatggctgta atacgaact ggaacaaatg gagaaaaacg gcggtggcgt tatcgtcaat   420
atggccagca ttcatggtat cgttgcggcc ccgctgagct tgcatatac ctctgcgaaa   480
cacgccgtgg ttggcctgac gaaaaacatt ggtgctgaat atggccagaa aaacatccgt   540
tgcaatgcgg tgtgcccggg ctacattgaa accccgctgc tggaatcact gacgaaagaa   600
atgaaagaag ccctgatctc gaaacacccg atgggtcgcc tgggcaaacc ggaagaagtg   660
gcagaactgg ttctgtttct gagttccgaa aaatcatcgt tcatgaccgg tggctattac   720
ctggtcgatg gtggctacac ggcagtg                                      747
```

<210> SEQ ID NO 164
<211> LENGTH: 249
<212> TYPE: PRT
<213> ORGANISM: Artificial sequence
<220> FEATURE:
<223> OTHER INFORMATION: Engineered sequence

<400> SEQUENCE: 164

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Ser Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80
```

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 165
<211> LENGTH: 747
<212> TYPE: DNA
<213> ORGANISM: Artificial sequence
<220> FEATURE:
<223> OTHER INFORMATION: Engineered sequence

<400> SEQUENCE: 165
atgggtatcc tggacaacaa agtcgcactg gttacgggcg ctggttcggg catcggtctg      60
gcggtggcac actcctacgc taaagaaggc gctaaagtca ttgtgtcaga tcgcaacgaa     120
gaccatggta ataaaaccgt tgaagatatt aaagcacagg cggtgaagc tagttttgtg     180 aaagcggaca ccagcaaccc ggaagaagtg gaagccctgg ttaaacgtac ggtcgaaatt     240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgttcct gagttccgaa aaatcatcgt tcatgaccgg tggctattac     720
ctggtcgatg gtggctacac ggcagtg                                         747

<210> SEQ ID NO 166
<211> LENGTH: 249
<212> TYPE: PRT
<213> ORGANISM: Artificial sequence
<220> FEATURE:
<223> OTHER INFORMATION: Engineered sequence

<400> SEQUENCE: 166

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Arg Asn Glu Asp His Gly Asn Lys Thr Val Glu
            35                  40                  45

Asp Ile Lys Ala Gln Gly Gly Glu Ala Ser Phe Val Lys Ala Asp Thr
        50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
            130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 167
<211> LENGTH: 747
<212> TYPE: DNA
<213> ORGANISM: Artificial sequence
<220> FEATURE:
<223> OTHER INFORMATION: Engineered sequence

<400> SEQUENCE: 167
atgggtatcc tggacaacaa agtcgcactg gttacgggcg ctggttcggg catcggtctg     60
gcggtggcac actcctacgc taaagaaggc gctaaagtca ttgtgtcaga tatcaacgaa    120
gacaagggta ataaaaccgt tgaagatatt aaagcacagg gcggtgaagc tagttttgtg    180
aaagcggaca ccagcaaccc ggaagaagtg gaagccctgg ttaaacgtac ggtcgaaatt    240
tatggtcgcc tggatgtggc atgcaacaat gctggcattg gcggtgaaca ggcactggct    300
ggtgattacg gcctggacag ctggcgtaaa gttctgtcta tcaatctgga cggtgtcttc    360
tatggctgta aatacgaact ggaacaaatg gagaaaaacg gcggtggcgt atcgtcaat    420 atggccagca ttcatggtat cgttgcggcc ccgctgagct ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa acccgctgc tggaatcact gacgaaagaa    600
atgaaagaag ccctgatctc gaaacaccag atgggtcgcc tgggcaaacc ggaagaagtg    660

```
gcagaactgg ttctgtttct gagttccgaa aaatcatcgt tcatgaccgg tggctattac    720
ctggtcgatg gtggctacac ggcagtg                                        747
```

<210> SEQ ID NO 168
<211> LENGTH: 249
<212> TYPE: PRT
<213> ORGANISM: Artificial sequence
<220> FEATURE:
<223> OTHER INFORMATION: Engineered sequence

<400> SEQUENCE: 168

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 169
<211> LENGTH: 747
<212> TYPE: DNA
<213> ORGANISM: Artificial sequence
<220> FEATURE:
<223> OTHER INFORMATION: Engineered sequence

<400> SEQUENCE: 169

```
atgggtatcc tggacaacaa agtcgcactg gttacgggcg ctggttcggg catcggtctg    60
gcggtggcac actcctacgc taaagaaggc gctaaagtca ttgtgtcaga tcgcaacgaa   120
gacaccggta ataaaaccgt tgaagatatt aaagcacagg gcggtgaagc tagttttgtg   180
```

-continued

```
aaagcggaca ccagcaaccc ggaagaagtg gaagccctgg ttaaacgtac ggtcgaaatt    240
tatggtcgcc tggatgtggc atgcaacaat gctggcattg cggtgaaca ggcactggct     300 ggtgattacg gcctggacag ctggcgtaaa gttctgtcta tcaatctgga cggtgtcttc    360
tatggctgta atacgaact ggaacaaatg gagaaaaacg gcggtggcgt tatcgtcaat     420
atggccagca ttcatggtat cgttgcggcc ccgctgagct ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgttttct gagttccgaa aaatcatcgt tcatgaccgg tggctattac    720
ctggtcgatg gtggctacac ggcagtg                                        747
```

<210> SEQ ID NO 170
<211> LENGTH: 249
<212> TYPE: PRT
<213> ORGANISM: Artificial sequence
<220> FEATURE:
<223> OTHER INFORMATION: Engineered sequence

<400> SEQUENCE: 170

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Arg Asn Glu Asp Thr Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 171
<211> LENGTH: 747
<212> TYPE: DNA
<213> ORGANISM: Artificial sequence
<220> FEATURE:
<223> OTHER INFORMATION: Engineered sequence

<400> SEQUENCE: 171

```
atgggtatcc tggacaacaa agtcgcactg gttacgggcg ctggttcggg catcggtctg      60
gcggtggcac actcctacgc taaagaaggc gctaaagtca ttgtgtcaga tcgcaacgaa     120
gacagcggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat     420
atggccagca ttcatggtat cgttgcggcc ccgctgagct ctgcatatac ctctgcgaaa     480
cacgccgtgg ttggcctgac gaaaaacatt ggtgctgaat atggccagaa aacatccgt     540
tgcaatgcgg tgtgcccggg ctacattgaa accccgctgc tggaatcact gacgaaagaa     600
atgaaagaag ccctgatctc gaaacaccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                        747
```

<210> SEQ ID NO 172
<211> LENGTH: 249
<212> TYPE: PRT
<213> ORGANISM: Artificial sequence
<220> FEATURE:
<223> OTHER INFORMATION: Engineered sequence

<400> SEQUENCE: 172

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Arg Asn Glu Asp Ser Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro

```
                180               185               190
Leu Leu Glu Ser Leu Thr Lys Glu Met Lys Glu Ala Leu Ile Ser Lys
            195                 200                 205

His Pro Met Gly Arg Leu Gly Lys Pro Glu Glu Val Ala Glu Leu Val
        210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 173
<211> LENGTH: 747
<212> TYPE: DNA
<213> ORGANISM: Artificial sequence
<220> FEATURE:
<223> OTHER INFORMATION: Engineered sequence

<400> SEQUENCE: 173
atgggtatcc tggacaacaa agtcgcactg gttacgggcg ctggttcggg catcggtctg      60
gcggtggcac actcctacgc taaagaaggc gctaaagtca ttgtgtcaga tatcagcgaa     120
gaccatggta taaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatgtggc atgcaacaat gctggcattg gcggtgaaca ggcactggct     300
ggtgattacg gcctggacag ctggcgtaaa gttctgtcta tcaatctgga cggtgtcttc     360
tatggctgta aatacgaact ggaacaaatg gagaaaaacg gcggtggcgt atcgtcaat     420 atggccagca ttcatggtat cgttgcggcc ccgctgagct ctgcatatac ctctgcgaaa     480
cacgccgtgg ttggcctgac gaaaaacatt ggtgctgaat atggccagaa aacatccgt     540 tgcaatgcgg tgtgcccggg ctacattgaa accccgctgc tggaatcact gacgaaagaa     600
atgaaagaag ccctgatctc gaaacaccg atgggtcgcc tggcaaaacc ggaagaagtg      660
gcagaactgg ttctgtttct gagttccgaa aaatcatcgt tcatgaccgg tggctattac     720
ctggtcgatg gtggctacac ggcagtg                                          747

<210> SEQ ID NO 174
<211> LENGTH: 249
<212> TYPE: PRT
<213> ORGANISM: Artificial sequence
<220> FEATURE:
<223> OTHER INFORMATION: Engineered sequence

<400> SEQUENCE: 174

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Ser Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
```

```
              100                 105                 110
Ser Ile Asn Leu Asp Gly Val Phe Tyr Gly Cys Lys Tyr Glu Leu Glu
            115                 120                 125

Gln Met Glu Lys Asn Gly Gly Val Ile Val Asn Met Ala Ser Ile
        130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 175
<211> LENGTH: 747
<212> TYPE: DNA
<213> ORGANISM: Artificial sequence
<220> FEATURE:
<223> OTHER INFORMATION: Engineered sequence

<400> SEQUENCE: 175

```
atgggtatcc tggacaacaa agtcgcactg gttacgggcg ctggttcggg catcggtctg    60
gcggtggcac actcctacgc taaagaaggc gctaaagtca ttgtgtcaga tatcaacgaa   120
gaccatggta taaaaccgt tgaagatatt aaagcacagg gcggtgaagc tagttttgtg    180
aaagcggaca ccagcaaccc ggaagaagtg aaagccctgg ttaaacgtac ggtcgaaatt   240
tatggtcgcc tggatgtggc atgcaacaat gctggcattg cggtgaaaca ggcactggct   300
ggtgattacg gcctggacag ctggcgtaaa gttctgtcta tcaatctgga cggtgtcttc   360
tatggctgta atacgaact ggaacaaatg gagaaaaacg gcggtggcgt tatcgtcaat    420
aacgccagca ttcatggtat cgttgcggcc ccgctgagct ctgcatatac ctctgcgaaa   480
cacgccgtgg ttggcctgac gaaaaacatt ggtgctgaat atggccagaa aaacatccgt   540
tgcaatgcgg tgtgcccggg ctacattgaa accccgctgc tggaatcact gacgaaagaa   600
atgaaagaag ccctgatctc gaaacacccg atgggtcgcc tgggcaaacc ggaagaagtg   660
gcagaactgg ttctgtttct gagttccgaa aaatcatcgt tcatgaccgg tggctattac   720
ctggtcgatg gtggctacac ggcagtg                                       747
```

<210> SEQ ID NO 176
<211> LENGTH: 249
<212> TYPE: PRT
<213> ORGANISM: Artificial sequence
<220> FEATURE:
<223> OTHER INFORMATION: Engineered sequence

<400> SEQUENCE: 176

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
```

```
               20                  25                  30
Val Ile Val Ser Asp Ile Asn Glu Asp His Gly Asn Lys Thr Val Glu
            35                  40                  45

Asp Ile Lys Ala Gln Gly Gly Glu Ala Ser Phe Val Lys Ala Asp Thr
        50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Asn Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 177
<211> LENGTH: 747
<212> TYPE: DNA
<213> ORGANISM: Artificial sequence
<220> FEATURE:
<223> OTHER INFORMATION: Engineered sequence

<400> SEQUENCE: 177

```
atgggtatcc tggacaacaa agtcgcactg gttacgggcg ctggttcggg cgtgggtctg     60
gcggtggcac actcctacgc taaagaaggc gctaaagtca ttgtgtcaga tatcaacgaa    120
gaccatggta ataaaaccgt tgaagatatt aaagcacagg gcggtgaagc tagttttgtg    180
aaagcggaca ccagcaaccc ggaagaagtg gaagccctgg ttaaacgtac ggtcgaaatt    240
tatggtcgcc tggatgtggc atgcaacaat gctggcattg gcggtgaaca ggcactggct    300
ggtgattacg gcctggacag ctggcgtaaa gttctgtcta tcaatctgga cggtgtcttc    360
tatgctgta aatacgaact ggaacaaatg gagaaaaacg gcggtggcgt tatcgtcaat    420
atggccagca ttcatggtat cgttgcggcc ccgctgagct ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747
```

<210> SEQ ID NO 178
<211> LENGTH: 249
<212> TYPE: PRT
<213> ORGANISM: Artificial sequence
<220> FEATURE:
<223> OTHER INFORMATION: Engineered sequence

<400> SEQUENCE: 178

| | | | | | | | | | | | | | | | |
|---|---|---|---|---|---|---|---|---|---|---|---|---|---|---|---|
| Met | Gly | Ile | Leu | Asp | Asn | Lys | Val | Ala | Leu | Val | Thr | Gly | Ala | Gly | Ser |
| 1 | | | | 5 | | | | | 10 | | | | | 15 | |
| Gly | Val | Gly | Leu | Ala | Val | Ala | His | Ser | Tyr | Ala | Lys | Glu | Gly | Ala | Lys |
| | | | 20 | | | | | 25 | | | | | 30 | | |
| Val | Ile | Val | Ser | Asp | Ile | Asn | Glu | Asp | His | Gly | Asn | Lys | Thr | Val | Glu |
| | | 35 | | | | | 40 | | | | | 45 | | | |
| Asp | Ile | Lys | Ala | Gln | Gly | Gly | Glu | Ala | Ser | Phe | Val | Lys | Ala | Asp | Thr |
| 50 | | | | | 55 | | | | | 60 | | | | | |
| Ser | Asn | Pro | Glu | Glu | Val | Glu | Ala | Leu | Val | Lys | Arg | Thr | Val | Glu | Ile |
| 65 | | | | 70 | | | | | 75 | | | | | 80 | |
| Tyr | Gly | Arg | Leu | Asp | Val | Ala | Cys | Asn | Asn | Ala | Gly | Ile | Gly | Gly | Glu |
| | | | 85 | | | | | 90 | | | | | 95 | | |
| Gln | Ala | Leu | Ala | Gly | Asp | Tyr | Gly | Leu | Asp | Ser | Trp | Arg | Lys | Val | Leu |
| | | | 100 | | | | | 105 | | | | | 110 | | |
| Ser | Ile | Asn | Leu | Asp | Gly | Val | Phe | Tyr | Gly | Cys | Lys | Tyr | Glu | Leu | Glu |
| | | 115 | | | | | 120 | | | | | 125 | | | |
| Gln | Met | Glu | Lys | Asn | Gly | Gly | Gly | Val | Ile | Val | Asn | Met | Ala | Ser | Ile |
| | 130 | | | | | 135 | | | | | 140 | | | | |
| His | Gly | Ile | Val | Ala | Ala | Pro | Leu | Ser | Ser | Ala | Tyr | Thr | Ser | Ala | Lys |
| 145 | | | | | 150 | | | | | 155 | | | | | 160 |
| His | Ala | Val | Val | Gly | Leu | Thr | Lys | Asn | Ile | Gly | Ala | Glu | Tyr | Gly | Gln |
| | | | | 165 | | | | | 170 | | | | | 175 | |
| Lys | Asn | Ile | Arg | Cys | Asn | Ala | Val | Cys | Pro | Gly | Tyr | Ile | Glu | Thr | Pro |
| | | | 180 | | | | | 185 | | | | | 190 | | |
| Leu | Leu | Glu | Ser | Leu | Thr | Lys | Glu | Met | Lys | Glu | Ala | Leu | Ile | Ser | Lys |
| | | | | 195 | | | | | 200 | | | | | 205 | |
| His | Pro | Met | Gly | Arg | Leu | Gly | Lys | Pro | Glu | Glu | Val | Ala | Glu | Leu | Val |
| | 210 | | | | | 215 | | | | | 220 | | | | |
| Leu | Phe | Leu | Ser | Ser | Glu | Lys | Ser | Ser | Phe | Met | Thr | Gly | Gly | Tyr | Tyr |
| 225 | | | | | 230 | | | | | 235 | | | | | 240 |
| Leu | Val | Asp | Gly | Gly | Tyr | Thr | Ala | Val | | | | | | | |
| | | | | 245 | | | | | | | | | | | |

<210> SEQ ID NO 179
<211> LENGTH: 747
<212> TYPE: DNA
<213> ORGANISM: Artificial sequence
<220> FEATURE:
<223> OTHER INFORMATION: Engineered sequence

<400> SEQUENCE: 179

| | | |
|---|---|---|
| atgggtatcc tggacaacaa agtcgcactg gttacgggcg ctggttcggg catcggtctg | 60 |
| gcggtggcac actcctacgc taaagaaggc gctaaagtca ttgtgtcaga tatcaacgaa | 120 |
| gaccatggta ataaaaccgt tgaagatatt aaagcacagg gcggtgaagc tagttttgtg | 180 |
| aaagcggaca ccagcaaccc ggaagaagtg gaagccctgg ttaaacgtac ggtcgaaatt | 240 |
| tatggtcgcc tggatgtggc atgcaacaat gctggcattg gcggtgaaca ggcactggct | 300 |

```
ggtgattacg gcctggacag ctggcgtaaa gttctgtcta tcaatctgga cggtgtcttc    360
tatggctgta aatacgaact ggaacaaatg gagaaaaacg gcggtggcgt tatcgtcaat    420
atcgccagca ttcatggtat cgttgcggcc ccgctgagct ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tggcaaaacc ggaagaagtg    660
gcagaactgg ttctgttttc tgagttccga aaaatcatcg tcatgaccgg tggctattac    720
ctggtcgatg gtggctacac ggcagtg                                       747
```

<210> SEQ ID NO 180
<211> LENGTH: 249
<212> TYPE: PRT
<213> ORGANISM: Artificial sequence
<220> FEATURE:
<223> OTHER INFORMATION: Engineered sequence

<400> SEQUENCE: 180

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Ile Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 181
<211> LENGTH: 747
<212> TYPE: DNA
<213> ORGANISM: Artificial sequence
<220> FEATURE:
<223> OTHER INFORMATION: Engineered sequence

<400> SEQUENCE: 181

| | |
|---|---:|
| atgggtatcc tggacaacaa agtcgcactg gttacgggcg ctggttcggg catcggtctg | 60 |
| gcggtggcac actcctacgc taaagaaggc gctaaagtca ttgtgtcaga tatcaacgaa | 120 |
| gaccatggta ataaaaccgt tgaagatatt aaagcacagg gcggtgaagc tagttttgtg | 180 |
| aaagcggaca ccagcaaccc ggaagaagtg gaagccctgg ttaaacgtac ggtcgaaatt | 240 |
| tatggtcgcc tggatgtggc atgcaacaat gctggcattg gcggtgaaca ggcactggct | 300 |
| ggtgattacg gcctggacag ctggcgtaaa gttctgtcta tcaatctgga cggtgtcttc | 360 |
| tatggctgta atacgaact ggaacaaatg gagaaaaacg gcggtggcgt tatcgtcaat | 420 |
| accgccagca ttcatggtat cgttgcggcc ccgctgagct ctgcatatac ctctgcgaaa | 480 |
| cacgccgtgg ttggcctgac gaaaaacatt ggtgctgaat atggccagaa aacatccgt | 540 |
| tgcaatgcgg tgtgcccggg ctacattgaa accccgctgc tggaatcact gacgaaagaa | 600 |
| atgaaagaag ccctgatctc gaaacaccg atgggtcgcc tgggcaaacc ggaagaagtg | 660 |
| gcagaactgg ttctgtttct gagttccgaa aaatcatcgt tcatgaccgg tggctattac | 720 |
| ctggtcgatg gtggctacac ggcagtg | 747 |

<210> SEQ ID NO 182
<211> LENGTH: 249
<212> TYPE: PRT
<213> ORGANISM: Artificial sequence
<220> FEATURE:
<223> OTHER INFORMATION: Engineered sequence

<400> SEQUENCE: 182

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Gln Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Thr Ala Ser Ile
    130                 135                 140

His Gly Ile Val Ala Ala Pro Leu Ser Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205
```

His Pro Met Gly Arg Leu Gly Lys Pro Glu Glu Val Ala Glu Leu Val
   210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245

<210> SEQ ID NO 183
<211> LENGTH: 747
<212> TYPE: DNA
<213> ORGANISM: Artificial sequence
<220> FEATURE:
<223> OTHER INFORMATION: Engineered sequence

<400> SEQUENCE: 183

| | |
|---|---|
| atgggtatcc tggacaacaa agtcgcactg gttacgggcg ctggttcggg catcggtctg | 60 |
| gcggtggcac actcctacgc taaagaaggc gctaaagtca ttgtgtcaga tatcaacgaa | 120 |
| gacaagggta taaaaccgt tgaagatatt aaagcacagg gcggtgaagc tagttttgtg | 180 |
| aaagcggaca ccgcgaaccc ggaagaagtg gaagccctgg ttaaacgtac ggtcgaaatt | 240 |
| tatggtcgcc tggatgtggc atgcaacaat gctggcattc tgggtgaaaa ggcactggct | 300 |
| ggtgattacg gcctggacag ctggcgtaaa gttctgtctg tgaatctgga cggtgtcttc | 360 |
| tatggctgta atacgaact ggaacaaatg gagaaaaacg gcggtggcgt tatcgtcaat | 420 |
| atggccagca ttcatggtat cgttgcgcag ccgctgaact ctgcatatac ctctgcgaaa | 480 |
| cacgccgtgg ttggcctgac gaaaaacatt ggtgctgaat atggccagaa aaacatccgt | 540 |
| tgcaatgcgg tggcgccggg ctacattgaa accccgctgc tggaatcact gacgaaagaa | 600 |
| atgaaagaag ccctgatctc gaaacacccg atgggtcgcc tgggcaaacc ggaagaagtg | 660 |
| gcagaactgg ttctgttct gagttccgaa aaatcatcgt tcatgaccgg tggctattac | 720 |
| ctggtcgatg gtggctacac ggcagtg | 747 |

<210> SEQ ID NO 184
<211> LENGTH: 249
<212> TYPE: PRT
<213> ORGANISM: Artificial sequence
<220> FEATURE:
<223> OTHER INFORMATION: Engineered sequence

<400> SEQUENCE: 184

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ala Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Leu Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

```
Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Ala Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 185
<211> LENGTH: 747
<212> TYPE: DNA
<213> ORGANISM: Artificial sequence
<220> FEATURE:
<223> OTHER INFORMATION: Engineered sequence

<400> SEQUENCE: 185

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccgcgaaccc ggaagaagtg aagccctgg ttaaacgtac ggtcgaaatt      240
tatggtcgcc tggatgtggc atgcaacaat gctggcattg gcggtgaaaa ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat      420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747
```

<210> SEQ ID NO 186
<211> LENGTH: 249
<212> TYPE: PRT
<213> ORGANISM: Artificial sequence
<220> FEATURE:
<223> OTHER INFORMATION: Engineered sequence

<400> SEQUENCE: 186

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45
```

```
Asp Ile Lys Ala Gln Gly Gly Glu Ala Ser Phe Val Lys Ala Asp Thr
 50                  55                  60

Ala Asn Pro Glu Glu Val Glu Ala Leu Val Lys Arg Thr Val Glu Ile
 65                  70                  75                  80

Tyr Gly Arg Leu Asp Val Ala Cys Asn Asn Ala Gly Ile Gly Gly Glu
                 85                  90                  95

Lys Ala Leu Ala Gly Asp Tyr Gly Leu Asp Ser Trp Arg Lys Val Leu
                100                 105                 110

Ser Ile Asn Leu Asp Gly Val Phe Tyr Gly Cys Lys Tyr Glu Leu Glu
                115                 120                 125

Gln Met Glu Lys Asn Gly Gly Val Ile Val Asn Met Ala Ser Ile
            130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
                180                 185                 190

Leu Leu Glu Ser Leu Thr Lys Glu Met Lys Glu Ala Leu Ile Ser Lys
                195                 200                 205

His Pro Met Gly Arg Leu Gly Lys Pro Glu Glu Val Ala Glu Leu Val
210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 187
<211> LENGTH: 747
<212> TYPE: DNA
<213> ORGANISM: Artificial sequence
<220> FEATURE:
<223> OTHER INFORMATION: Engineered sequence

<400> SEQUENCE: 187

```
atgggtatcc tggacaacaa agtcgcactg gttacgggcg ctggttcggg catcggtctg    60
gcggtggcac actcctacgc taaagaaggc gctaaagtca ttgtgtcaga tatcaacgaa   120
gaccgcggta ataaaaccgt tgaagatatt aaagcacagg gcggtgaagc tagttttgtg   180
aaagcggaca ccagcaaccc ggaagaagtg gaagccctgg ttaaacgtac ggtcgaaatt   240
tatggtcgcc tggatgtggc atgcaacaat gctggcattg gcggtgaaaa ggcactggct   300
ggtgattacg gcctggacag ctggcgtaaa gttctgtctg tgaatctgga cggtgtcttc   360
tatggctgta aatacgaact ggaacaaatg gagaaaaacg gcggtggcgt tatcgtcaat   420
atggccagca ttcatggtat cgttgcgcag ccgctgaact ctgcatatac ctctgcgaaa   480
cacgccgtgg ttggcctgac gaaaaacatt ggtgctgaat atggccagaa aaacatccgt   540
tgcaatgcgg tgtgcccggg ctacattgaa accccgctgc tggaatcact gacgaaagaa   600
atgaaagaag ccctgatctc gaaacacccg atgggtcgcc tggcaaaacc ggaagaagtg   660
gcagaactgg ttctgtttct gagttccgaa aaatcatcgt tcatgaccgg tggctattac   720
ctggtcgatg gtggctacac ggcagtg                                       747
```

<210> SEQ ID NO 188
<211> LENGTH: 249

```
<212> TYPE: PRT
<213> ORGANISM: Artificial sequence
<220> FEATURE:
<223> OTHER INFORMATION: Engineered sequence

<400> SEQUENCE: 188

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Arg Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 189
<211> LENGTH: 747
<212> TYPE: DNA
<213> ORGANISM: Artificial sequence
<220> FEATURE:
<223> OTHER INFORMATION: Engineered sequence

<400> SEQUENCE: 189
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta taaaaccgt tgaagatatt aaagcacagg gcggtgaagc tagttttgtg     180
aaagcggaca ccgcgaaccc ggaagaagtg gaagccctgg ttaaacgtac ggtcgaaatt     240
tatggtcgcc tggatgtggc atgcaacaat gctggcattc tgggtgaaaa ggcactggct     300
ggtgattacg gcctggacag ctggcgtaaa gttctgtcta tcaatctgga cggtgtcttc     360
tatggctgta aatacgaact ggaacaaatg gagaaaaacg gcggtggcgt tatcgtcaat     420
```

```
aacgccagca ttcatggtat cgttgcgcag ccgctgaact ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa acccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747
```

<210> SEQ ID NO 190
<211> LENGTH: 249
<212> TYPE: PRT
<213> ORGANISM: Artificial sequence
<220> FEATURE:
<223> OTHER INFORMATION: Engineered sequence

<400> SEQUENCE: 190

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ala Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Leu Gly Glu
                85                  90                  95

Lys Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Asn Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 191
<211> LENGTH: 747
<212> TYPE: DNA
<213> ORGANISM: Artificial sequence
<220> FEATURE:
<223> OTHER INFORMATION: Engineered sequence

<400> SEQUENCE: 191

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccgcggta ataaaaccgt tgaagatatt aaagcacagg gcggtgaagc tagttttgtg     180
aaagcggaca ccgcgaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta aatacgaact ggaacaaatg gagaaaaacg gcggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aacatccgt     540 tgcaatgcgg tgtgcccggg ctacattgaa accccgctgc tggaatcact gacgaaagaa     600
atgaaagaag ccctgatctc gaaacaccog atgggtcgcc tgggcaaacc ggaagaagtg     660
gcagaactgg ttctgtttct gagttccgaa aaatcatcgt tcatgaccgg tggcccgtac     720
ctggtcgatg gtggctacac ggcagtg                                         747
```

<210> SEQ ID NO 192
<211> LENGTH: 249
<212> TYPE: PRT
<213> ORGANISM: Artificial sequence
<220> FEATURE:
<223> OTHER INFORMATION: Engineered sequence

<400> SEQUENCE: 192

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
                20                  25                  30

Val Ile Val Ser Asp Ile Asn Glu Asp Arg Gly Asn Lys Thr Val Glu
            35                  40                  45

Asp Ile Lys Ala Gln Gly Gly Glu Ala Ser Phe Val Lys Ala Asp Thr
        50                  55                  60

Ala Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220
```

```
Leu Phe Leu Ser Ser Glu Lys Ser Ser Phe Met Thr Gly Gly Pro Tyr
225                 230                 235                 240

Leu Val Asp Gly Gly Tyr Thr Ala Val
            245
```

<210> SEQ ID NO 193
<211> LENGTH: 747
<212> TYPE: DNA
<213> ORGANISM: Artificial sequence
<220> FEATURE:
<223> OTHER INFORMATION: Engineered sequence

<400> SEQUENCE: 193

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta aatacgaact ggaacaaatg gagaaaaacg gcggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747
```

<210> SEQ ID NO 194
<211> LENGTH: 249
<212> TYPE: PRT
<213> ORGANISM: Artificial sequence
<220> FEATURE:
<223> OTHER INFORMATION: Engineered sequence

<400> SEQUENCE: 194

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140
```

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245

<210> SEQ ID NO 195
<211> LENGTH: 747
<212> TYPE: DNA
<213> ORGANISM: Artificial sequence
<220> FEATURE:
<223> OTHER INFORMATION: Engineered sequence

<400> SEQUENCE: 195

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcacagg gcggtgaagc tagttttgtg     180
aaagcggaca ccgcgaaccc ggaagaagtg gaagccctgg ttaaacgtac ggtcgaaatt     240
tatggtcgcc tggatgtggc atgcaacaat gctggcattg cggtgaaaaa ggcactggct     300
ggtgattacg gcctggacag ctggcgtaaa gttctgtcta tcaatctgga cggtgtcttc     360
tatggctgta aatacgaact ggaacaaatg gagaaaaacg gcggtggcgt atcgtcaat     420 atggccagca ttcatggtat cgttgcgcag ccgctgaact ctgcatatac ctctgcgaaa     480
cacgccgtgg ttggcctgac taaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747
```

<210> SEQ ID NO 196
<211> LENGTH: 249
<212> TYPE: PRT
<213> ORGANISM: Artificial sequence
<220> FEATURE:
<223> OTHER INFORMATION: Engineered sequence

<400> SEQUENCE: 196

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

```
Ala Asn Pro Glu Glu Val Glu Ala Leu Val Lys Arg Thr Val Glu Ile
 65                  70                  75                  80

Tyr Gly Arg Leu Asp Val Ala Cys Asn Asn Ala Gly Ile Gly Gly Glu
                 85                  90                  95

Lys Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Ala Leu Ile Ser Lys
        195                 200                 205

His Pro Met Gly Arg Leu Gly Lys Pro Glu Glu Val Ala Glu Leu Val
210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 197
<211> LENGTH: 747
<212> TYPE: DNA
<213> ORGANISM: Artificial sequence
<220> FEATURE:
<223> OTHER INFORMATION: Engineered sequence

<400> SEQUENCE: 197

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccgcggta ataaaaccgt tgaagatatt aaagcacagg gcggtgaagc tagttttgtg     180
aaagcggaca ccgcgaaccc ggaagaagtg gaagccctgg ttaaacgtac ggtcgaaatt     240
tatggtcgcc tggatgtggc atgcaacaat gctggcattc tgggtgaaaa ggcactggct     300
ggtgattacg gcctggacag ctggcgtaaa gttctgtctg tgaatctgga cggtgtcttc     360
tatggctgta aatacgaact ggaacaaatg gagaaaaacg gcggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tggcaaaacc ggaagaagtg     660
gcagaactgg ttctgtttct gagttccgaa aaatcatcgt tcatgaccgg tggcccgtac     720
ctggtcgatg gtggctacac ggcagtg                                         747
```

<210> SEQ ID NO 198
<211> LENGTH: 249
<212> TYPE: PRT
<213> ORGANISM: Artificial sequence
<220> FEATURE:
<223> OTHER INFORMATION: Engineered sequence

<400> SEQUENCE: 198

Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
                20                  25                  30
Val Ile Val Ser Asp Ile Asn Glu Asp Arg Gly Asn Lys Thr Val Glu
            35                  40                  45
Asp Ile Lys Ala Gln Gly Gly Glu Ala Ser Phe Val Lys Ala Asp Thr
        50                  55                  60
Ala Asn Pro Glu Glu Val Glu Ala Leu Val Lys Arg Thr Val Glu Ile
65                  70                  75                  80
Tyr Gly Arg Leu Asp Val Ala Cys Asn Asn Ala Gly Ile Leu Gly Glu
                85                  90                  95
Lys Ala Leu Ala Gly Asp Tyr Gly Leu Asp Ser Trp Arg Lys Val Leu
                100                 105                 110
Ser Val Asn Leu Asp Gly Val Phe Tyr Gly Cys Lys Tyr Glu Leu Glu
            115                 120                 125
Gln Met Glu Lys Asn Gly Gly Val Ile Val Asn Met Ala Ser Ile
130                 135                 140
His Gly Ile Val Ala Gln Pro Leu Asn Ser Ala Tyr Thr Ser Ala Lys
145                 150                 155                 160
His Ala Val Val Gly Leu Thr Lys Asn Ile Gly Ala Glu Tyr Gly Gln
                165                 170                 175
Lys Asn Ile Arg Cys Asn Ala Val Cys Pro Gly Tyr Ile Glu Thr Pro
                180                 185                 190
Leu Leu Glu Ser Leu Thr Lys Glu Met Lys Glu Ala Leu Ile Ser Lys
            195                 200                 205
His Pro Met Gly Arg Leu Gly Lys Pro Glu Glu Val Ala Glu Leu Val
        210                 215                 220
Leu Phe Leu Ser Ser Glu Lys Ser Ser Phe Met Thr Gly Gly Pro Tyr
225                 230                 235                 240
Leu Val Asp Gly Gly Tyr Thr Ala Val
                245

<210> SEQ ID NO 199
<211> LENGTH: 747
<212> TYPE: DNA
<213> ORGANISM: Artificial sequence
<220> FEATURE:
<223> OTHER INFORMATION: Engineered sequence

<400> SEQUENCE: 199

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccgcggta taaaaccgt tgaagatatt aaagcacagg gcggtgaagc tagttttgtg     180
aaagcggaca ccgcgaaccc ggaagaagtg gaagccctgg ttaaacgtac ggtcgaaatt     240
tatggtcgcc tggatgtggc atgcaacaat gctggcattc tgggtgaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt tatcgtcaat     420
aacgccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
```

```
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747
```

<210> SEQ ID NO 200
<211> LENGTH: 249
<212> TYPE: PRT
<213> ORGANISM: Artificial sequence
<220> FEATURE:
<223> OTHER INFORMATION: Engineered sequence

<400> SEQUENCE: 200

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Arg Gly Asn Lys Thr Val Glu
        35                  40                  45

Asp Ile Lys Ala Gln Gly Gly Glu Ala Ser Phe Val Lys Ala Asp Thr
    50                  55                  60

Ala Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Leu Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Gly Val Ile Val Asn Asn Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 201
<211> LENGTH: 747
<212> TYPE: DNA
<213> ORGANISM: Artificial sequence
<220> FEATURE:
<223> OTHER INFORMATION: Engineered sequence

<400> SEQUENCE: 201

```
atgggtatcc tggacaacaa agtcgcactg gttacgggcg ctggttcggg catcggtctg     60
gcggtggcac actcctacgc taaagaaggc gctaaagtca ttgtgtcaga tatcaacgaa    120
```

-continued

```
gaccgcggta ataaaaccgt tgaagatatt aaagcacagg gcggtgaagc tagttttgtg    180
aaagcggaca tcagcaaccc ggaagaagtg gaagccctgg ttaaacgtac ggtcgaaatt    240
tatggtcgcc tggatgtggc atgcaacaat gctggcattc ttggtgaaaa ggcactggct    300
ggtgattacg gcctggacag ctggcgtaaa gttctgtctg tgaatctgga cggtgtcttc    360
tatggctgta atacgaact ggaacaaatg gagaaaacg gcggtggcgt atcgtcaat       420 atggccagca ttcatggtat cgttgcgcag ccgctgaact ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggcccgtac    720
ctggtcgatg gtggctacac ggcagtg                                       747
```

<210> SEQ ID NO 202
<211> LENGTH: 249
<212> TYPE: PRT
<213> ORGANISM: Artificial sequence
<220> FEATURE:
<223> OTHER INFORMATION: Engineered sequence

<400> SEQUENCE: 202

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Arg Gly Asn Lys Thr Val Glu
        35                  40                  45

Asp Ile Lys Ala Gln Gly Gly Glu Ala Ser Phe Val Lys Ala Asp Ile
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Leu Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Pro Tyr
225                 230                 235                 240

Leu Val Asp Gly Gly Tyr Thr Ala Val
```

<210> SEQ ID NO 203
<211> LENGTH: 747
<212> TYPE: DNA
<213> ORGANISM: Artificial sequence
<220> FEATURE:
<223> OTHER INFORMATION: Engineered sequence

<400> SEQUENCE: 203

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccgcggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt tatcgtcaat     420
atggccagca ttcatggtat cgttgcgcag ccgctgaact ctgcatatac ctctgcgaaa     480
cacgccgtgt ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tggcaaaacc ggaagaagtg     660
gcagaactgg ttctgtttct gagttccgaa aaatcatcgt tcatgaccgg tggcccgtac     720
ctggtcgatg tggctacac ggcagtg                                         747
```

<210> SEQ ID NO 204
<211> LENGTH: 249
<212> TYPE: PRT
<213> ORGANISM: Artificial sequence
<220> FEATURE:
<223> OTHER INFORMATION: Engineered sequence

<400> SEQUENCE: 204

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Arg Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
```

```
              165                 170                 175
Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Pro Tyr
225                 230                 235                 240

Leu Val Asp Gly Gly Tyr Thr Ala Val
            245

<210> SEQ ID NO 205
<211> LENGTH: 747
<212> TYPE: DNA
<213> ORGANISM: Artificial sequence
<220> FEATURE:
<223> OTHER INFORMATION: Engineered sequence

<400> SEQUENCE: 205
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatgtggc atgcaacaat gctggcattc tgggtgaaaa ggcactggct     300
ggtgattacg gcctggacag ctggcgtaaa gttctgtctg tgaatctgga cggtgtcttc     360
tatggctgta aatacgaact ggaacaaatg gagaaaaacg gcggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aacatccgt     540
tgcaatgcgg tgtgcccggg ctacattgaa accccgctgc tggaatcact gacgaaagaa     600
atgaaagaag ccctgatctc gaaacacccg atgggtcgcc tggcaaaacc ggaagaagtg     660
gcagaactgg ttctgttttct gagttccgaa aaatcatcgt tcatgaccgg tggctattac     720
ctggtcgatg gtggctacac ggcagtg                                        747

<210> SEQ ID NO 206
<211> LENGTH: 249
<212> TYPE: PRT
<213> ORGANISM: Artificial sequence
<220> FEATURE:
<223> OTHER INFORMATION: Engineered sequence

<400> SEQUENCE: 206

Met Gly Ile Leu Asp Asn Lys Val Ala Leu Val Thr Gly Ala Gly Ser
1               5                  10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Leu Gly Glu
```

85                  90                  95

Lys Ala Leu Ala Gly Asp Tyr Gly Leu Asp Ser Trp Arg Lys Val Leu
               100                 105                 110

Ser Val Asn Leu Asp Gly Val Phe Tyr Gly Cys Lys Tyr Glu Leu Glu
               115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 207
<211> LENGTH: 747
<212> TYPE: DNA
<213> ORGANISM: Artificial sequence
<220> FEATURE:
<223> OTHER INFORMATION: Engineered sequence

<400> SEQUENCE: 207
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccgcggta taaaaccgt tgaagatatt aaagcacagg gcggtgaagc tagttttgtg     180
aaagcggaca ccagcaaccc ggaagaagtg aagccctgg ttaaacgtac ggtcgaaatt     240
tatggtcgcc tggatgtggc atgcaacaat gctggcattc tgggtgaaaa ggcactggct     300
ggtgattacg gcctggacag ctggcgtaaa gttctgtctg tgaatctgga cggtgtcttc     360
tatggctgta aatacgaact ggaacaaatg gagaaaaacg gcggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747

<210> SEQ ID NO 208
<211> LENGTH: 249
<212> TYPE: PRT
<213> ORGANISM: Artificial sequence
<220> FEATURE:
<223> OTHER INFORMATION: Engineered sequence

<400> SEQUENCE: 208

Met Gly Ile Leu Asp Asn Lys Val Ala Leu Val Thr Gly Ala Gly Ser

```
1               5                   10                  15
Gly Ile Gly Leu Ala Val Ala His Ser Tyr Ala Lys Glu Gly Ala Lys
            20                  25                  30

Val Ile Val Ser Asp Ile Asn Glu Asp Arg Gly Asn Lys Thr Val Glu
            35                  40                  45

Asp Ile Lys Ala Gln Gly Gly Glu Ala Ser Phe Val Lys Ala Asp Thr
 50                  55                  60

Ser Asn Pro Glu Glu Val Glu Ala Leu Val Lys Arg Thr Val Glu Ile
 65                  70                  75                  80

Tyr Gly Arg Leu Asp Val Ala Cys Asn Asn Ala Gly Ile Leu Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
            115                 120                 125

Gln Met Glu Lys Asn Gly Gly Val Ile Val Asn Met Ala Ser Ile
130                 135                 140

His Gly Ile Val Ala Gln Pro Leu Asn Ser Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
            195                 200                 205

His Pro Met Gly Arg Leu Gly Lys Pro Glu Glu Val Ala Glu Leu Val
210                 215                 220

Leu Phe Leu Ser Ser Glu Lys Ser Phe Met Thr Gly Gly Tyr Tyr
225                 230                 235                 240

Leu Val Asp Gly Gly Tyr Thr Ala Val
                245
```

<210> SEQ ID NO 209
<211> LENGTH: 747
<212> TYPE: DNA
<213> ORGANISM: Artificial sequence
<220> FEATURE:
<223> OTHER INFORMATION: Engineered sequence

<400> SEQUENCE: 209

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta taaaaccgt tgaagatatt aaagcacagg gcggtgaagc tagttttgtg      180
aaagcggaca ccgcgaaccc ggaagaagtg aagccctgg ttaaacgtac ggtcgaaatt      240
tatggtcgcc tggatgtggc atgcaacaat gctggcattc tgggtgaaaa ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat      420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa acccgctgc tggaatcact gacgaaagaa      600
atgaaagaag ccctgatctc gaaacaccg atgggtcgcc tgggcaaacc ggaagaagtg      660
```

```
gcagaactgg ttctgtttct gagttccgaa aaatcatcgt tcatgaccgg tggctattac    720
ctggtcgatg gtggctacac ggcagtg                                        747
```

<210> SEQ ID NO 210
<211> LENGTH: 249
<212> TYPE: PRT
<213> ORGANISM: Artificial sequence
<220> FEATURE:
<223> OTHER INFORMATION: Engineered sequence

<400> SEQUENCE: 210

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ala Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Leu Gly Glu
                85                  90                  95

Lys Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 211
<211> LENGTH: 747
<212> TYPE: DNA
<213> ORGANISM: Artificial sequence
<220> FEATURE:
<223> OTHER INFORMATION: Engineered sequence

<400> SEQUENCE: 211

```
atgggtatcc tggacaacaa agtcgcactg gttacgggcg ctggttcggg catcggtctg    60
gcggtggcac actcctacgc taagaaggc gctaaagtca ttgtgtcaga tatcaacgaa   120
gaccgcggta taaaaccgt tgaagatatt aagcacagg gcggtgaagc tagttttgtg    180
aaagcggaca ccgcgaaccc ggaagaagtg gaagccctgg ttaaacgtac ggtcgaaatt   240
```

```
tatggtcgcc tggatgtggc atgcaacaat gctggcattg gcggtgaaaa ggcactggct    300
ggtgattacg gcctggacag ctggcgtaaa gttctgtctg tgaatctgga cggtgtcttc    360
tatggctgta atacgaact ggaacaaatg gagaaaaacg gcggtggcgt tatcgtcaat     420
atggccagca ttcatggtat cgttgcgcag ccgctgaact ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                       747
```

<210> SEQ ID NO 212
<211> LENGTH: 249
<212> TYPE: PRT
<213> ORGANISM: Artificial sequence
<220> FEATURE:
<223> OTHER INFORMATION: Engineered sequence

<400> SEQUENCE: 212

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Arg Gly Asn Lys Thr Val Glu
        35                  40                  45

Asp Ile Lys Ala Gln Gly Gly Glu Ala Ser Phe Val Lys Ala Asp Thr
    50                  55                  60

Ala Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 213

<211> LENGTH: 747
<212> TYPE: DNA
<213> ORGANISM: Artificial sequence
<220> FEATURE:
<223> OTHER INFORMATION: Engineered sequence

<400> SEQUENCE: 213

| | | | | | |
|---|---|---|---|---|---|
| atgggtatcc | tggacaacaa | agtcgcactg | gttacgggcg | ctggttcggg | catcggtctg | 60 |
| gcggtggcac | actcctacgc | taaagaaggc | gctaaagtca | ttgtgtcaga | tatcaacgaa | 120 |
| gaccgcggta | ataaaaccgt | tgaagatatt | aaagcacagg | gcggtgaagc | tagttttgtg | 180 |
| aaagcggaca | ccagcaaccc | ggaagaagtg | gaagccctgg | ttaaacgtac | ggtcgaaatt | 240 |
| tatggtcgcc | tggatgtggc | atgcaacaat | gctggcattc | tgggtgaaaa | ggcactggct | 300 |
| ggtgattacg | gcctggacag | ctggcgtaaa | gttctgtctg | tgaatctgga | cggtgtcttc | 360 |
| tatggctgta | aatacgaact | ggaacaaatg | gagaaaaacg | gcggtggcgt | tatcgtcaat | 420 |
| atggccagca | ttcatggtat | cgttgcgcag | ccgctgaact | ctgcatatac | ctctgcgaaa | 480 |
| cacgccgtgg | ttggcctgac | gaaaaacatt | ggtgctgaat | atggccagaa | aaacatccgt | 540 |
| tgcaatgcgg | tgtgcccggg | ctacattgaa | accccgctgc | tggaatcact | gacgaaagaa | 600 |
| atgaaagaag | ccctgatctc | gaaacacccg | atgggtcgcc | tggcaaaacc | ggaagaagtg | 660 |
| gcagaactgg | ttctgtttct | gagttccgaa | aaatcatcgt | tcatgaccgg | tgccccgtac | 720 |
| ctggtcgatg | gtggctacac | ggcagtg | | | | 747 |

<210> SEQ ID NO 214
<211> LENGTH: 249
<212> TYPE: PRT
<213> ORGANISM: Artificial sequence
<220> FEATURE:
<223> OTHER INFORMATION: Engineered sequence

<400> SEQUENCE: 214

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Arg Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Leu Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
            195                 200                 205

His Pro Met Gly Arg Leu Gly Lys Pro Glu Glu Val Ala Glu Leu Val
        210                 215                 220

Leu Phe Leu Ser Ser Glu Lys Ser Ser Phe Met Thr Gly Gly Pro Tyr
225                 230                 235                 240

Leu Val Asp Gly Gly Tyr Thr Ala Val
                245

<210> SEQ ID NO 215
<211> LENGTH: 747
<212> TYPE: DNA
<213> ORGANISM: Artificial sequence
<220> FEATURE:
<223> OTHER INFORMATION: Engineered sequence

<400> SEQUENCE: 215

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt tatcgtcaat      420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tggcaaaacc ggaagaagtg     660
gcagaactgg ttctgttct gagttccgaa aaatcatcgt tcatgaccgg tggctattac     720
ctggtcgatg gtggctacac ggcagtg                                         747
```

<210> SEQ ID NO 216
<211> LENGTH: 249
<212> TYPE: PRT
<213> ORGANISM: Artificial sequence
<220> FEATURE:
<223> OTHER INFORMATION: Engineered sequence

<400> SEQUENCE: 216

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 217
<211> LENGTH: 747
<212> TYPE: DNA
<213> ORGANISM: Artificial sequence
<220> FEATURE:
<223> OTHER INFORMATION: Engineered sequence

<400> SEQUENCE: 217
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccgcgaaccc ggaagaagtg aagccctgg ttaaacgtac ggtcgaaatt      240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta aatacgaact ggaacaaatg gagaaaaacg gcggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aacatccgt     540
tgcaatgcgg tgtgcccggg ctacattgaa accccgctgc tggaatcact gacgaaagaa     600
atgaaagaag ccctgatctc gaaacaccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                        747

<210> SEQ ID NO 218
<211> LENGTH: 249
<212> TYPE: PRT
<213> ORGANISM: Artificial sequence
<220> FEATURE:
<223> OTHER INFORMATION: Engineered sequence

<400> SEQUENCE: 218

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
         35                  40                  45

Asp Ile Lys Ala Gln Gly Gly Glu Ala Ser Phe Val Lys Ala Asp Thr
 50                  55                  60

Ala Asn Pro Glu Glu Val Glu Ala Leu Val Lys Arg Thr Val Glu Ile
 65                  70                  75                  80

Tyr Gly Arg Leu Asp Val Ala Cys Asn Asn Ala Gly Ile Gly Gly Glu
             85                  90                  95

Lys Ala Leu Ala Gly Asp Tyr Gly Leu Asp Ser Trp Arg Lys Val Leu
             100                 105                 110

Ser Val Asn Leu Asp Gly Val Phe Tyr Gly Cys Lys Tyr Glu Leu Glu
             115                 120                 125

Gln Met Glu Lys Asn Gly Gly Val Ile Val Asn Met Ala Ser Ile
130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                 165                 170                 175

Lys Asn Ile Arg Cys Asn Ala Val Cys Pro Gly Tyr Ile Glu Thr Pro
             180                 185                 190

Leu Leu Glu Ser Leu Thr Lys Glu Met Lys Glu Ala Leu Ile Ser Lys
             195                 200                 205

His Pro Met Gly Arg Leu Gly Lys Pro Glu Glu Val Ala Glu Leu Val
210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 219
<211> LENGTH: 747
<212> TYPE: DNA
<213> ORGANISM: Artificial sequence
<220> FEATURE:
<223> OTHER INFORMATION: Engineered sequence

<400> SEQUENCE: 219
atgggtatcc tggacaacaa agtcgcactg gttacgggcg ctggttcggg catcggtctg       60
gcggtggcac actcctacgc taaagaaggc gctaaagtca ttgtgtcaga tatcaacgaa      120
gaccatggta ataaaaccgt tgaagatatt aaagcacagg gcggtgaagc tagttttgtg      180
aaagcggaca ccagcaaccc ggaagaagtg aagccctgg ttaaacgtac ggtcgaaatt       240
tatggtcgcc tggatgtggc atgcaacaat gctggcattg gcggtgaaaa ggcactggct      300
ggtgattacg gcctggacag ctggcgtaaa gttctgtcta gcaatctgga cggtgtcttc      360
tatggctgta atacgaact ggaacaaatg gagaaaaacg gcggtggcgt atcgtcaat        420 atggccagca ttcatggtat cgttgcgcag ccgctgaact ctgcatatac ctctgcgaaa      480
cacgccgtgg ttggcctgac gaaaaacatt ggtgctgaat atggccagaa aaacatccgt      540
tgcaatgcgg tgtgcccggg ctacattgaa accccgctgc tggaatcact gacgaaagaa      600
atgaaagaag ccctgatctc gaaacaccg atgggtcgcc tgggcaaacc ggaagaagtg       660
gcagaactgg ttctgtttct gagttccgaa aaatcatcgt tcatgaccgg tggctattac      720
ctggtcgatg gtggctacac ggcagtg                                          747

<210> SEQ ID NO 220
<211> LENGTH: 249
<212> TYPE: PRT
<213> ORGANISM: Artificial sequence
<220> FEATURE:
<223> OTHER INFORMATION: Engineered sequence

<400> SEQUENCE: 220

```
Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
                20                  25                  30
Val Ile Val Ser Asp Ile Asn Glu Asp His Gly Asn Lys Thr Val Glu
            35                  40                  45
Asp Ile Lys Ala Gln Gly Gly Glu Ala Ser Phe Val Lys Ala Asp Thr
        50                  55                  60
Ser Asn Pro Glu Glu Val Glu Ala Leu Val Lys Arg Thr Val Glu Ile
65                  70                  75                  80
Tyr Gly Arg Leu Asp Val Ala Cys Asn Asn Ala Gly Ile Gly Gly Glu
                85                  90                  95
Lys Ala Leu Ala Gly Asp Tyr Gly Leu Asp Ser Trp Arg Lys Val Leu
            100                 105                 110
Ser Ser Asn Leu Asp Gly Val Phe Tyr Gly Cys Lys Tyr Glu Leu Glu
        115                 120                 125
Gln Met Glu Lys Asn Gly Gly Gly Val Ile Val Asn Met Ala Ser Ile
    130                 135                 140
His Gly Ile Val Ala Gln Pro Leu Asn Ser Ala Tyr Thr Ser Ala Lys
145                 150                 155                 160
His Ala Val Val Gly Leu Thr Lys Asn Ile Gly Ala Glu Tyr Gly Gln
                165                 170                 175
Lys Asn Ile Arg Cys Asn Ala Val Cys Pro Gly Tyr Ile Glu Thr Pro
            180                 185                 190
Leu Leu Glu Ser Leu Thr Lys Glu Met Lys Glu Ala Leu Ile Ser Lys
        195                 200                 205
His Pro Met Gly Arg Leu Gly Lys Pro Glu Glu Val Ala Glu Leu Val
    210                 215                 220
Leu Phe Leu Ser Ser Glu Lys Ser Ser Phe Met Thr Gly Gly Tyr Tyr
225                 230                 235                 240
Leu Val Asp Gly Gly Tyr Thr Ala Val
                245
```

<210> SEQ ID NO 221
<211> LENGTH: 747
<212> TYPE: DNA
<213> ORGANISM: Artificial sequence
<220> FEATURE:
<223> OTHER INFORMATION: Engineered sequence

<400> SEQUENCE: 221

```
atgggtatcc tggacaacaa agtcgcactg gttacgggcg ctggttcggg catcggtctg    60
gcggtggcac actcctacgc taaagaaggc gctaaagtca ttgtgtcaga tatcaacgaa   120
gaccatggta ataaaaccgt tgaagatatt aaagcacagg gcggtgaagc tagttttgtg   180
aaagcggaca ccaccaaccc ggaagaagtg gaagccctgg ttaaacgtac ggtcgaaatt   240
tatggtcgcc tggatgtggc atgcaacaat gctggcattg gcggtgaaaa ggcactggct   300
ggtgattacg gcctggacag ctggcgtaaa gttctgtcta tcaatctgga cggtgtcttc   360
```

```
tatggctgta aatacgaact ggaacaaatg agaaaaaacg gcggtggcgt tatcgtcaat    420
atggccagca ttcatggtat cgttgcgcag ccgctgaact ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747
```

<210> SEQ ID NO 222
<211> LENGTH: 249
<212> TYPE: PRT
<213> ORGANISM: Artificial sequence
<220> FEATURE:
<223> OTHER INFORMATION: Engineered sequence

<400> SEQUENCE: 222

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Thr Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 223
<211> LENGTH: 747
<212> TYPE: DNA
<213> ORGANISM: Artificial sequence
<220> FEATURE:

<223> OTHER INFORMATION: Engineered sequence

<400> SEQUENCE: 223

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg cgggtgaaaa ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat      420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                        747
```

<210> SEQ ID NO 224
<211> LENGTH: 249
<212> TYPE: PRT
<213> ORGANISM: Artificial sequence
<220> FEATURE:
<223> OTHER INFORMATION: Engineered sequence

<400> SEQUENCE: 224

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Ala Gly Glu
                85                  90                  95

Lys Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205
```

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 225
<211> LENGTH: 747
<212> TYPE: DNA
<213> ORGANISM: Artificial sequence
<220> FEATURE:
<223> OTHER INFORMATION: Engineered sequence

<400> SEQUENCE: 225

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg aaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt atcgtcaat     420
atggccagca ttcatggtat cgttgcgcag ccgctgaact ctgcatatac ctctgcgaaa     480
cacgccgtgg ttggcctgac gaaaaacatt ggtgctgatt atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgttcct gagttccgaa aaatcatcgt tcatgaccgg tggctattac     720
ctggtcgatg gtggctacac ggcagtg                                        747
```

<210> SEQ ID NO 226
<211> LENGTH: 249
<212> TYPE: PRT
<213> ORGANISM: Artificial sequence
<220> FEATURE:
<223> OTHER INFORMATION: Engineered sequence

<400> SEQUENCE: 226

Met Gly Ile Leu Asp Asn Lys Val Ala Leu Val Thr Gly Ala Gly Ser
1               5                  10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

```
Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Asp Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 227
<211> LENGTH: 747
<212> TYPE: DNA
<213> ORGANISM: Artificial sequence
<220> FEATURE:
<223> OTHER INFORMATION: Engineered sequence

<400> SEQUENCE: 227

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg aagccctggt taaacgtac ggtcgaaatt      240
tatggtcgcc tggatgtggc atgcaacaat gctggcattg cggtgaaaa ggcactggct      300
ggtgattacg gcctggacag ctggcgtaaa gttctgtcta tcaatctgga cggtgtcttc     360
tatggctgta atacgaact ggaacaaatg gagaaaacg gcggtggcgt tatcgtcaat       420
atggccagca ttcatggtat cgttgcgcag ccgctgaact ctgcatatac ctctgcgaaa     480
cacgccgtgg ttggcctgac gaaaaacatt ggtgctgatt atggccagaa aaacatccgt    540
tgcaatgcgg tgtgcccggg ctacattgaa acccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg cgggctacac ggcagtg                                         747
```

<210> SEQ ID NO 228
<211> LENGTH: 249
<212> TYPE: PRT
<213> ORGANISM: Artificial sequence
<220> FEATURE:
<223> OTHER INFORMATION: Engineered sequence

<400> SEQUENCE: 228

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
                20                  25                  30

Val Ile Val Ser Asp Ile Asn Glu Asp His Gly Asn Lys Thr Val Glu
            35                  40                  45
```

Asp Ile Lys Ala Gln Gly Gly Glu Ala Ser Phe Val Lys Ala Asp Thr
    50              55                  60

Ser Asn Pro Glu Glu Val Glu Ala Leu Val Lys Arg Thr Val Glu Ile
65              70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
            115                 120                 125

Gln Met Glu Lys Asn Gly Gly Val Ile Val Asn Met Ala Ser Ile
130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Asp Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
            195                 200                 205

His Pro Met Gly Arg Leu Gly Lys Pro Glu Glu Val Ala Glu Leu Val
210                 215                 220

Leu Phe Leu Ser Ser Glu Lys Ser Ser Phe Met Thr Gly Gly Tyr Tyr
225                 230                 235                 240

Leu Val Asp Ala Gly Tyr Thr Ala Val
                245

<210> SEQ ID NO 229
<211> LENGTH: 747
<212> TYPE: DNA
<213> ORGANISM: Artificial sequence
<220> FEATURE:
<223> OTHER INFORMATION: Engineered sequence

<400> SEQUENCE: 229
atgggtatcc tggacaacaa agtcgcactg gttacgggcg ctggttcggg catcggtctg        60
gcggtggcac actcctacgc taaagaaggc gctaaagtca ttgtgtcaga tatcaacgaa       120
gaccatggta taaaaccgt tgaagatatt aaagcacagg gcggtgaagc tagttttgtg       180
aaagcggaca ccagcaaccc ggaagaagtg aagccctgg ttaaacgtac ggtcgaaatt       240
tatggtcgcc tggatgtggc atgcaacaat gctggcattg gcggtgaaaa ggcactggct       300
ggtgattacg gcctggacag ctggcgtaaa gttctgtcta tcaatctgga cggtgtcttc       360
tatggctgta atacgaact ggaacaaatg gagaaaaacg gcggtggcgt atcgtcaat       420 atggccagca ttcatggtat cgttgcgcag ccgctgaact ctgcatatac ctctgcgaaa       480
cacgccgtgg ttggcctgac gaaacatatt ggtgctgaat atggccagaa aaacatccgt       540
tgcaatgcgg tgtgcccggg ctacattgaa accccgctgc tggaatcact gacgaaagaa       600
atgaaagaag ccctgatctc gaaacacccg agcggtcgcc tgggcaaacc ggaagaagtg       660
gcagaactgg ttctgttcct gagttccgaa aaatcatcgt tcatgaccgg tggctattac       720
ctggtcgata ccggctacac ggcagtg                                         747

<210> SEQ ID NO 230
<211> LENGTH: 249
<212> TYPE: PRT

<213> ORGANISM: Artificial sequence
<220> FEATURE:
<223> OTHER INFORMATION: Engineered sequence

<400> SEQUENCE: 230

Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
            20                  25                  30
Val Ile Val Ser Asp Ile Asn Glu Asp His Gly Asn Lys Thr Val Glu
        35                  40                  45
Asp Ile Lys Ala Gln Gly Gly Glu Ala Ser Phe Val Lys Ala Asp Thr
    50                  55                  60
Ser Asn Pro Glu Glu Val Glu Ala Leu Val Lys Arg Thr Val Glu Ile
65                  70                  75                  80
Tyr Gly Arg Leu Asp Val Ala Cys Asn Asn Ala Gly Ile Gly Gly Glu
                85                  90                  95
Lys Ala Leu Ala Gly Asp Tyr Gly Leu Asp Ser Trp Arg Lys Val Leu
            100                 105                 110
Ser Ile Asn Leu Asp Gly Val Phe Tyr Gly Cys Lys Tyr Glu Leu Glu
        115                 120                 125
Gln Met Glu Lys Asn Gly Gly Val Ile Val Asn Met Ala Ser Ile
    130                 135                 140
His Gly Ile Val Ala Gln Pro Leu Asn Ser Ala Tyr Thr Ser Ala Lys
145                 150                 155                 160
His Ala Val Val Gly Leu Thr Lys His Ile Gly Ala Glu Tyr Gly Gln
                165                 170                 175
Lys Asn Ile Arg Cys Asn Ala Val Cys Pro Gly Tyr Ile Glu Thr Pro
            180                 185                 190
Leu Leu Glu Ser Leu Thr Lys Glu Met Lys Glu Ala Leu Ile Ser Lys
        195                 200                 205
His Pro Ser Gly Arg Leu Gly Lys Pro Glu Glu Val Ala Glu Leu Val
    210                 215                 220
Leu Phe Leu Ser Ser Glu Lys Ser Ser Phe Met Thr Gly Gly Tyr Tyr
225                 230                 235                 240
Leu Val Asp Thr Gly Tyr Thr Ala Val
                245

<210> SEQ ID NO 231
<211> LENGTH: 747
<212> TYPE: DNA
<213> ORGANISM: Artificial sequence
<220> FEATURE:
<223> OTHER INFORMATION: Engineered sequence

<400> SEQUENCE: 231
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta taaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcgtgg gcggtgaaaa ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat     420
atggccagca ttcatggtat cgttgcgcag ccgctgaact ctgcatatac ctctgcgaaa     480

```
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747
```

```
<210> SEQ ID NO 232
<211> LENGTH: 249
<212> TYPE: PRT
<213> ORGANISM: Artificial sequence
<220> FEATURE:
<223> OTHER INFORMATION: Engineered sequence

<400> SEQUENCE: 232
```

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Val Gly Gly Glu
                85                  90                  95

Lys Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

```
<210> SEQ ID NO 233
<211> LENGTH: 747
<212> TYPE: DNA
<213> ORGANISM: Artificial sequence
<220> FEATURE:
<223> OTHER INFORMATION: Engineered sequence

<400> SEQUENCE: 233
```

```
atgggtatcc tggacaacaa agtcgcactg gttacgggcg ctggttcggg catcggtctg    60
gcggtggcac actcctacgc taaagaaggc gctaaagtca ttgtgtcaga tatcaacgaa   120
gaccatggta ataaaaccgt tgaagatatt aaagcacagg gcggtgaagc tagttttgtg   180
aaagcggaca ccagcaaccc ggaagaagtg gaagccctgg ttaaacgtac ggtcgaaatt   240
tatggtcgcc tggatgtggc atgcaacaat gctggcattg gcggtgaaaa ggcactggct   300
ggtgattacg gcctggacag ctggcgtaaa gttctgtcta tcaatctgga cggtgtcttc   360
tatggctgta atacgaact  ggaacaaatg gagaaaaacg gcggtggcgt tatcgtcaat   420
atggccagca ttcatggtat cgttgcgcag ccgctgaact ctgcatatac ctctgcgaaa   480
cacgccgtgg ttggcctgac gaaaaacatt ggtgctgaat atggccagaa aaacatccgt   540
tgcaatgcgg tgtgcccggg ctacattgaa accccgctgc tggaatcact gacgaaagaa   600
atgaaagaag ccctgatctc gaaacacccg atgggtcgcc tgggcaaacc ggaagaagtg   660
gcagaactgg ttctgtttct gagttccgaa aaatcatcgt tcatgaccgg tggctattac   720
ctggtcgatc cgggctacac ggcagtg                                       747
```

<210> SEQ ID NO 234
<211> LENGTH: 249
<212> TYPE: PRT
<213> ORGANISM: Artificial sequence
<220> FEATURE:
<223> OTHER INFORMATION: Engineered sequence

<400> SEQUENCE: 234

Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
            20                  25                  30
Val Ile Val Ser Asp Ile Asn Glu Asp His Gly Asn Lys Thr Val Glu
        35                  40                  45
Asp Ile Lys Ala Gln Gly Gly Glu Ala Ser Phe Val Lys Ala Asp Thr
    50                  55                  60
Ser Asn Pro Glu Glu Val Glu Ala Leu Val Lys Arg Thr Val Glu Ile
65                  70                  75                  80
Tyr Gly Arg Leu Asp Val Ala Cys Asn Asn Ala Gly Ile Gly Gly Glu
                85                  90                  95
Lys Ala Leu Ala Gly Asp Tyr Gly Leu Asp Ser Trp Arg Lys Val Leu
            100                 105                 110
Ser Ile Asn Leu Asp Gly Val Phe Tyr Gly Cys Lys Tyr Glu Leu Glu
        115                 120                 125
Gln Met Glu Lys Asn Gly Gly Gly Val Ile Val Asn Met Ala Ser Ile
    130                 135                 140
His Gly Ile Val Ala Gln Pro Leu Asn Ser Ala Tyr Thr Ser Ala Lys
145                 150                 155                 160
His Ala Val Val Gly Leu Thr Lys Asn Ile Gly Ala Glu Tyr Gly Gln
                165                 170                 175
Lys Asn Ile Arg Cys Asn Ala Val Cys Pro Gly Tyr Ile Glu Thr Pro
            180                 185                 190
Leu Leu Glu Ser Leu Thr Lys Glu Met Lys Glu Ala Leu Ile Ser Lys
        195                 200                 205
His Pro Met Gly Arg Leu Gly Lys Pro Glu Glu Val Ala Glu Leu Val
    210                 215                 220
Leu Phe Leu Ser Ser Glu Lys Ser Ser Phe Met Thr Gly Gly Tyr Tyr

Leu Val Asp Pro Gly Tyr Thr Ala Val
            245

<210> SEQ ID NO 235
<211> LENGTH: 747
<212> TYPE: DNA
<213> ORGANISM: Artificial sequence
<220> FEATURE:
<223> OTHER INFORMATION: Engineered sequence

<400> SEQUENCE: 235
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gaccatggta ataaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatgtggc atgcaacaat gctggcattg gcggtgaaaa ggcactggct     300
ggtgattacg gcctggacag ctggcgtaaa gttctgtcta tcaatctgga cggtgtcttc     360
tatggctgta atacgaact ggaacaaatg gagaaaaacg gcggtggcgt tatcgtcaat      420
atggccagca ttcatggtat cgttgcgcag ccgctgaact ctgcatatac ctctgcgaaa     480
cacgccgtgg ttggcctgac gaaaaacatt ggtgctgatt atggccagaa aaacatccgt     540
tgcaatgcgg tgtgcccggg ctacattgaa accccgctgc tggaatcact gacgaaagaa     600
atgaaagaag ccctgatctc gaaacacccg aacggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747

<210> SEQ ID NO 236
<211> LENGTH: 249
<212> TYPE: PRT
<213> ORGANISM: Artificial sequence
<220> FEATURE:
<223> OTHER INFORMATION: Engineered sequence

<400> SEQUENCE: 236

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp His Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Ile Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys

```
              145                 150                 155                 160
His Ala Val Val Gly Leu Thr Lys Asn Ile Gly Ala Asp Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Asn Gly Arg Leu Gly Lys Pro Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 237
<211> LENGTH: 747
<212> TYPE: DNA
<213> ORGANISM: Artificial sequence
<220> FEATURE:
<223> OTHER INFORMATION: Engineered sequence

<400> SEQUENCE: 237
atgggtatcc tggacaacaa agtcgcactg gttacgggcg ctggttcggg catcggtcag    60
gcggtggcac actcctacgc taaagaaggc gctaaagtca ttgtgtcaga tatcaacgaa   120
gacaagggta ataaaaccgt tgaagatatt aaagcacagg gcggtgaagc tagttttgtg   180
aaagcggaca ccagcaaccc ggaagaagtg gaagccctgg ttaaacgtac ggtcgaaatt   240
tatggtcgcc tggatgtggc atgcaacaat gctggcattg gcggtgaaaa ggcactggct   300
ggtgattacg gcctggacag ctggcgtaaa gttctgtctg tgaatctgga cggtgtcttc   360
tatggctgta atacgaact ggaacaaatg agaaaaacg gcggtggcgt tatcgtcaat    420
atggccagca ttcatggtat cgttgcgcag ccgctgaact ctgcatatac ctctgcgaaa   480
cacgccgtgg ttggcctgac gaaaaacatt ggtgctgaat atggccagaa aaacatccgt   540
tgcaatgcgg tgtgcccggg ctacattgaa accccgctgc tggaatcact gacgaaagaa   600
atgaaagaag ccctgatctc gaaacaccg atgggtcgcc tgggcaaacc ggaagaagtg    660
gcagaactgg ttctgtttct gagttccgaa aaatcatcgt tcatgaccgg tggctattac   720
ctggtcgatg gtggctacac ggcagtg                                       747

<210> SEQ ID NO 238
<211> LENGTH: 249
<212> TYPE: PRT
<213> ORGANISM: Artificial sequence
<220> FEATURE:
<223> OTHER INFORMATION: Engineered sequence

<400> SEQUENCE: 238

Met Gly Ile Leu Asp Asn Lys Val Ala Leu Val Thr Gly Ala Gly Ser
1               5                  10                  15

Gly Ile Gly Gln Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
```

```
              65                  70                  75                  80
Tyr Gly Arg Leu Asp Val Ala Cys Asn Asn Ala Gly Ile Gly Gly Glu
                85                  90                  95
Lys Ala Leu Ala Gly Asp Tyr Gly Leu Asp Ser Trp Arg Lys Val Leu
            100                 105                 110
Ser Val Asn Leu Asp Gly Val Phe Tyr Gly Cys Lys Tyr Glu Leu Glu
        115                 120                 125
Gln Met Glu Lys Asn Gly Gly Val Ile Val Asn Met Ala Ser Ile
    130                 135                 140
His Gly Ile Val Ala Gln Pro Leu Asn Ser Ala Tyr Thr Ser Ala Lys
145                 150                 155                 160
His Ala Val Val Gly Leu Thr Lys Asn Ile Gly Ala Glu Tyr Gly Gln
                165                 170                 175
Lys Asn Ile Arg Cys Asn Ala Val Cys Pro Gly Tyr Ile Glu Thr Pro
            180                 185                 190
Leu Leu Glu Ser Leu Thr Lys Glu Met Lys Glu Ala Leu Ile Ser Lys
        195                 200                 205
His Pro Met Gly Arg Leu Gly Lys Pro Glu Glu Val Ala Glu Leu Val
    210                 215                 220
Leu Phe Leu Ser Ser Glu Lys Ser Ser Phe Met Thr Gly Gly Tyr Tyr
225                 230                 235                 240
Leu Val Asp Gly Gly Tyr Thr Ala Val
                245

<210> SEQ ID NO 239
<211> LENGTH: 747
<212> TYPE: DNA
<213> ORGANISM: Artificial sequence
<220> FEATURE:
<223> OTHER INFORMATION: Engineered sequence

<400> SEQUENCE: 239
atgggtatcc tggacaacaa agtcgcactg gttacgggcg ctggttcggg catcggtctg      60
gcggtggcac actcctacgc taaagaagcc gctaaagtca ttgtgtcaga tatcaacgaa     120
gacaagggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt tatcgtcaat      420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747

<210> SEQ ID NO 240
<211> LENGTH: 249
<212> TYPE: PRT
<213> ORGANISM: Artificial sequence
<220> FEATURE:
<223> OTHER INFORMATION: Engineered sequence
```

<400> SEQUENCE: 240

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Ala Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 241
<211> LENGTH: 747
<212> TYPE: DNA
<213> ORGANISM: Artificial sequence
<220> FEATURE:
<223> OTHER INFORMATION: Engineered sequence

<400> SEQUENCE: 241

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaaagccagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta aatacgaact ggaacaaatg gagaaaaacg gcggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
```

| | | |
|---|---|---|
| atgaaagaag ccctgatctc gaaacacccg atgggtcgcc tgggcaaacc ggaagaagtg | 660 |
| gcagaactgg ttctgtttct gagttccgaa aaatcatcgt tcatgaccgg tggctattac | 720 |
| ctggtcgatg gtggctacac ggcagtg | 747 |

<210> SEQ ID NO 242
<211> LENGTH: 249
<212> TYPE: PRT
<213> ORGANISM: Artificial sequence
<220> FEATURE:
<223> OTHER INFORMATION: Engineered sequence

<400> SEQUENCE: 242

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ser Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 243
<211> LENGTH: 747
<212> TYPE: DNA
<213> ORGANISM: Artificial sequence
<220> FEATURE:
<223> OTHER INFORMATION: Engineered sequence

<400> SEQUENCE: 243

| | | |
|---|---|---|
| atgggtatcc tggacaacaa agtcgcactg gttacgggcg ctggttcggg catcggtctg | 60 |
| gcggtggcac actcctacgc taaagaaggc gctaaagtca ttgtgtcaga tatcaacgaa | 120 |

```
gacaagggta ataaaaccgt tgaagatatt aaagcacagg gcggtgaagc tagttttgtg    180
aaagcggaca ccagcaaccc ggaagaagtg gaagccctgg ttaaacgtac gcgggaaatt    240
tatggtcgcc tggatgtggc atgcaacaat gctggcattg gcggtgaaaa ggcactggct    300
ggtgattacg gcctggacag ctggcgtaaa gttctgtctg tgaatctgga cggtgtcttc    360
tatggctgta atacgaact ggaacaaatg gagaaaacg gcggtggcgt tatcgtcaat      420
atggccagca ttcatggtat cgttgcgcag ccgctgaact ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacaccccg atgggtcgcc tgggcaaacc ggaagaagtg   660
gcagaactgg ttctgtttct gagttccgaa aaatcatcgt tcatgaccgg tggctattac    720
ctggtcgatg gtggctacac ggcagtg                                       747
```

<210> SEQ ID NO 244
<211> LENGTH: 249
<212> TYPE: PRT
<213> ORGANISM: Artificial sequence
<220> FEATURE:
<223> OTHER INFORMATION: Engineered sequence

<400> SEQUENCE: 244

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Arg Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 245
<211> LENGTH: 747
<212> TYPE: DNA
<213> ORGANISM: Artificial sequence
<220> FEATURE:
<223> OTHER INFORMATION: Engineered sequence

<400> SEQUENCE: 245

```
atgggtatcc tggacaacaa agtcgcactg gttacgggcg ctggttcggg catcggtctg    60
gcggtggcac actcctacgc taaagaaggc gctaaagtca ttgtgtcaga tatcaacgaa   120
gacaagggta ataaaaccgt tgaagatatt aaagcccaga acggtgaagc tagttttgtg   180
aaagcggaca ccagcaaccc ggaagaagtg aagccctgg ttaaacgtac ggtcgaaatt    240
tatggtcgcc tggatgtggc atgcaacaat gctggcattg gcggtgaaaa ggcactggct   300
ggtgattacg gcctggacag ctggcgtaaa gttctgtctg tgaatctgga cggtgtcttc   360
tatggctgta atacgaact ggaacaaatg gagaaaaacg gcggtggcgt tatcgtcaat    420
atggccagca ttcatggtat cgttgcgcag ccgctgaact ctgcatatac ctctgcgaaa   480
cacgccgtgg ttggcctgac gaaaaacatt ggtgctgaat atggccagaa aaacatccgt   540
tgcaatgcgg tgtgcccggg ctacattgaa accccgctgc tggaatcact gacgaaagaa   600
atgaaagaag ccctgatctc gaaacacccg atgggtcgcc tgggcaaacc ggaagaagtg   660
gcagaactgg ttctgttcct gagttccgaa aaatcatcgt tcatgaccgg tggctattac   720
ctggtcgatg gtggctacac ggcagtg                                      747
```

<210> SEQ ID NO 246
<211> LENGTH: 249
<212> TYPE: PRT
<213> ORGANISM: Artificial sequence
<220> FEATURE:
<223> OTHER INFORMATION: Engineered sequence

<400> SEQUENCE: 246

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Asn Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175
```

```
Lys Asn Ile Arg Cys Asn Ala Val Cys Pro Gly Tyr Ile Glu Thr Pro
            180                 185                 190
Leu Leu Glu Ser Leu Thr Lys Glu Met Lys Glu Ala Leu Ile Ser Lys
        195                 200                 205
His Pro Met Gly Arg Leu Gly Lys Pro Glu Val Ala Glu Leu Val
    210                 215                 220
Leu Phe Leu Ser Ser Glu Lys Ser Ser Phe Met Thr Gly Gly Tyr Tyr
225                 230                 235                 240
Leu Val Asp Gly Gly Tyr Thr Ala Val
                245

<210> SEQ ID NO 247
<211> LENGTH: 747
<212> TYPE: DNA
<213> ORGANISM: Artificial sequence
<220> FEATURE:
<223> OTHER INFORMATION: Engineered sequence

<400> SEQUENCE: 247
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta taaaaccgt  tgaagatatt aaacaccagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact  ggaacaaatg gagaaaaacg gcggtggcgt atcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aacatccgt     540
tgcaatgcgg tgtgcccggg ctacattgaa accccgctgc tggaatcact gacgaaagaa     600
atgaaagaag ccctgatctc gaaacaccg  atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747

<210> SEQ ID NO 248
<211> LENGTH: 249
<212> TYPE: PRT
<213> ORGANISM: Artificial sequence
<220> FEATURE:
<223> OTHER INFORMATION: Engineered sequence

<400> SEQUENCE: 248

Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
            20                  25                  30
Val Ile Val Ser Asp Ile Asn Glu Asp Lys Gly Asn Lys Thr Val Glu
        35                  40                  45
Asp Ile Lys His Gln Gly Gly Glu Ala Ser Phe Val Lys Ala Asp Thr
    50                  55                  60
Ser Asn Pro Glu Glu Val Glu Ala Leu Val Lys Arg Thr Val Glu Ile
65                  70                  75                  80
Tyr Gly Arg Leu Asp Val Ala Cys Asn Asn Ala Gly Ile Gly Gly Glu
                85                  90                  95
```

```
Lys Ala Leu Ala Gly Asp Tyr Gly Leu Asp Ser Trp Arg Lys Val Leu
                100                 105                 110

Ser Val Asn Leu Asp Gly Val Phe Tyr Gly Cys Lys Tyr Glu Leu Glu
            115                 120                 125

Gln Met Glu Lys Asn Gly Gly Val Ile Val Asn Met Ala Ser Ile
        130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 249
<211> LENGTH: 747
<212> TYPE: DNA
<213> ORGANISM: Artificial sequence
<220> FEATURE:
<223> OTHER INFORMATION: Engineered sequence

<400> SEQUENCE: 249

```
atgggtatcc tggacaacaa agtcgcactg gttacgggcg ctggttcggg catcggtctg     60
gcggtggcac actcctacgc taaagaaggc gctaaagtca ttgtgtcaga tatcaacgaa    120
gacaagggta ataaaaccgt tgaagatatt aaaggccagg cggtgaagc tagttttgtg    180
aaagcggaca ccagcaaccc ggaagaagtg gaagccctgg ttaaacgtac ggtcgaaatt    240
tatggtcgcc tggatgtggc atgcaacaat gctggcattg cggtgaaaa ggcactggct    300
ggtgattacg gcctggacag ctggcgtaaa gttctgtctg tgaatctgga cggtgtcttc    360
tatggctgta atacgaact ggaacaaatg gagaaaaacg gcggtggcgt atcgtcaat    420
atggccagca ttcatggtat cgttgcgcag ccgctgaact ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgttcct gagttccgaa aaatcatcgt tcatgaccgg tggctattac    720
ctggtcgatg gtggctacac ggcagtg                                       747
```

<210> SEQ ID NO 250
<211> LENGTH: 249
<212> TYPE: PRT
<213> ORGANISM: Artificial sequence
<220> FEATURE:
<223> OTHER INFORMATION: Engineered sequence

<400> SEQUENCE: 250

```
Met Gly Ile Leu Asp Asn Lys Val Ala Leu Val Thr Gly Ala Gly Ser
1               5                   10                  15
```

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Gly Gln Gly Gly Glu Ala Ser Phe Val Lys Ala Asp Thr
50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 251
<211> LENGTH: 747
<212> TYPE: DNA
<213> ORGANISM: Artificial sequence
<220> FEATURE:
<223> OTHER INFORMATION: Engineered sequence

<400> SEQUENCE: 251
atgggtatcc tggacaacaa agtcgcactg gttacgggcg ctggttcggg catcggtctg     60
gcggtggcac actcctacgc taaagaaggc gctaaagtca ttgtgtcaga tatcaacgaa    120
gacaagggta ataaaaccgt tgaagatatt aaagcacagg gcggtgaagc tagttttgtg    180
aaagcggaca ccagcaaccc ggaagaagtg aagccctgg ttaaacgtac ggtcgaaaac     240
tatggtcgcc tggatgtggc atgcaacaat gctggcattg gcgtgaaaa ggcactggct     300 ggtgattacg gcctggacag ctggcgtaaa gttctgtctg tgaatctgga cggtgtcttc    360
tatggctgta atacgaact ggaacaaatg gagaaaaacg gcggtggcgt tatcgtcaat     420
atggccagca ttcatggtat cgttgcgcag ccgctgaact ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tggcaaaacc ggaagaagtg    660
gcagaactgg ttctgttttct gagttccgaa aaatcatcgt tcatgaccgg tggctattac    720

```
ctggtcgatg gtggctacac ggcagtg                                        747
```

<210> SEQ ID NO 252
<211> LENGTH: 249
<212> TYPE: PRT
<213> ORGANISM: Artificial sequence
<220> FEATURE:
<223> OTHER INFORMATION: Engineered sequence

<400> SEQUENCE: 252

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Asn
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 253
<211> LENGTH: 747
<212> TYPE: DNA
<213> ORGANISM: Artificial sequence
<220> FEATURE:
<223> OTHER INFORMATION: Engineered sequence

<400> SEQUENCE: 253

```
atgggtatcc tggacaacaa agtcgcactg gttacgggcg ctggttcggg catcggtctg     60
gcggtggcac actcctacgc taaagaaggc gctaaagtca ttgtgtcaga tatcaacgaa    120
gacaagggta ataaaaccgt tgaagatatt aaagcacagg gcggtgaagc tagttttgtg    180
aaagcggaca ccagcaaccc ggaagaagtg gaagccctgg ttaaacgtac ggtcgaaaag    240
```

```
tatggtcgcc tggatgtggc atgcaacaat gctggcattg gcggtgaaaa ggcactggct    300
ggtgattacg gcctggacag ctggcgtaaa gttctgtctg tgaatctgga cggtgtcttc    360
tatggctgta atacgaact ggaacaaatg gagaaaaacg gcggtggcgt tatcgtcaat     420
atggccagca ttcatggtat cgttgcgcag ccgctgaact ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747
```

<210> SEQ ID NO 254
<211> LENGTH: 249
<212> TYPE: PRT
<213> ORGANISM: Artificial sequence
<220> FEATURE:
<223> OTHER INFORMATION: Engineered sequence

<400> SEQUENCE: 254

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Lys
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 255
<211> LENGTH: 747

<212> TYPE: DNA
<213> ORGANISM: Artificial sequence
<220> FEATURE:
<223> OTHER INFORMATION: Engineered sequence

<400> SEQUENCE: 255

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta taaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattaca agctggacag ctggcgtaaa gttctgtctg tgaatctgga cggtgtcttc     360
tatggctgta atacgaact ggaacaaatg gagaaaaacg gcggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747
```

<210> SEQ ID NO 256
<211> LENGTH: 249
<212> TYPE: PRT
<213> ORGANISM: Artificial sequence
<220> FEATURE:
<223> OTHER INFORMATION: Engineered sequence

<400> SEQUENCE: 256

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Lys Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190
```

Leu Leu Glu Ser Leu Thr Lys Glu Met Lys Glu Ala Leu Ile Ser Lys
            195                 200                 205

His Pro Met Gly Arg Leu Gly Lys Pro Glu Gly Val Ala Glu Leu Val
        210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 257
<211> LENGTH: 747
<212> TYPE: DNA
<213> ORGANISM: Artificial sequence
<220> FEATURE:
<223> OTHER INFORMATION: Engineered sequence

<400> SEQUENCE: 257

| | |
|---|---|
| atgggtatcc tggacaacaa agtcgcactg gttacgggcg ctggttcggg catcggtctg | 60 |
| gcggtggcac actcctacgc taaagaaggc gctaaagtca ttgtgtcaga tatcaacgaa | 120 |
| gacaagggta ataaaaccgt tgaagatatt aaagcacagg gcggtgaagc tagttttgtg | 180 |
| aaagcggaca ccagcaaccc ggaagaagtg gaagccctgg ttaaacgtac ggtcgaaatt | 240 |
| tatggtcgcc tggatgtggc atgcaacaat gctggcattg gcggtgaaaa ggcactggct | 300 |
| ggtgattacc ggctggacag ctggcgtaaa gttctgtctg tgaatctgga cggtgtcttc | 360 |
| tatggctgta atacgaact ggaacaaatg gagaaaaacg gcggtggcgt atcgtcaat | 420 |
| atggccagca ttcatggtat cgttgcgcag ccgctgaact ctgcatatac ctctgcgaaa | 480 |
| cacgccgtgg ttggcctgac gaaaaacatt ggtgctgaat atggccagaa aaacatccgt | 540 |
| tgcaatgcgg tgtgcccggg ctacattgaa accccgctgc tggaatcact gacgaaagaa | 600 |
| atgaaagaag ccctgatctc gaaacaccg atgggtcgcc tgggcaaacc ggaagaagtg | 660 |
| gcagaactgg ttctgtttct gagttccgaa aaatcatcgt tcatgaccgg tggctattac | 720 |
| ctggtcgatg gtggctacac ggcagtg | 747 |

<210> SEQ ID NO 258
<211> LENGTH: 249
<212> TYPE: PRT
<213> ORGANISM: Artificial sequence
<220> FEATURE:
<223> OTHER INFORMATION: Engineered sequence

<400> SEQUENCE: 258

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Arg Leu Asp Ser Trp Arg Lys Val Leu
            100                 105                 110

```
Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

```
<210> SEQ ID NO 259
<211> LENGTH: 747
<212> TYPE: DNA
<213> ORGANISM: Artificial sequence
<220> FEATURE:
<223> OTHER INFORMATION: Engineered sequence

<400> SEQUENCE: 259
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacc cgctggacag ctggcgtaaa gttctgtctg tgaatctgga cggtgtcttc     360
tatggctgta atacgaact ggaacaaatg gagaaaaacg gcggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747
```

```
<210> SEQ ID NO 260
<211> LENGTH: 249
<212> TYPE: PRT
<213> ORGANISM: Artificial sequence
<220> FEATURE:
<223> OTHER INFORMATION: Engineered sequence

<400> SEQUENCE: 260

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30
```

Val Ile Val Ser Asp Ile Asn Glu Asp Lys Gly Asn Lys Thr Val Glu
         35                  40                  45

Asp Ile Lys Ala Gln Gly Gly Glu Ala Ser Phe Val Lys Ala Asp Thr
 50                  55                  60

Ser Asn Pro Glu Glu Val Glu Ala Leu Val Lys Arg Thr Val Glu Ile
 65                  70                  75                  80

Tyr Gly Arg Leu Asp Val Ala Cys Asn Asn Ala Gly Ile Gly Gly Glu
                 85                  90                  95

Lys Ala Leu Ala Gly Asp Tyr Pro Leu Asp Ser Trp Arg Lys Val Leu
            100                 105                 110

Ser Val Asn Leu Asp Gly Val Phe Tyr Gly Cys Lys Tyr Glu Leu Glu
            115                 120                 125

Gln Met Glu Lys Asn Gly Gly Val Ile Val Asn Met Ala Ser Ile
        130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 261
<211> LENGTH: 747
<212> TYPE: DNA
<213> ORGANISM: Artificial sequence
<220> FEATURE:
<223> OTHER INFORMATION: Engineered sequence

<400> SEQUENCE: 261
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcacagg gcggtgaagc tagttttgtg     180
aaagcggaca ccagcaaccc ggaagaagtg aagccctggt taaacgtac ggtcgaaatt      240 tatggtcgcc tggatgtggc atgcaacaat gctggcattg gcggtgaaaa ggcactggct     300
ggtgattaca ccctggacag ctggcgtaaa gttctgtctg tgaatctgga cggtgtcttc     360
tatggctgta aatacgaact ggaacaaatg gagaaaaacg gcggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aacatccgt     540 tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747

<210> SEQ ID NO 262
<211> LENGTH: 249
<212> TYPE: PRT
<213> ORGANISM: Artificial sequence
<220> FEATURE:
<223> OTHER INFORMATION: Engineered sequence

<400> SEQUENCE: 262

```
Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
            20                  25                  30
Val Ile Val Ser Asp Ile Asn Glu Asp Lys Gly Asn Lys Thr Val Glu
        35                  40                  45
Asp Ile Lys Ala Gln Gly Gly Glu Ala Ser Phe Val Lys Ala Asp Thr
    50                  55                  60
Ser Asn Pro Glu Glu Val Glu Ala Leu Val Lys Arg Thr Val Glu Ile
65                  70                  75                  80
Tyr Gly Arg Leu Asp Val Ala Cys Asn Asn Ala Gly Ile Gly Gly Glu
                85                  90                  95
Lys Ala Leu Ala Gly Asp Tyr Thr Leu Asp Ser Trp Arg Lys Val Leu
            100                 105                 110
Ser Val Asn Leu Asp Gly Val Phe Tyr Gly Cys Lys Tyr Glu Leu Glu
        115                 120                 125
Gln Met Glu Lys Asn Gly Gly Val Ile Val Asn Met Ala Ser Ile
    130                 135                 140
His Gly Ile Val Ala Gln Pro Leu Asn Ser Ala Tyr Thr Ser Ala Lys
145                 150                 155                 160
His Ala Val Val Gly Leu Thr Lys Asn Ile Gly Ala Glu Tyr Gly Gln
                165                 170                 175
Lys Asn Ile Arg Cys Asn Ala Val Cys Pro Gly Tyr Ile Glu Thr Pro
            180                 185                 190
Leu Leu Glu Ser Leu Thr Lys Glu Met Lys Glu Ala Leu Ile Ser Lys
        195                 200                 205
His Pro Met Gly Arg Leu Gly Lys Pro Glu Glu Val Ala Glu Leu Val
    210                 215                 220
Leu Phe Leu Ser Ser Glu Lys Ser Ser Phe Met Thr Gly Gly Tyr Tyr
225                 230                 235                 240
Leu Val Asp Gly Gly Tyr Thr Ala Val
                245
```

<210> SEQ ID NO 263
<211> LENGTH: 747
<212> TYPE: DNA
<213> ORGANISM: Artificial sequence
<220> FEATURE:
<223> OTHER INFORMATION: Engineered sequence

<400> SEQUENCE: 263

| | | | | |
|---|---|---|---|---|
| atgggtatcc tggacaacaa agtcgcactg gttacgggcg ctggttcggg catcggtctg | | | | 60 |
| gcggtggcac actcctacgc taaagaaggc gctaaagtca ttgtgtcaga tatcaacgaa | | | | 120 |
| gacaagggta taaaaccgt tgaagatatt aaagcacagg gcggtgaagc tagttttgtg | | | | 180 |
| aaagcggaca ccagcaaccc ggaagaagtg gaagccctgg ttaaacgtac ggtcgaaatt | | | | 240 |
| tatggtcgcc tggatgtggc atgcaacaat gctggcattg gcggtgaaaa ggcactggct | | | | 300 |
| ggtgattacc acctggacag ctggcgtaaa gttctgtctg tgaatctgga cggtgtcttc | | | | 360 |

```
tatggctgta aatacgaact ggaacaaatg gagaaaaacg gcggtggcgt tatcgtcaat    420
atggccagca ttcatggtat cgttgcgcag ccgctgaact ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacaccgg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                       747
```

<210> SEQ ID NO 264
<211> LENGTH: 249
<212> TYPE: PRT
<213> ORGANISM: Artificial sequence
<220> FEATURE:
<223> OTHER INFORMATION: Engineered sequence

<400> SEQUENCE: 264

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr His Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 265
<211> LENGTH: 747
<212> TYPE: DNA
<213> ORGANISM: Artificial sequence
<220> FEATURE:
<223> OTHER INFORMATION: Engineered sequence

<400> SEQUENCE: 265

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta taaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaaca agggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747
```

<210> SEQ ID NO 266
<211> LENGTH: 249
<212> TYPE: PRT
<213> ORGANISM: Artificial sequence
<220> FEATURE:
<223> OTHER INFORMATION: Engineered sequence

<400> SEQUENCE: 266

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Lys Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
```

```
         210                 215                 220
Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 267
<211> LENGTH: 747
<212> TYPE: DNA
<213> ORGANISM: Artificial sequence
<220> FEATURE:
<223> OTHER INFORMATION: Engineered sequence

<400> SEQUENCE: 267
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta taaaaccgt tgaagatatt aaagcacagg gcggtgaagc tagttttgtg      180
aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaacc acggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aacatccgt     540 tgcaatgcgg tgtgcccggg ctacattgaa accccgctgc tggaatcact gacgaaagaa     600
atgaaagaag ccctgatctc gaaacaccc g atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747

<210> SEQ ID NO 268
<211> LENGTH: 249
<212> TYPE: PRT
<213> ORGANISM: Artificial sequence
<220> FEATURE:
<223> OTHER INFORMATION: Engineered sequence

<400> SEQUENCE: 268

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn His Gly Gly Val Ile Val Asn Met Ala Ser Ile
```

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Tyr Tyr
225                 230                 235                 240

Leu Val Asp Gly Gly Tyr Thr Ala Val
            245

<210> SEQ ID NO 269
<211> LENGTH: 747
<212> TYPE: DNA
<213> ORGANISM: Artificial sequence
<220> FEATURE:
<223> OTHER INFORMATION: Engineered sequence

<400> SEQUENCE: 269
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaaca ccggtggcgt tatcgtcaat      420
atggccagca ttcatggtat cgttgcgcag ccgctgaact ctgcatatac ctctgcgaaa     480
cacgccgtgg ttggcctgac gaaaaacatt ggtgctgaat atggcagaa aaacatccgt      540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                          747

<210> SEQ ID NO 270
<211> LENGTH: 249
<212> TYPE: PRT
<213> ORGANISM: Artificial sequence
<220> FEATURE:
<223> OTHER INFORMATION: Engineered sequence

<400> SEQUENCE: 270

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr

```
                    50                  55                  60
Ser Asn Pro Glu Glu Val Glu Ala Leu Val Lys Arg Thr Val Glu Ile
 65                  70                  75                  80

Tyr Gly Arg Leu Asp Val Ala Cys Asn Asn Ala Gly Ile Gly Gly Glu
                 85                  90                  95

Lys Ala Leu Ala Gly Asp Tyr Gly Leu Asp Ser Trp Arg Lys Val Leu
                100                 105                 110

Ser Val Asn Leu Asp Gly Val Phe Tyr Gly Cys Lys Tyr Glu Leu Glu
            115                 120                 125

Gln Met Glu Lys Asn Thr Gly Gly Val Ile Val Asn Met Ala Ser Ile
        130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
                180                 185                 190

Leu Leu Glu Ser Leu Thr Lys Glu Met Lys Glu Ala Leu Ile Ser Lys
            195                 200                 205

His Pro Met Gly Arg Leu Gly Lys Pro Glu Glu Val Ala Glu Leu Val
        210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 271
<211> LENGTH: 747
<212> TYPE: DNA
<213> ORGANISM: Artificial sequence
<220> FEATURE:
<223> OTHER INFORMATION: Engineered sequence

<400> SEQUENCE: 271
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaacc gcggtggcgt tatcgtcaat      420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                          747

<210> SEQ ID NO 272
<211> LENGTH: 249
<212> TYPE: PRT
<213> ORGANISM: Artificial sequence
```

<220> FEATURE:
<223> OTHER INFORMATION: Engineered sequence

<400> SEQUENCE: 272

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
                20                  25                  30

Val Ile Val Ser Asp Ile Asn Glu Asp Lys Gly Asn Lys Thr Val Glu
            35                  40                  45

Asp Ile Lys Ala Gln Gly Gly Glu Ala Ser Phe Val Lys Ala Asp Thr
        50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
                100                 105                 110

Ser Val Asn Leu Asp Gly Val Phe Tyr Gly Cys Lys Tyr Glu Leu Glu
            115                 120                 125

Gln Met Glu Lys Asn Arg Gly Gly Val Ile Val Asn Met Ala Ser Ile
        130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
                180                 185                 190

Leu Leu Glu Ser Leu Thr Lys Glu Met Lys Glu Ala Leu Ile Ser Lys
            195                 200                 205

His Pro Met Gly Arg Leu Gly Lys Pro Glu Glu Val Ala Glu Leu Val
        210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 273
<211> LENGTH: 747
<212> TYPE: DNA
<213> ORGANISM: Artificial sequence
<220> FEATURE:
<223> OTHER INFORMATION: Engineered sequence

<400> SEQUENCE: 273
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120 gacaaggta ataaaaccgt tgaagatatt aaagcacagg gcggtgaagc tagtttttgtg     180 aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt tatcgtcaat     420
atggccagca ttcatggtat cgttgcgcag ccgctgaact ctgcatatac ctctgcgaaa     480

```
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
gcgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                         747
```

<210> SEQ ID NO 274
<211> LENGTH: 249
<212> TYPE: PRT
<213> ORGANISM: Artificial sequence
<220> FEATURE:
<223> OTHER INFORMATION: Engineered sequence

<400> SEQUENCE: 274

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Ala Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 275
<211> LENGTH: 747
<212> TYPE: DNA
<213> ORGANISM: Artificial sequence
<220> FEATURE:
<223> OTHER INFORMATION: Engineered sequence

<400> SEQUENCE: 275

```
atgggtatcc tggacaacaa agtcgcactg gttacgggcg ctggttcggg catcggtctg     60
```

```
gcggtggcac actcctacgc taaagaaggc gctaaagtca ttgtgtcaga tatcaacgaa    120
gacaagggta ataaaaccgt tgaagatatt aaagcacagg gcggtgaagc tagttttgtg    180
aaagcggaca ccagcaaccc ggaagaagtg gaagccctgg ttaaacgtac ggtcgaaatt    240
tatggtcgcc tggatgtggc atgcaacaat gctggcattg gcggtgaaaa ggcactggct    300
ggtgattacg gcctggacag ctggcgtaaa gttctgtctg tgaatctgga cggtgtcttc    360 tatgctgta aatacgaact ggaacaaatg gagaaaaacg gcggtggcgt tatcgtcaat    420
atggccagca ttcatggtat cgttgcgcag ccgctgaact ctgcatatac ctctgcgaaa    480
cacgccgtgg ttggcctgac gaaaaacatt ggtgctgaat atggccagaa aacatccgt    540 tgcaatgcgg tgtgcccggg ctacattgaa accccgctgc tggaatcact gacgaaagaa    600
gagaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747
```

<210> SEQ ID NO 276
<211> LENGTH: 249
<212> TYPE: PRT
<213> ORGANISM: Artificial sequence
<220> FEATURE:
<223> OTHER INFORMATION: Engineered sequence

<400> SEQUENCE: 276

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Glu Lys Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Phe Met Thr Gly Gly Tyr Tyr
225                 230                 235                 240
```

Leu Val Asp Gly Gly Tyr Thr Ala Val
            245

<210> SEQ ID NO 277
<211> LENGTH: 747
<212> TYPE: DNA
<213> ORGANISM: Artificial sequence
<220> FEATURE:
<223> OTHER INFORMATION: Engineered sequence

<400> SEQUENCE: 277

| | | |
|---|---|---|
| atgggtatcc tggacaacaa agtcgcactg gttacgggcg ctggttcggg catcggtctg | 60 |
| gcggtggcac actcctacgc taaagaaggc gctaaagtca ttgtgtcaga tatcaacgaa | 120 |
| gacaagggta ataaaaccgt tgaagatatt aaagcacagg gcggtgaagc tagttttgtg | 180 |
| aaagcggaca ccagcaaccc ggaagaagtg aagccctgg ttaaacgtac ggtcgaaatt | 240 |
| tatggtcgcc tggatgtggc atgcaacaat gctggcattg gcggtgaaaa ggcactggct | 300 |
| ggtgattacg gcctggacag ctggcgtaaa gttctgtctg tgaatctgga cggtgtcttc | 360 |
| tatggctgta atacgaact ggaacaaatg gagaaaaacg gcggtggcgt tatcgtcaat | 420 |
| atggccagca ttcatggtat cgttgcgcag ccgctgaact ctgcatatac ctctgcgaaa | 480 |
| cacgccgtgg ttggcctgac gaaaaacatt ggtgctgaat atggccagaa aacatccgt | 540 |
| tgcaatgcgg tgtgcccggg ctacattgaa accccgctgc tggaatcact gacgaaagaa | 600 |
| atgaaagaag acctgatctc gaaacacccg atgggtcgcc tgggcaaacc ggaagaagtg | 660 |
| gcagaactgg ttctgtttct gagttccgaa aaatcatcgt tcatgaccgg tggctattac | 720 |
| ctggtcgatg gtggctacac ggcagtg | 747 |

<210> SEQ ID NO 278
<211> LENGTH: 249
<212> TYPE: PRT
<213> ORGANISM: Artificial sequence
<220> FEATURE:
<223> OTHER INFORMATION: Engineered sequence

<400> SEQUENCE: 278

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

```
His Ala Val Val Gly Leu Thr Lys Asn Ile Gly Ala Glu Tyr Gly Gln
            165                 170                 175

Lys Asn Ile Arg Cys Asn Ala Val Cys Pro Gly Tyr Ile Glu Thr Pro
        180                 185                 190

Leu Leu Glu Ser Leu Thr Lys Glu Met Lys Glu Asp Leu Ile Ser Lys
    195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Tyr Tyr
225                 230                 235                 240

Leu Val Asp Gly Gly Tyr Thr Ala Val
            245
```

<210> SEQ ID NO 279
<211> LENGTH: 747
<212> TYPE: DNA
<213> ORGANISM: Artificial sequence
<220> FEATURE:
<223> OTHER INFORMATION: Engineered sequence

<400> SEQUENCE: 279

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaaa acctgatctc gaaacacccg atgggtcgcc tggcaaaacc ggaagaagtg     660
gcagaactgg ttctgtttct gagttccgaa aaatcatcgt tcatgaccgg tggctattac     720
ctggtcgatg gtggctacac ggcagtg                                         747
```

<210> SEQ ID NO 280
<211> LENGTH: 249
<212> TYPE: PRT
<213> ORGANISM: Artificial sequence
<220> FEATURE:
<223> OTHER INFORMATION: Engineered sequence

<400> SEQUENCE: 280

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80
```

Tyr Gly Arg Leu Asp Val Ala Cys Asn Asn Ala Gly Ile Gly Gly Glu
            85                  90                  95

Lys Ala Leu Ala Gly Asp Tyr Gly Leu Asp Ser Trp Arg Lys Val Leu
        100                 105                 110

Ser Val Asn Leu Asp Gly Val Phe Tyr Gly Cys Lys Tyr Glu Leu Glu
            115                 120                 125

Gln Met Glu Lys Asn Gly Gly Val Ile Val Asn Met Ala Ser Ile
130                 135                 140

His Gly Ile Val Ala Gln Pro Leu Asn Ser Tyr Thr Ser Ala Lys
145                 150                 155                 160

His Ala Val Val Gly Leu Thr Lys Asn Ile Gly Ala Glu Tyr Gly Gln
            165                 170                 175

Lys Asn Ile Arg Cys Asn Ala Val Cys Pro Gly Tyr Ile Glu Thr Pro
        180                 185                 190

Leu Leu Glu Ser Leu Thr Lys Glu Met Lys Glu Asn Leu Ile Ser Lys
            195                 200                 205

His Pro Met Gly Arg Leu Gly Lys Pro Glu Glu Val Ala Glu Leu Val
210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245

<210> SEQ ID NO 281
<211> LENGTH: 747
<212> TYPE: DNA
<213> ORGANISM: Artificial sequence
<220> FEATURE:
<223> OTHER INFORMATION: Engineered sequence

<400> SEQUENCE: 281
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt atcgtcaat      420 atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctggcctc gaaacacccg atgggtcgcc tgggcaaacc ggaagaagtg     660
gcagaactgg ttctgttct gagttccgaa aaatcatcgt tcatgaccgg tggctattac     720
ctggtcgatg gtggctacac ggcagtg                                        747

<210> SEQ ID NO 282
<211> LENGTH: 249
<212> TYPE: PRT
<213> ORGANISM: Artificial sequence
<220> FEATURE:
<223> OTHER INFORMATION: Engineered sequence

<400> SEQUENCE: 282

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
                20                  25                  30

Val Ile Val Ser Asp Ile Asn Glu Asp Lys Gly Asn Lys Thr Val Glu
            35                  40                  45

Asp Ile Lys Ala Gln Gly Gly Glu Ala Ser Phe Val Lys Ala Asp Thr
        50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
                100                 105                 110

Ser Val Asn Leu Asp Gly Val Phe Tyr Gly Cys Lys Tyr Glu Leu Glu
            115                 120                 125

Gln Met Glu Lys Asn Gly Gly Val Ile Val Asn Met Ala Ser Ile
        130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
                180                 185                 190

Leu Leu Glu Ser Leu Thr Lys Glu Met Lys Glu Ala Leu Ala Ser Lys
                195                 200                 205

His Pro Met Gly Arg Leu Gly Lys Pro Glu Val Ala Glu Leu Val
210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 283
<211> LENGTH: 747
<212> TYPE: DNA
<213> ORGANISM: Artificial sequence
<220> FEATURE:
<223> OTHER INFORMATION: Engineered sequence

<400> SEQUENCE: 283
atgggtatcc tggacaacaa agtcgcagtg gttacgggcg ctggttcggg catcggtctg      60
gcggtggcac actcctacgc taaagaaggc gctaaagtca ttgtgtcaga tatcaacgaa     120
gacaagggta taaaaccgt tgaagatatt aaagcacagg gcggtgaagc tagttttgtg      180
aaagcggaca ccagcaaccc ggaagaagtg aagcccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt tatcgtcaat      420
atggccagca ttcatggtat cgttgcgcag ccgctgaact ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa acccgctgc tggaatcact gacgaaagaa     600

```
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747
```

<210> SEQ ID NO 284
<211> LENGTH: 249
<212> TYPE: PRT
<213> ORGANISM: Artificial sequence
<220> FEATURE:
<223> OTHER INFORMATION: Engineered sequence

<400> SEQUENCE: 284

```
Met Gly Ile Leu Asp Asn Lys Val Ala Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 285
<211> LENGTH: 747
<212> TYPE: DNA
<213> ORGANISM: Artificial sequence
<220> FEATURE:
<223> OTHER INFORMATION: Engineered sequence

<400> SEQUENCE: 285

```
atgggtatcc tggacaacaa agtcgcactg gttacgggcg ctggttcggg catcggtctg     60
gcgtcggcac actcctacgc taagaaaggc gctaaagtca ttgtgtcaga tatcaacgaa    120
gacaagggta taaaaaccgt tgaagatatt aaagcacagg gcggtgaagc tagttttgtg    180
```

-continued

```
aaagcggaca ccagcaaccc ggaagaagtg gaagccctgg ttaaacgtac ggtcgaaatt      240
tatggtcgcc tggatgtggc atgcaacaat gctggcattg gcggtgaaaa ggcactggct      300
ggtgattacg gcctggacag ctggcgtaaa gttctgtctg tgaatctgga cggtgtcttc      360
tatggctgta aatacgaact ggaacaaatg gagaaaaacg gcggtggcgt tatcgtcaat      420
atggccagca ttcatggtat cgttgcgcag ccgctgaact ctgcatatac ctctgcgaaa      480
cacgccgtgg ttggcctgac gaaaaacatt ggtgctgaat atggccagaa aaacatccgt      540
tgcaatgcgg tgtgcccggg ctacattgaa accccgctgc tggaatcact gacgaaagaa      600
atgaaagaag ccctgatctc gaaacacccg atgggtcgcc tgggcaaacc ggaagaagtg      660
gcagaactgg ttctgtttct gagttccgaa aaatcatcgt tcatgaccgg tggctattac      720
ctggtcgatg gtggctacac ggcagtg                                          747
```

<210> SEQ ID NO 286
<211> LENGTH: 249
<212> TYPE: PRT
<213> ORGANISM: Artificial sequence
<220> FEATURE:
<223> OTHER INFORMATION: Engineered sequence

<400> SEQUENCE: 286

```
Met Gly Ile Leu Asp Asn Lys Val Ala Leu Val Thr Gly Ala Gly Ser
1               5                   10                  15

Gly Ile Gly Leu Ala Ser Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Val Ala Glu Leu Val
    210                 215                 220

Leu Phe Leu Ser Ser Glu Lys Ser Ser Phe Met Thr Gly Tyr Tyr
225                 230                 235                 240

Leu Val Asp Gly Gly Tyr Thr Ala Val
                245
```

<210> SEQ ID NO 287
<211> LENGTH: 747
<212> TYPE: DNA
<213> ORGANISM: Artificial sequence
<220> FEATURE:
<223> OTHER INFORMATION: Engineered sequence

<400> SEQUENCE: 287

```
atgggtatcc tggacaacaa agtcgcactg gttacgggcg ctggttcggg catcggtctg      60
gcggtggcac actcctacgc taaagaaggc gctaaagtca ttgcttcaga tatcaacgaa     120
gacaagggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgttttct gagttccgaa aaatcatcgt tcatgaccgg tggctattac     720
ctggtcgatg gtggctacac ggcagtg                                          747
```

<210> SEQ ID NO 288
<211> LENGTH: 249
<212> TYPE: PRT
<213> ORGANISM: Artificial sequence
<220> FEATURE:
<223> OTHER INFORMATION: Engineered sequence

<400> SEQUENCE: 288

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Ala Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175
```

```
Lys Asn Ile Arg Cys Asn Ala Val Cys Pro Gly Tyr Ile Glu Thr Pro
                180                 185                 190

Leu Leu Glu Ser Leu Thr Lys Glu Met Lys Glu Ala Leu Ile Ser Lys
            195                 200                 205

His Pro Met Gly Arg Leu Gly Lys Pro Glu Glu Val Ala Glu Leu Val
        210                 215                 220

Leu Phe Leu Ser Ser Glu Lys Ser Phe Met Thr Gly Tyr Tyr
225                 230                 235                 240

Leu Val Asp Gly Gly Tyr Thr Ala Val
                245

<210> SEQ ID NO 289
<211> LENGTH: 747
<212> TYPE: DNA
<213> ORGANISM: Artificial sequence
<220> FEATURE:
<223> OTHER INFORMATION: Engineered sequence

<400> SEQUENCE: 289
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcacagg gcggtgaagc tagttttcg      180 aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aacatccgt     540 tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                          747

<210> SEQ ID NO 290
<211> LENGTH: 249
<212> TYPE: PRT
<213> ORGANISM: Artificial sequence
<220> FEATURE:
<223> OTHER INFORMATION: Engineered sequence

<400> SEQUENCE: 290

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Ser Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95
```

```
Lys Ala Leu Ala Gly Asp Tyr Gly Leu Asp Ser Trp Arg Lys Val Leu
                100                 105                 110
Ser Val Asn Leu Asp Gly Val Phe Tyr Gly Cys Lys Tyr Glu Leu Glu
            115                 120                 125
Gln Met Glu Lys Asn Gly Gly Gly Val Ile Val Asn Met Ala Ser Ile
        130                 135                 140
His Gly Ile Val Ala Gln Pro Leu Asn Ser Ala Tyr Thr Ser Ala Lys
145                 150                 155                 160
His Ala Val Val Gly Leu Thr Lys Asn Ile Gly Ala Glu Tyr Gly Gln
                165                 170                 175
Lys Asn Ile Arg Cys Asn Ala Val Cys Pro Gly Tyr Ile Glu Thr Pro
            180                 185                 190
Leu Leu Glu Ser Leu Thr Lys Glu Met Lys Glu Ala Leu Ile Ser Lys
        195                 200                 205
His Pro Met Gly Arg Leu Gly Lys Pro Glu Glu Val Ala Glu Leu Val
    210                 215                 220
Leu Phe Leu Ser Ser Glu Lys Ser Phe Met Thr Gly Gly Tyr Tyr
225                 230                 235                 240
Leu Val Asp Gly Gly Tyr Thr Ala Val
                245
```

<210> SEQ ID NO 291
<211> LENGTH: 747
<212> TYPE: DNA
<213> ORGANISM: Artificial sequence
<220> FEATURE:
<223> OTHER INFORMATION: Engineered sequence

<400> SEQUENCE: 291

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta taaaaccgt tgaagatatt aaagcacagg gcggtgaagc tagttttatg     180
aaagcggaca ccagcaaccc ggaagaagtg aagccctgg ttaaacgtac ggtcgaaatt      240
tatggtcgcc tggatgtggc atgcaacaat gctggcattg cggtgaaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt atcgtcaat      420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa acccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747
```

<210> SEQ ID NO 292
<211> LENGTH: 249
<212> TYPE: PRT
<213> ORGANISM: Artificial sequence
<220> FEATURE:
<223> OTHER INFORMATION: Engineered sequence

<400> SEQUENCE: 292

```
Met Gly Ile Leu Asp Asn Lys Val Ala Leu Val Thr Gly Ala Gly Ser
1               5                   10                  15
```

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Met Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

```
<210> SEQ ID NO 293
<211> LENGTH: 747
<212> TYPE: DNA
<213> ORGANISM: Artificial sequence
<220> FEATURE:
<223> OTHER INFORMATION: Engineered sequence

<400> SEQUENCE: 293
```

| | | |
|---|---|---:|
| atgggtatcc tggacaacaa agtcgcactg gttacgggcg ctggttcggg catcggtctg | | 60 |
| gcggtggcac actcctacgc taaagaaggc gctaaagtca ttgtgtcaga tatcaacgaa | | 120 |
| gacaagggta taaaaccgt tgaagatatt aaagcacagg gcggtgaagc tagttttgtg | | 180 |
| aaagcggaca ccagcaaccc ggaagaagtg gaagccatgg ttaaacgtac ggtcgaaatt | | 240 |
| tatggtcgcc tggatgtggc atgcaacaat gctggcattg gcggtgaaaa ggcactggct | | 300 |
| ggtgattacg gcctggacag ctggcgtaaa gttctgtctg tgaatctgga cggtgtcttc | | 360 |
| tatgctgta aatacgaact ggaacaaatg gagaaaaacg gcggtggcgt tatcgtcaat | | 420 |
| atggccagca ttcatggtat cgttgcgcag ccgctgaact ctgcatatac ctctgcgaaa | | 480 |
| cacgccgtgg ttggcctgac gaaaaacatt ggtgctgaat atggccagaa aaacatccgt | | 540 |
| tgcaatgcgg tgtgcccggg ctacattgaa accccgctgc tggaatcact gacgaaagaa | | 600 |
| atgaaagaag ccctgatctc gaaacacccg atgggtcgcc tgggcaaacc ggaagaagtg | | 660 |
| gcagaactgg ttctgttttct gagttccgaa aaatcatcgt tcatgaccgg tggctattac | | 720 | ctggtcgatg gtggctacac ggcagtg 747

<210> SEQ ID NO 294
<211> LENGTH: 249
<212> TYPE: PRT
<213> ORGANISM: Artificial sequence
<220> FEATURE:
<223> OTHER INFORMATION: Engineered sequence

<400> SEQUENCE: 294

```
Met Gly Ile Leu Asp Asn Lys Val Ala Leu Val Thr Gly Ala Gly Ser
1               5                   10                  15
Gly Ile Gly Leu Ala Val Ala His Ser Tyr Ala Lys Glu Gly Ala Lys
            20                  25                  30
Val Ile Val Ser Asp Ile Asn Glu Asp Lys Gly Asn Lys Thr Val Glu
        35                  40                  45
Asp Ile Lys Ala Gln Gly Gly Glu Ala Ser Phe Val Lys Ala Asp Thr
    50                  55                  60
Ser Asn Pro Glu Glu Val Glu Ala Met Val Lys Arg Thr Val Glu Ile
65                  70                  75                  80
Tyr Gly Arg Leu Asp Val Ala Cys Asn Asn Ala Gly Ile Gly Gly Glu
                85                  90                  95
Lys Ala Leu Ala Gly Asp Tyr Gly Leu Asp Ser Trp Arg Lys Val Leu
            100                 105                 110
Ser Val Asn Leu Asp Gly Val Phe Tyr Gly Cys Lys Tyr Glu Leu Glu
        115                 120                 125
Gln Met Glu Lys Asn Gly Gly Gly Val Ile Val Asn Met Ala Ser Ile
    130                 135                 140
His Gly Ile Val Ala Gln Pro Leu Asn Ser Ala Tyr Thr Ser Ala Lys
145                 150                 155                 160
His Ala Val Val Gly Leu Thr Lys Asn Ile Gly Ala Glu Tyr Gly Gln
                165                 170                 175
Lys Asn Ile Arg Cys Asn Ala Val Cys Pro Gly Tyr Ile Glu Thr Pro
            180                 185                 190
Leu Leu Glu Ser Leu Thr Lys Glu Met Lys Glu Ala Leu Ile Ser Lys
        195                 200                 205
His Pro Met Gly Arg Leu Gly Lys Pro Glu Glu Val Ala Glu Leu Val
    210                 215                 220
Leu Phe Leu Ser Ser Glu Lys Ser Ser Phe Met Thr Gly Gly Tyr Tyr
225                 230                 235                 240
Leu Val Asp Gly Gly Tyr Thr Ala Val
                245
```

<210> SEQ ID NO 295
<211> LENGTH: 747
<212> TYPE: DNA
<213> ORGANISM: Artificial sequence
<220> FEATURE:
<223> OTHER INFORMATION: Engineered sequence

<400> SEQUENCE: 295
atgggtatcc tggacaacaa agtcgcactg gttacgggcg ctggttcggg catcggtctg     60
gcggtggcac actcctacgc taaagaaggc gctaaagtca ttgtgtcaga tatcaacgaa    120
gacaagggta ataaaaccgt tgaagatatt aaagcacagg gcggtgaagc tagttttgtg    180
aaagcggaca ccagcaaccc ggaagaagtg gaagccctgg ttaaacgtac ggtcgaaatt    240
tatggtcgcc tggatgtggc atgcaacaat gctggcattg gcggtgaaaa ggcactggct    300

```
ggtgattacg gcctggacag ctggcgtaaa gttctgtctg tgaatctgga cggtgtcttc    360
tatggctgta aatacgaact ggaacaaatg gagaaaaacg gcggtggcgt tatcgtcaat    420
atgtctagca ttcatggtat cgttgcgcag ccgctgaact ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747
```

<210> SEQ ID NO 296
<211> LENGTH: 249
<212> TYPE: PRT
<213> ORGANISM: Artificial sequence
<220> FEATURE:
<223> OTHER INFORMATION: Engineered sequence

<400> SEQUENCE: 296

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ser Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 297
<211> LENGTH: 747
<212> TYPE: DNA

<213> ORGANISM: Artificial sequence
<220> FEATURE:
<223> OTHER INFORMATION: Engineered sequence

<400> SEQUENCE: 297

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcaaccg gcggtgaagc tagttttgtg     180
aaagcggaca ccagcaaccc ggaagaagtg aagccctgg ttaaacgtac ggtcgaaatt      240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt tatcgtcaat      420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                        747
```

<210> SEQ ID NO 298
<211> LENGTH: 249
<212> TYPE: PRT
<213> ORGANISM: Artificial sequence
<220> FEATURE:
<223> OTHER INFORMATION: Engineered sequence

<400> SEQUENCE: 298

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Thr Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
```

```
            195                 200                 205
His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 299
<211> LENGTH: 747
<212> TYPE: DNA
<213> ORGANISM: Artificial sequence
<220> FEATURE:
<223> OTHER INFORMATION: Engineered sequence

<400> SEQUENCE: 299

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aacatccgt     540
tgcaatgcgg tgtgcccggg ctacattgaa accccgctgc tggaatcact gacgaaagaa     600
atgaaagaag ccctgatctc gaaacaccg atgggtcgcc tgggcaggcc ggaagaagtg     660
gcagaactgg ttctgttcct gagttccgaa aaatcatcgt tcatgaccgg tggctattac     720
ctggtcgatg gtggctacac ggcagtg                                         747
```

<210> SEQ ID NO 300
<211> LENGTH: 249
<212> TYPE: PRT
<213> ORGANISM: Artificial sequence
<220> FEATURE:
<223> OTHER INFORMATION: Engineered sequence

<400> SEQUENCE: 300

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
```

```
                115                 120                 125
Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Arg Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245
```

<210> SEQ ID NO 301
<211> LENGTH: 747
<212> TYPE: DNA
<213> ORGANISM: Artificial sequence
<220> FEATURE:
<223> OTHER INFORMATION: Engineered sequence

<400> SEQUENCE: 301

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatgtggc atgcaacaat gctggcattg cggtgaaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt tatcgtcaat      420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc gagcgaagtg     660
gcagaactgg ttctgttct gagttccgaa aaatcatcgt tcatgaccgg tggctattac      720
ctggtcgatg gtggctacac ggcagtg                                         747
```

<210> SEQ ID NO 302
<211> LENGTH: 249
<212> TYPE: PRT
<213> ORGANISM: Artificial sequence
<220> FEATURE:
<223> OTHER INFORMATION: Engineered sequence

<400> SEQUENCE: 302

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
                20                  25                  30

Val Ile Val Ser Asp Ile Asn Glu Asp Lys Gly Asn Lys Thr Val Glu
```

```
                35                  40                  45
Asp Ile Lys Ala Gln Gly Gly Glu Ala Ser Phe Val Lys Ala Asp Thr
 50                  55                  60

Ser Asn Pro Glu Glu Val Glu Ala Leu Val Lys Arg Thr Val Glu Ile
 65                  70                  75                  80

Tyr Gly Arg Leu Asp Val Ala Cys Asn Asn Ala Gly Ile Gly Gly Glu
                 85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Ser Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 303
<211> LENGTH: 747
<212> TYPE: DNA
<213> ORGANISM: Artificial sequence
<220> FEATURE:
<223> OTHER INFORMATION: Engineered sequence

<400> SEQUENCE: 303
atgggtatcc tggacaacaa agtcgcactg gttacgggcg ctggttcggg catcggtctg    60
gcggtggcac actcctacgc taagaaggc gctaaagtca ttgtgtcaga tatcaacgaa   120
gacaagggta taaaaccgt tgaagatatt aaagcacagg cggtgaagc tagttttgtg    180 aaagcggaca ccagcaaccc ggaagaagtg gaagccctgg ttaaacgtac ggtcgaaatt   240
tatggtcgcc tggatgtggc atgcaacaat gctggcattg gcggtgaaaa ggcactggct   300
ggtgattacg gcctggacag ctggcgtaaa gttctgtctg tgaatctgga cggtgtcttc   360
tatggctgta atacgaact ggaacaaatg gagaaaaacg gcggtggcgt tatcgtcaat    420
atggccagca ttcatggtat cgttgcgcag ccgctgaact ctgcatatac ctctgcgaaa   480
cacgccgtgg ttggcctgac gaaaaacatt ggtgctgaat atggccagaa aaacatccgt   540
tgcaatgcgg tgtgcccggg ctacattgac accccgctgc tggaatcact gacgaaagaa   600
atgaaagaag ccctgatctc gaaacacccg atgggtcgcc tgggcaaacc ggaagaagtg   660
gcagaactgg ttctgtttct gagttccgaa aaatcatcgt tcatgaccgg tggctattac   720
ctggtcgatg gtggctacac ggcagtg                                       747

<210> SEQ ID NO 304
```

<211> LENGTH: 249
<212> TYPE: PRT
<213> ORGANISM: Artificial sequence
<220> FEATURE:
<223> OTHER INFORMATION: Engineered sequence

<400> SEQUENCE: 304

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Asp Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 305
<211> LENGTH: 747
<212> TYPE: DNA
<213> ORGANISM: Artificial sequence
<220> FEATURE:
<223> OTHER INFORMATION: Engineered sequence

<400> SEQUENCE: 305
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta taaaaccgt tgaagatatt aaagcacagg gcggtgaagc tagttttgtg      180
aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta aatacgaact ggaacaaatg gagaaaaacg gcggtggcgt tatcgtcaat     420

```
atggccagca ttcatggtat cgttgcgcag ccgctgaact ctgcatatac ctctgcgaaa    480
cacgccgtga ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747
```

<210> SEQ ID NO 306
<211> LENGTH: 249
<212> TYPE: PRT
<213> ORGANISM: Artificial sequence
<220> FEATURE:
<223> OTHER INFORMATION: Engineered sequence

<400> SEQUENCE: 306

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Ile Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 307
<211> LENGTH: 747
<212> TYPE: DNA
<213> ORGANISM: Artificial sequence
<220> FEATURE:
<223> OTHER INFORMATION: Engineered sequence

<400> SEQUENCE: 307

```
atgggtatcc tggacaacaa agtcgcactg gttacgggcg ctggttcggg catcggtctg    60
gcggtggcac actcctacgc taaagaaggc gctaaagtca ttgtgtcaga tatcaacgaa   120
gacaagggta ataaaaccgt tgaagatatt aaagcacagg gcggtgaagc tagttttgtg   180
aaagcggaca ccagcaaccc ggaagaagtg aaagccctgg ttaaacgtac ggtcgaaatt   240
tatggtcgcc tggatgtggc atgcaacaat gctggcattg gcggtgaaaa ggcactggct   300
ggtgattacg gcctggacag ctggcgtaaa gttctgtctg tgaatctgga cggtgtcttc   360
tatggctgta atacgaact ggaacaaatg gagaaaaacg gcggtggcgt tatcgtcaat   420
atggccagca ttcatggtat cgttgcgcag ccgctgaact ctgcatatac ctctgcgaaa   480
cacgccgtgc tgggcctgac gaaaaacatt ggtgctgaat atggccagaa aaacatccgt   540
tgcaatgcgg tgtgcccggg ctacattgaa accccgctgc tggaatcact gacgaaagaa   600
atgaaagaag ccctgatctc gaaacacccg atgggtcgcc tgggcaaacc ggaagaagtg   660
gcagaactgg ttctgtttct gagttccgaa aaatcatcgt tcatgaccgg tggctattac   720
ctggtcgatg gtggctacac ggcagtg                                       747
```

<210> SEQ ID NO 308
<211> LENGTH: 249
<212> TYPE: PRT
<213> ORGANISM: Artificial sequence
<220> FEATURE:
<223> OTHER INFORMATION: Engineered sequence

<400> SEQUENCE: 308

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Leu Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220
```

Leu Phe Leu Ser Ser Glu Lys Ser Phe Met Thr Gly Gly Tyr Tyr
225                 230                 235                 240

Leu Val Asp Gly Gly Tyr Thr Ala Val
            245

<210> SEQ ID NO 309
<211> LENGTH: 747
<212> TYPE: DNA
<213> ORGANISM: Artificial sequence
<220> FEATURE:
<223> OTHER INFORMATION: Engineered sequence

<400> SEQUENCE: 309
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaacg gcggtggcgt tatcgtcaat     420
atggccagca ttcatggtat cgttgcgcag ccgctgaact ctgcatatac ctctgcgaaa     480
cacgccgtgg ttggcctgac gaaaaacatt ggtgctgaat atggccagaa aacatccgt     540
tgcaatgcga cttgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                         747

<210> SEQ ID NO 310
<211> LENGTH: 249
<212> TYPE: PRT
<213> ORGANISM: Artificial sequence
<220> FEATURE:
<223> OTHER INFORMATION: Engineered sequence

<400> SEQUENCE: 310

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
            165                 170                 175

Lys Asn Ile Arg Cys Asn Ala Thr Cys Pro Gly Tyr Ile Glu Thr Pro
        180                 185                 190

Leu Leu Glu Ser Leu Thr Lys Glu Met Lys Glu Ala Leu Ile Ser Lys
    195                 200                 205

His Pro Met Gly Arg Leu Gly Lys Pro Glu Glu Val Ala Glu Leu Val
210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245

<210> SEQ ID NO 311
<211> LENGTH: 747
<212> TYPE: DNA
<213> ORGANISM: Artificial sequence
<220> FEATURE:
<223> OTHER INFORMATION: Engineered sequence

<400> SEQUENCE: 311
atgggtatcc tggacaacaa agtcgcactg gttacgggcg ctggttcggg catcggtctg    60
gcggtggcac actcctacgc taaagaaggc gctaaagtca ttgtgtcaga tatcaacgaa   120
gacaagggta taaaaccgt tgaagatatt aaagcacagg gcggtgaagc tagttttgtg   180
aaagcggaca ccagcaaccc ggaagaagtg aagccctgg ttaaacgtac ggtcgaaatt   240
tatggtcgcc tggatgtggc atgcaacaat gctggcattg gcggtgaaaa ggcactggct   300
ggtgattacg gcctggacag ctggcgtaaa gttctgtctg tgaatctgga cggtgtcttc   360
tatggctgta atacgaact ggaacaaatg gagaaaaacg gcggtggcgt tatcgtcaat   420
atggccagca ttcatggtat cgttgcgcag ccgctgaact ctgcatatac ctctgcgaaa   480
cacgccgtgg ttggcctgac gaaaaacatt ggtgctgaat atggccagaa aaacatccgt   540
tgcaatgcgg tgtgcccggg ctacattgaa accccgctgc tggaatcact gacgaaagaa   600
atgaaagaag ccctgatctc gaaacacccg atgggtcgcc tgggcaaacc ggaagaagtg   660
gcagaactgt cgctgtttct gagttccgaa aaatcatcgt tcatgaccgg tggctattac   720
ctggtcgatg gtggctacac ggcagtg                                       747

<210> SEQ ID NO 312
<211> LENGTH: 249
<212> TYPE: PRT
<213> ORGANISM: Artificial sequence
<220> FEATURE:
<223> OTHER INFORMATION: Engineered sequence

<400> SEQUENCE: 312

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
            85                  90                  95

Lys Ala Leu Ala Gly Asp Tyr Gly Leu Asp Ser Trp Arg Lys Val Leu
        100                 105                 110

Ser Val Asn Leu Asp Gly Val Phe Tyr Gly Cys Lys Tyr Glu Leu Glu
    115                 120                 125

Gln Met Glu Lys Asn Gly Gly Val Ile Val Asn Met Ala Ser Ile
130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Ser
210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245

<210> SEQ ID NO 313
<211> LENGTH: 747
<212> TYPE: DNA
<213> ORGANISM: Artificial sequence
<220> FEATURE:
<223> OTHER INFORMATION: Engineered sequence

<400> SEQUENCE: 313
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta taaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt atcgtcaat     420 atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactga cgctgtttct gagttccgaa aaatcatcgt tcatgaccgg tggctattac     720
ctggtcgatg gtggctacac ggcagtg                                          747

<210> SEQ ID NO 314
<211> LENGTH: 249
<212> TYPE: PRT
<213> ORGANISM: Artificial sequence
<220> FEATURE:

<223> OTHER INFORMATION: Engineered sequence

<400> SEQUENCE: 314

| Met | Gly | Ile | Leu | Asp | Asn | Lys | Val | Ala | Leu | Val | Thr | Gly | Ala | Gly | Ser |
|---|---|---|---|---|---|---|---|---|---|---|---|---|---|---|---|
| 1 | | | | 5 | | | | | 10 | | | | | 15 | |

| Gly | Ile | Gly | Leu | Ala | Val | Ala | His | Ser | Tyr | Ala | Lys | Glu | Gly | Ala | Lys |
| | | | 20 | | | | | 25 | | | | | 30 | | |

| Val | Ile | Val | Ser | Asp | Ile | Asn | Glu | Asp | Lys | Gly | Asn | Lys | Thr | Val | Glu |
| | | 35 | | | | | 40 | | | | | 45 | | | |

| Asp | Ile | Lys | Ala | Gln | Gly | Gly | Glu | Ala | Ser | Phe | Val | Lys | Ala | Asp | Thr |
| | 50 | | | | | 55 | | | | | 60 | | | | |

| Ser | Asn | Pro | Glu | Glu | Val | Glu | Ala | Leu | Val | Lys | Arg | Thr | Val | Glu | Ile |
| 65 | | | | | 70 | | | | | 75 | | | | | 80 |

| Tyr | Gly | Arg | Leu | Asp | Val | Ala | Cys | Asn | Asn | Ala | Gly | Ile | Gly | Gly | Glu |
| | | | | 85 | | | | | 90 | | | | | 95 | |

| Lys | Ala | Leu | Ala | Gly | Asp | Tyr | Gly | Leu | Asp | Ser | Trp | Arg | Lys | Val | Leu |
| | | | 100 | | | | | 105 | | | | | 110 | | |

| Ser | Val | Asn | Leu | Asp | Gly | Val | Phe | Tyr | Gly | Cys | Lys | Tyr | Glu | Leu | Glu |
| | | | 115 | | | | | 120 | | | | | 125 | | |

| Gln | Met | Glu | Lys | Asn | Gly | Gly | Val | Ile | Val | Asn | Met | Ala | Ser | Ile |
| | 130 | | | | | 135 | | | | | 140 | | | |

| His | Gly | Ile | Val | Ala | Gln | Pro | Leu | Asn | Ser | Ala | Tyr | Thr | Ser | Ala | Lys |
| 145 | | | | | 150 | | | | | 155 | | | | | 160 |

| His | Ala | Val | Val | Gly | Leu | Thr | Lys | Asn | Ile | Gly | Ala | Glu | Tyr | Gly | Gln |
| | | | | 165 | | | | | 170 | | | | | 175 | |

| Lys | Asn | Ile | Arg | Cys | Asn | Ala | Val | Cys | Pro | Gly | Tyr | Ile | Glu | Thr | Pro |
| | | | 180 | | | | | 185 | | | | | 190 | | |

| Leu | Leu | Glu | Ser | Leu | Thr | Lys | Glu | Met | Lys | Glu | Ala | Leu | Ile | Ser | Lys |
| | | | 195 | | | | | 200 | | | | | 205 | | |

| His | Pro | Met | Gly | Arg | Leu | Gly | Lys | Pro | Glu | Glu | Val | Ala | Glu | Leu | Thr |
| | 210 | | | | | 215 | | | | | 220 | | | | |

| Leu | Phe | Leu | Ser | Ser | Glu | Lys | Ser | Ser | Phe | Met | Thr | Gly | Gly | Tyr | Tyr |
| 225 | | | | | 230 | | | | | 235 | | | | | 240 |

| Leu | Val | Asp | Gly | Gly | Tyr | Thr | Ala | Val |
| | | | | 245 | | | | |

<210> SEQ ID NO 315
<211> LENGTH: 747
<212> TYPE: DNA
<213> ORGANISM: Artificial sequence
<220> FEATURE:
<223> OTHER INFORMATION: Engineered sequence

<400> SEQUENCE: 315

| atgggtatcc tggacaacaa agtcgcactg gttacgggcg ctggttcggg catcggtctg | 60 |
|---|---|
| gcggtggcac actcctacgc taaagaaggc gctaaagtca ttgtgtcaga tatcaacgaa | 120 |
| gacaagggta taaaaccgt tgaagatatt aaagcacagg gcggtgaagc tagtttttgtg | 180 |
| aaagcggaca ccagcaaccc ggaagaagtg gaagccctgg ttaaacgtac ggtcgaaatt | 240 |
| tatggtcgcc tggatgtggc atgcaacaat gctggcattg gcggtgaaaa ggcactggct | 300 |
| ggtgattacg gcctggacag ctggcgtaaa gttctgtctg tgaatctgga cggtgtcttc | 360 |
| tatggctgta aattttcgct ggaacaaatg gagaaaaacg gcggtggcgt tatcgtcaat | 420 |
| atggccagca ttcatggtat cgttgcgcag ccgctgaact ctgcatatac ctctgcaaaa | 480 |
| cacgccgtgg ttggcctgac gaaaaacatt ggtgctgaat atggccagaa aaacatccgt | 540 |

```
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg tggctacac ggcagtg                                         747
```

<210> SEQ ID NO 316
<211> LENGTH: 249
<212> TYPE: PRT
<213> ORGANISM: Artificial sequence
<220> FEATURE:
<223> OTHER INFORMATION: Engineered sequence

<400> SEQUENCE: 316

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Phe Ser Leu Glu
        115                 120                 125

Gln Met Glu Lys Asn Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 317
<211> LENGTH: 747
<212> TYPE: DNA
<213> ORGANISM: Artificial sequence
<220> FEATURE:
<223> OTHER INFORMATION: Engineered sequence

<400> SEQUENCE: 317

```
atgggtatcc tggacaacaa agtcgcactg gttacgggcg ctggttcggg catcggtctg    60
```

```
gcggtggcac actcctacgc taaagaaggc gctaaagtca ttgtgtcaga tatcaacgaa    120
gacaagggta ataaaaccgt tgaagatatt aaagcacagg gcggtgaagc tagttttgtg    180
aaagcggaca ccagcaaccc ggaagaagtg aaagccctgg ttaaacgtac ggtcgaaatt    240
tatggtcgcc tggatgtggc atgcaacaat gctggcattg gcggtgaaaa ggcactggct    300
ggtgattacg gcctggacag ctggcgtaaa gttctgtctg tgaatctgga cggtgtcttc    360
tatggctgta aatttgaact ggaacaaatg gagaaaaacg gcggtggcgt tatcgtcaat    420
atggccagca ttcatggtat cgttgcgcag ccgctgaact ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tggcaaaacc ggaagaagtg    660
gcagaactgg ttctgtttct gagttccgaa aaatcatcgt tcatgaccgg tggctattac    720
ctggtcgatg gtggctacac ggcagtg                                         747
```

<210> SEQ ID NO 318
<211> LENGTH: 249
<212> TYPE: PRT
<213> ORGANISM: Artificial sequence
<220> FEATURE:
<223> OTHER INFORMATION: Engineered sequence

<400> SEQUENCE: 318

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Phe Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240
```

Leu Val Asp Gly Gly Tyr Thr Ala Val
            245

<210> SEQ ID NO 319
<211> LENGTH: 747
<212> TYPE: DNA
<213> ORGANISM: Artificial sequence
<220> FEATURE:
<223> OTHER INFORMATION: Engineered sequence

<400> SEQUENCE: 319

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcacagg gcggtgaagc tagttttgtg     180
aaagcggaca ccagcaaccc ggaagaagtg aagccctgg ttaaacgtac ggtcgaaatt      240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta atacacgct ggaacaaatg agaaaaacg gcggtggcgt tatcgtcaat       420
atggccagca ttcatggtat cgttgcgcag ccgctgaact ctgcatatac ctctgcgaaa     480
cacgccgtgg ttggcctgac gaaaaacatt ggtgctgaat atggccagaa aacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgttct gagttccgaa aaatcatcgt tcatgaccgg tggctattac      720
ctggtcgatg gtggctacac ggcagtg                                         747
```

<210> SEQ ID NO 320
<211> LENGTH: 249
<212> TYPE: PRT
<213> ORGANISM: Artificial sequence
<220> FEATURE:
<223> OTHER INFORMATION: Engineered sequence

<400> SEQUENCE: 320

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Thr Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

```
His Ala Val Val Gly Leu Thr Lys Asn Ile Gly Ala Glu Tyr Gly Gln
            165                 170                 175

Lys Asn Ile Arg Cys Asn Ala Val Cys Pro Gly Tyr Ile Glu Thr Pro
        180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245
```

<210> SEQ ID NO 321
<211> LENGTH: 747
<212> TYPE: DNA
<213> ORGANISM: Artificial sequence
<220> FEATURE:
<223> OTHER INFORMATION: Engineered sequence

<400> SEQUENCE: 321

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta taaaaccgt tgaagatatt aaagcacagg gcggtgaagc tagttttgtg     180
aaagcggaca ccagcaaccc ggaagaagtg aagccctgg ttaaacgtac ggtcgaaatt     240
tatggtcgcc tggatgtggc atgcaacaat gctggcattg cggtgaaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt tatcgtcgtg     420
atggccagca ttcatggtat cgttgcgcag ccgctgaact ctgcatatac ctctgcgaaa     480
cacgccgtgg ttggcctgac gaaaaacatt ggtgctgaat atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                          747
```

<210> SEQ ID NO 322
<211> LENGTH: 249
<212> TYPE: PRT
<213> ORGANISM: Artificial sequence
<220> FEATURE:
<223> OTHER INFORMATION: Engineered sequence

<400> SEQUENCE: 322

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80
```

Tyr Gly Arg Leu Asp Val Ala Cys Asn Asn Ala Gly Ile Gly Gly Glu
            85                  90                  95

Lys Ala Leu Ala Gly Asp Tyr Gly Leu Asp Ser Trp Arg Lys Val Leu
        100                 105                 110

Ser Val Asn Leu Asp Gly Val Phe Tyr Gly Cys Lys Tyr Glu Leu Glu
        115                 120                 125

Gln Met Glu Lys Asn Gly Gly Val Ile Val Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 323
<211> LENGTH: 747
<212> TYPE: DNA
<213> ORGANISM: Artificial sequence
<220> FEATURE:
<223> OTHER INFORMATION: Engineered sequence

<400> SEQUENCE: 323
atgggtatcc tggacaacaa agtcgcactg gttacgggcg ctggttcggg catcggtctg     60
gcggtggcac actcctacgc taaagaaggc gctaaagtca ttgtgtcaga tatcaacgaa    120
gacaagggta taaaaccgt tgaagatatt aaagcacagg cggtgaagc tagttttgtg      180 aaagcggaca ccagcaaccc ggaagaagtg aaagccctgg ttaaacgtac ggtcgaaatt    240
tatggtcgcc tggatgtggc atgcaacaat gctggcattg gcggtgaaaa ggcactggct    300
ggtgattacg gcctggacag ctggcgtaaa gttctgtctg tgaatctgga cggtgtcttc    360
tatggctgta atacgctct ggaacaaatg agaaaaacg gcggtggcgt tatcgtcaat     420
atggccagca ttcatggtat cgttgcgcag ccgctgaact ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa accccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                        747

<210> SEQ ID NO 324
<211> LENGTH: 249
<212> TYPE: PRT
<213> ORGANISM: Artificial sequence
<220> FEATURE:
<223> OTHER INFORMATION: Engineered sequence

<400> SEQUENCE: 324

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
            35                  40                  45

Asp Ile Lys Ala Gln Gly Gly Glu Ala Ser Phe Val Lys Ala Asp Thr
        50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
            85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Ala Leu Glu
            115                 120                 125

Gln Met Glu Lys Asn Gly Gly Val Ile Val Asn Met Ala Ser Ile
            130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
            165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Gly Ala Leu Ile Ser Lys
            195                 200                 205

His Pro Met Gly Arg Leu Gly Lys Pro Glu Glu Val Ala Glu Leu Val
210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
            245

<210> SEQ ID NO 325
<211> LENGTH: 747
<212> TYPE: DNA
<213> ORGANISM: Artificial sequence
<220> FEATURE:
<223> OTHER INFORMATION: Engineered sequence

<400> SEQUENCE: 325
atgggtatcc tggacaacaa agtcgcactg gttacgggcg ctggttcggg catcggtctg     60
gcggtggcac actcctacgc taaagaaggc gctaaagtca ttgtgtcaga tatcaacgaa    120
gacaagggta taaaaccgt tgaagatatt aaagcacagg gcggtgaagc tagttttgtg    180
aaagcggaca ccagcaaccc ggaagaagtg gaagccctgg ttaaacgtac ggtcgaaatt    240
tatggtcgcc tggatgtggc atgcaacaat gctggcattg gcggtgaaaa ggcactggct    300
ggtgattacg gcctggacag ctggcgtaaa gttctgtctg tgaatctgga cggtgtcttc    360
tatggctgta atattctcct ggaacaaatg gagaaaaacg gcggtggcgt tatcgtcaat    420
atggccagca ttcatggtat cgttgcgcag ccgctgaact ctgcatatac ctctgcgaaa    480
cacgccgtgg ttggcctgac gaaaaacatt ggtgctgaat atggccagaa aaacatccgt    540
tgcaatgcgg tgtgcccggg ctacattgaa acccgctgc tggaatcact gacgaaagaa    600
atgaaagaag ccctgatctc gaaacacccg atgggtcgcc tgggcaaacc ggaagaagtg    660
gcagaactgg ttctgtttct gagttccgaa aaatcatcgt tcatgaccgg tggctattac    720
ctggtcgatg gtggctacac ggcagtg                                         747

<210> SEQ ID NO 326
<211> LENGTH: 249
<212> TYPE: PRT
<213> ORGANISM: Artificial sequence
<220> FEATURE:
<223> OTHER INFORMATION: Engineered sequence

<400> SEQUENCE: 326

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Ser Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 327
<211> LENGTH: 747
<212> TYPE: DNA
<213> ORGANISM: Artificial sequence
<220> FEATURE:
<223> OTHER INFORMATION: Engineered sequence

<400> SEQUENCE: 327
atgggtatcc tggacaacaa agtcgcactg gttacgggcg ctggttcggg catcggtctg    60
gcggtggcac actcctacgc taaagaaggc gctaaagtca ttgtgtcaga tatcaacgaa    120
gacaagggta ataaaaccgt tgaagatatt aaagcacagg gcggtgaagc tagttttgtg    180

```
aaagcggaca ccagcaaccc ggaagaagtg gaagccctgg ttaaacgtac ggtcgaaatt      240
tatggtcgcc tggatgtggc atgcaacaat gctggcattg gcggtgaaaa ggcactggct      300
ggtgattacg gcctggacag ctggcgtaaa gttctgtctg tgaatctgga cggtgtcttc      360
tatggctgta aatttgttct ggaacaaatg gagaaaaacg gcggtggcgt tatcgtcaat      420
atggccagca ttcatggtat cgttgcgcag ccgctgaact ctgcatatac ctctgcgaaa      480
cacgccgtgg ttggcctgac gaaaaacatt ggtgctgaat atggccagaa aaacatccgt      540
tgcaatgcgg tgtgcccggg ctacattgaa accccgctgc tggaatcact gacgaaagaa      600
atgaaagaag ccctgatctc gaaacacccg atgggtcgcc tgggcaaacc ggaagaagtg      660
gcagaactgg ttctgttttc tgagttccga aaaatcatcg tcatgaccgg tggctattac      720
ctggtcgatg gtggctacac ggcagtg                                          747
```

<210> SEQ ID NO 328
<211> LENGTH: 249
<212> TYPE: PRT
<213> ORGANISM: Artificial sequence
<220> FEATURE:
<223> OTHER INFORMATION: Engineered sequence

<400> SEQUENCE: 328

```
Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Phe Val Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Glu Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```

<210> SEQ ID NO 329
<211> LENGTH: 747
<212> TYPE: DNA
<213> ORGANISM: Artificial sequence
<220> FEATURE:
<223> OTHER INFORMATION: Engineered sequence

<400> SEQUENCE: 329

```
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta ataaaaccgt tgaagatatt aaagcacagg gcggtgaagc tagttttgtg     180
aaagcggaca ccagcaaccc ggaagaagtg gaagccctgg ttaaacgtac ggtcgaaatt     240
tatggtcgcc tggatgtggc atgcaacaat gctggcattg cgggtgaaaa ggcactggct     300
ggtgattacg gcctggacag ctggcgtaaa gttctgtctg tgaatctgga cggtgtcttc     360
tatggctgta atacgaact ggaacaaatg gagaaaaacg gcggtggcgt tatcgtcaat      420
atggccagca ttcatggtat cgttgcgcag ccgctgaact ctgcatatac ctctgcgaaa     480
cacgccgtgg ttggcctgac gaaaaacatt ggtgctgatt atggccagaa aacatccgt      540
tgcaatgcgg tgtgcccggg ctacattgaa accccgctgc tggaatcact gacgaaagaa     600
atgaaagaag ccctgatctc gaaacaccg atgggtcgcc tgggcaaacc ggaagaagtg      660
gcagaactgg ttctgtttct gagttccgaa aaatcatcgt tcatgaccgg tggctattac     720
ctggtcgatg gtggctacac ggcagtg                                          747
```

<210> SEQ ID NO 330
<211> LENGTH: 249
<212> TYPE: PRT
<213> ORGANISM: Artificial sequence
<220> FEATURE:
<223> OTHER INFORMATION: Engineered sequence

<400> SEQUENCE: 330

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
            20                  25                  30

Val Ile Val Ser Asp Ile Asn Glu Asp Lys Gly Asn Lys Thr Val Glu
        35                  40                  45

Asp Ile Lys Ala Gln Gly Gly Glu Ala Ser Phe Val Lys Ala Asp Thr
    50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Ala Gly Glu
                85                  90                  95

Lys Ala Leu Ala Gly Asp Tyr Gly Leu Asp Ser Trp Arg Lys Val Leu
            100                 105                 110

Ser Val Asn Leu Asp Gly Val Phe Tyr Gly Cys Lys Tyr Glu Leu Glu
        115                 120                 125

Gln Met Glu Lys Asn Gly Gly Gly Val Ile Val Asn Met Ala Ser Ile
    130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Asp Tyr Gly Gln
                165                 170                 175

Lys Asn Ile Arg Cys Asn Ala Val Cys Pro Gly Tyr Ile Glu Thr Pro

```
                180             185             190
Leu Leu Glu Ser Leu Thr Lys Glu Met Lys Glu Ala Leu Ile Ser Lys
                    195                 200                 205

His Pro Met Gly Arg Leu Gly Lys Pro Glu Glu Val Ala Glu Leu Val
            210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245

<210> SEQ ID NO 331
<211> LENGTH: 747
<212> TYPE: DNA
<213> ORGANISM: Artificial sequence
<220> FEATURE:
<223> OTHER INFORMATION: Engineered sequence

<400> SEQUENCE: 331
atgggtatcc tggacaacaa agtcgcactg gttacgggcg ctggttcggg catcggtctg      60
gcggtggcac actcctacgc taaagaaggc gctaaagtca ttgtgtcaga tatcaacgaa     120
gacaagggta taaaaccgt tgaagatatt aaagcacagg gcggtgaagc tagttttgtg     180
aaagcggaca ccagcaaccc ggaagaagtg aagccctgg ttaaacgtac ggtcgaaatt     240
tatggtcgcc tggatgtggc atgcaacaat gctggcattg gcggtgaaaa ggcactggct     300
ggtgattacg gcctggacag ctggcgtaaa gttctgtctg tgaatctgga cggtgtcttc     360
tatggctgta aatacgaact ggaacaaatg gagaaaaacg gcggtggcgt atcgtcaat     420 atggccagca ttcatggtat cgttgcgcag ccgctgaact ctgcatatac ctctgcgaaa     480
cacgccgtgg ttggcctgac gaaaaacatt ggtgctgatt atggccagaa aaacatccgt     540
tgcaatgcgg tgtgcccggg ctacattgaa accccgctgc tggaatcact gacgaaagaa     600
atgaaagaag ccctgatctc gaaacacccg atgggtcgcc tgggcaaacc ggaagaagtg     660
gcagaactgg ttctgtttct gagttccgaa aaatcatcgt tcatgaccgg tggctattac     720
ctggtcgatg gtggctacac ggcagtg                                        747

<210> SEQ ID NO 332
<211> LENGTH: 249
<212> TYPE: PRT
<213> ORGANISM: Artificial sequence
<220> FEATURE:
<223> OTHER INFORMATION: Engineered sequence

<400> SEQUENCE: 332

Met Gly Ile Leu Asp Asn Lys Val Ala Leu Val Thr Gly Ala Gly Ser
1               5                   10                  15

Gly Ile Gly Leu Ala Val Ala His Ser Tyr Ala Lys Glu Gly Ala Lys
                20                  25                  30

Val Ile Val Ser Asp Ile Asn Glu Asp Lys Gly Asn Lys Thr Val Glu
            35                  40                  45

Asp Ile Lys Ala Gln Gly Gly Glu Ala Ser Phe Val Lys Ala Asp Thr
        50                  55                  60

Ser Asn Pro Glu Glu Val Glu Ala Leu Val Lys Arg Thr Val Glu Ile
65                  70                  75                  80

Tyr Gly Arg Leu Asp Val Ala Cys Asn Asn Ala Gly Ile Gly Gly Glu
                85                  90                  95

Lys Ala Leu Ala Gly Asp Tyr Gly Leu Asp Ser Trp Arg Lys Val Leu
```

-continued

```
                    100                 105                 110
Ser Val Asn Leu Asp Gly Val Phe Tyr Gly Cys Lys Tyr Glu Leu Glu
            115                 120                 125

Gln Met Glu Lys Asn Gly Gly Gly Val Ile Val Asn Met Ala Ser Ile
        130                 135                 140

His Gly Ile Val Ala Gln Pro Leu Asn Ser Ala Tyr Thr Ser Ala Lys
145                 150                 155                 160

His Ala Val Val Gly Leu Thr Lys Asn Ile Gly Ala Asp Tyr Gly Gln
                165                 170                 175

Lys Asn Ile Arg Cys Asn Ala Val Cys Pro Gly Tyr Ile Glu Thr Pro
            180                 185                 190

Leu Leu Glu Ser Leu Thr Lys Glu Met Lys Glu Ala Leu Ile Ser Lys
        195                 200                 205

His Pro Met Gly Arg Leu Gly Lys Pro Glu Glu Val Ala Glu Leu Val
    210                 215                 220

Leu Phe Leu Ser Ser Glu Lys Ser Ser Phe Met Thr Gly Gly Tyr Tyr
225                 230                 235                 240

Leu Val Asp Gly Gly Tyr Thr Ala Val
                245
```